(12) United States Patent
Fray et al.

(10) Patent No.: US 6,350,907 B1
(45) Date of Patent: Feb. 26, 2002

(54) MATRIX METALLOPROTEASE INHIBITORS

(75) Inventors: Michael Jonathan Fray; Roger Peter Dickinson; Kevin Neil Dack, all of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/546,756

(22) Filed: Apr. 11, 2000

Related U.S. Application Data

(63) Continuation-in-part of application No. 09/424,402, filed as application No. PCT/EP98/08565 on Dec. 23, 1998, now abandoned.

(30) Foreign Application Priority Data

Jan. 9, 1998 (GB) .............................................. 9800510
Jun. 2, 1998 (GB) .............................................. 9811843

(51) Int. Cl.[7] ........................ C07C 259/04; A61K 31/16
(52) U.S. Cl. ........................ 562/623; 564/153; 514/357; 514/399; 514/419; 514/438; 514/520; 514/524; 514/563; 514/575; 546/337; 548/388.1; 548/495; 549/76; 549/77; 549/296; 558/414; 562/448
(58) Field of Search ................................. 572/623, 448; 514/575, 563, 357, 399, 438, 419, 520, 524; 546/337; 548/338.1, 495; 549/76, 77, 296; 558/414; 562/623, 448; 564/153

(56) References Cited

U.S. PATENT DOCUMENTS

| | | | | |
|---|---|---|---|---|
| 5,840,974 A | * | 11/1998 | Whittaker et al. | 562/623 |
| 5,917,090 A | * | 6/1999 | Huxley et al. | 562/623 |

FOREIGN PATENT DOCUMENTS

| | | |
|---|---|---|
| WO | 9402446 | 2/1994 |
| WO | 9402447 | 2/1994 |
| WO | 9412169 | 6/1994 |
| WO | 9425434 | 11/1994 |
| WO | 9425435 | 11/1994 |
| WO | 9509841 | 4/1995 |
| WO | 9512603 | 5/1995 |
| WO | 9519956 | 7/1995 |
| WO | 9519961 | 7/1995 |
| WO | 9519965 | 7/1995 |
| WO | 9532944 | 12/1995 |
| WO | 9616027 | 5/1996 |
| WO | 9633165 | 10/1996 |
| WO | 9633166 | 10/1996 |
| WO | 9635712 | 11/1996 |
| WO | 9635714 | 11/1996 |
| WO | 9702239 | 1/1997 |

OTHER PUBLICATIONS

Beckett and Whittaker, 1998, Exp. Opin. Patents 8(3):259–282, "Matrix metalloproteinase inhibitors 1998".
Levy et al., 1998, J. Med. Chem. 41:199–223, "Matrix metalloproteinase inhibitors: a structure–activity study".
Bender, 1997, slide presentation at $2^{nd}$ Winter Conference on Medicinal and Bioorganic Chemistry, Steamboat Springs, Colorado.

* cited by examiner

Primary Examiner—Shailendra Kumar
(74) Attorney, Agent, or Firm—Peter C. Richardson; Paul H. Ginsburg; Elsa Djuardi

(57) ABSTRACT

Compounds of formula (I):

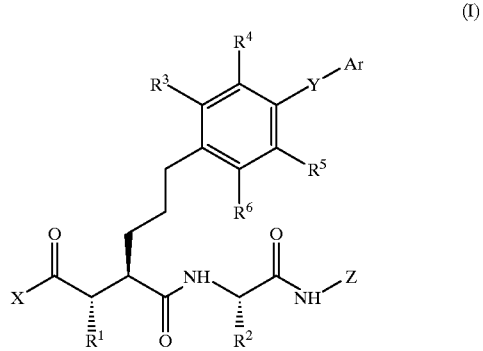

or pharmaceutically acceptable salts thereof, or solvates of either entity, wherein the substituents have the values described herein, are useful as matrix metalloprotease (MMP) inhibitors

37 Claims, No Drawings

MATRIX METALLOPROTEASE INHIBITORS

This application is a continuation-in-part of application Ser. No. 09/424,402, filed Nov. 23, 1999, now abandoned, which is the U.S. national stage of PCT/EP98/08565, which has an international filing date of Dec. 23, 1998, and which claims priority from GB 9800510.1, which was filed on Jan. 9, 1998, and GB 9811843.3, which was filed on Jun. 2, 1998.

This invention relates to certain compounds, and their pharmaceutically acceptable salts, which inhibit matrix metalloproteases (MMPs), particularly MMP-3, MMP-12 and MMP-13. They are therefore useful in the treatment of mammals having conditions alleviable by inhibition of MMPs, especially MMP-3, MMP-12 and MMP-13.

MMPs constitute a family of structurally similar zinc-containing metalloproteases, which are involved in the remodelling, repair and degradation of extracellular matrix proteins, both as part of normal physiological processes and in pathological conditions. Since they have high destructive potential, the MMPs are usually under close regulation, and failure to maintain MMP regulation has been implicated as a component of a number of conditions. Examples of conditions where MMPs are thought to be important are those involving bone restructuring, embryo implantation in the uterus, infiltration of immune cells into inflammatory sites, ovulation, spermatogenesis, tissue remodelling during wound repair and organ differentiation such as such as in venous and diabetic ulcers, pressure sores, colon ulcers for example ulcerative colitis and Crohn's disease, duodenal ulcers, fibrosis, local invasion of tumours into adjacent areas, metastatic spread of tumour cells from primary to secondary sites, and tissue destruction in arthritis, skin disorders such as dystrophic epidermolysis bulosa, dermatitis herpetiformis, or conditions caused by or complicated by embolic phenomena, such as chronic or acute cardiac or cerebral infarctions.

Conditions where MMP-3 and MMP-13 have been implicated include tissue destruction such as in venous and diabetic ulcers, pressure sores, colon ulcers for example ulcerative colitis and Crohn's disease, duodenal ulcers, and tissue destruction in arthritis, skin disorders such as dystrophic epidermolysis bulosa, dermatitis herpetiformis, or conditions caused by or complicated by embolic phenomena, such as chronic or acute cardiac or cerebral infarctions.

Another important function of certain MMPs is to activate other enzymes, including other MMPs, by cleaving the pro-domain from their protease domain. Thus, certain MMPs act to regulate the activities of other MMPs, so that over-production in one MMP may lead to excessive proteolysis of extracellular matrix by another.

Excessive production of MMP-3 is thought to be responsible for pathological tissue breakdown which underlies a number of diseases and conditions. For example, MMP-3 has been found in the synovium and cartilage of osteoarthritis and rheumatoid arthritis patients, thus implicating MMP-3 in the joint damage caused by these diseases. (See K. L. Sirum, C. E Brinkerhoff, Biochemistry, 1989, 28, 8691; Z. Gunja-Smith, H. Nagasse, J. F. Woessner, Biochem. J., 1989, 258, 115). MMP-13 is also thought to play an important role in the pathology of osteoarthritis and rheumatoid arthritis (M. Stahle-Backdahle, B. Sandstedt, K. Bruce, A. Lindahl, M. G. Jimenez, J. A. Vega, C. Lopez Otin, Lab. Invest., 1997, 76, 717–28; O. Lindy, Y. T. Konttinen, T. Sorsa, Y. Ding, S. Santavirta, A. Ceponis, C. Lopez Otin, Arthritis Rheum. 1997, 40, 1391–9).

Over-expression of MMP-3 is also thought to be responsible for much of the tissue damage and chronicity of chronic wounds, such as venous and diabetic ulcers, and pressure sores. (See M. Vaalamo, M. Weckroth, P. Puoakkainen, J. Kere, P. Saarinen, J. Lauharanta, U. K. Saarialho-Kere, Brit. J Dermatology, 1996, 135, 52–59).

During the healing of normal and chronic wounds, MMP-1 is expressed by migrating keratinocytes at the wound edges (U. K. Saarialho-Kere, S. O. Kovacs, A. P. Pentland, J Clin. Invest. 1993, 92, 2858–66). There is evidence which suggests MMP-1 is required for keratinocyte migration on a collagen type I matrix in vitro, and is completely inhibited by the presence of the non-selective MMP inhibitor SC44463 ((N4-hydroxy)-N1-[(1S)-2-(4-methoxyphenyl)methyl-1-((1R)-methylamino)carbonyl)]-(2R)-2-(2-methylpropyl)butanediamide) (B. K. Pilcher, J. A. Dumin, B. D. Sudbeck, S. M. Krane, H. G. Welgus, W.C. Parks, J. Cell Biol., 1997, 137, 1–13). Keratinocyte migration in vivo is essential for effective wound healing to occur.

MMP-2 and MMP-9 appear to play important roles in wound healing during the extended remodelling phase and the onset of re-epithelialisation, respectively (M. S. Agren, Brit. J. Dermatology, 1994, 131, 634–40; T. Salo, M. Mäkänen, M. Kylmäniemi, Lab. Invest., 1994, 70, 176–82). The potent, non-selective MMP inhibitor BB94 ((2S,3R)-5-methyl-3-{[(1S)-1-(methylcarbamoyl)-2-phenylethyl]carbamoyl}-2-[(2-thienylthio)methyl]hexanohydroxamic acid, batimastat), inhibits endothelial cell invasion of basement membrane, thereby inhibiting angiogenesis (G. Tarboletti, A. Garofalo, D. Belotti, T. Drudis, P. Borsotti, E. Scanziani, P. D. Brown, R. Giavazzi, J. Natl. Cancer Inst., 1995, 87, 293–8). There is evidence that this process requires active MMP-2 and/or 9.

Thus, non-selective MMP inhibitors which inhibit MMPs 1 and/or 2 and/or 9 would be expected to impair wound healing. As described above, MNP-14 is responsible for the activation of MMP-2, and thus inhibition of MMP-14 might also result in impaired wound healing.

The production of MMP-3 has also been thought to be involved in tissue damage in conditions where there is ulceration of the colon (as in ulcerative colitis and Crohn's disease, see S. L. Pender, S. P. Tickle, A. J. Docherty, D. Howie, N. C. Wathen, T. T. MacDonald, J. Immunol., 1997, 158, 1582; C. J. Bailey, R. M. Hembry, A. Alexander, M. H. Irving, M. E. Grant, C. A. Shuttleworth, J. Clin. Pathol., 1994, 47, 113–6), or duodenum (see U. K. Saarialho-Kere, M. Vaalamo, P. Puolakkainen, K. Airola, W. C. Parks, M. L. Kaajalainen-Lindsberg, Am. J. Pathol., 1996, 148, 519–26). It is also likely that MMP-1 and MMP-2 are required during the healing phase of these conditions. A selective MMP-3 inhibitor would be more effective than a non-selective inhibitor.

MMP-3 has also been implicated in skin diseases such as dystrophic epidermolysis bullosa (T. Sato, K. Nomura, I. Hashimoto, Arch. Dermatol. Res., 1995, 287, 428) and dermatitis herpetiformis (K. Airola, M. Vaalamo, T. Reunala, U. K. Saarialho-Kere, J. Invest. Dermatology, 1995, 105, 184–9).

Rupture of atherosclerotic plaques by MMP-3 can lead to cardiac or cerebral infarction. (F. Mach, et al., Circulation, 1997, 96, 396–9.) Thus, MMP-3 inhibitors may find utility in the treatment of conditions caused by or complicated by embolic phenomena, such as chronic or acute cardiac or cerebral infarctions. MMP-12 (macrophage elastase) is thought to contribute to the pathology of atherosclerosis, gastro-intestinal ulcers and emphysema. For example, in a rabbit model of developing atherosclerosis, MMP-12 is expressed abundantly by macrophage foam cells (S. Matsumoto, et al, Am.J.Pathol. 1998, 153, 109). MMP-12 is also expressed abundantly by macrophages in the vicinity of shedding mucosal epithelium in human gastro-intestinal ulcers, such as those found in patients with ulcerative colitis and Crohn's disease (M. Vaalamo, et al, *Am.J.Pathol.*, 1998, 152, 1005). MMP-12 is thought to be important for the progression of lung damage by cigarette smoke. In a model of cigarette smoke-induced emphysema, mice lacking the gene for MMP-12 were resistant to developing the condition whereas wild-typemice suffered significant lung damage (R D Hautamaki, et al, *Science*, 1997, 277, 2002).

For recent reviews of MMPs, see Zask et al, *Current Pharmaceutical Design*, 1996, 2, 624–661; Beckett, *Exp. Opin. Ther. Patents*, 1996, 6, 1305–1315; and Beckett et al, Drug Discovery Today, vol 1(no.1), 1996, 16–26.

Alternative names for various MMPs and substrates acted on by these are shown in the table below (Zask et al, supra).

| Enzyme | Other names | Preferred substrates |
|---|---|---|
| MMP-1 | Collagenase-1, interstitial collagenase | Collagens I, II, III, VII, X, gelatins |
| MMP-2 | Gelatinase A, 72 kDa gelatinase | Gelatins, collagens IV, V, VII, X, elastin, fibronectin; activates pro-MMP-13 |
| MMP-3 | Stromelysin-1 | Proteoglycans, laminin, fibronectin, gelatins. |
| MMP-7 | Pump, Matrilysin | Proteoglycans, laminin, fibronectin, gelatins, collagen IV, elastin, activates pro-MMP-1 and -2. |
| MMP-8 | Collagenase-2, neutrophil collagenase | Collagens I, II, III |
| MMP-9 | Gelatinase B, 92 kDa gelatinase | Gelatins, collagens IV, V, elastin |
| MMP-12 | Macrophage metalloelastase | Elastin, collagen IV, fibronectin, activates pro-MMP-2 & 3. |
| MMP-13 | Collagenase-3 | Collagens I, II, III, gelatins |
| MMP-14 | MT-MMP-1 | Activates pro-MMP-2 & 13, gelatins |
| MMP-15 | MT-MMP-2 | unknown |
| MMP-16 | MT-MMP-3 | Activates pro-MMP-2 |
| MMP-17 | MT-MMP-4 | unknown |

A number of publications, including some of those mentioned in the reviews above, describe compounds of the general formula shown below as MMP inhibitors.

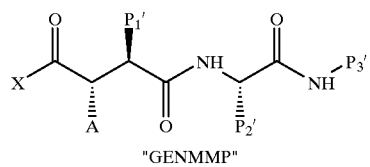

"GENMMP"

wherein "A" is known as the "alpha" group and XCO is is a zinc-binding group such as a carboxylic acid or hydroxamic acid moiety.

The review by Beckett et al, mentioned above, states that a vast range of groups can be tolerated at the $P_2'$ position without significantly affecting the behaviour of the compounds.

International Patent Application publication nos. WO96/33165 and WO96/33161 (British Biotech Pharmaceuticals Ltd.) generically disclose compounds of formula "GENMMP" above where, inter alia $P_1'$ is optionally substituted phenyl($C_1$–$C_6$)alkyl and $P_3'$ is a group $CHR^xR^y$ where $R^x$ and $R^y$ represent optionally substituted phenyl or heteroaryl rings. These compounds are said to be selective inhibitors of MMP-3 and MMP-7 relative to human fibroblast collagenase (MMP-1) and 72 KDa gelatinase (MMP-2).

International Patent Application publication no. WO96/16027 (Syntex Inc. and Agouron Pharmaceuticals Inc.) discloses MMP inhibitors of the general formula "GENMMP" as shown above wherein COX includes $CO_2H$ and CONHOH, $P_1'$ is a group $R_2X$ which includes optionally substituted aryl($C_{0-4}$ alkylene), and $P_3'$ is $(CH_2)_pR^7$ where p is 0 to 4, provided that when p is not 0 then $R^2X$ is biphenylalkyl, and $R^7$ is aryl or heteroaryl. Compounds where p is 0, 2 or 3 are said to be preferred, and compounds where p is 0 and COX is $CO_2H$ or CONHOH are preferred for matrilysin (i.e. MMP-7) inhibition.

A number of compounds from said publication WO96/16027 of general formula "GENMMP" have been disclosed by the Agouron group (2nd Winter Conference on Medicinal and Bioorganic Chemistry, Steamboat Springs, Colo., USA, January 1997) e.g. wherein X is OH, $P_1'$ is an optionally 4'-substituted biarylpropyl group, $P_2'$ is isobutyl and $P_3'$ is 4-methoxycarbonylphenyl. Such compounds were reported to have poor to moderate MMP-3/MMP-2 selectivity. It was found that use of an alpha-substituent and replacement of the 4-methoxycarbonylphenyl moiety with a 4-methylthiophenyl group greatly enhanced the MMP-3/MMP-2 selectivity.

The review by Beckett (above) also mentions an Agouron compound (#31 of the review) of general formula "GENMMP" wherein X is OH, $P_1'$ is biphenylpropyl, $P_2'$ is t-butyl, and $P_3'$ is 4-pyridyl. This compound has almost identical $K_i$ values for MMP-3 and MMP-2, so is not selective for MMP-3 over MMP-2.

International Patent Application no. WO95/12603 (Syntex) discloses compounds, said to be MMP-3 and MMP-7 inhibitors, of formula "GENMMP" above, where $P_3'$ is a substituted phenyl moiety and $P_1'$ includes arylalkyl.

We have now found a group of MMP inhibitor compounds with good activity for MMP-3, MMP-12 and MMP-13, and good selectivity for MMP-3 over other MMPs such as MMPs-1, 2, 9 and 14. It has been found, for this group of compounds, that the MMP-3 selectivity is remarkably dependent on a particular combination of $P_1'$ and $P_3'$ substituents, which effect could not have been predicted from the art mentioned above.

Thus, according to the present invention, there are provided compounds of formula (I):

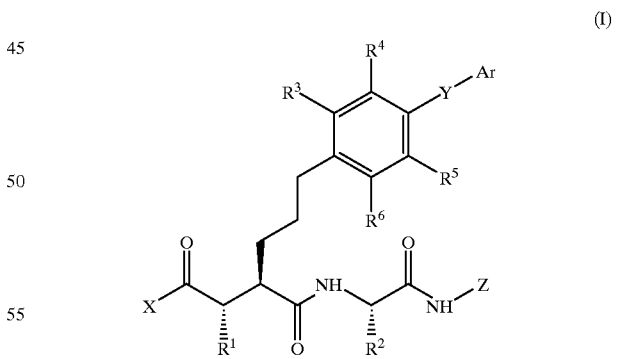

(I)

and pharmaceutically acceptable salts thereof, wherein
$R^1$ is H, OH, $C_{1-4}$ alkyl, $C_{1-4}$ alkoxy, or $C_{2-4}$ alkenyl,
$R^2$ is $C_{1-6}$ alkyl optionally substituted by fluoro, indolyl, imidazolyl, $SO_2(C_{1-4}$ alkyl), $C_{5-7}$ cycloalkyl,
or by an optionally protected OH, SH, $CONH_2$, $CO_2H$, $NH^2$ or NHC(=NH)$NH_2$ group, $C_{5-7}$ cycloalkyl optionally substituted by $C_{1-6}$ alkyl,
or is benzyl optionally substituted by optionally protected OH, $C_{1-6}$ alkoxy, benzyloxy or benzylthio, wherein the optional protecting groups for said OH, SH, CONH$_2$, NH$_2$ and NHC(=NH)NH$_2$ groups are selected from C$_{1-6}$ alkyl, benzyl, C$_{1-6}$ alkanoyl,
and where the optional protecting groups for said CO$_2$H is selected from C$_{1-6}$ alkyl or benzyl, R$^3$, R$^5$ and R$^6$ are each independently selected from H and F,
R$^4$ is CH$_3$, Cl or F,
X is HO or HONH,
Y is a direct link or O.
Z is either a group of formula (a):

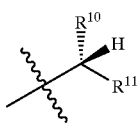

where R$^{10}$ is C$_{1-4}$ alkyl, C$_{1-4}$ alkoxymethyl, hydroxy(C$_{2-4}$ alkyl), carboxy(C$_{1-4}$ alkyl) or (amino or dimethylamino)C$_{2-4}$ alkyl,
and R$^{11}$ is phenyl, naphthyl or pyridyl optionally substituted by up to three substituents independently selected from halo and methyl;
or (b)

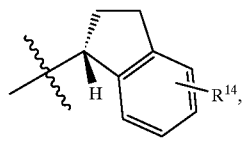

R$^{14}$ is H, OH, CH$_3$ or halo,
Ar is a group of formula (c), (d) or (e):

(c)

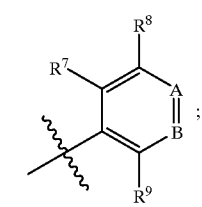

(d)

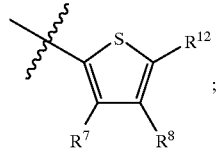

(e)

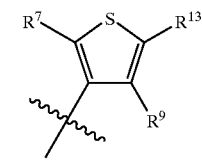

wherein
A is N or CR$^{12}$,
B is N or CR$^{13}$,
provided that A and B are not both N,
R$^7$ and R$^9$ are each independently H or F, R$^8$, R$^{12}$ and R$^{13}$ are each independently H, CN, C$_{1-6}$ alkyl, hydroxy(C$_{1-6}$ alkyl), hydroxy(C$_{1-6}$)alkoxy, C$_{1-6}$ alkoxy (C$_{1-6}$)alkoxy,(amino or dimethylamino)C$_{1-6}$ allyl, CONH$_2$, OH, halo, C$_{1-6}$ alkoxy, (C$_{1-6}$ alkoxy)methyl, piperazinylcarbonyl, piperidinyl, C(NH$_2$)=NOH or C(=NH)NHOH, with the proviso that at least two of R$^8$, R$^{12}$ and R$^{13}$ are H.

"Alkyl" groups, including the alkyl moiety of "alkoxy" groups, and "alkenyl" groups, can be straight or branched where the number of carbon atoms allows.

"Halo" means F, Cl, Br or I.

The compounds of the present invention are MMP inhibitors, and are especially potent and selective MMP-3 inhibitors, especially with good selectivity over MMPs-1,2,9 and/or 14. In addition, certain of the compounds of the invention have useful MMP-12 and/or MMP-13 inhibitory activity.

Preferably, R$^1$ is H, OH, C$_{1-4}$ alkyl or C$_{1-4}$alkoxy.
More preferably, R$^1$ is H, OH, n-propyl or ethoxy.
Most preferably R$^1$ is H.
Preferably R$^2$ is C$_{1-6}$ alkyl optionally substituted by indolyl, C$_{1-6}$ alkylthio, SO$_2$(C$_{1-4}$alkyl), C$_{5-7}$ cycloalkyl, OH or SH, C$_{5-7}$ cycloalkyl optionally substituted by C$_{1-6}$ alkyl, or R$^2$ is benzyl.

More preferably R$^2$ is C$_{1-6}$ alkyl optionally substituted by OH, SO$_2$(C$_{1-4}$ alkyl) or C$_{5-7}$ cycloalkyl, cyclohexyl optionally substituted by C$_{1-6}$ alkyl, or R$^2$ is benzyl.

Yet more preferably, R$^2$ is cyclohexylmethyl, isopropyl, 1-methylcyclohexyl, t-butyl, C(CH$_3$)$_2$SO$_2$CH$_3$, benzyl or C(CH$_3$)$_2$OH.

Further yet more preferably R$^2$ is isopropyl, t-butyl or benzyl.

Most preferably, R$^2$ is t-butyl.
Preferably, Z is a group of formula (a):

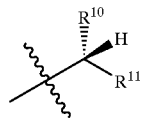

where R$^{10}$ is C$_{1-4}$ alkyl, C$_{1-4}$ alkoxymethyl or hydroxy(C$_{2-4}$ alkyl) and R$^{11}$ is phenyl or pyridyl, optionally substituted by up to three substituents independently selected from halo and methyl,
or Z is

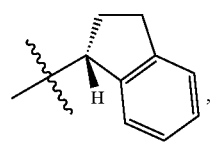

More preferably Z is a group of formula (a):

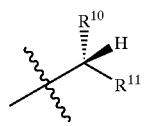

where $R^{10}$ is $C_{1-4}$ alkyl, $C_{1-4}$ alkoxymethyl or hydroxy($C_{2-4}$ alkyl), and $R^{11}$ is phenyl, pyridin-4-yl or pyridin-3-yl, or Z is

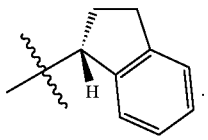

Yet more preferably Z is a group of formula (a):

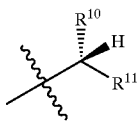

where $R^{10}$ is $CH_3$, $CH_2OCH_3$, or $CH_2OH$, and $R^{11}$ is phenyl, pyridin-4-yl or pyridin-3-yl, or Z is

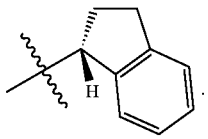

Most preferably, Z is a group of formula

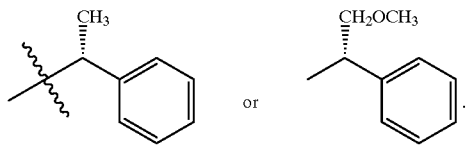

Preferably $R^3$ is H.
Preferably $R^4$ is F when Y is O.
Preferably $R^4$ is Cl or $CH_3$ when Y is a direct link.
Preferably $R^5$ is H.
Preferably $R^6$ is H.
Preferably Ar is a group of formula (c),

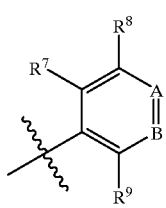

(c)

wherein
A is $CR^{12}$ and B is $CR^{13}$,
$R^7$ and $R^9$ are each independently H or F,
$R^8$ and $R^{13}$ are each independently H, F, Cl, CN, $CONH_2$, $CH_3$ or $OCH_3$, and
$R^{12}$ is H, $C_{1-6}$ alkyl, CN, hydroxy($C_{2-6}$ alkyl), (amino or dimethylamino)$C_{2-6}$ alkyl, $CONH_2$, OH, halo, $C_{1-6}$ alkoxy, ($C_{1-6}$ alkoxy)methyl, piperazinylcarbonyl, piperidinyl, $C(NH_2)NOH$ or $C(=NH)NHOH$.

More preferably Ar is a group of formula (c),

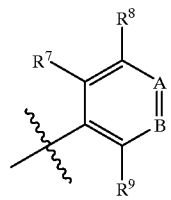

(c)

wherein A is $CR^{12}$, B is $CR^{13}$, and $R^7$, $R^8$ and $R^9$ are H.
Yet more preferably, Ar is a group of formula (c),

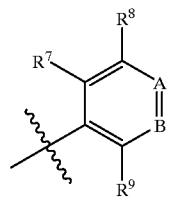

(c)

wherein
A is $CR^{12}$, B is $CR^{13}$, $R^7$, $R^8$ and $R^9$ are H,
$R^{12}$ is H, $C_{1-6}$ alkyl, CN, hydroxy($C_{2-6}$ alkyl), (amino or dimethylamino)$C_{2-6}$ alkyl, $CONH_2$, OH, halo, $C_{1-6}$ alkoxy, ($C_{1-6}$ alkoxy)methyl, $C(NH_2)=NOH$ or $C(=NH)NHOH$, and $R^{13}$ is H, $OCH_3$, CN, $CONH_2$, $CH_3$ or F.

Further yet more preferably Ar is phenyl, 3-methoxyphenyl, 4-cyanophenyl, 3-cyanophenyl, 3-carbamoylphenyl or 4-hydroxyamidinophenyl. Most preferably, Ar is phenyl or 3-methoxyphenyl.

A preferred group of substances are those where the substituents have the values mentioned in the Examples, viz.:
$R^1$ is H, OH, n-propyl or ethoxy,
$R^2$ is t-butyl, isopropyl or benzyl,
Z is a group of formula

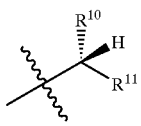

where $R^{10}$ is $CH_3$, $CH_2OCH_3$, or $CH_2OH$, and $R^{11}$ is phenyl, pyridin-4-yl or pyridin-3-yl, or Z is

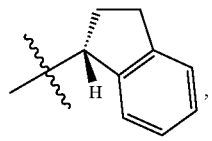

$R^3$ is H,
$R^4$ is $CH_3$, Cl or F,
$R^5$ is H,
$R^6$ is H,
and Ar is phenyl, 3-methoxyphenyl, 4-cyanophenyl, 3-cyanophenyl, 3-carbamoylphenyl or 4-hydroxyamidinophenyl, and the salts thereof.

Another preferred group are the compounds are those of the Examples below, and the salts thereof.

The most preferred substances are selected from Examples 3, 4, 8, 14, 15, 16, 22, 29, 30, 31 and 32 below, and the salts thereof.

Pharmaceutically-acceptable salts are well known to those skilled in the art, and for example include those mentioned in the art cited above, and by Berge et al, in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

Pharmaceutically acceptable base addition salts are well known to those skilled in the art, and for example include those mentioned in the art cited above, and can be formed from bases which form non-toxic salts and include the aluminium, calcium, lithium, magnesium, potassium, sodium and zinc salts, and salts of non-toxic amines such as diethanolamnine.

Certain of the compounds of the formula (I) may exist as geometric isomers. The compounds of the formula (I) may possess one or more asymmetric centres, apart from the specified centres in formula (I), and so exist in two or more stereoisomeric forms. The present invention includes all the individual stereoisomers and geometric isomers of the compounds of formula (I), apart from the specified centres in formula (I), including the group Z, and mixtures thereof.

Another aspect of the invention is a pharmaceutical composition comprising a compound or salt according to the above definitions and a pharmaceutically-acceptable adjuvant, diluent or carrier.

Yet another aspect of the invention is a compound or salt according to the above definitions for use as a medicament.

A further aspect of the invention is the use of a compound or salt according to the above definitions for the manufacture of a medicament for the treatment of a condition mediated by one or more matrix metalloproteases, especially MMP-3 and/or MMP-12 and/or MMP-13.

Yet another aspect of the invention is a method of treatment of a condition mediated by one or more matrix metalloproteases, especially MMP-3 and/or MMP-12 and/or MMP-13.

It is to be appreciated that reference to treatment includes prophylaxis as well as the alleviation of established symptoms of MMP-mediated conditions.

The invention further provides Methods for the production of compounds of the invention, which are described below and in the Examples. The skilled man will appreciate that the compounds of the invention could be made by methods other than those specifically described herein, by adaptation of the methods herein described in the sections below and/or adaptation thereof, and of methods known in the art. Suitable guides to synthesis, functional group transformations, use of protecting groups, etc. are, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and PGM Wuts, John Wiley and Sons Inc. (1991), and P J Kocienski, in "Protecting Groups", Georg Thieme Verlag (1994).

In the Methods below, unless otherwise specified, the substituents are as defined above with reference to the compounds of formula (I) above.

Method 1

Compounds of formula (I) where X is OH can be obtained via the corresponding compound of formula (II) below where $X_1$ is a group capable of being transformed to a carboxy group in conditions which do not result in substantial transformation of the other parts of the compound (II). A suitable example of such a group is $CO_2$(t-butyl or methyl). The t-butyl group can be cleaved by reaction with an acid such as hydrogen chloride or trifluoroacetic acid (TFA) in a suitable solvent such as anhydrous dichloromethane or dioxane, at a suitable temperature such as between 0° C. and 20° C. The methyl ester can be hydrolysed by a hydroxide such as lithium hydroxide, in a suitable solvent system such as a tetrahydrofuran/water mixture, suitably at room temperature.

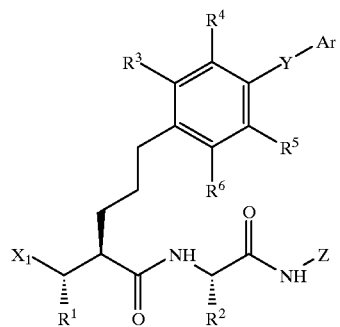

(II)

Compounds of formula (II) may be made by methods known in the art, and exemplified in the Preparations below, for example by coupling of suitable amine and acid derivatives, which are available by known chemistry.

Method 2

Compounds of formula (I) where X is NHOH can be obtained from the corresponding compounds of formula (I) where X is OH via treatment of the compounds of formula (I) where X is OH with hydroxylamine, such as by generation from a hydroxylamine salt such as the hydrochloride, by a suitable base such as a tertiary amine, e.g. diisopropylethylamine, in a suitable solvent such as N,N-dimethylformamide (DMF), and a coupling agent such as N-[(dimethylamino)-1H-1,2,3-triazolo[4,5-b]pyridin-1-ylmethylene]-N-methylmethaninium hexafluorophosphate N-oxide ("HATU", which reagent is described in *Tet.Letts.* (1994) 35, 2279), at a suitable temperature such as from 0–20° C.

Compounds of formula (I) where X is OH may be made by conventional methods and the methods described herein.

Method 3

Compounds of formula (I) where X is NHOH can be obtained from the corresponding compounds of formula (I) where X is OH via treatment of the compounds of formula (I) where X is OH with O-allylhydroxylamine, such as by generation from a O-allylhydroxylamine salt such as the hydrochloride, by a suitable base such as a tertiary amine e.g. diisopropylethylamine, in a suitable solvent such as N,N-dimethylformamide (DMF) or dichloromethane, and a coupling agent, e.g. a peptide coupling agent such as 7-azabenzotriazol-1-yloxytris(pyrrolidino)phosphonium hexafluorophosphate ("PyAOP"), at a suitable temperature such as from 0–20° C. This stage gives compounds of formula (III) below.

This coupling method is generally described in *Tet.Letts.* (1994) 35, 2279.

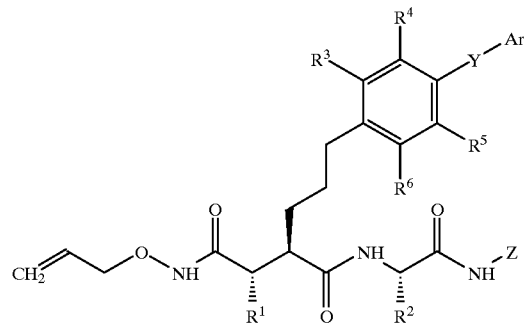

(III)

Compounds of formula (III) can be transformed into compounds of formula (I) where X is NHOH by treatment with ammonium formate in the presence of a suitable catalyst such as bis(triphenylphosphine)palladium(II) acetate, in a suitable solvent such as aqueous ethanol, at a suitable temperature such as the refluxing temperature of aqueous ethanol.

Method 4

Compounds of formula (I) where X is NHOH and R¹ is OH can be made via reaction of a compound of formula (IV) with hydroxylamine, for example via generation from a hydroxylamine salt such as the hydrochloride with a suitable base such as sodium methoxide in a suitable solvent such as methanol.

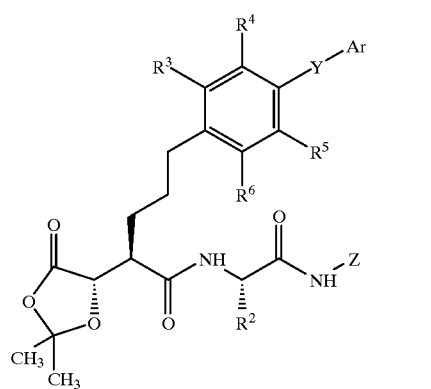

(IV)

Compounds of formula (IV) may be made by conventional methods as are exempllified in the Preparations below.

Method 5

Compounds of formula (I) may be made from compounds of formula (V) below via cross-coupling with a compound of formula (VI) below:

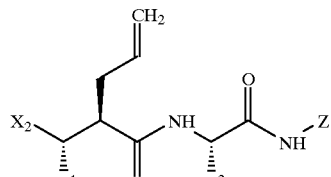

(V)

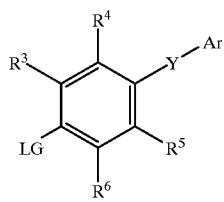

(VI)

where $X_2$ is a protected acid such as the t-butyl or methyl ester group and LG is a cross-coupling leaving group such as I, Br or $OSO_2CF_3$. The cross-coupling reaction can be carried out in the presence of a catalyst such as bis(tri-o-tolyl)phosphine palladium(II) acetate with a suitable base such as triethylamine, in a suitable solvent such as acetonitrile or DMF, at a suitable temperature such as between 50–150° C. This type of reaction is generally described by Heck in *Tet.Letts.* (1984) 25, 2271, and numerous other articles.

Compounds of the formula (V) can be made by conventional methods such as by adaptation of those described in the Preparations below.

Compounds of the formula (VI) can be made by conventional methods such as by adaptation of those described in the Preparations below, and by reference to the following articles: *Synthesis* (1984) 709; *J Chem Soc Perkin Trans I* (1977) 1841; *J Org Chem* (1994) 59, 6095; ibid, (1979) 44, 4444 and *Tet.Letts.* (1997) 38, 1749.

The resultant product from this reaction is a mixture of compounds of formula (VIIa) and (VIIb) wherein $X_2$ is defined as above for compounds of formula (V).

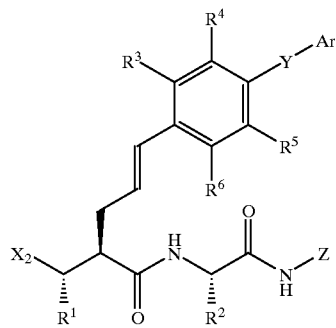

(VIIa)

-continued

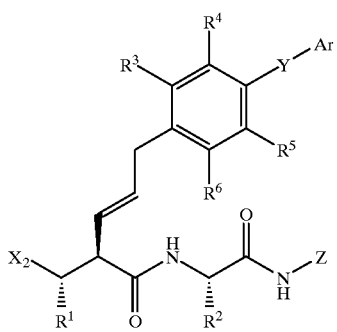

(VIIb)

The compounds of formula (VIIa) and (VIIb) can be transformed into a compound of formula (I) where X is OH, by reduction of the olefinic bond using conventional methods, such as hydrogenation in the presence of a catalyst, or by reaction with diimide, which may be generated, for example, from p-toluenesulphonyl hydrazide, and deprotection of the protected acid moiety $X_2$.

It will be apparent to those skilled in the art that other protection and subsequent deprotection regimes during synthesis of a compound of the invention may be achieved by conventional techniques, for example as described in the volumes by Greene and Wuts, and Kocienski, supra.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Certain compounds of the invention may be interconverted into certain other compounds of the invention by well-known methods from the literature.

Compounds of the invention are available by either the methods described herein in the Methods and Examples or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

The compounds and salts of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

For human use, the compounds of formula (I) or their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract. The compounds or salts can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride). Such formulation techniques are well-known in the art.

All such formulations may also contain appropriate stabilisers and preservatives.

For oral and parenteral administration to human patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

For topical administration to human patients with chronic wounds, the daily dosage level of the compounds, in suspension or other formulation, could be from 0.01 to 50mg/ml, preferably from 0.3 to 30 mg/ml.

The physician in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

Test Methods

The ability of compounds to inhibit the cleavage of fluorogenic peptides by MMPs 1, 2, 3, 9 12, 13 and 14 is described below.

The assays for MMPs 2, 3, 9, and 14 are based upon the original protocol described by Knight et al. (*Fed.Euro.Biochem.Soc.*, 296 (3), 263–266; 1992) with the slight modifications given below.

Inhibition of MMP-1

(i) Enzyme Preparation

Catalytic domain MMP-1 was prepared at Pfizer Central Research. A stock solution of MMP-1 (1 $\mu$M) was activated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 $\mu$M $ZnSO_4$, 0.05% Brij 35) pH 7.5 to a concentration of 10 nM. The final concentration of enzyme used in the assay was 1 nM.

(ii) Substrate

The fluorogenic substrate used in this assay was Dnp-Pro-β-cyclohexyl-Ala-Gly-Cys(Me)-His-Ala-Lys(N-Me-Ala)-$NH_2$ as originally described by Bickett et al (*Anal. Biochem*, 212, 58–64, 1993). The final substrate concentration used in the assay was 10 $\mu$M.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG LabTechnologies, Aylesbury, UK) at an excitation wavelength of 355 nm and emission wavelength of 440 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-2, MMP-3 and MMP-9

(i) Enzyme Preparation

Catalytic domain MMP-2, MMP-3 and MMP-9 were prepared at Pfizer Central Research. A stock solution of MMP-2, MMP-3 or MMP-9 (1 $\mu$M) was activated by the addition of aminophenylmercuric acetate (APMA). For MMP-2 and MMP-9, a final concentration of 1 mM APMA was added, followed by incubation for 1 hour at 37° C. MMP-3 was activated by the addition of 2 mM APMA, followed by incubation for 3 hours at 37° C. The enzymes were then diluted in Tris-HCl assay buffer (100 mM Tris, 100 mM NaCl, 10 mM $CaCl_2$ and 0.16% Brij 35, pH 7.5), to a concentration of 10 nM. The final concentration of enzyme used in the assays was 1 nM.

(ii) Substrate

The fluorogenic substrate used in this screen was Mca-Arg-Pro-Lys-Pro-Tyr-Ala-Nva-Trp-Met-Lys(Dnp)-$NH_2$ (Bachem Ltd, Essex, UK) as originally described by Nagase et al (*J.Biol.Chem.*, 269(33), 20952–20957, 1994). This substrate was selected because it has a balanced hydrolysis rate against MMPs 2, 3 and 9 ($k_{cat}/k_m$ of 54,000, 59,400 and 55,300 $s^{-1}$ $M^{-1}$ respectively). The final substrate concentration used in the assay was 5 $\mu$M.

(iii) Determination of Enzyme Inhibition

Test compounds were dissolved in dimethyl sulphoxide and diluted with test buffer solution (as above) so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence using a fluorimeter (Fluostar; BMG LabTechnologies, Aylesbury, UK) at an excitation wavelength of 328 nm and emission wavelength of 393 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-12 (Human Macrophage Elastase)

(i) Enzyme Preparation

Catalytic domain MMP-12 (200 $\mu$g/ml) was used. MMP-12 was diluted in Tris-HCl assay buffer (50 mM Tris, 200 mM NaCl, 5 mM $CaCl_2$, 20 $\mu$M $ZnSO_4$, 0.02% Brij 35) pH 7.4 to 240 ng/ml. The final concentration of enzyme used in the assay was 60 ng/ml.

(ii) Substrate

The fluorogenic substrate used in this assay was DNP-Pro-Cha-Gly-Cys(Me)-His-Ala-Lys(NMA)-$NH_2$. The final substrate concentration used in the assay was 10 $\mu$M.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate and allowed to equilibrate for 15 minutes at room temperature in an orbital shaker prior to the addition of substrate. Plates were then incubated for 2 hours at room temperature prior to the determination of fluorescence (substrate cleavage) using a fluorimeter at an excitation wavelength of 360 nm and emission wavelength of 460 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-13

(i) Enzyme Preparation

Human recombinant MMP-13 was prepared by PanVera Corporation (Madison, Wis.) and characterized at Pfizer (Groton, Conn.). A 1.9 mg/ml stock was activated with 2 mM APMA for 2 hours at 37° C. MMP-13 was then diluted in assay buffer (50 mM Tris, 200 mM NaCl, 5 mM $CaCl_2$, 20 $\mu$M $ZnCl_2$ and 0.02% Brij 35) at pH 7.5 to a concentration of 5.3 nM. The final concentration of enzyme used in the assay was 1.3 nM.

(ii) Substrate.

The fluorogenic substrate used in this screen was Dnp-Pro-Cha-Gly-Cys(Me)-His-Ala-Lys(NMA)-$NH_2$. The final substrate concentration used in the assay was 10 $\mu$M.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate. The addition of substrate to each well initiated the reaction. Fluorescence intensity was determined on a 96 well plate fluorometer (Cytofluor II; PerSeptive Biosystems, Inc, Framingham, Mass.) at an excitation wavelength of 360 nm and emission wavelength of 460 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-14

(i) Enzyme Preparation

Catalytic domain MMP-14 was purchased from Prof Tschesche, Department of Biochemistry, Faculty of Chemistry, University of Bielefeld, Germany. A 10 $\mu$M enzyme stock solution was activated for 20 minutes at 25°

C. following the addition of 5 μg/ml of trypsin (Sigma, Dorset, UK). The trypsin activity was then neutralised by the addition of 50 μg/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assay was 1 nM.

(ii) Substrate

The fluorogenic substrate used in this screen was Mca-Pro-Leu-Gly-Leu-Dpa-Ala-Arg-$NH_2$ (Bachem Ltd, Essex, UK) as described by Will et al (*J.Biol.Chem.*, 271(29), 17119–17123, 1996). The final substrate concentration used in the assay was 10 μM.

Determination of enzyme inhibition by test compounds was performed as described for MMPs 2, 3 and 9.

Some activity data for certain compounds of the Examples are presented in the Table below.

| | "MMP-x" inhibitor $IC_{50}$/nM | | | | | | |
|---|---|---|---|---|---|---|---|
| Ex. | x = 3 | x = 2 | x = 1 | x = 12 | x = 13 | x = 14 | x = 9 | 3/2sel* |
| 1 | 101 | 10803 | 85 | | | | | 107 |
| 2 | 13.5 | 1269 | 6000 | | 130 | 5650 | 1908 | 94 |

*Selectivity for MMP-3 over MMP-2

The compounds of Examples 3, 4, 8, 14, 15, 16, 22, 29, 30, 31 and 32 had MMP-3/MMP-2 selectivities in the range 195–930.

EXAMPLES AND PREPARATIONS

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (IR) spectra were measured using a Nicolet Magna 550 Fourier transform infra-red spectrometer. Flash chromatography refers to column chromatography on silica gel (Kieselgel 60, 230–400 mesh, from E. Merck, Darmstadt. Kieselgel 60 $F_{254}$ plates from E. Merck were used for TLC, and compounds were visualised using UV light, 5% aqueous potassium permanagate or Dragendorffs reagent (oversprayed with aqueous sodium nitrite). Hexane refers to a mixture of hexanes (hplc grade) b.p. 65–70° C. Ether refers to diethyl ether. Acetic acid refers to glacial acetic acid. 1-Hydroxy-7-aza-1H-1,2,3-benzotriazole (HOAt), N-[(dimethylamino)-1H-1,2,3-triazolo[4,5-b]pyridin-1-ylmethylene]-N-methylmethaninium hexafluorophosphate N-oxide (HATU) and 7-azabenzotriazol-1-yloxytris(pyrrolidino)phosphonium hexafluorophosphate (PyAOP) were purchased from PerSeptive Biosystems U.K. Ltd. "DIPE" refers to diisopropyl ether. Reverse-phase silica gel for flash chromatography was obtained from Fluka (Fluka 100, $C_{18}$, 40–63μ). Pentane refers to h.p.l.c. grade n-pentane (b.pt.35–37° C.).

CAUTION: Certain derivatives of 4-aminobiphenyl are described in the Preparations below. 4-aminobiphenyl is a known human carcinogen. Thus, analogues should be handled with due care. For leading references, see Yuta, K., Jurs, P. C., *J Med. Chem.* (1981), 24(3), 241–51; You, Z., Brezzell, M. D., Das, S. K., Hooberman, B. H., Sinsheimer, J. E. *Mutat. Res.* (1994), 320(1–2), 45–58; Hecht, S. S., et al, *J Med. Chem.* (1979), 22(8), 981–7.

Example 1

(3R)-3-({[(1S)-2,2-dimethyl-1-({[(1R)-1-phenylethyl]amino}carbonyl)propyl]amino}carbonyl)-6-[(3-methyl-4-phenyl)phenyl]hexanoic acid

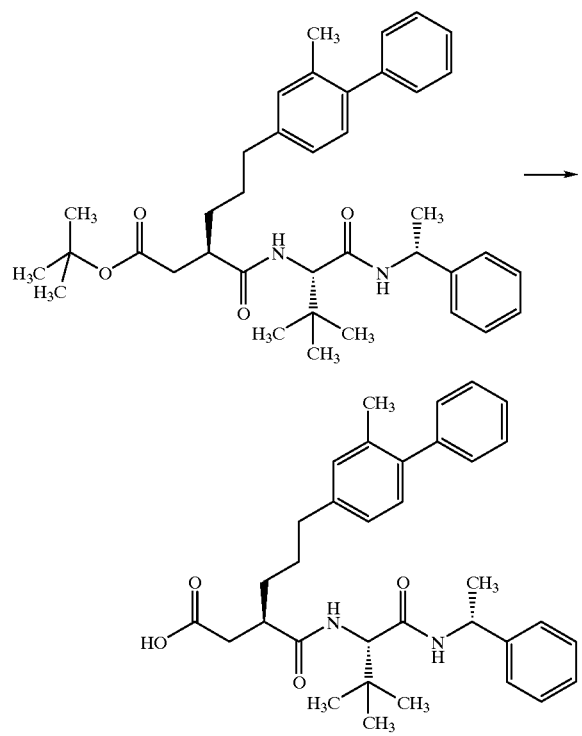

Trifluoroacetic acid (5 mL) was added dropwise over 5 min to a stirred solution of tert-butyl (3R)-3-({[(1S)-2,2-dimethyl-1-({[(1R)-1-phenylethyl]amino}carbonyl)propyl]amino}carbonyl)-6-[3-methyl-(4-phenyl)phenyl]hexanoate (Preparation 3) (285 mg, 0.47 mmol) in anhydrous dichloromethane (5 mnL) under nitrogen at 20° C. The solution was stirred for 4 h and concentrated under reduced pressure. The residue was dissolved in toluene and concentrated under reduced pressure (twice), and triturated with ether to give a colourless solid (210 mg, 82%).

m.p. 160–162° C. (from ethyl acetate).

$R_f$ 0.17 (hexane/ether/acetic acid=50:50:1)

HPLC retention time 7.3 min (Phenomenex Magellen $C_{18}$ silanised silica gel (5μ), eluting with acetonitrile/water/trifluoroacetic acid=70:30:0.1 (1 mL/min), detection by u.v. (220 nm).

$\delta_H$ (400 MHz, $CD_3OD$)(exchangeable hydrogens only partially exchanged) 1.02 (9H, s), 1.44 (3H, d, J=7 Hz), 1.52 (4H, m), 2.16 (3H, s), 2.37 (1H, dd, J=4 and 15 Hz), 2.50 (2H, m), 2.60 (1H, dd, J=9 and 15 Hz), 2.84 (1H, m), 4.37 (1H, d, J=10 Hz), 4.99 (1H, pentet, J=7 Hz), 6.94 (1H, d, J=8 Hz), 7.00 (2H, s and d, J=8 Hz, overlapping), 7.13 (1H, t, J=7 Hz 7.16 (2H, t, J=7 Hz), 7.23 (4H, t, J=7 Hz), 7.29 (1H, t, J=7 Hz), 7.38 (2H, t, J=7 Hz), 7.72 (1H, br d), 8.45 (1H, br d).

LRMS (thermospray) m/z=543 ($MH^+$)

FTIR $\nu_{max}$ (KBr disc) 3290, 2980, 2930, 1707, 1661, 1633, 1553, 700 $cm^{-1}$

| Found: | C, 75.22; | H, 7.73; | N, 5.16; |
| --- | --- | --- | --- |
| $C_{34}H_{42}N_2O_4$ requires | C, 75.25; | H, 7.80; | N, 5.16% |

Example 2

(2R)-2-{3-[3-Chloro-(4-phenyl)phenyl]propyl}-N1-[(1S)-2,2-dimethyl-1-({[(1R)-1-phenylethyl]amino}carbonyl)propyl]-(N4-hydroxy)butanediamide.

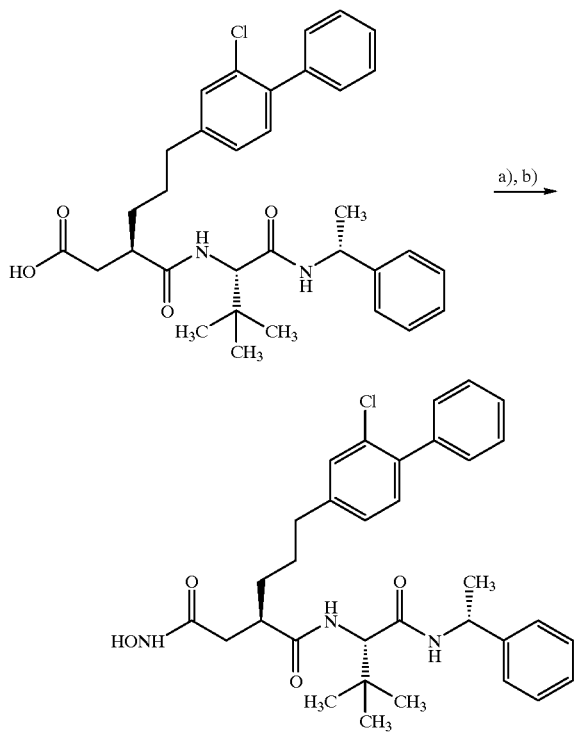

a) O-Allylhydroxylamine hydrochloride (17 mg, 0.152 mmol) was added to a stirred solution of (3R)-6-[(3-chloro-4-phenyl)phenyl]-3-({[(1S)-2,2-dimethyl-1-({[(1R)-1-phenylethyl]amino}carbonyl)propyl]amino}carbonyl)hexanoic acid (Preparation 4) (66 mg, 0.117 mmol) and diisopropylethylamine (78 μL, 0.456 mmol) in anhydrous dichloromethane (1 mL) under nitrogen at 0° C. 7-Azabenzotriazol-1-yloxytris(pyrrolidino)phosphonium hexafluorophosphate (79 mg, 0.152 mmol) was added in one portion, and the mixture was stirred at 0° C. for 2 h, then allowed to warm to room temperature. After an additional 1 h, the mixture was poured into ethyl acetate (25 mL) and washed sequentially with 5% aqueous citric acid (2×10 mL), saturated aqueous sodium bicarbonate (2×10 mL). The organic solution was dried ($Na_2SO_4$) and concentrated under reduced pressure. The solid residue was suspended in ether (3 mL) and filtered to give (2R)-2-{3-[3-chloro-(4-phenyl)phenyl]propyl}-N1-[(1S)-2,2-dimethyl-1-({[(1R)-1-phenylethyl]amino}carbonyl)propyl]-(N4-3-propenyloxy)butanediamide (58 mg, 82%) as a white solid.

$R_f$ 0.45 (ethyl acetate:hexane=2:1).

$δ_H$ (400 MHz, $CDCl_3$) 0.98 (9H, s), 1.46 (3H, d, J=6.5 Hz), 1.48 (4H, m), 2.17 (1H, m), 2.39 (1H, m), 2.50 (2H, m), 2.74 (1H, m), 4.13 (1H, d, J=8 Hz), 4.29 (2H, d, J=6 Hz), 5.06 (1H, pentet, J=6.5 Hz), 5.29 (2H, br d), 5.87 (2H, m and br d overlapping), 6.45 (1H, br s), 6.97 (1H, d, J=8 Hz), 7.19 (7H, complex), 7.35 (5H, complex), 8.36 (1H, br s).

LRMS (thermospray) m/z=618 ($MH^+$, weak).

b) A stirred mixture of (2R)-2-{3-[3-chloro-(4-phenyl)phenyl]propyl}-N1-[(1S)-2,2-dimethyl-1-({[(1R)-1-phenylethyl]amino}carbonyl)propyl]-(N4-3-propenyloxy)butanediamide (56 mg, 0.091 mmol) and ammonium formate (59 mg, 0.93 mmol) in ethanol/water (4:1, 4 mL) was heated to reflux under nitrogen to give a colourless solution. Bis(triphenylphosphine)palladium acetate (3.4 mg, 0.00465 mmol) was added, and the mixture was heated under reflux for 40 min. After being cooled, the brown solution was diluted with ethyl acetate (25 mL) and washed with saturated aqueous sodium chloride (2×10 mL), dried ($Na_2SO_4$) and concentrated under reduced pressure. The residue was purified by column chromatography ($C_{18}$ silanised silica gel (40–63μ, eluting with methanol:water=5:1) to give (2R)-2-{3-[3-chloro-(4-phenyl)phenyl]propyl}-N1-[(1S)-2,2-dimethyl-1({[(1R)-1-phenylethyl]amino}carbonyl)propyl]-(N4-hydroxy)butanediamide (46 mg, 88%) as a colourless solid.

m.p. 107–109° C.

$R_f$ 0.43 ($C_{18}$ silanised silica gel, methanol:water=5:1)

$δ_H$ (400 MHz, $CD_3OD$) 0.98 (9H, s), 1.39 (3H, d, J=6.5 Hz), 1.47 (4H, m), 2.13 (1H, dd, J=6 and 14 Hz), 2.31 (1H, dd, J=9 and 14 Hz), 2.48 (2H, m), 2.85 (1H, m), 4.32 (1H,s), 4.96 (1H, q, J=6.5 Hz), 6.80 (1H, d, J=8 Hz), 7.11 (4H, complex), 7.22 (3H, complex) (5H, complex).

LRMS (thermospray) m/z=578 ($MH^+$, weak), 562 ($MH^+$–O)

| Found: | C, 67.69; | H, 6.90; | N, 7.19; |
| --- | --- | --- | --- |
| $C_{33}H_{40}ClN_3O_4 \cdot 0.5H_2O$ requires | C, 67.51; | H, 7.04; | N, 7.16% |

Example 3

N1-[(1S)-2,2-Dimethyl-1-({[(1R)-1-phenylethyl]amino}carbonyl) propyl]-(4N-hydroxy)-(2R)-2-{3-[3-methyl-(4-phenyl)phenyl]propyl}butanediamide.

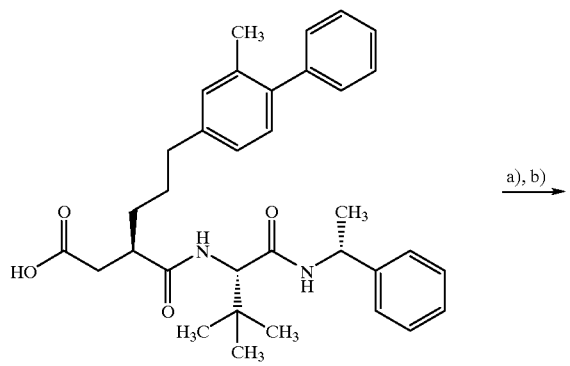

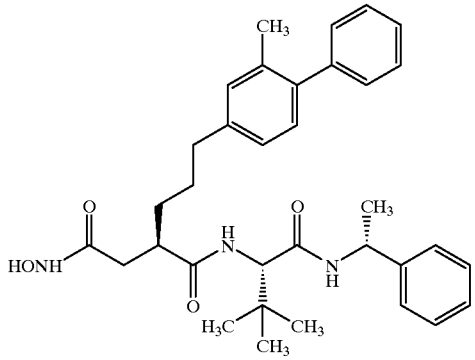

a) O-Allylhydroxylamine hydrochloride (295 mg, 2.69 mmol) was added to a stirred solution of (3R)-3-({[(1S)-2,2-dimethyl-1-({[(1R)-1-phenylethyl]amino}carbonyl)propyl]amino}carbonyl)-6-[(3-methyl-4-phenyl)phenyl]hexanoic acid (Example 1) (974 mg, 1.79 mmol) and diisopropylethylamine (1.56 mL, 8.97 mmol) in anhydrous dimethylformamide (25 mL) under nitrogen at 0° C. 7-Azabenzotriazol-1-yloxytris(pyrrolidino)phosphonium hexafluorophosphate (1.40 gm, 2.69 mmol) was added in one portion, and the mixture was allowed to warm to room temperature. After an additional 4.25 h, the mixture was poured into ethyl acetate (500 mL) and washed with saturated aqueous sodium bicarbonate (2×200 mL). The aqueous washings were extracted with ethyl acetate (2×100 mL). The combined organic solutions were dried (Na₂SO₄) and concentrated under reduced pressure. The solid residue was suspended in ether (3 mL) and filtered, then recrystallised from ethyl acetate to give N1-[(1S)-2,2-dimethyl-1-({[(1R)-1-phenylethyl]amino}carbonyl)propyl]-(2R)-2-{3-[3-methyl-(4-phenyl)phenyl]propyl}-(N4-3-propenyloxy)butanediamide (640 mg, 60%) as a white solid.

$R_f$ 0.31 (ethyl acetate/hexane=1:1).

$\delta_H$ (400 MHz, CDCl₃) 1.00 (9H, s), 1.48 (3H, d, J=6.5 Hz), 1.56 (4H, m), 2.22 (3H, s), 2.42 (1H, m), 2.52 (3H, m), 2.80 (1H, m), 4.20 (1H, d, J=8 Hz), 4.29 (2H, d, J=5 Hz), 5.07(1H, pentet, J=6.5 Hz), 5.28 (2H, br), 5.90 (1H, m), 6.13 (1H, br s), 6.61 (1H, br d), 6.95 (1H, d, J=8 Hz), 7.00 (1H, s), 7.10 (1H, d, J=8 Hz), 7.25 (8H, complex), 7.38 (2H, t, J=7 Hz), 8.69 (1H, br s).

LRMS (thermospray) m/z=598 (MH⁺, weak), 542 (MH₂⁺–allyloxy, base peak).

b) A stirred mixture of N1-[(1S)-2,2-dimethyl-1-({[(1R)-1-phenylethyl]amino}carbonyl)propyl]-(2R)-2-{3-[3-methyl-(4-phenyl)phenyl]propyl}-(N4-3-propenyloxy)butanediamide (794 mg, 1.32 mmol) and ammonium formate (419 mg, 6.64 mmol) in ethanol/water (4:1, 25 mL) was heated to reflux under nitrogen to give a colourless solution. Bis(triphenylphosphine)palladium acetate (40 mg, 0.066 mmol) was added, and the mixture was heated under reflux for 90 min. After being cooled, the brown solution was diluted with ethyl acetate (250 mL) and washed with saturated aqueous sodium chloride (2×100 mL), dried (Na₂SO₄) and concentrated under reduced pressure. The residue was purified by column chromatography (C₁₈ silanised silica gel, eluting with methanol:water=5:1) and then by trituration with methanol/diisopropyl ether to give N1-[(1S)-2,2-dimethyl-1-({[(1R)-1-phenylethyl]amino}carbonyl)propyl]-(N4-hydroxy)-(2R)-2-{3-[3-methyl-(4-phenyl)phenyl]propyl}butanediamide (440 mg, 59%) as a colourless solid.

m.p. 114–116.5° C.

$R_f$ 0.23 (C₁₈ silanised silica gel, methanol:water=5:1)

$\delta_H$ (400 MHz, DMSO-d₆) 0.85 (9H, s), 1.24 (3H, d, J=7 Hz), 1.31 (1H, m), 1.44 (3H, m), 1.98 (1H, dd, J=7 and 13 Hz), 2.11 (1H, m, and 3H, s overlapping), 2.42 (2H, m), 2.77 (1H, m), 4.26 (1H, d, 10 Hz), 4.87 (1H, pentet, J=7 Hz), 6.91 (1H, d, J=8 Hz), 6.97 (2H, s and d, J=8 Hz, overlapping), 7.18 (7H, complex), 7.29 (1H, t, J=6 Hz), 7.35 (2H, t, J=8 Hz), 7.64 (1H, br d), 8.23 (1H, br d), 8.44 (1H, s), 10.28 (1H, br s).

LRMS (thermospray) m/z=558 (MH⁺, weak), 542 (MH⁺–O)

FTIR $\nu_{max}$ (KBr disc) 3290, 2970, 2930, 1643, 1540, 700 cm⁻¹

| Found: | C, 72.60; | H, 8.02; | N, 7.31; |
| C₃₄H₄₃N₃O₄·0.25H₂O requires | C, 72.63; | H, 7.80; | N, 7.47% |

Example 4

N1-[(1S)-2,2-Dimethyl-1-({[(1R)-1-phenylethyl]amino}carbonyl) propyl]-(2R)-2[3-(3-fluoro-4-phenoxyphenyl)propyl]-(N4-hydroxy)butanediamide

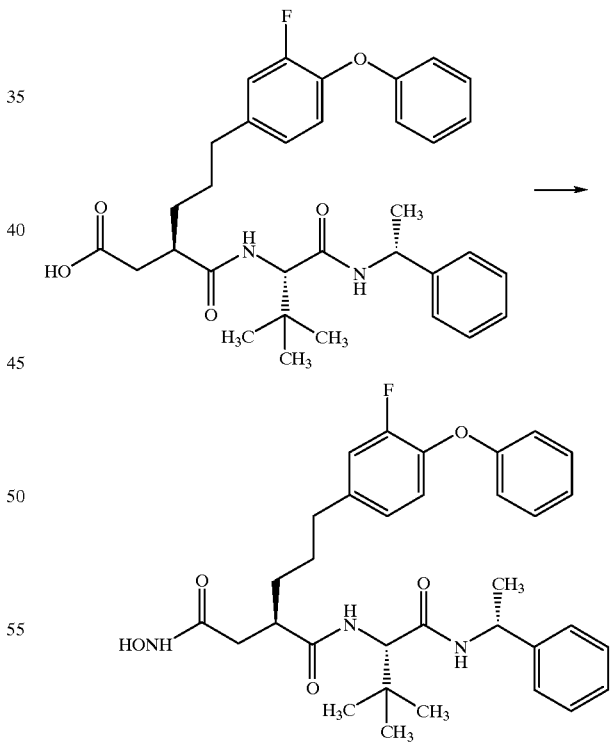

N-[(Dimethylamino)-1H-1,2,3-triazolo[4,5-b]pyridin-1-ylmethylene]-N-methylmethaninium hexafluorophosphate N-oxide (740 mg, 1.95 mmol) was added to a stirred solution of (3R)-3-({[(1S)-2,2-dimethyl-1-({[(1R)-1-phenylethyl]amino}carbonyl)propyl]amino}carbonyl)-6-(3-fluoro-4- phenoxyphenyl)hexanoic acid (Preparation 5) (731 mg, 1.30 mmol) and diisopropylethylamine (220 μL, 1.30 mmol) in anhydrous dimethylformamide (10 mL) at 0° C. under nitrogen. After 25 min, hydroxylamine hydrochloride (271 mg, 3.90 mmol) was added followed by diisopropylethylamine (880 μL, 5.20 mmol). The resulting mixture was stirred at 20° C. for 16 h, poured into ethyl acetate (150 mL) and washed with pH 7 phosphate buffer solution (3×50 mL), saturated aqueous sodium chloride (50 mL), dried (Na$_2$SO$_4$), and concentrated under reduced pressure. The residue was recrystallised from dichloromethane/diisopropyl ether to give the title compound as a colourless solid (275 mg, 24%). Further purification of a sample (130 mg) by preparative hplc (Phenomenex C$_{18}$ Magellan column, 150×20 mm, 5μ packing, 20 mL/min acetonitrile:aqueous phosphate buffer (8.3 mM, pH 7.2)=1:1, retention time 13.5 min), then trituration with diisopropyl ether, filtration and drying in vacuo at 50° C. gave 50 mg of a white solid.

m.p. 136–137° C.

R$_f$ 0.39 (dichloromethane:methanol:conc. aq. ammonia= 90:10:1)

δ$_H$ (400 MHz, CD$_3$OD) 1.02 (9H, s), 1.42 (3H, d, J=7 Hz), 1.48 (3H, m), 1.58 (1H, m), 2.16 (1H, dd, J=6 and 14 Hz), 2.34 (1H, dd, J=8 and 14 Hz), 2.49 (2H, m), 2.86 (1H, m), 4.34 (1H, s), 4.99 (1H, q, J=7 Hz), 6.86 (4H, m), 6.94 (1H, d, J=11.5 Hz), 7.04 (1H, t, J=7 Hz), 7.12 (1H, t, J=7 Hz), 7.18 (2H, t, J=7 Hz), 7.27 (4H, m).

LRMS (thermospray) m/z=535 (MH$^+$–HNCO)

FTIR ν$_{max}$. (KBr disc) 3290, 2970, 2930, 1644, 1508, 1490, 1220, 700 cm$^{-1}$

| Found: | C, 68.14; | H, 6.94; | N, 7.21; |
|---|---|---|---|
| C$_{33}$H$_{40}$FN$_3$O$_5$·0.25H$_2$O requires | C, 68.08; | H, 7.01; | N, 7.22% |

Example 5

N1-[(1S)-2,2-Dimethyl-1-({[(1R)-1-phenylethyl] amino}carbonyl) propyl]-(N4-hydroxy)-(2R)-2[3-(3-methyl-4-phenoxyphenyl)propyl]butanediamide

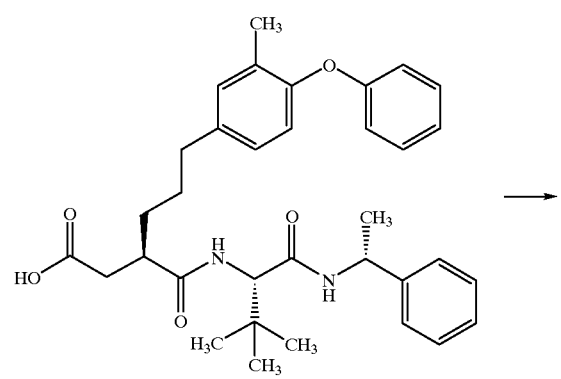

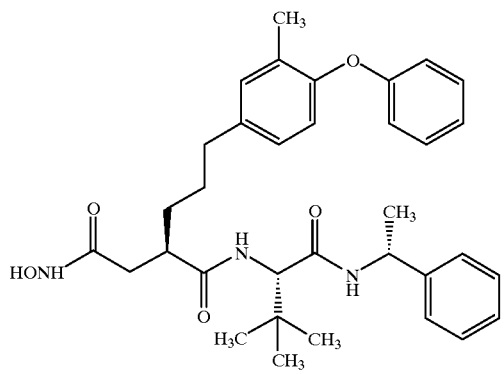

N-[(Dimethylamino)-1H-1,2,3-triazolo[4,5-b]pyridin-1-ylmethylene]-N-methylmethaninium hexafluorophosphate N-oxide (655 mg, 1.72 mmol) was added to a stirred solution of (3R)-3-({[(1S)-2,2-dimethyl-1-({[(1R)-1-phenylethyl] amino}carbonyl)propyl]amino}carbonyl)-6-(3-methyl-4-phenoxyphenyl)hexanoic acid (Preparation 6) (640 mg, 1.15 mmol) and diisopropylethylamine (198 μL, 1.15 mmol) in anhydrous dimethylformamide (5 mL) at 20° C. under nitrogen. After 25 min, hydroxylamine hydrochloride (239 mg, 3.44 mmol) was added followed by diisopropylethylamine (792 μL, 4.60 mmol). The resulting mixture was stirred at 20° C. for 48 h, poured into ethyl acetate (150 mL) and washed with pH 7 phosphate buffer solution (3×50 mL), saturated aqueous sodium chloride (50 mL), dried (MgSO$_4$), and concentrated under reduced pressure. The crude product was purified by flash chromatography. Firstly, chromatography eluting with dichloromethane:methanol:conc. aq. ammonia=90:10:1 gave a yellow oil. Further purification by flash chromatography (eluting with dichloromethane:methanol=95:5) gave an orange oil, which crystallised from dichloromethane/diisopropyl ether to give the title compound (25 mg, 4%).

R$_f$ 0.27 (dichloromethane:methanol=90:10)

δ$_H$ (300 MHz, CDCl$_3$) 0.98 (9H, s), 1.31 (3H, d, J=7 Hz), 1.60 (4H, m), 2.16 (3H, s), 2.24 (1H, m), 2.47 (3H, m), 2.82 (1H, m), 4.17 (1H, d, J=9 Hz), 5.05 (1H, pentet, J=7 Hz), 6.31 (1H, br d), 6.77 (1H, d, J=8 Hz), 6.85 (2H, d, J=8 Hz), 6.97 (1H, s), 7.02 (1H, t, J=8 Hz), 7.22 (9H, complex), 9.50 (1H, br s).

LRMS (thermospray) m/z=573 (M$^+$, weak), 531 (MH$^+$–O).

Example 6

N1-[(1S)-2,2-Dimethyl-1-({[(1R)-1-phenylethyl]amino}carbonyl) propyl]-(3S)-ethoxy-(2R)-2[3-(3-fluoro-4-phenoxyphenyl)propyl]-(N4-hydroxy)butanediamide

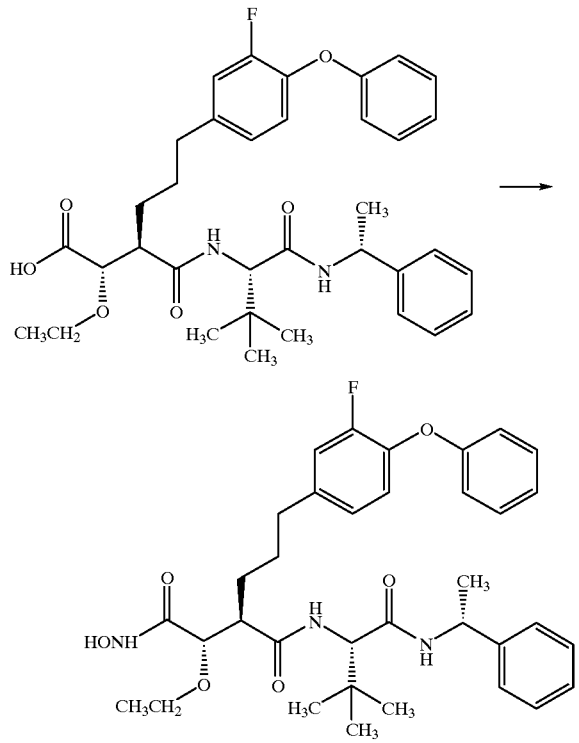

N-[(Dimethylamino)1H-1,2,3-triazolo[4,5-b]pyridin-1-ylmethylene]-N-methylmethaniniumn hexafluorophosphate N-oxide (88 mg, 0.232 mmol) was added to a stirred solution of (2S,3R)-3-([[(1S)-2,2-dimethyl-1-([[(1R)-1-phenylethyl]aminocarbonyl)propyl]aminocarbonyl)-2-ethoxy-6-(3-fluoro-4-phenoxyphenyl)hexanoic acid (Preparation 8)(94 mg, 0.155 mmol) and diisopropylethylamine (54 μL, 0.31 mmol) in anhydrous dimethylformarnide (2.5 mL) at 0° C. under nitrogen. After 45 min, hydroxylamine hydrochloride (32 mg, 0.465 mmol) was added followed by diisopropylethylamine (81 μL, 0.465 mmol). The resulting mixture was stirred at 0° C. for 5 h, poured into ethyl acetate (50 mL) and washed with pH 7 phosphate buffer solution (3×30 mL), saturated aqueous sodium chloride (30 mL), dried (MgSO$_4$), and concentrated under reduced pressure. The residue was purified by flash chromatography (eluting with dichloromethane:methanol:conc. aq. ammonia=95:5:0.5) to give the title compound as a colourless foam (43 mg, 34%).

$R_f$ 0.32 (dichloromethane:methanol:conc. aq. ammonia=95:5:0.5)

$\delta_H$ (400 MHz, CD$_3$OD) 1.04 (9H, s), 1.12 (3H, t, J=7 Hz), 1.32 (1H, m), 1.42 (3H, d, j=7 Hz), 1.46 (2H, m), 1.53 (1H, m), 2.42 (1H, dt, J=14 and 7 Hz), 2.54 (1H, ddd, J=7, 9 and 14 Hz), 2.74 (1H, dt, J=10 and 7.5 Hz), 3.32 (1H, m, partially obscured by CHD$_2$OD peak), 3.49 (1H, dq, J=10 and 7 Hz), 3.69 (1H, d, J=10 Hz), 4.39 (1H, s), 5.00 (1H, q, J=7 Hz), 6.84 (4H, complex), 6.92 (1H, dd, J=12 and 2 Hz), 7.04 (1H, t, J=8 Hz), 7.14 (3H, complex), 7.26 (4H, complex).

LRMS (thermospray) m/z=606 (MH$^+$−O), 533 (base peak, MNa$^+$-(Ph(CH$_3$)CHNH$_2$)

HRMS (positive ion electrospray) Found: m/z=644.3113 C$_{35}$H$_{44}$FNaN$_3$O$_6$ requires 644.3112.

| Found: | C, 66.79; | H, 7.05; | N, 6.66; |
|---|---|---|---|
| C$_{35}$H$_{44}$FN$_3$O$_6$.0.5H$_2$O requires | C, 66.65; | H, 7.17; | N, 6.66% |

Example 7

(2S,3R)-3-({[(1S)-2,2-Dimethyl-1-({[(1R)-1-phenylethyl]amino}carbonyl)-6-[(3-methyl-4-phenyl)phenyl]-2propylhexanoic acid

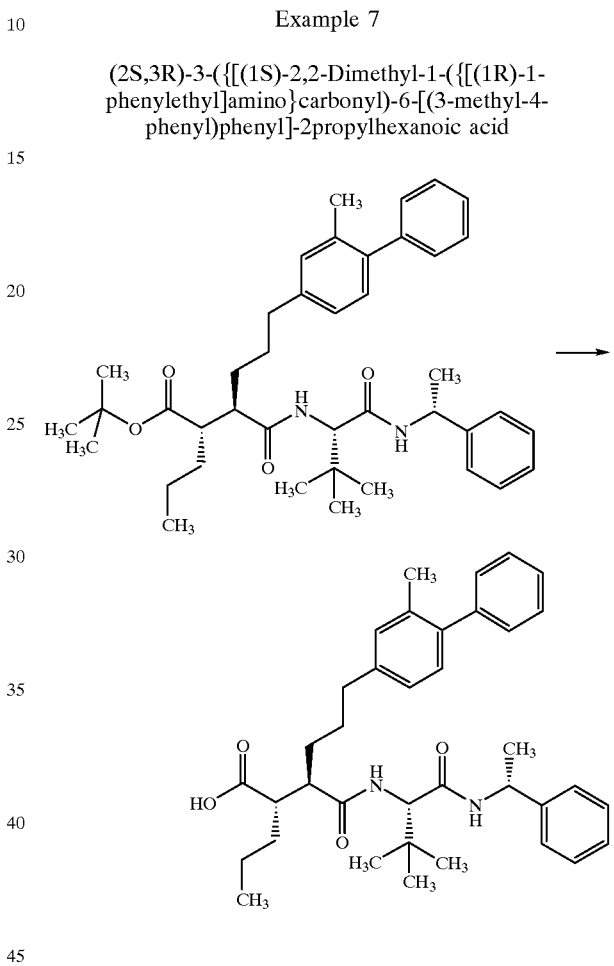

According to the method of Example 1, tert-butyl (2S,3R)-3-({[(1S)-2,2-dimethyl-1-({[(1R)-1-phenylethyl]amino}carbonyl)propyl]amino}carbonyl)-6-[3-methyl-(4-phenyl)phenyl]-2-propylhexanoate (Preparation 13) (360 mg, 0.56 mmol) was treated with trifluoroacetic acid in anhydrous dichloromethane to give the title compound as a colourless solid (163 mg, 50%), after recrystallisation from methanol. The mother liquors yielded a second crop of crystals (45 mg, 14%) from methanol.

m.p. 212–215° C. (from methanol).

$R_f$ 0.4 (dichloromethane/methanol/acetic acid=90:10:1)

$\delta_H$ (400 MHz, DMSO-d$_6$) 0.77 (3H, t, J=6 Hz), 0.92 (9H, s), 1.13 (1H, m), 1.29 (3H, d, J=6.5 Hz, and 3H, m, overlapping), 1.61 (4H, m), 2.13 (3H, s), 2.35 (2H, m), 2.45 (1H, m), 2.66 (1H, br t, J=8 Hz), 2.60 (1H, dd, J=9 and 15 Hz), 4.34 (1H, d, J=9 Hz), 4.90 (1H, pentet, J=6.5 Hz), 6.89 (1H, d, J=7 Hz), 6.97 (2H, s and d, J=8 Hz, overlapping), 7.25 (7H, complex), 7.31 (1H, t, J 7 Hz), 7.39 (2H, m), 7.94 (1H, br d), 8.29 (1H, br d), 11.66 (1H, br s).

LRMS (thermospray) m/z=586 (MH$^+$)

FTIR $v_{max}$ (KBr disc) 1710, 1630, cm$^{-1}$

| Found: | C, 72.60; | H, 8.14; | N, 4.59; |
|---|---|---|---|
| C$_{37}$H$_{48}$N$_2$O$_4$.0.33MeOH.1.25H$_2$O requires | C, 72.62; | H, 8.45; | N, 4.54% |

Example 8

N1-[(1S)-2,2-Dimethyl-1-({[(1R)-1-phenylethyl]amino}carbonyl) propyl]-(N4-hydroxy)-(2R)-2{3-[3-methyl-(4-phenyl)phenyl]propyl}-(3S)-propylbutanediamide.

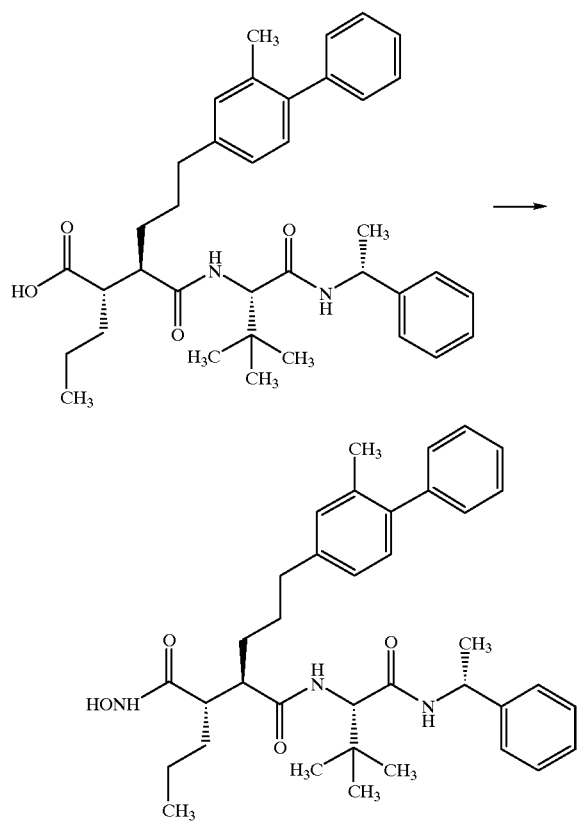

According to the method of Example 4, reaction of (2S, 3R)-3-({[(1S)-2,2-dimethyl-1-({[(1R)-1-phenylethyl]amino}carbonyl)propyl]amino}carbonyl)-6-[(3-methyl-4-phenyl)phenyl]-2-propylhexanoic acid ((Example 7) 130 mg, 0.22 mmol) with hydroxylamine hydrochloride (45.9 mg, 0.66 mmol) at 20° C. for 5 h, followed by the same work-up and trituration of the crude product with ether gave the title compound (64 mg, 49%) as a colourless solid.

R$_f$ 0.31 (dichloromethane:methanol:conc. aq. ammonia=90:10:1)

δ$_H$ (400 MHz, DMSO-d$_6$) 0.74 (3H, t, J=6.5 Hz), 0.92 (9H, s), 1.03 (1H, m), 1.16 (2H, m). 1.24 (3H, d, J=7.5 Hz, and 1H, m overlapping), 1.37 (3H, m), 1.44 (1H, m), 2.12 (3H, s and 1H, m, overlapping), 2.33 (1H, m), 2.44 (1H, m), 2.61 (1H, m), 4.31 (1H, d, J=9 Hz), 4.89 (1H, pentet, J=7.5 Hz), 6.88 (1H, d, J=8 Hz), 6.95 (1H, s), 6.97 (1H, d, J=8 Hz), 7.13 (3H, m), 7.22 (4H, m), 7.30 (1H, t, J=8 Hz), 7.38 (2H, t, J=8 Hz),), 7.88 (1H, br d), 8.18 (1H, br d), 8.73 (1H, br s), 10.28 (1H, br s).

LRMS (thermospray) m/z=556 (base peak, MNH$_4^+$−HCONHOH)

| Found: | C, 72.14; | H, 8.18; | N, 6.85; |
|---|---|---|---|
| C$_{37}$H$_{49}$N$_3$O$_4$.0.75H$_2$O requires | C, 72.46; | H, 8.30; | N, 6.85% |

FTIR $v_{max}$ (KBr disc) 3290, 2970, 2930, 1637, 1530, 700 cm$^{-1}$

Example 9

(N4,3S)-Dihydroxy-N1-[(1S)2,2-dimethyl-1-({[(1R)-1-phenylethyl]amino}carbonyl)propyl]-(2R)-2[3-(3-fluoro-4-phenoxyphenyl)propyl]butanediamide

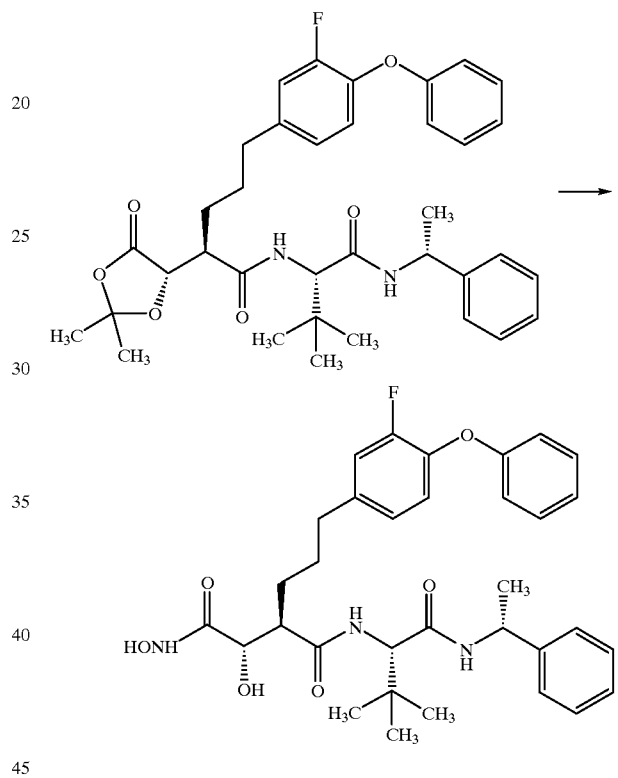

Sodium methoxide (35 mg, 0.67 mmol) was added to a solution of anhydrous hydroxylamine hydrochloride (45 mg, 0.67 mmol) in anhydrous methanol (1 mL) under nitrogen at room temperature. The mixture was stirred for 2 h and filtered rapidly through a pad of Arbocel filter aid, washing with anhydrous methanol (1 mL). (2R)-2-[(4S)-2,2-Dimethyl-5-oxo-1,3-dioxolan-4-yl]-N-[(1S)-2,2-dimethyl-1-({[(1R)-1-phenylethyl]amino}carbonyl)propyl]-5-[(3-fluoro-4-phenoxy)phenyl]pentanamide (Preparation 15) (103 mg, 0.16 mmol) with anhydrous methanol (1 niL) were added, and the mixture was stirred at room temperature for 18 h. The solution was concentrated under reduced pressure, and the residue purified by flash chromatography, first on C$_{18}$ silanised silica gel (40–63μ) eluting with methanol:water=4:1, and then on normal phase silica gel (gradient elution with dichloromethane:methanol). The product was obtained as a colourless solid (25 mg, 26%).

m.p. 90–95° C.

R$_f$ 0.38 (dichloromethane:methanol=90:10)

δ$_H$ (300 MHz, CD$_3$OD) 1.03 (9H, s), 1.45 (3H, d, J=7 Hz), 1.52 (3H, m), 1.66 (1H, m), 2.53 (2H, m), 2.77 (1H, m), 4.02

(1H, d, J=8 Hz), 4.36 (1H, s), 5.01 (1H, q, J=7 Hz), 6.87 (4H, complex), 6.97 (1H, d, J=12 Hz), 7.04 (1H, t, J=8 Hz), 7.16 (3H, complex), 7.28 (4H, complex).

LRMS (thermospray) m/z=533 (base peak, MH$^+$−HONHCO)

| Found: | C, 65.94; | H, 6.89; | N, 6.95; |
|---|---|---|---|
| $C_{33}H_{40}FN_3O_6 \cdot 0.4H_2O$ requires | C, 65.96; | H, 6.84; | N, 6.99% |

Example 10

(N4,3S)-Dihydroxy-N1-[(1S)2,2-dimethyl-1-({[(1R)-1-phenylethyl]amino}carbonyl)propyl]-(2R)-2{3-[3-methyl-(4-phenyl)phenyl]propyl}butanediamide.

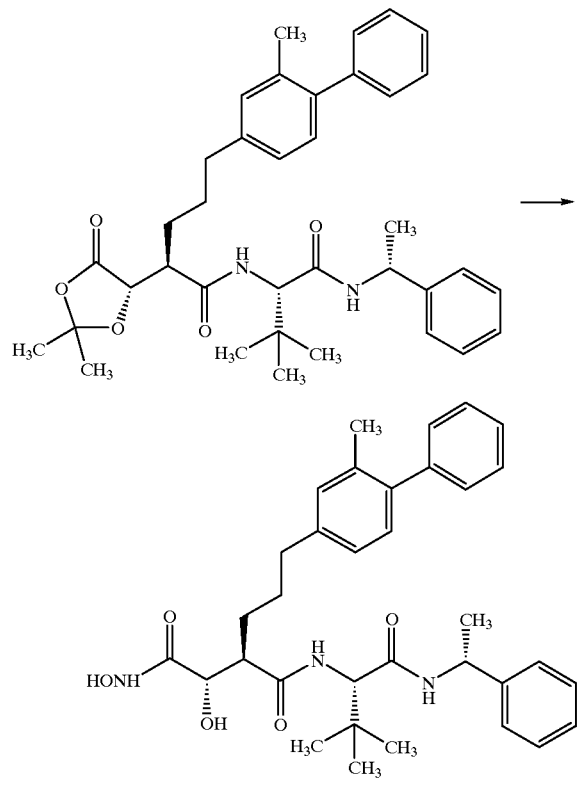

According to the method of Example 9, (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]-5-[(3-methyl- 4-phenyl)phenyl]pentanamide (Preparation 16) (440 mg, 0.73 mmol) was reacted with hydroxylamine at room temperature for 18 h. The solution was concentrated under reduced pressure, and the residue purified by flash chromatography ($C_{18}$ silanised silica gel (40–63µ) eluting with methanol:water=4:1 then 5:1) to give a colourless solid (339 mg, 81%).

m.p. 95–97° C.

$R_f$ 0.16 (dichloromethane:methanol=95:5)

$\delta_H$ (300 MHz, CDCl$_3$) 0.98 (9H, s), 1.50 (3H, d, J=7 Hz), 1.65 (3H, m), 1.89 (1H, m), 2.23 (3H, s), 2.58 (2H, br t, J=6 Hz), 3.27 (1H, m), 4.15 (1H, d), 4.20 (1H, br s), 5.09 (1H, pentet, J=7 Hz), 5.32 (1H, br s), 6.20 (1H, br d), 6.98 (1H, d, J=8 Hz), 7.01 (1H, s) 7.10 (1H, d, J=8 Hz), 7.31 (10H, complex), 7.86 (br d), 9.50 (1H, br s).

LRMS (thermospray) m/z=514 (base peak, MH$^+$−HONHCO)

| Found: | C, 70.50; | H, 7.58; | N, 7.23; |
|---|---|---|---|
| $C_{34}H_{43}N_3O_5 \cdot 0.25H_2O$ requires | C, 70.62; | H, 7.58; | N, 7.27% |

Example 11

(2R)-N1-[(1S)-2,2-Dimethyl-1-({[(1R)-1-phenylethyl]amino}carbonyl)propyl]-2{3-[3-fluoro-(4-phenyl)phenyl]propyl}-(N4-hydroxy)butanediamide.

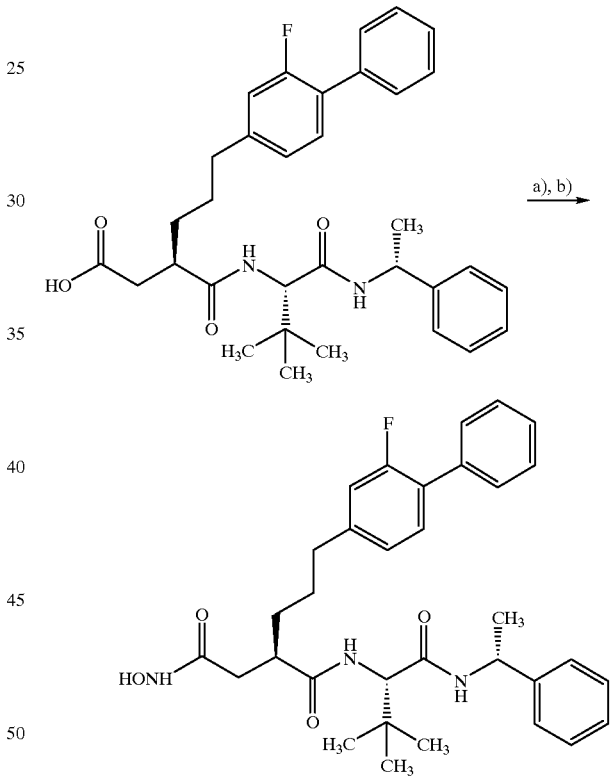

a) According to the method of Example 2, (3R)-3-({[(1S)-2,2-dimethyl-1-({[(1R)-1-phenylethyl]amino}carbonyl)propyl]amino}carbonyl)-6-[(3-fluoro-4-phenyl)phenyl]hexanoic acid (Preparation 17)(426 mg, 0.78 mmol) was reacted with O-allylhydroxylamine hydrochloride (128 mg, 1.17 mmol). Purification of the crude product by flash chromatography (gradient elution with hexane:isopropanol) followed by trituration with ether and ethyl acetate gave (2R)-N1-[(1S)-2,2-dimethyl-1-({[(1R)-1-phenylethyl]amino}carbonyl)propyl]-2-{$^3$-[$^3$-fluoro-(4-phenyl)phenyl]propyl}-(N4-3-propenyloxy)butanediamide (260 mg, 55%) as a white solid.

m.p. 182–186° C.

$R_f$ 0.32 (hexane:isopropanol=10:1).

$\delta_H$ (400 MHz, DMSO-$d_6$) 0.87 (9H, s), 1.26 (3H, d, J=6.5 Hz), 1.28 (1H, m), 1.43 (3H, m), 1.97 (1H, m), 2.13 (1H, m), 2.50 (2H, m), 2.84 (1H, m), 4.16 (2H, m), 4.27 (1H, d, J=9 Hz 4.87 (1H, pentet, J=6.5 Hz), 5.15 (1H, d, J=10 Hz), 5.20 (1H, d, J=17 Hz), 5.85 (1H, m), 6.97 (2H, m), 7.13 (4H, complex), 7.29 (2H, m), 7.45 (4H, m), 7.65 (1H, br s), 8.26 (1H, br s), 10.37 (1H, br s).

LRMS (thermospray) m/z=602 (MH$^+$).

| Found: | C, 70.91; | H, 7.33; | N, 6.84; |
|---|---|---|---|
| $C_{36}H_{44}FN_3O_4 \cdot 0.5H_2O$ requires | C, 70.80; | H, 7.43; | N, 6.88% | b) According to the method of Example 2, (2R)-N1-[(1S)-2,2-dimethyl-1-({[(1R)-1-phenylethyl]amino}carbonyl) propyl]-2-{$^3$-[$^3$-fluoro-(4-phenyl)phenyl]propyl}-(N4-3-propenyloxy)butanediamide (210 mg, 0.35 mmol) was reacted with ammonium formate (110 mg, 1.75 mmol) in ethanol/water (4:1, 5 mL) under palladium catalysts at reflux for 2 h. After work-up, the residue was purified by flash chromatography (gradient elution with dichloromethane:methanol:conc. aq. ammonia) and trituration with ether to give (2R)-N1-[(1S)-2,2-dimethyl-1-({[(1R)-1-phenylethyl]amino}carbonyl)propyl]-2-{3-[3-fluoro-(4-phenyl)phenyl]propyl}-(N4-hydroxy)butanediamide (120 mg, 61%) as a colourless solid.

$R_f$ 0.25 (dichloromethane:methanol:conc. aq. ammonia=90:10:1)

$\delta_H$ (400 MHz, DMSO-$d_6$) 0.87 (9H, s), 1.25 (3H, d, J=6.5 Hz), 1.31 (1H, m), 1.44 (3H, m), 2.00 (1H, dd, J=7 and 15 Hz), 2.13 (1H, dd, J=4 and 15 Hz), 2.48 (2H, m), 2.80 (1H,1 m), 4.26 (1H, d, J=9 Hz), 4.87 (1H, pentet, J=6.5 Hz), 6.97 (2H, m), 7.06 (1H, t, J=8 Hz), 7.20 (2H, m), 7.30 (2H, m), 7.43 (4H, complex), 7.66 (1H, br d), 8.23 (1H. br d), 8.58 (1H, s), 10.27 (1H, br s).

LRMS (thermospray) m/z=563 (MH$^+$)

| Found: | C, 70.02; | H, 7.25; | N, 7.52; |
|---|---|---|---|
| $C_{33}H_{40}FN_3O_4 \cdot 0.25H_2O$ requires | C, 70.00; | H, 7.21; | N, 7.42% |

Example 12

(3R)-3-({[(1S)-2,2-Dimethyl-1-({[(1R)-1-phenylethyl]amino}carbonyl)-(2S)-ethoxy-6-[(3-methyl-4-phenyl)phenyl]hexanoic acid

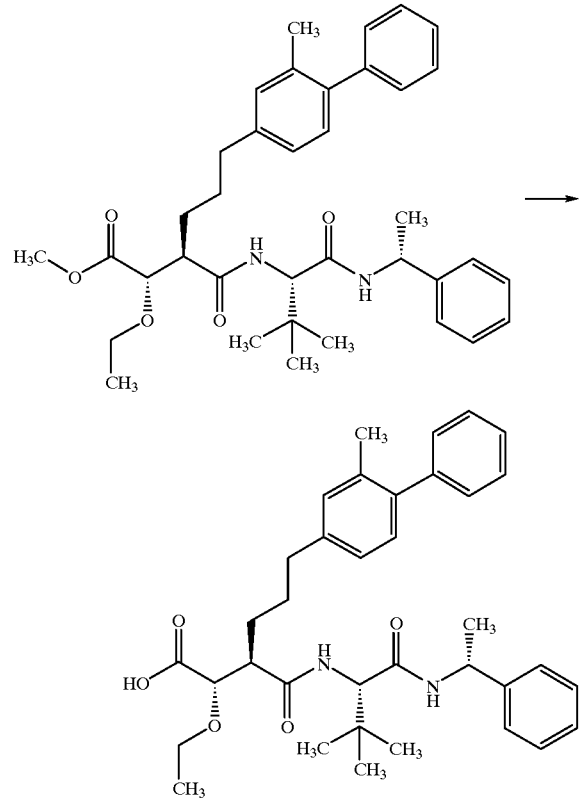

Lithium hydroxide hydrate (30 mg, 0.71 mmol) was added to a suspension of methyl (2S,3R)-3-({[(1S)-2,2-dimethyl-1-({[(1R)-1-phenylethyl]amino}carbonyl)propyl]amino}carbonyl)-2-ethoxy-6-[(3-methyl-4-phenyl)phenyl] hexanoate (Preparation 18)(384 mg, 0.64 mmol) in tetrahydrofuran:water=3:2 (10 mL) and the mixture was stirred at room temperature for 2 h. The solution was acidified with 1M hydrochloric acid and extracted with ethyl acetate (3×30 mL). The combined extracts were dried (Na$_2$SO$_4$), and concentrated under reduced pressure. Trituration with ether gave the title compound (196 mg, 52%) as a colourless solid.

$\delta_H$ (400 MHz, CD$_3$OD) (the exchangeable hydrogens only partially exchanged) 1.02 (9H, s), 1.16 (3H, t, J=7 Hz), 1.42 (3H, d, J=7 Hz), 1.52 (3H, m), 1.65 (1H, m), 2.16 (3H, s), 2.50 (2H, m), 2.74 (1H, m), 3.39 (1H, m), 3.58 (1H, m), 3.90 (1H, d, J=9 Hz), 4.38 (1H, d, J=9 Hz), 5.00 (1H, pentet, J=7 Hz), 6.92 (2H, m), 7.00 (2H, m), 7.20 (7H, complex), 7.38 (2H, t, J=7), 7.86 (1H, br d), 8.35 (1H, br d).

| Found: | C, 73.11; | H, 7.89; | N, 4.79; |
|---|---|---|---|
| $C_{36}H_{46}N_2O_5 \cdot 0.25H_2O$ requires | C, 73.12; | H, 7.92; | N, 4.74% |

Example 13

N1-[(1S)-2,2-Dimethyl-1-({[(1R)-1-phenylethyl]amino}carbonyl)propyl]-(3S)-ethoxy-(N4-hydroxy)-(2R)-2{3-[3-methyl-(4-phenyl)phenyl]propyl}butanediamide.

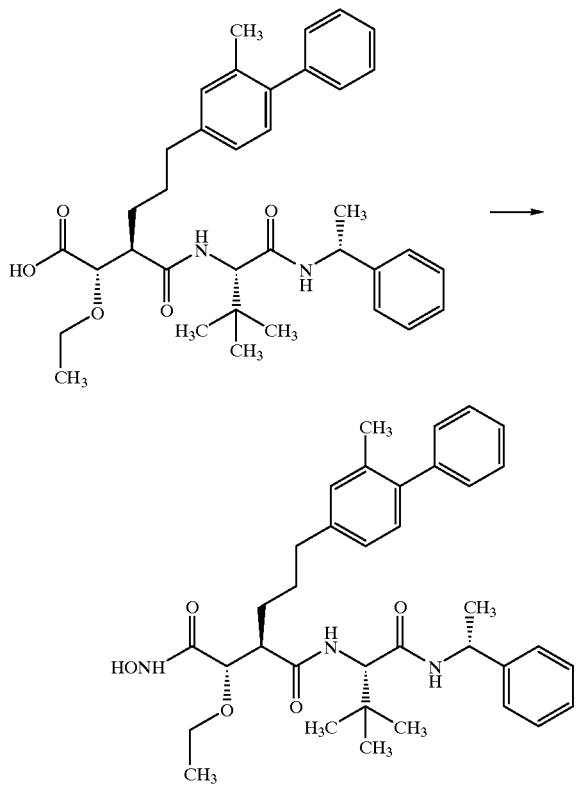

N-[(Dimethylamino)-1H-1,2,3-triazolo[4,5-b]pyridin-1-ylmethylene]-N-methylmethaninium hexafluorophosphate N-oxide (164 mg, 0.43 mmol) was added to a stirred solution of (2S,3R)-3-({[(1S)-2,2-dimethyl-1-({[(1R)-1-phenylethyl]amino}carbonyl)propyl]amino}carbonyl)-2-ethoxy-6-[(3-methyl-4-phenyl)phenyl]hexanoic acid (Example 12)(169 mg, 0.29 mmol) and diisopropylethylamine (50 μL, 0.29 mmol) in anhydrous dimethylformamide (3 mL) at 0° C. under nitrogen. After 60 min, hydroxylamine hydrochloride (60 mg, 0.86 mmol) was added followed by diisopropylethylamine (81 μL, 0.465 mmol). The resulting mixture was stirred at 20° C. for 16 h, diluted with ether and washed with water. The aqueous layer was extracted with ether (two portions) and ethyl acetate. The combined organic solutions were washed with water, dried ($Na_2SO_4$), and concentrated under reduced pressure. The residue was purified by repeated flash chromatography (eluting with dichloromethane:methanol:conc. aq. ammonia=97.5:2.5:0.5, then 96:4:0.5) to give the title compound as a colourless foam (20 mg, 11%).

$R_f$ 0.25 (dichloromethane:methanol:conc. aq. ammonia= 90:10:1)

$\delta_H$ (300 MHz, $CDCl_3$) 0.97 (9H, s), 1.31 (3H, t, J=7 Hz), 1.55 (3H, d, J=7 Hz), 1.71 (3H m), 1.84 (1H, m), 2.23 (3H, s), 2.65 (2H, m), 2.84 (1H, m), 3.48 (1H, pentet, J=7 Hz), 3.76 (1H, m), 3.95 (1H, d, J=7 Hz), 3.98 (1H, d, J=10 Hz), 5.12 (1H, q, J=7 Hz), 6.47 (1H. br d), 7.02 (2H, m), 7.13 (1H, d, J=8 Hz), 7.30 (10H, complex), 9.65 (1H, br s).

HRMS (positive ion electrospray) Found: m/z=624.3403 $C_{36}H_{47}NaN_3O_5$ requires 624.3413.

Example 14

(3R)-3-(}[(1S)-2,2-Dimethyl-1-(}[(1S)-2methoxy-1-phenylethyl]amino}carbonyl)-propyl]amino}cabonyl)-6-[(3-methyl-4-phenyl)phenyl]hexanoic acid

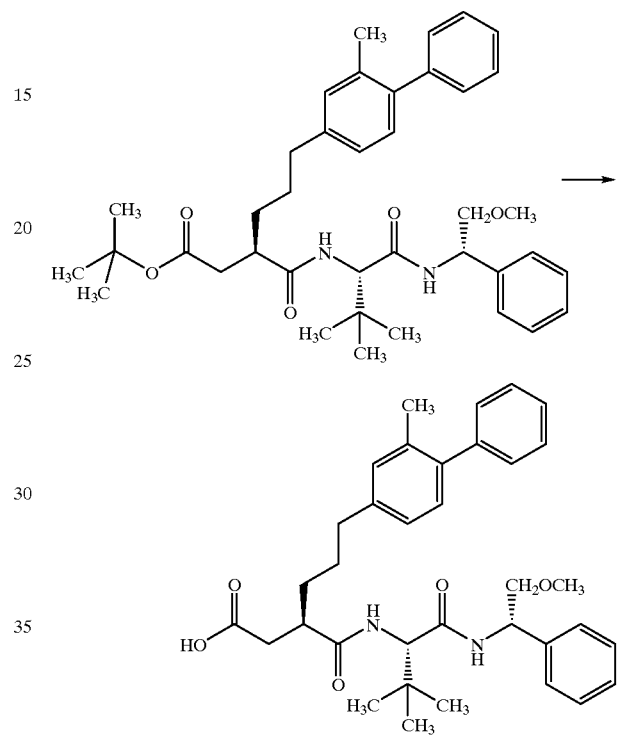

According to the method of Example 1, tert-butyl (3R)-3-({[(1 S)-2,2-dimethyl-1-({[(1S)-2-methoxy-1-phenylethyl]amino}carbonyl)propyl]amino}carbonyl)-6-[3-methyl-(4-phenyl)phenyl]-hexanoate (Preparation 19)(535 mg, 0.85 mmol) was treated with trifluoroacetic acid in anhydrous dichloromethane at room temperature for 2 h. The residue was dissolved in toluene and concentrated under reduced pressure (twice), and recrystallised from ethyl acetate to give a colourless solid (387 mg, 80%).

m.p. 184–186° C. (from ethyl acetate).

$R_f$ 0.47 (hexane/ether/acetic acid=50:50:1)

$\delta_H$ (400 MHz, $CD_3OD$)(exchangeable hydrogens only partially exchanged) 1.03 (9H, s), 1.51 (4H, m), 2.15 (3H, s), 2.36 (1H, dd, J=5 and 17 Hz), 2.46 (2H, m), 2.60 (1H, dd, J=10 and 17 Hz), 2.82 (1H, m), 3.32 (3H, s), 3.57 (2H, d, J=7 Hz), 4.42 (1H, d, J=10 Hz), 5.10 (1H, q, J=7 Hz), 6.87 (1H, d, J=8 Hz), 6.98 (2H, s and d, J=8 Hz, overlapping), 7.22 (8H, complex), 7.39 (2H, t, J=7 Hz), 7.74 (1H, br d), 8.48 (1H, br d).

LRMS (thermospray) m/z=573 ($MH^+$)

FTIR $\nu_{max}$ (KBr disc) 3300, 2960, 2930, 1711, 1639, 1543, 700 $cm^{-1}$

| Found: | C, 73.32; | H, 7.73; | N, 4.80; |
| $C_{35}H_{44}N_2O_5$ requires: | C, 73.40; | H, 7.74; | N, 4.89% |

| Found: | C, 71.77; | H, 7.69; | N, 4.61; |
| $C_{36}H_{46}N_2O_6$ requires: | C, 71.73; | H, 7.69; | N, 4.65%. |

Example 15

(3R)-3-({[(1 s)-2,2-Dimethyl-1-({[(1S)-2methoxy-1-phenylethyl]amino}carbonyl)propyl]amino}carbonyl)-6-(3'-methoxy-2methylbiphen-4-yl)hexanoic acid

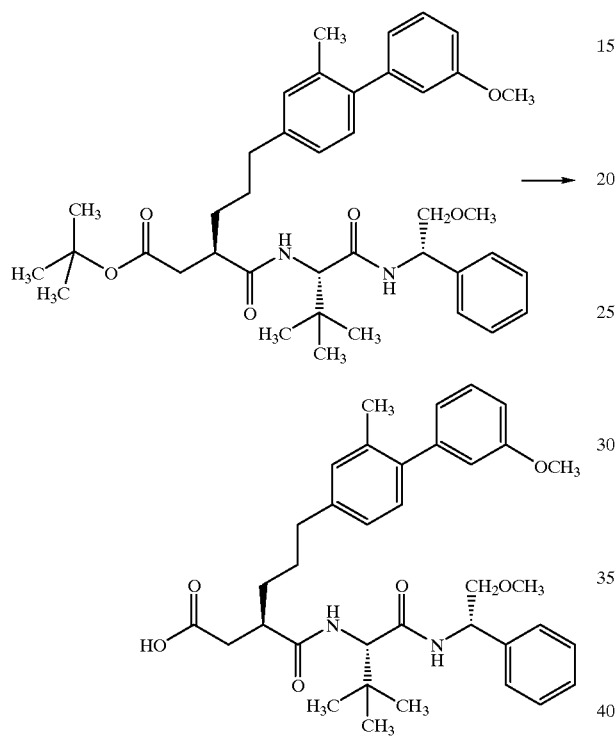

According to the method of Example 1 tert-butyl (3R)-3-({[(1 s)-2,2-dimethyl-1-({[(1S)-1-methoxy-1-phenylethyl]amino}carbonyl)propyl]amino}carbonyl)-6-(3'-methoxy-2-methylbiphen-4-yl)hexanoate (Preparation 21)(660 mg, 1.0 mmol) was treated with trifluoroacetic acid in anhydrous dichloromethane at room temperature for 3 h. The residue was dissolved in toluene and concentrated under reduced pressure (twice), and recrystallised from ethyl acetate to give a colourless solid (326 mg, 54%/O). Recrystallisation of the mother liquors gave an additional 107 mg (18%).

m.p. 155.5–157.5° C. (from ethyl acetate).

$R_f$ 0.34 (hexane/ether/acetic acid=50:50:1)

$\delta_H$ (400 MHz, $CD_3OD$)(exchangeable hydrogens only partially exchanged) 1.03 (9H, s), 1.51 (4H, m), 2.16 (3H, s), 2.37 (1H, dd, J=5 and 17 Hz), 2.47 (2H, m), 2.59 (1H, dd, J=10 and 17 Hz), 2.83 (1H, m), 3.32 (3H, s), 3.57 (2H, d, J=7 Hz), 3.80 (3H, s), 4.43 (1H, d, J=10 Hz), 5.10 (1H, q, J=7 Hz), 6.77 (1H, s), 6.80 (1H, d, J=7 Hz), 6.87 (2H, m), 6.97 (2H, m), 7.16 (3H, m), 7.28 (3H, m), 7.74 (1H, br d), 8.50 (1H, br d).

LRMS (thermospray) m/z=603 ($MH^+$)

FTIR $v_{max.}$ (KBr disc) 3300, 2960, 2930, 1711, 1640, 1545, 1484, 1217, 1211, 700 $cm^{-1}$

Example 16

(2R)-N-1-[(1S)-2,2-Dimethyl-1-({[(1S)-2methoxy-1-phenylethyl]amino}carbonyl)propyl]-2{3-[3-methyl-4-phenyl)phenyl]propyl}-(N-4-hydroxy)butanediamide.

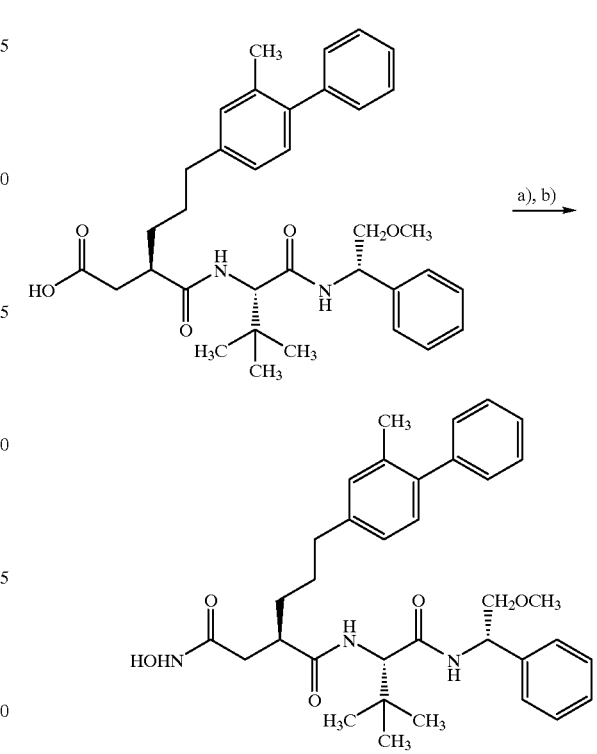

a) According to the method of Example 2, (3R)-3-({[(1S)-2,2-dimethyl-1-({[(1S)-2-methoxy-1-phenylethyl]amino}carbonyl)propyl]amino}carbonyl)-6-[(3-methyl-4-phenyl)phenyl]hexanoic acid (Example 14) (347 mg, 0.61 mmol) was reacted with O-allylhydroxylamine hydrochloride (81 mg, 0.73 mmol). Purification of the crude product by flash chromatography (eluting with hexane:ethyl acetate=2:1) followed by trituration with ether and ethyl acetate gave (2R)-N1-[(1)-2,2-dimethyl-1-({[(1S)-2-methoxy-1-phenylethyl]amino}carbonyl)propyl]-2-{3-[(3-methyl-4-phenyl)phenyl]propyl}-(N4-3-propenyloxy)butanediamide (306 mg, 80%) as a white solid.

m.p. 117–120° C.

$R_f$ 0.28 (hexane:ethyl acetate=1:2).

$\delta_H$ (400 MHz, $CDCl_3$) 1.02 (9H, s), 1.40–1.70 (4H, complex), 2.20 (3H, s, and 1H, m overlapping), 2.34–2.60 (3H, complex), 2.76 (1H, m), 3.36 (3H, s), 3.63 (2H, d, J=5 Hz), 4.28 (1H, d, J=9.5 Hz), 4.34 (2H, d, J=6 Hz), 5.12 (1H, dt, J=7.5 and 5 Hz), 5.30 (2H, m), 5.90 (1H, m), 6.44 (1H, d, J=7.5 Hz and 1H, br s overlapping), 6.94 (1H, m), 6.98 (1H, s), 7.08 (1H, d, J=7 Hz), 7.18–7.38 (8H, complex), 7.40 (2H, m), 8.50 (1H, br s).

LRMS (thermospray) m/z=628 ($MH^+$).

b) A stirred mixture of (2R)-N1-[(1S)-2,2-dimethyl-1-({[(1S)-2-methoxy-1-phenylethyl]amino}carbonyl)propyl]-2-{3-[(3-methyl-4-phenyl)phenyl]propyl}-(N4-3-propenyloxy)butanediamide (300 mg, 0.48 mmol) and ammonium formate (300 mg, 4.76 mmol) was dissolved in hot ethanol/water (4:1, 6 mL) to give a colourless solution. A solution of palladium acetate (4 mg, 0.018 mmol) and triphenylphosphine (9.6 mg, 0.037 mmol) in ethanol/water (4:1, 2 mL) was added, and the mixture was heated under reflux for 60 min. After being cooled, the brown solution was diluted with ethyl acetate (100 mL) and washed with saturated aqueous sodium chloride (2×50 mL), dried (MgSO$_4$) and concentrated under reduced pressure. The residue was purified by column chromatography (C$_{18}$ silanised silica gel (40–63μ), eluting with methanol:water=4:1) then triturated with diisopropyl ether to give (2R)-N1-[(1S)-2,2-dimethyl-1-({[(1S)-2-methoxy-1-phenylethyl]amino}carbonyl)propyl]-2-{3-[(3-methyl-4-phenyl)phenyl]propyl}-(N4-hydroxy)butanediamide (226 mg, 80%) as a white solid.

m.p. 92–96° C.

R$_f$ 0.57 (dichloromethane:methanol:conc. aq. ammonia=90:10:1)

δ$^H$ (400 MHz, CH$_3$OD) 1.02 (9H, s), 1.40–1.68 (4H, m), 2.17 (3H, s), 2.20 (1H, m), 2.36 (1H m), 2.48 (2H, m), 2.86 (1H, m), 3.30 (3H, s), 3.58 (2H, d, J=6.5 Hz), 4.40 (1H, s), 5.10 (1H, t, J=6.5 Hz), 6.88 (1H, m), 6.98 (2H, m), 7.10–7.36 (8H, complex), 7.39 (2H, m).

LRMS (thermospray) m/z=588 (MH$^+$)

| Found: | C, 70.95; | H, 7.85; | N, 7.00; |
|---|---|---|---|
| C$_{35}$H$_{45}$N$_3$O$_5$.0.25H$_2$O requires | C, 70.98; | H, 7.74; | N, 7.09% |

Examples 17 and 18

(N4,3S)-Dihydroxy-N1-[(1S)-2,2-dimethyl-1-({[(1R)-1-phenylethyl]amino}carbonyl)propyl]-(2R)-2{3-[4-(4-cyanophenyl)-3-methylphenyl]propyl}butanediamide and (N4,3S)-dihydroxy-N1-[(1S)-2,2-dimethyl-1-({[(1R)-1-phenylethyl]amino}carbonyl)propyl]-(3R)-{-[4-(4-hydroxyamidino)phenyl-3-methylphenyl]propyl}butanediamide.

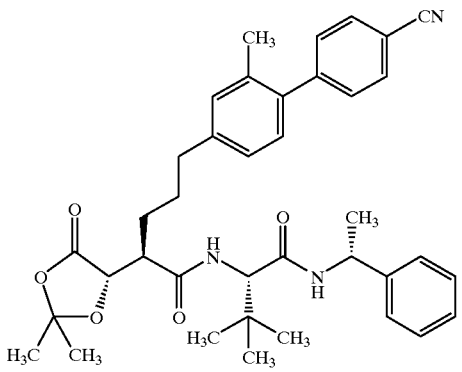

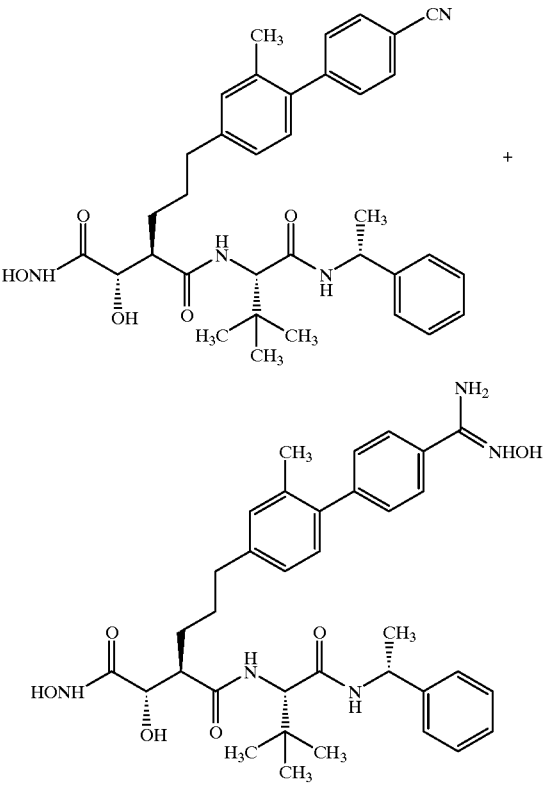

According to the method of Example 9, (2R)-5-{[4-(4-cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide (Preparation 22) (384 mg, 0.62 mmol) was reacted with hydroxylamine at room temperature for 18 h. The solution was concentrated under reduced pressure, and the residue purified by column chromatography (C$_{18}$ silanised silica gel (40–63μ) eluting with methanol:water=70:30 then 80:20) to give two fractions. The first eluted product was identified as (N4, 3S)-dihydroxy-N1-[(1S)-2,2-dimethyl-1-({[(1R)-1-phenylethyl]amino}carbonyl)propyl]-(2R)-2-{3-[4-(4-cyanophenyl)-3-methylphenyl]propyl}butanediamide, R$_f$ 0.38 (dichloromethane:methanol=90:10), which was triturated with diisopropylether to give a white solid (115 mg, 31%).

m.p. 103–109° C.

δ$_H$ (400 MHz, DMSO-d$_6$) 0.92 (9H, s), 1.25 (1H, m), 1.26 (3H, d, J=7.5 Hz), 1.40–1.54 (3H, m), 2.14 (3H, s), 2.40 (1H, m), 2.44 (1H, m), 2.70 (1H, m), 3.76 (1H, t, J=7.5 Hz), 4.34 (1H, d, J=9.5 Hz), 4.90 (1H, pentet, J=7.5 Hz), 5.24 (1H, d, J=7.5 Hz), 6.98 (1H, m), 7.00 (2H, m), 7.10 (3H, m), 7.20 (2H, m), 7.46 (2H, d, J=8 Hz), 7.58 (1H, d, J=9.5 Hz), 7.82 (2H, d, J=8 Hz), 8.26 (1H, d, J=7.5 Hz), 8.80 (1H, br s), 10.56 (1H, br s).

LRMS (thermospray) m/z=538 (base peak, M$^+$–HONHCO)

| Found: | C, 69.26; | H, 7.15; | N, 9.10; |
|---|---|---|---|
| C$_{35}$H$_{42}$N$_4$O$_5$.0.1EtOAc.0.4H$_2$O requires | C, 69.16; | H, 7.15; | N, 9.11% |

The second eluted product was identified as (N4, 3S)-dihydroxy-N1-[(1S)-2,2-dimethyl-1-({[(1R)-1-phenylethyl]

amino}carbonyl)propyl]-(2R)-2-{3-[4-(4-hydroxamidino)phenyl-3-methylphenyl]propyl}butanediamide, R$_f$ 0.20 (dichloromethane:methanol=90:10), as a white solid (84 mg, 21%).

m.p. 131–135° C.

δ$_H$ (400 MHz, DMSO-d$_6$) 0.90 (9H, s), 1.24 (1H, m, and 3H, d, J=7 Hz overlapping), 1.38–1.58 (3H, m), 2.16 (3H, s), 2.40 (1H, m), 2.44 (1H, m), 2.58 (1H, m), 3.76 (1H, t, J=7 Hz), 4.34 (1H, d, J=10.5 Hz), 4.90 (1H, pentet, J=7 Hz), 5.24 (1H, d, J=7 Hz), 5.80 (2H, s), 6.96 (1H, m), 7.00 (2H, m), 7.04–7.20 (3H, m), 7.21 (2H, m), 7.46 (2H, d, J=8 Hz), 7.58 (1H, d, J=10.5 Hz), 7.70 (2H, d, J=8 Hz), 8.24 (1H, d, J=7 Hz), 8.80 (1H, br s), 9.60 (1H, s), 10.58 (1H, br s).

LRMS (thermospray) m/z 632 (MH$^+$)

| Found: | C, 64.86; | H, 7.21; | N, 10.28; |
|---|---|---|---|
| C$_{35}$H$_{45}$N$_5$O$_6$.0.1CH$_3$OH.0.9H$_2$O requires | C, 64.74; | H, 7.31; | N, 10.75% |

Example 19

(N4,3S)-Dihydroxy-N1-[(1S)-2,2-dimethyl-1-({[(1R)-1-phenylethyl]amino}carbonyl)propyl]-(2R)-2{3-[4-(3-cyanophenyl)-3-methylphenyl]propyl}butanediamide.

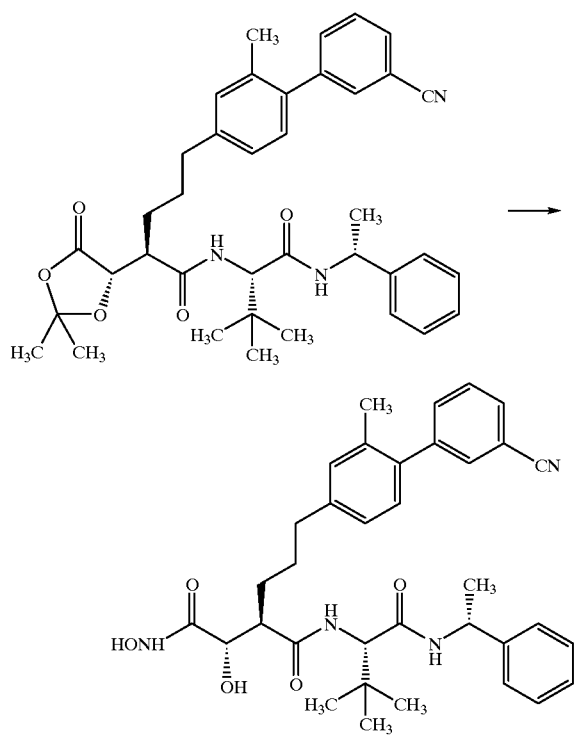

Sodium methoxide (43 mg, 0.80 mmol) was added to a solution of anhydrous hydroxylamine hydrochloride (56 mg, 0.80 mmol) in anhydrous methanol (1 mL) under nitrogen at room temperature. The mixture was stirred for 2.5 h and filtered rapidly through a pad of Arbocel filter aid, washing with anhydrous methanol (1 mL). (2R)-5-{[4-(3-Cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide (Preparation 24) (123 mg, 0.20 mmol) in anhydrous methanol (1 mL) was added to the mixture at 4° C. and stirred for 15 min. The mixture was warmed to room temperature and stirred for 9 h. The solution was concentrated under reduced pressure and the residue purified by column chromatography (C$_{18}$ silanised silica gel (40–63μ) eluting with methanol:water=3:1). The residue was azeotroped with ethanol, then ethyl acetate and triturated with diisopropyl ether to give the title compound as a non-crystalline white solid (58 mg, 48%). No distinct melting point.

R$_f$ 0.11 (dichloromethane:methanol:conc. aq. ammonia=90:10:1)

δ$_H$ (400 MHz, DMSO-d$_6$) 0.92 (9H, s), 1.24 (1H, m and 3H, d, J=7 Hz overlapping), 1.38–1.54 (3H, m), 2.14 (3H, s), 2.40 (1H, m), 2.48 (1H, m), 2.70 (1H, m), 3.76 (1H, t, J=7.5 Hz), 4.34 (1H, d, J=9.5 Hz), 4.90 (1H, pentet, J=7 Hz), 5.22 (1H, d, J=7.5 Hz), 6.98 (1H, d, J=7 Hz), 7.02 (2H, m), 7.14 (3H, m), 7.22 (2H, d, J 7 Hz), 7.58 (1H, d,=9.5 Hz), 7.60 (2H, d, J=5 Hz), 7.72 (1H, s), 7.80 (1H, m), 8.26 (1H, d, J=7 Hz), 8.80 (1H, br s), 10.56 (1H, br s).

LRMS (thermospray) m/z=599 (MH$^+$), 538 (base peak, M$^+$–HONHCO)

| Found: | C, 69.12; | H, 7.20; | N, 9.04; |
|---|---|---|---|
| C$_{35}$H$_{42}$N$_4$O$_5$.0.5H$_2$O requires | C, 69.17; | H, 7.13; | N, 9.22% |

Example 20

(2R)-2{3-[4-(3-Carbamoylphenyl)-3-methylphenyl]propyl}-(N4,3S)-dihydroxy-N1-[(1S)-2,2-dimethyl-1-({[(1R)-1-phenylethyl]amino}carbonyl)propyl]butanediamide.

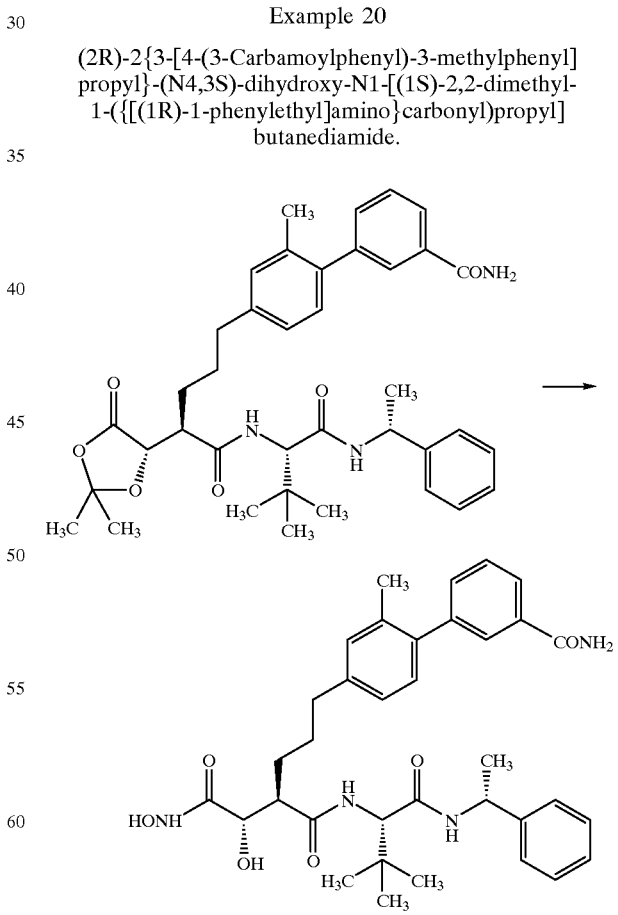

According to the method of Example 19, (2R)-5-{[4-(3-carbamoylphenyl)-3-methyl]phenyl-2-[(4S)-2,2-dimethyl- 5-oxo-1,3-dioxolan-4-yl]-N-[(1S)-2,2-dimethyl-1-({[(1R)-1-phenylethyl]amino}carbonyl)propyl]pentanamide (Preparation 26) (126 mg, 0.20 mmol) was reacted with hydroxylamine at room temperature for 13 h. The solution was concentrated under reduced pressure and the residue purified by column chromatography ($C_{18}$ silanised silica gel (40–63μ) eluting with methanol:water=3:2). The residue was azeotroped with ethanol, then ethyl acetate and triturated with diethyl ether to give the title compound as a white solid (74 mg, 60%).

m.p. 85–100° C.

$R_f$ 0.04 (dichloromethane:methanol:conc. aq. ammonia= 90:10:1)

$\delta_H$ (400 MHz, DMSO-$d_6$) 0.94 (9H, s), 1.24 (1H, m and 3H, d, J=7 Hz overlapping), 1.43 (3H, m), 2.14 (3H, s), 2.40 (1H, m), 2.50 (1H, m), 2.70 (1H, m), 3.76 (1H, t, J=7 Hz), 4.36 (1H, d, J=10 Hz), 4.90 (1H, pentet, J=7 Hz), 5.24 (1H, d, J=7.5 Hz), 6.98 (1H, d, J=7 Hz), 7.02 (2H, m), 7.14 (3H, m), 7.20 (2H, m), 7.34 (1H, s), 7.40 (1H, d, J=7 Hz), 7.46 (1H, d, J=7 Hz), 7.58 (1H, d, J=10 Hz), 7.80 (1H, s), 7.82 (1H, d, J=7 Hz), 7.98 (1H, s), 8.26 (1H, d, J=7 Hz), 8.90 (1H, s), 10.60 (1H, s).

LRMS (thermospray) m/z=617 (MH$^+$)

| Found: | C, 65.35; | H, 7.29; | N, 8.57; |
|---|---|---|---|
| $C_{35}H_{44}N_4O_6 \cdot 1.33H_2O$ requires | C, 65.61; | H, 7.34; | N, 8.74% |

Example 21

(3R)-3-[({({[(1S)-2Methoxy-1-phenylethyl]amino}carbonyl)-[(1S)-2methyl]-1-propyl}amino)carbonyl]-6-[3-methyl-(4-phenyl)phenyl]hexanoic acid.

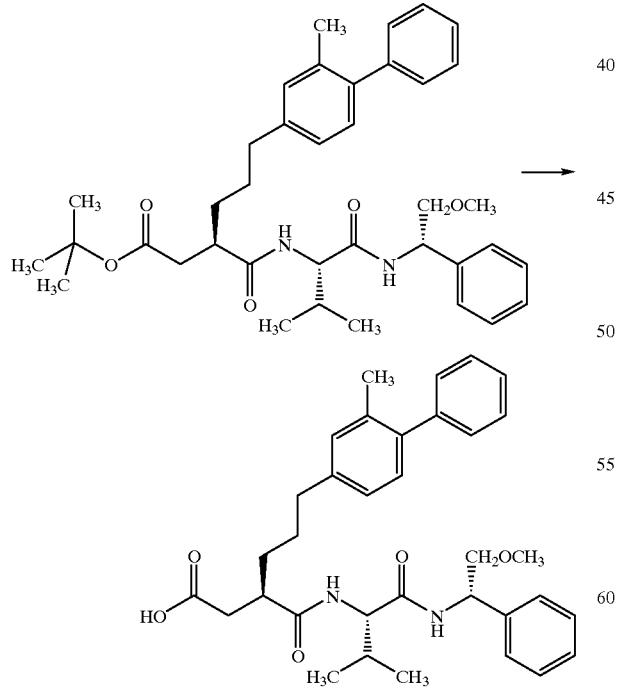

According to the method of Example 1, tert-butyl (3R)-3-[({({[(1S)-2-methoxy-1-phenylethyl]amino}carbonyl)-[(1S)-2-methyl]-1-propyl}amino)carbonyl]-6-[3-methyl-(4-phenyl)phenyl]hexanoate (Preparation 28) (700 mg, 1.14 mmol) was treated with trifluoroacetic acid in anhydrous dichloromethane at room temperature for 4 h. The residue was azeotroped with toluene (twice), and recrystallised from diethyl ether to give the title compound as a colourless solid (506 mg, 79%).

m.p. 141–144° C.

$R_f$ 0.28 (pentane:ethyl acetate:acetic acid=50:50: 1)

$\delta_H$ (400 MHz, DMSO-$d_6$) 0.83 (3H, d, J=8 Hz), 0.85 (3H, d, J=8 Hz), 1.36 (1H, m), 1.48 (3H, m), 1.94 (1H, octet, J=8 Hz), 2.18 (3H, s), 2.22 (1H, m), 2.42 (3H, m), 2,76 (1H, m), 3.20 (3H, s), 3.44 (2H, d, J=7.5 Hz), 4.20 (1H, t, J=8 Hz), 5.00 (1H, q, J=7.5 Hz), 6.94 (1H, m), 7.00 (2H, m), 7.12–7.38 (8H, complex), 7.40 (2H, m), 7.90 (1H, d, J=8 Hz), 8.02 (1H, d, J=7.5 Hz), 12.04 (1H, br s).

LRMS (thermospray) m/z=559 (MH$^+$)

| Found: | C, 72.86; | H, 7.52; | N, 5.04; |
|---|---|---|---|
| $C_{34}H_{42}N_2O_5$ requires | C, 73.09; | H, 7.58; | N, 5.01% |

Example 22

(3R)-3-({[({[(1S)-2Methoxy-1-phenylethyl]amino}carbonyl)-(1S)-2phenylethyl]amino}carbonyl)-6-[3-methyl-(4-phenyl) phenyl] hexanoic acid.

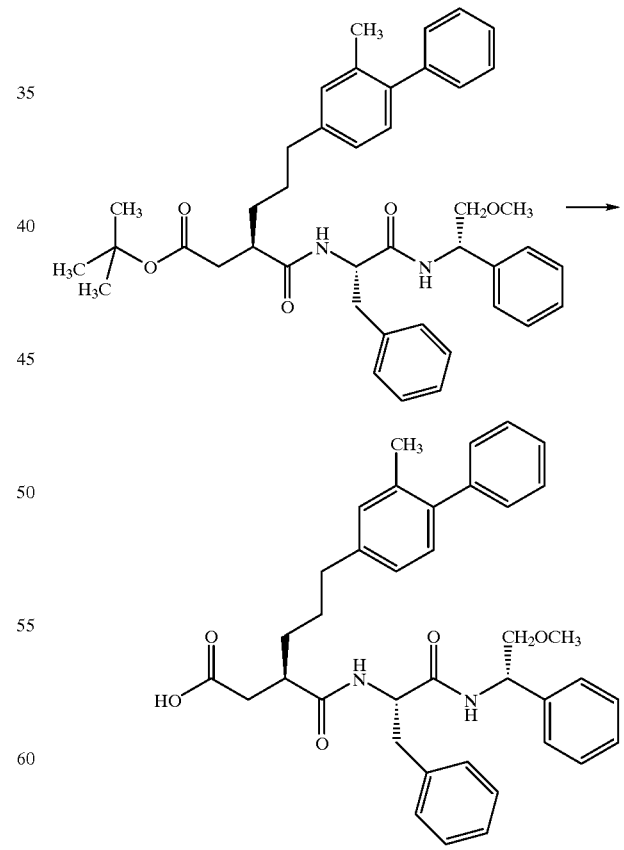

According to the method of Example 1, tert-butyl (3R)-3-({[({[(1S)-2-methoxy-1-phenylethyl]amino}carbonyl)-

(1S)-2-phenylethyl]amino}carbonyl)-6-[3-methyl-(4-phenyl)phenyl]hexanoate (Preparation 30)(920 mg, 1.39 mmol) was treated with trifluoroacetic acid in anhydrous dichloromethane at room temperature for 4 h. The residue was azeotroped with toluene (twice), and recrystallised from diethyl ether to give the title compound as a colourless solid (665 mg, 79%).

m.p. 152–157° C.

$R_f$ 0.27 (pentane:ethyl acetate:acetic acid=50:50:1)

δH (400 MHz, DMSO-$d_6$) 1.30–1.50 (4H, m), 2.16 (3H, s), 2.18 (1H, m), 2.30 (1H, m), 2.42 (2H, m), 2.62 (1H, m), 2.84 (1H, m), 2.98 (1H, m), 3.18 (3H, s), 3.38 (2H, d, J=6 Hz), 4.60 (1H, dt, J=6 and 8.5 Hz), 4.98 (1H, q, J=8 Hz), 6.94 (1H, m), 7.00 (2H, m), 7.12–7.38 (13H, complex), 7.40 (2H, m), 8.08 (1H, d, J=8.5 Hz), 8.20 (1H, d, J=8 Hz), 12.05 (1H, br s).

LRMS (thermospray) m/z=607 (MH+)

| Found: | C, 75.02; | H, 6.96; | N, 4.63; |
| $C_{38}H_{42}N_2O_5$ requires | C, 75.22; | H, 6.98; | N, 4.62% |

Example 23

(3R)-3-({[(1S)-2,2-Dimethyl-1-{[(1R)-1-(4-pyridyl)ethylamino]carbonyl}propyl]amino}carbonyl)-6-[(3-methyl-4-phenyl)phenyl]hexanoic acid hydrochloride.

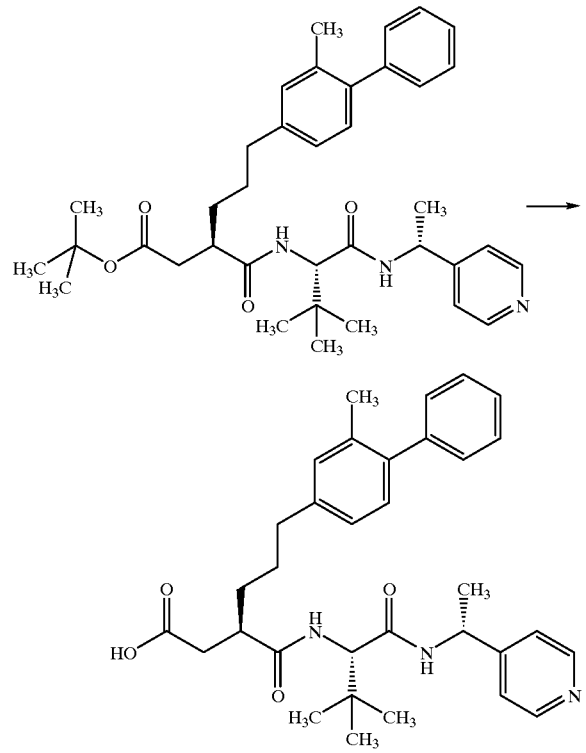

Hydrogen chloride gas was bubbled in to a solution of tert-butyl-(3R)-3-({[(1S)-2,2-dimethyl-1-{[(1R)-1-(4-pyridyl)ethylamino]carbonyl}propyl]amino}carbonyl)-6-[(3-methyl-4-phenyl)phenyl]hexanoate (Preparation 31) (285 mg, 0.47 mmol) in dioxane (15 mL) under nitrogen at 0° C., until saturated. The solution was stirred for 3 h at 0° C., then concentrated under reduced pressure. The residue was triturated with diethyl ether to give the title compound as a white solid (390 mg, 88%).

m.p. 132° C. (dec.).

$R_f$ 0.16 (ethyl acetate:hexane:acetic acid=75:25:1)

δ$_H$ (400 MHz, $CD_3OD$) 1.06 (9H, s), 1.50 (4H, m and 3H, d, J=7 Hz, overlapping), 2.16 (3H, s), 2.40–2.60 (3H, m), 2.64 (1H, m), 2.90 (1H, m), 4.32 (1H, d, J=10 Hz), 5.16 (1H, pentet, J=7 Hz), 6.86 (1H, m), 6.98 (2H, m), 7.21 (2H, m), 7.30 (1H, m), 7.40 (2H, m), 7.90 (1H, d, J=10 Hz), 7.96 (2H, d, J=8 Hz), 8.56 (2H, d, J=8 Hz), 8.90 (1H, d, J=7 Hz).

LRMS (thermospray) m/z=544 (MH+)

| Found: | C, 65.43; | H, 7.28; | N, 6.72; |
| $C_{33}H_{41}N_3O_4 \cdot HCl \cdot 1.5H_2O$ requires | C, 65.28; | H, 7.47; | N, 6.92% |

Example 24

N1-[(1S)-2,2-Dimethyl-1-([(1R)-1-(3-pyridyl)ethylamino]carbonyl) propyl]-(N4-hydroxy)-(2R)-2}3-[3-methyl-(4-phenyl)phenyl] propyl}bytanediamide.

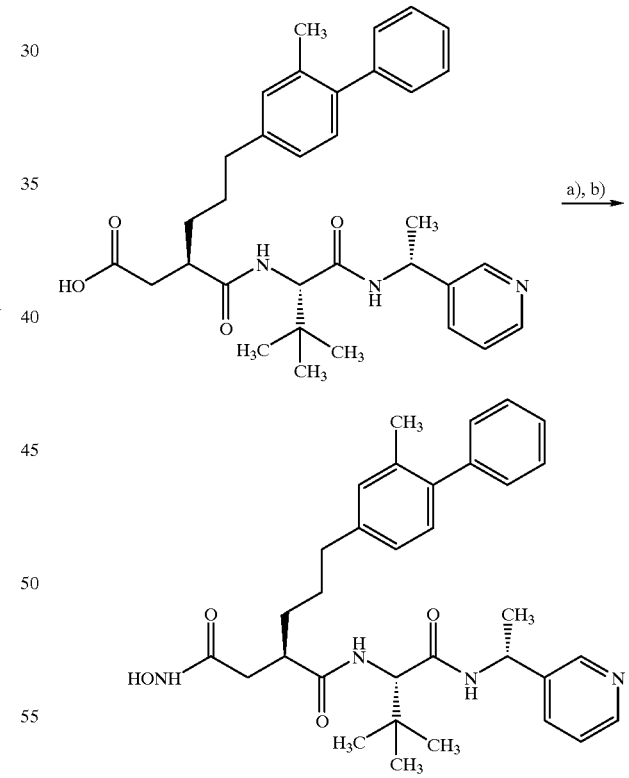

a) According to the method of Example 2, (3R)-3-({[(1S)-2,2-dimethyl-1-{[(1R)-1-(3-pyridyl)ethylamino]carbonyl}propyl]amino}carbonyl)-6-[(3-methyl-4-phenyl)phenyl]-hexanoic acid (Preparation 32) (330 mg, 0.57 mmol) was reacted with O-allylhydroxylamine hydrochloride (76 mg, 0.68 mmol). Purification of the crude product by recrystallisation from hot ethyl acetate gave N1-[(1S)-2,2-dimethyl-1-([(1R)-1-(3-pyridyl)ethylamino]carbonyl)

propyl]-(N4-3-propenyloxy)-(2R)-2-{3-[3-methyl-(4-phenyl)phenyl]propyl}butanediamide (219 mg, 64%) as a white solid.

m.p. 187–189° C.

R$_f$ 0.21 (ethyl acetate).

δ$_H$ (400 MHz, DMSO-d$_6$) 0.90 (9H, s), 1.32 (3H, d, J=7.5 Hz), 1.42 (4H, m), 2.04 (1H, m), 2.16 (3H, s), 2.18 (1H, m), 2.46 (2H, m), 2.86 (1H, m), 4.20 (2H, m), 4.28 (1H, d, J=9 Hz), 4.96 (1H, m), 5.20 (2H, m), 5.88 (1H, m), 6.94 (1H, m), 7.00 (2H, m), 7.18 (1H, m), 7.26 (2H, m), 7.32 (1H, m), 7.40 (2H, m), 7.60 (1H, m), 7.70 (1H, m), 8.38 (1H, m), 8.40 (1H, d, J=7.5 Hz), 8.48 (1H, s), 10.85 (1H, s).

LRMS (APCI) m/z=599 (MH$^+$).

b) According to the method of Example 2, N1-[(1S)-2,2-dimethyl-1-([(1R)-1-(3-pyridyl)ethylamino]carbonyl)propyl]-(N4-3-propenyloxy)-(2R)-2-{3-[3-methyl-(4-phenyl)phenyl]propyl}butanediamide (219 mg, 0.37 mmol) was reacted with ammonium formate (230 mg, 3.66 mmol) in ethanol/water (4:1, 8 mL) under palladium catalysis at reflux for 1.25 h. After work-up, the residue was purified by column chromatography (C$_{18}$ silanised silica gel (40–63μ), eluting with methanol:water=4:1) and triturated with diisopropyl ether to give N1-[(1S)-2,2-dimethyl-1-([(1R)-1-(3-pyridyl)ethylamino]carbonyl)propyl]-(N4-hydroxy)-(2R)-2-{3-[3-methyl-(4-phenyl)phenyl]propyl}butanediamide (122 mg, 60%) as a white solid.

m.p. 112–114° C.

R$_f$ 0.33 (C$_{18}$ silanised silica, methanol:water=5:1)

δ$_H$ (400 MHz, CH$_3$OD) 1.01 (9H, s), 1.46 (3H, d, J=7 Hz), 1.40–1.64 (4H, m), 2.16 (3H, s), 2.20 (1H, m), 2.36 (1H, m), 2.50 (2H, m), 2.88 (1H, m), 4.32 (1H, s), 5.02 (1H, q, J=7 Hz), 6.92 (1H, m), 7.00 (2H, m), 7.18 (1H, m), 7.22 (2H, m), 7.32 (1H, m), 7.40 (2H, m), 7.72 (1H, m), 8.28 (1H, m), 8.48 (1H, s).

LRMS (thermospray) m/z=559 (MH$^+$)

| Found: | C, 70.13; | H, 7.83; | N, 9.48; |
|---|---|---|---|
| C$_{33}$H$_{42}$N$_4$O$_4$.0.33H$_2$O.0.33DIPE requires | C, 70.20; | H, 7.80; | N, 9.63% |

Example 25

(N4,3S)-Dihydroxy-N1-[(1S)-2,2-dimethyl-1-({[(1R)-1-(4-pyridyl)ethyl]amino}carbonyl)propyl]-(2R)-2}3-[3-methyl-(4-phenyl)phenyl]propyl}butanediamide.

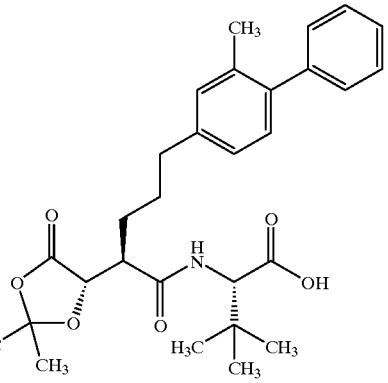

a)

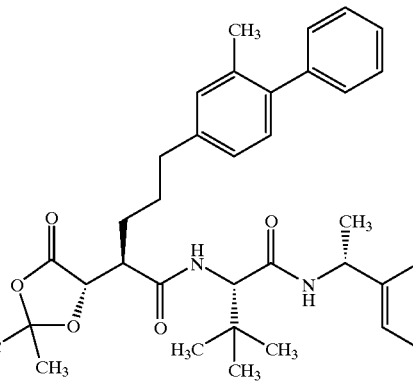

b)

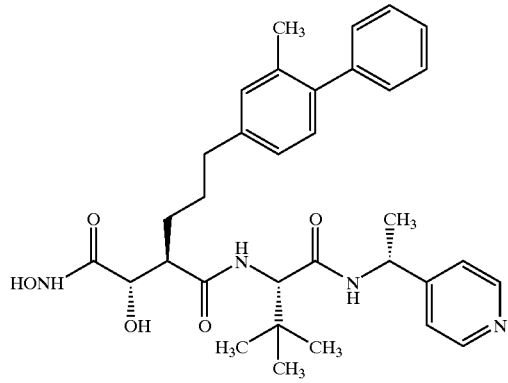

(R)-(+)-1-(4-Pyridyl)ethylamine was prepared by the method of J. Amer. Chem. Soc., 1973, 95, 811, by recrystallising the (−)-tartaric acid salt of the racemic amine, [α]$_D^{20}$=−16.7° (c=0.20, H$_2$O). The free base was liberated by dissolving the tartrate salt in excess aqueous sodium hydroxide saturated with sodium chloride and extracting several times with dichloromethane. The free base was used immediately without purification.

a) 7-Azabenzotriazol-1-yloxytris(pyrrolidino)phosphonium hexafluorophosphate (208 mg, 0.40 mmol) was added to a stirred solution of (2R)-N-[(1S)1-(carboxy)-2,2-dimethylpropyl]-2-[(4S)-2,2-dimethyl-5-oxo-1,3-dioxolan-4-yl]-5-[(3-methyl-4-phenyl)phenyl]pentanamide (Preparation 33)(198 mg, 0.40 mmol), (R)-(+)1-(4-pyridyl)

ethylamine (49 mg, 0.40 mmol) and collidine (53 μL, 0.40 mmol) in anhydrous dichloromethane (4 mL) under nitrogen at 0° C. After 1 h, the solution was stirred at 20° C. for 3 h. The mixture was poured into ethyl acetate (100 mL) and water (100 mL), solid sodium chloride was added to give phase separation. The layers were separated and organic layer washed with 5% aqueous sodium bicarbonate (2×75 mL) adding further solid sodium chloride. The organic solution was dried ($Na_2SO_4$) and concentrated under reduced pressure. The residue was purified by flash chromatography (gradient elution with hexane:ethyl acetate=5:1 to 1:5), to give a solid which was triturated with diisopropyl ether to give (2R)-2-[(4S)-2,2-dimethyl-5-oxo-1,3-dioxolan-4-yl]-N-[(1S)-2,2-dimethyl-1-({[(1R)-1-(4-pyridyl)ethyl]amino}carbonyl)propyl]-5-[(3-methyl-4-phenyl)phenyl]pentanamide (104 mg, 43%) as a white solid.

m.p. 167–170° C.

$R_f$ 0.10(hexane:ethyl acetate=1:3)

$\delta_H$ (400 MHz, DMSO-$d_6$) 0.92 (9H, s), 1.34 (3H, d, J=7 Hz), 1.45 (3H, s and 2H, m, overlapping), 1.56 (3H, s and 1H, m overlapping), 1.72–1.82 (1H, m), 2.14 (3H, s), 2.40–2.60 (2H, m), 2.98 (1H, m), 4.40 (1H, d, J=9 Hz), 4.46 (1H, d, J=9 Hz), 4.90 (1H, pentet, J=7 Hz), 6.94 (1H, m), 7.00 (2H, m), 7.20 (2H, d, J=5.5 Hz), 7.30 (3H, m), 7.40 (2H, m), 7.86 (1H, d, J=9 Hz), 8.30 (2H, d, J=5.5 Hz), 8.58 (1H, d, J=7 Hz).

LRMS (thermospray) m/z=600 ($MH^+$).

| Found: | C, 69.04; | H, 7.31; | N, 6.68; |
| $C_{36}H_{45}N_3O_5$.1.2$H_2O$.0.13EtOAc requires | C, 69.32; | H, 7.71; | N, 6.64% | b) According to the method of Example 19, (2R)-2-[(4S)-2,2-dimethyl-5-oxo-1,3-dioxolan-4-yl]-N-[(1S)-2,2-dimethyl-1-({[(1R)-1-(4-pyridyl)ethyl]amino}carbonyl)propyl]-5-[(3-methyl-4-phenyl)phenyl]pentanamide (from a), above) (86 mg, 0.14 mmol) was reacted with hydroxylamine at room temperature for 18 h. The solution was concentrated under reduced pressure and purified by column chromatography ($C_{18}$ silanised silica gel (40–63μ) eluting with methanol:water=3:1). The residue was azeotroped with ethanol, then ethyl acetate and triturated with diisopropyl ether to give the title compound as a white solid (45 mg, 56%).

m.p. 100–110° C.

$R_f$ 0.10 (dichloromethane:methanol:conc. aq. ammonia=90:10:1)

$\delta_H$ (400 MHz, DMSO-$d_6$) 0.92 (9H, s), 1.26 (1H, m and 3H, d, J=7 Hz, overlapping), 1.36–1.60 (3H, m), 2.10 (3H, s), 2.40 (1H, m), 2.48 (1H, m), 2.70 (1H, m), 3.80 (1H, t, J=7.5 Hz), 4.34 (1H, d, J=9.5 Hz), 4.88 (1H, pentet, J=7 Hz), 5.24 (1H, d, J=7.5 Hz), 6.90 (1H, m), 6.98 (2H, m), 7.20 (2H, d, J=5.5 Hz), 7.28 (3H, m), 7.40 (2H, m), 7.60 (1H, d, J=9.5 Hz), 8.32 (2H, d, J=5.5 Hz), 8.42 (1H, d, J=7 Hz), 8.80 (1H, s), 10.60 (1H, br s).

| Found: | C, 67.88; | H, 7.44; | N, 9.42; |
| $C_{33}H_{42}N_4O_5$.0.5$H_2O$ requires | C, 67.90; | H, 7.43; | N, 9.06% |

Example 26

(N4,3S)-Dihydroxy-N1-[(1S)-2,2-dimethyl-1-({[(1R)-1-(3-pyridyl)ethyl]amino}carbonyl)propyl]-(2R)-2}3-[3-methyl-(4-phenyl)phenyl]propyl}butanediamide.

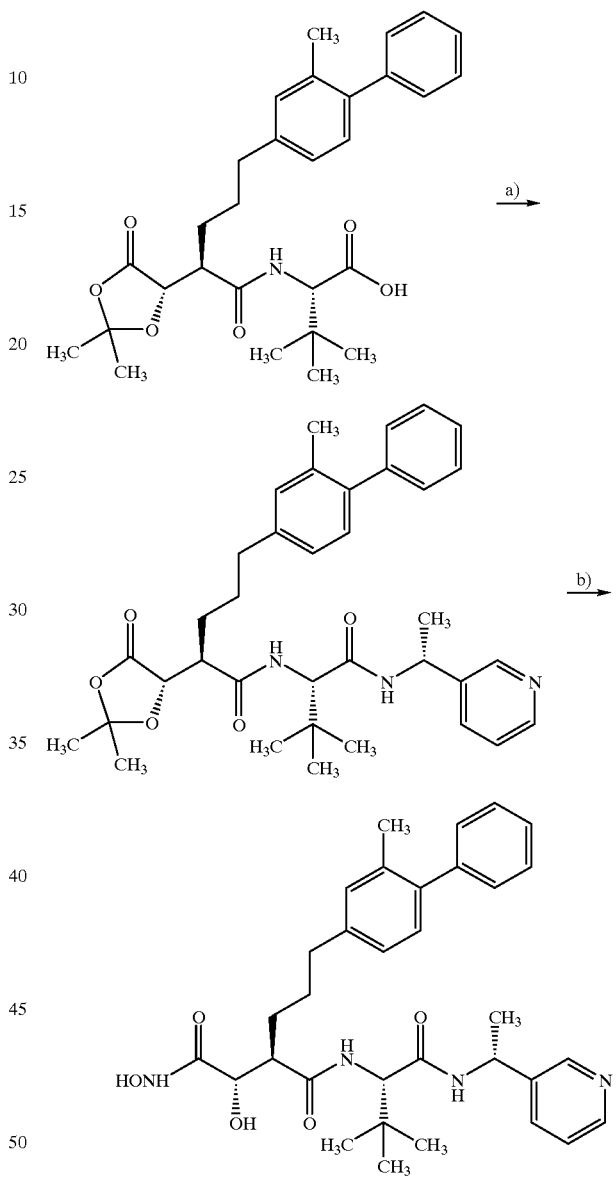

(R)-(+)-1-(3-Pyridyl)ethylamine was prepared by the method of J. Amer. Chem. Soc., 1973, 95, 811, by recrystallising of the (−)-tartaric acid salt of the racemic amine, $[\alpha]_D^{20}$=−20.1° (c=1.67, $H_2O$). The free base was liberated by dissolving the tartrate salt in excess aqueous 1M sodium hydroxide saturated with sodium chloride and extracting several times with dichloromethane. The free base was used immediately without purification.

a) According to the method of Example 25(a), of (2R)-N-[(1S)-1-(carboxy)-2,2-dimethylpropyl]-2-[(4S)-2,2-dimethyl-5-oxo-1,3-dioxolan-4-yl]-5-[(3-methyl-4-phenyl)phenyl]pentanamide (Preparation 33)(86 mg, 0.14 mmol) was reacted with (R)-(+)-1-(3-pyridyl)ethylamine free base (49 mg, 0.40 mmol) at room temperature for 3 h, followed by the same work up and trituration of the crude product with diisopropyl ether to give (2R)-2-[(4S)-2,2-dimethyl-5-oxo-1,3-dioxolan-4-yl]-N-[(1S)-2,2-dimethyl-1-({[(1R)-1-(3-pyridyl)ethyl]amino}carbonyl)propyl]-5-[(3-methyl-4-phenyl)phenyl]pentanamide (165 mg, 69%) as a white solid.

m.p. 172–176° C.

$R_f$ 0.10 (hexane:ethyl acetate=1:3)

$\delta_H$ (400 MHz, DMSO-$d_6$) 0.92 (9H, s), 1.35 (3H, d, J=7.5 Hz), 1.45 (2H, m and 3H, s overlapping), 1.55 (1H, m and 3H, s overlapping), 1.75 (1H, m), 2.12 (3H, s), 2.38–2.58 (2H, m), 2.95 (1H, m), 4.35 (1H, d, J=10 Hz), 4.45 (1H, d, J=9.5 Hz), 4.98 (1H, pentet, J=7.5 Hz), 6.94 (1H, m), 7.00 (2H, m), 7.10 (1H, m), 7.25 (2H, m), 7.35 (1H, m), 7.40 (2H, m), 7.68 (1H, d, J=8 Hz), 7.82 (1H, d, J=9.5 Hz), 8.32 (1H, m), 8.45 (1H, s), 8.55 (1H, d, J=7.5 Hz).

LRMS (thermospray) m/z=600 (MH$^+$)

b) According to the method of Example 19, (2R)-2-[(4S)-2,2-dimethyl-5-oxo-1,3-dioxolan-4-yl]-N-[(1S)-2,2-dimethyl-1-({[(1R)-1-(3-pyridyl)ethyl]amino}carbonyl)propyl]-5-[(3-methyl-4-phenyl)phenyl]pentanamide (from a), above) (142 mg, 0.24 mmol) was reacted with hydroxylamine at room temperature for 17 h. The solution was concentrated under reduced pressure and purified by column chromatography (C$_{18}$ silanised silica gel (40–63μ) gradient elution with methanol:water=60:40 to 80:20) to give a buff solid. This solid was purified again by reverse-phase chromatography(eluting with methanol:water=75:25). The product was then azeotroped with ethanol, ethyl acetate and triturated with diisopropyl ether to give the title compound as a white solid (50 mg, 36%).

m.p. 85–95° C.

$R_f$ 0.11 (dichloromethane:methanol:conc. aq. ammonia=90:10:1)

$\delta_H$ (400 MHz, DMSO-$d_6$) 0.90 (9H, s), 1.25 (1H, m), 1.30 (3H, d, J=7 Hz), 1.36–1.55 (3H, m), 2.15 (3H, s), 2.40 (2H, m), 2.70 (1H, m), 3.78 (1H, t, J=7.5 Hz), 4.30 (1H, d, J=9.5 Hz), 4.94 (1H, pentet, J=7 Hz), 5.24 (1H, d, J=7.5 Hz), 6.90 (1H, m), 7.00 (2H, m), 7.12 (1H, m), 7.20–7.38 (3H, m), 7.40 (2H, m), 7.60 (2H, m), 8.32 (1H, m), 8.38 (1H, d, J=7 Hz), 8.50 (1H, s), 8.82 (1H, br s), 10.55 (1H, br s).

LRMS (thermospray) m/z=514 (base peak, M$^+$-HONHCO)

| Found: | C, 67.52; | H, 7.44; | N, 9.52; |
| C$_{33}$H$_{42}$N$_4$O$_5$.0.67H$_2$O requires | C, 67.57; | H, 7.44; | N, 9.55% |

Example 27

(N4,3S)-Dihydroxy-N1-[(1S)-2,2-dimethyl-1-({[(1S)-2hydroxy-1-phenylethyl]amino}carbonyl)propyl]-(2R)-2}3-[3-methyl-(4-phenyl)phenyl]propyl}butanediamide.

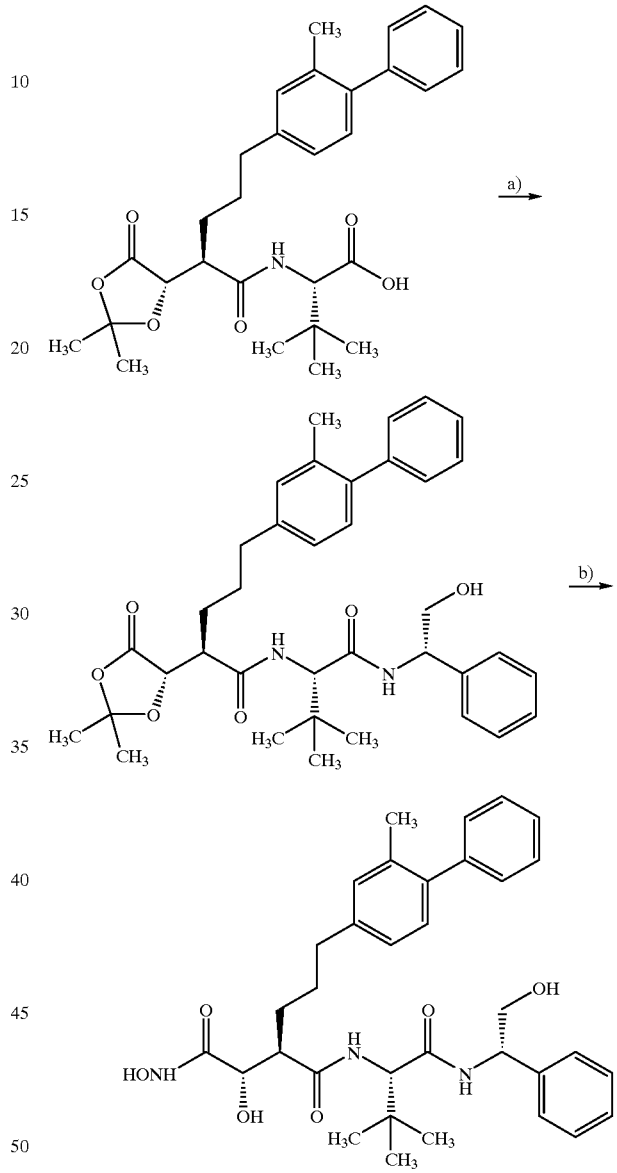

a) According to the method of Example 25(a), (2R)-N-[(1S)1-(carboxy)-2,2-dimethylpropyl]-2-[(4S)-2,2-dimethyl-5-oxo-1,3-dioxolan-4-yl]-5-[(3-methyl-4-phenyl)phenyl]pentanamide (Preparation 33)(150 mg, 0.30 mmol) was reacted with (S)-(+)-2-phenylglycinol (41 mg, 0.30 mmol) at room temperature for 3 h. The mixture was poured into ethyl acetate (75 mL) and washed with 0.5M aqueous sodium dihydrogenphosphate (2×50 mL)(solid sodium chloride was added to give phase separation). The organic solution was dried (Na$_2$SO$_4$) and concentrated under reduced pressure. The residual oil was triturated with diethyl ether to give (2R)-2-[(4S)-2,2-dimethyl-5-oxo-1,3-dioxolan-4-yl]-N-[(1S)-2,2-dimethyl-1-({[(1S)-2-hydroxy-1-phenylethyl]amino}carbonyl)propyl]-5-[(3-methyl-4-phenyl)phenyl]pentanamide (80 mg, 43%) as a white solid.

m.p. 206–209° C.

$R_f$ 0.33 (hexane:ethyl acetate:acetic acid=50:50:1)

$\delta_H$(400 MHz, DMSO-$d_6$) 0.95 (9H, s), 1.42 (2H, m and 3H, s overlapping), 1.56 (1H, m and 3H, s overlapping), 1.75 (1H, m), 2.16 (3H, s), 2.48 (2H, m), 2.95 (1H, m), 3.55 (2H, m), 4.40 (1H, d, J=9.5 Hz), 4.48 (1H, d, J=9.5 Hz), 4.75 (1H, t, J=5.5 Hz), 4.84 (1H, q, J=7 Hz), 6.94 (1H, m), 7.00 (2H, m), 7.10 (3H, m), 7.20 (2H, m), 7.30 (3H, m), 7.40 (2H, m), 7.80 (1H, d, J=9.5 Hz), 8.32 (1H, d, J=7 Hz).

LRMS (thermospray) m/z=615 (MH$^+$)

| Found: | C, 71.46; | H, 7.53; | N, 4.59; |
|---|---|---|---|
| $C_{37}H_{46}N_2O_6 \cdot 0.33H_2O$ requires | C, 71.59; | H, 7.58; | N, 4.51% | b) According to the method of Example 19, (2R)-2-[(4S)-2,2-dimethyl-5-oxo-1,3-dioxolan-4-yl]-N-[(1S)-2,2-dimethyl-1-({[(1S)-2-hydroxy-1-phenylethyl]amino}carbonyl)propyl]-5-[(3-methyl-4-phenyl)phenyl]pentanamide (from a), above) (66 mg, 0.11 mmol) was reacted with hydroxylamine at room temperature for 17 h. The solution was concentrated under reduced pressure and purified by column chromatography ($C_{18}$ silanised silica gel (40–63μ) gradient elution with methanol:water=60:40 to 80:20). The residue was azeotroped with ethanol, then with ethyl acetate and triturated with diisopropyl ether to give the title compound as a buff solid (35 mg, 54%).

m.p. 80–90° C.

$R_f$ 0.06 (dichloromethane:methanol:conc. aq. ammonia=90:10:1)

$\delta_H$ (400 MHz, DMSO-$d_6$) 0.92 (9H, s), 1.22 (1H, m), 1.30–1.55 (3H, m), 2.15 (3H, s), 2.40 (2H, m), 2.68 (1H, m), 3.56 (2H, m), 3.78 (1H, t, J=7.5 Hz), 4.38 (1H, d, J=9.5 Hz), 4.75 (1H, m), 4.82 (1H, q, J=7.5 Hz), 5.22 (1H, d, J=7.5 Hz), 6.90 (1H, m), 7.00 (2H, m), 7.15 (3H, m), 7.20–7.38 (5H, m), 7.40 (2H, m), 7.58 (1H, d, J=9.5 Hz), 8.20 (1H, d, J=7.5 Hz), 8.80 (1H, br s), 10.58 (1H, br s).

LRMS (thermospray) m/z=529 (base peak, M$^+$–HONHCO)

| Found: | C, 67.91; | H, 7.71; | N, 6.58; |
|---|---|---|---|
| $C_{34}H_{43}N_3O_6 \cdot 0.67H_2O \cdot 0.25DIPE$ requires | C, 67.99; | H, 7.69; | N, 6.70% |

Example 28

(N4,3S)-Dihydroxy-N1-[(1S)-2,2-dimethyl-1-({[(1R)-2,3-dihydro-1H-inden-1-yl]amino}carbonyl)propyl]-(2R)-2}3-[3-methyl-(4-phenyl)phenyl]propyl}butanediamide.

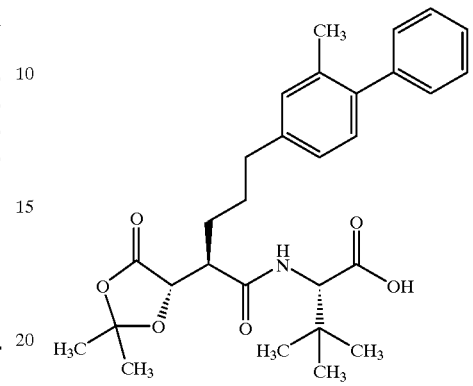

a)

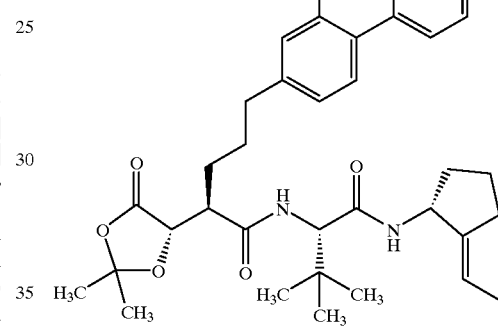

b)

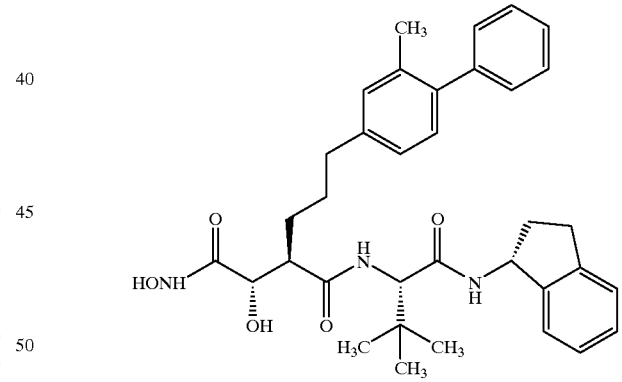

a) According to the method of Example 25(a), (2R)-N-[(1S)1-(carboxy)-2,2dimethylpropyl]-2-[(4S)-2,2-dimethyl-5-oxo-1,3-dioxolan-4-yl]-5-[(3-methyl-4-phenyl)phenyl]pentanamide (Preparation 33)(150 mg, 0.30 mmol) was reacted with (R)-(−)-1-aminoindan (40 mg, 0.30 mmol) at room temperature for 3 h. The mixture was poured into ethyl acetate (75 mL) and washed with 0.5M aqueous sodium dihydrogenphosphate (2×50 mL) and 5% aqueous sodium bicarbonate (50 mL)(solid sodium chloride was added to give phase separation). The organic solution was dried (Na$_2$SO$_4$) and concentrated under reduced pressure. The residual oil was purified by flash chromatography (gradient elution with hexane:ethyl acetate=10:1 to 2:1) and then triturated with diisopropyl ether to give (2R)-2-[(4S)-2,2- dimethyl-5-oxo-1,3-dioxolan-4-yl]-N-[(1S)-2,2-dimethyl-1-({[(1R)-2,3-dihydro- 1H-inden-1-yl]amino}carbonyl)propyl]-5-[(3-methyl-4-phenyl)phenyl]pentanamide as a white solid (135 mg, 74%).

R$_f$ 0.76 (hexane:ethyl acetate:acetic acid=50:50:1)

$\delta_H$ (400 MHz, CDCl$_3$) 1.02 (9H, s), 1.55 (3H, s), 1.60 (3H, s), 1.65–2.00 (5H, complex), 2.20 (3H, s), 2.60 (1H, m), 2.66 (3H, m), 2.86 (1H, m), 2.95 (1H, m), 4.20 (1H, d, J=10 Hz), 4.54 (1H, d, J=7 Hz), 5.42 (1H, q, J=8 Hz), 5.82 (1H, d, J=7 Hz), 6.62 (1H, d, J=8 Hz), 7.00–7.40 (12H, complex).

| Found: | C, 74.06; | H, 7.61; | N, 4.47; |
| --- | --- | --- | --- |
| C$_{38}$H$_{46}$N$_2$O$_5$.0.33EtOAc requires | C, 73.81; | H, 7.66; | N, 4.38% | b) According to the method of Example 19, (2R)-2-[(4S)-2,2-dimethyl-5-oxo-1,3-dioxolan-4-yl]-N-[(1S)-2,2-dimethyl-1-({[(1R)-2,3-dihydro-1H-inden-1-yl]amino}carbonyl)propyl]-5-[(3-methyl-4-phenyl)phenyl]pentanamide (from a), above) (105 mg, 0.17 mmol) was reacted with hydroxylamine at room temperature for 17 h. The solution was concentrated under reduced pressure and purified by columnchromatography (C$_{18}$ silanised silica gel (40–63μ) gradient elution with methanol:water=60:40 to 85:15). The residue was azeotroped with ethanol, then ethyl acetate and triturated with diisopropyl ether to give the title compound as a buff solid (60 mg, 60%).

m.p. 100–120° C.

R$_f$ 0.10 (dichloromethane:methanol:conc. aq. ammonia=90:10:1)

$\delta_H$ (400 MHz, DMSO-d$_6$) 0.92 (9H, s), 1.26 (1H, m), 1.42–1.60 (3H, m), 1.65 (1H, m), 2.15 (3H, s), 2.22 (1H, m), 2.40–2.62 (2H, m), 2.72 (2H, m), 2.80 (1H, m), 3.80 (1H, t, J=8 Hz), 4.30 (1H, d, J=9.5 Hz), 5.25 (2H, m), 6.90–7.45 (12H, complex), 7.62 (1H, d, J=9.5 Hz), 8.20 (1H, d, J=8.5 Hz), 8.80 (1H, s), 10.58 (1H, br s).

LRMS (thermospray) m/z=526 (base peak, MH$^+$−HONHCO)

| Found: | C, 70.94; | H, 7.50; | N, 6.81; |
| --- | --- | --- | --- |
| C$_{35}$H$_{43}$N$_3$O$_5$.0.33H$_2$O requires | C, 71.05; | H, 7.44; | N, 7.10% |

Example 29

(N4,3S)-Dihydroxy-N1-[(1S)-2,2-dimethyl-1-({[(1S)-2methoxy-1-phenylethyl]amino}carbonyl)propyl]-(2R)-2{3-[3-methyl-(4-phenyl)phenyl]propyl}butanediamide.

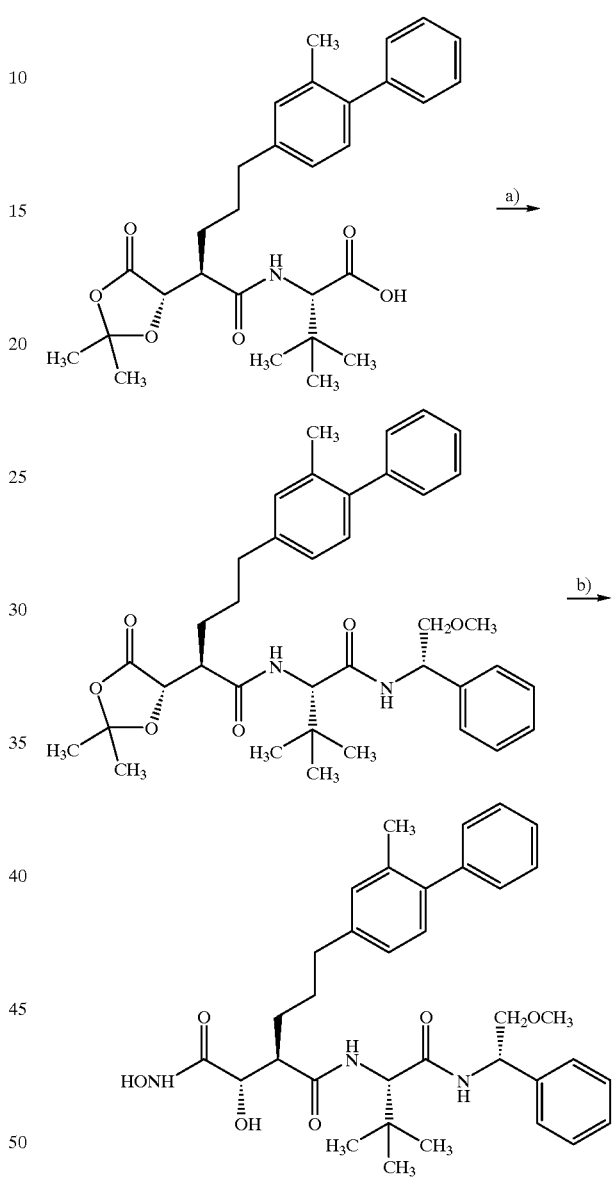

a) According to the method of Example 25(a), (2R)-N-[(1S)-1-(carboxy)-2,2-dimethylpropyl]-2-[(4S)-2,2-dimethyl-5-oxo-1,3-dioxolan-4-yl]-5-[(3-methyl-4-phenyl)phenyl]pentanamide (Preparation 33)(198 mg, 0.40 mmol) was reacted with (1S)-2-methoxy-1-phenylethylamine (61 mg, 0.40 mmol) at room temperature for 3 h. The mixture was poured into ethyl acetate (75 mL) and washed with 0.5M aqueous sodium dihydrogenphosphate (2×50 mL) and 5% aqueous sodium bicarbonate (50 mL)(solid sodium chloride was added to give phase separation). The organic solution was dried (Na$_2$SO$_4$) and concentrated under reduced pressure. The residual oil was purified by flash chromatography (gradient elution with hexane: ethyl acetate=4:1 to 1:1) and triturated with diisopropyl ether to give (2R)-2-[(4S)-2,2-dimethyl-5-oxo-1,3-dioxolan-4-yl]-N-[(1S)-2,2-dimethyl-1-({[(1S)-2-methoxy-1-phenylethyl]amino}carbonyl)propyl]-5-[(3-methyl-4-phenyl)phenyl]pentanamide as a white solid (172 mg, 68%).

$R_f$ 0.53 (hexane:ethyl acetate:acetic acid=50:50:1)

$\delta_H$ (400 MHz, CDCl$_3$) 1.02 (9H, s), 1.50 (3H, s), 1.55 (3H, s), 1.54 (2H, m), 1.90 (2H, m), 2.20 (3H, s), 2.60 (3H, m), 3.30 (3H, s), 3.60 (2H, d, J=5 Hz), 4.28 (1H, d, J=9 Hz), 4.50 (1H, d, J=6 Hz), 5.10 (1H, dt, J=5 and 7 Hz), 6.36 (1H, d, J=7 Hz), 6.50 (1H, d, J=9 Hz), 6.98 (1H, d, J=8 Hz), 7.01 (1H, s), 7.10 (1H, d, J=8 Hz), 7.15–7.36 (8H, complex), 7.40 (2H, m).

LRMS (thermospray) m/z=629 (MH$^+$), 651 (MNa$^+$).

| Found: | C, 72.41; | H, 7.76; | N, 4.50; |
| C$_{38}$H$_{48}$N$_2$O$_6$ requires | C, 72.49; | H, 7.72; | N, 4.48% | b) According to the method of Example 9, (2R)-2-[(4S)-2,2-dimethyl-5-oxo-1,3-dioxolan-4-yl]-N-[(1S)-2,2-dimethyl-1-({[(1S)-2-methoxy-1-phenylethyl]amino}carbonyl)propyl]-5-[(3-methyl-4-phenyl)phenyl]pentanamide (from a), above) (142 mg, 0.22 mmol) was reacted with hydroxylamine at room temperature for 17 h. The solution was concentrated under reduced pressure and purified by column chromatography (C$_{18}$ silanised silica gel (40–63μ) eluting with methanol:water=3:1). The residue was azeotroped with ethanol, then ethyl acetate and triturated with diisopropyl ether to give the title compound as a white solid (109 mg, 82%).

m.p. 100–110° C.

$R_f$ 0.07 (dichloromethane:methanol:conc. aq. ammonia=90:10:1)

$\delta_H$ (400 MHz, DMSO-d$_6$) 0.90 (9H, s), 1.20 (1H, m), 1.30–1.50 (3H, m), 2.10 (3H, s), 2.38 (1H, m), 2.44 (1H, m), 2.65 (1H, m), 3.17 (3H, s), 3.45 (2H, d, J=7.5 Hz), 3.75 (1H, t, J=8 Hz), 4.40 (1H, d, J=9.5 Hz), 5.00 (1H, q, J=7.5 Hz), 5.22 (1H, d, J=8 Hz), 6.90 (1H, d), 6.98 (2H, m), 7.15 (3H, m), 7.25 (4H, m), 7.35 (1H, m), 7.40 (2H, m), 7.58 (1H, d, J=9.5 Hz), 8.35 (1H, d, J=7.5 Hz), 8.80 (1H, br s), 10.58 (1H, br s).

LRMS (thermospray) m/z=575 (MH$^+$), 514 (M$^+$-HONHCO).

| Found: | C, 68.71; | H, 7.64; | N, 6.65; |
| C$_{35}$H$_{45}$N$_3$O$_6$·0.5H$_2$O requires | C, 68.60; | H, 7.57; | N, 6.86% |

Example 30

(N4,3S)-Dihydroxy-N1-[(1S)-2,2-dimethyl-1-({[(1R)-1-phenylethyl]amino}carbonyl)propyl]-(2R)-2{3-[3'-methoxy-2methylbiphen-4-yl)propyl]}butanediamide.

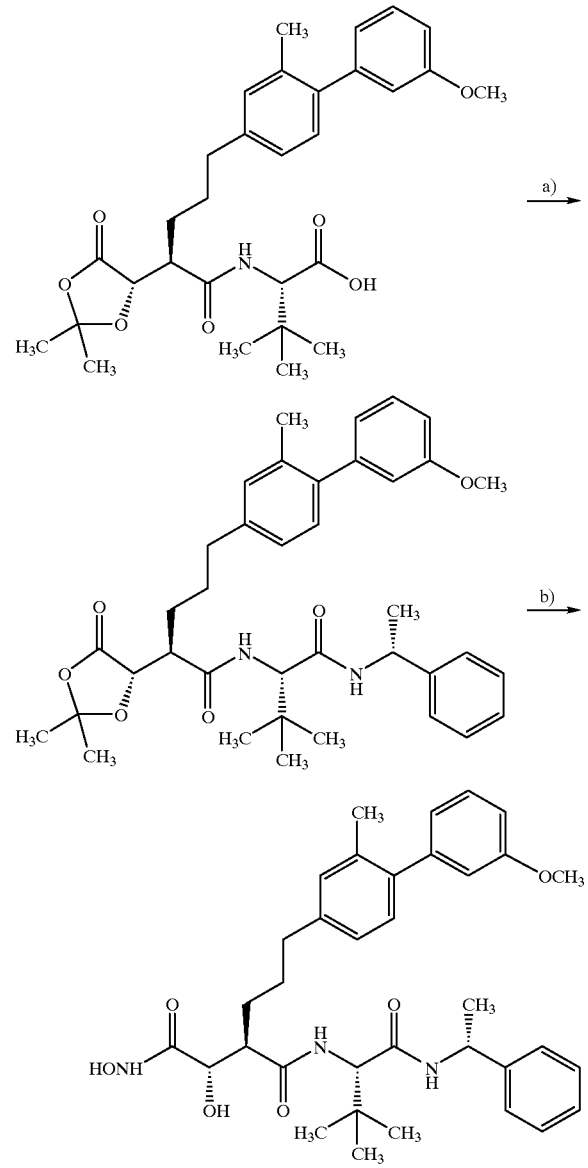

a) According to the method of Example 25(a), (2R)-N-[(1S)-1-(carboxy)-2,2-dimethylpropyl]-2-[(4S)-2,2-dimethyl-5-oxo-1,3-dioxolan-4-yl]-5-[(3'-methoxy-2-methylbiphen-4-yl)propyl]pentanamide (Preparation 34) (150 mg, 0.28 mmol) was reacted with (R)-1-phenylethylamine (35 μl, 0.28 mmol) at room temperature for 2.5 h. The mixture was poured into ethyl acetate (75 mL) and washed with 0.5M aqueous sodium dihydrogenphosphate (2×50 mL) and 5% aqueous sodium bicarbonate (50 mL) (solid sodium chloride was added to give phase separation). The organic solution was dried (Na$_2$SO$_4$) and concentrated under reduced pressure. The residual oil was purified by flash chromatography (eluting with hexane:ethyl acetate=35:65) to give (2R)-2-[(4S)-2,2-dimethyl-5-oxo- 1,3-dioxolan-4-yl]-N-[(1S)-2,2-dimethyl-1-({[(1R)-1-phenylethyl]amino}carbonyl)propyl]-5-[(3'-methoxy-2-methylbiphen-4-yl)propyl]pentanamide as a white solid (133 mg, 76%).

$R_f$ 0.49 (hexane:ethyl acetate:acetic acid=50:50:1) $\delta_H$ (300 MHz, CDCl$_3$) 1.00 (9H, s), 1.40–1.60 (11H, complex), 1.62 (1H, m), 1.90 (1H, m), 2.21 (3H, s), 2.60 (3H, m), 3.80 (3H, s), 4.18 (1H, d, J=9 Hz), 4.45 (1H, d, J=7 Hz), 5.05 (1H, pentet, J=7.5 Hz), 5.85 (1H, d, J=7.5 Hz), 6.50 (1H, d, J=9 Hz), 6.84 (3H, m), 7.00 (2H, m), 7.14 (1H, d, J=9.5 Hz), 7.18–7.40 (6H, complex).

LRMS (thermospray) m/z=646 (MNH$_4^+$).

b) According to the method of Example 19, (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]-5-[(3'-methoxy-2-methylbiphen-4-yl)propyl]pentanamide (from a), above) (133 mg, 0.21 mmol) was reacted with hydroxylamine (59 mg, 0.85 mmol) at room temperature for 18 h. The solution was concentrated under reduced pressure, the residue purified by column chromatography (C$_{18}$ silanised silica gel (40–63$\mu$), gradient elution with methanol:water=3:2 to 4:1), then triturated with diisopropyl ether to give the title compound as a white solid (57 mg, 45%).

m.p. 98–100° C.

$R_f$ 0.20 (dichloromethane:methanol=95:5)

$\delta_H$ (400 MHz, DMSO-d$_6$) 0.92 (9H, s), 1.18–1.30 (1H, m), 1.25 (3H, d, J=7.5 Hz), 1.38–1.58 (3H, m), 2.15 (3H, s), 2.40 (1H, m), 2.46 (1H, m), 2.70 (1H, m), 3.76 (4H, m), 4.35 (1H, d, J=9.5 Hz), 4.90 (1H, pentet, J=7.5 Hz), 5.22 (1H, d, J=8 Hz), 6.75–7.40 (12H, complex), 7.58 (1H, d, J=9.5 Hz), 8.26 (1H, d, J=7.5 Hz), 8.80 (1H, s), 10.58 (1H, s).

LRMS (thermospray) m/z=621 (MNH$_4^+$)

| Found: | C, 69.17; | H, 7.55; | N, 6.87; |
|---|---|---|---|
| C$_{35}$H$_{45}$N$_3$O$_6$.0.2H$_2$O requires | C, 69.22; | H, 7.53; | N, 6.92% |

Example 31

(N4,3S)-Dihydroxy-N1-[(1S)-2,2-dimethyl-1-({[(1S)-2phenylethyl]amino}carbonyl)propyl]-(2R)-2{3-[3'-methoxy-2methylbiphen-4-yl)propyl]}butanediamide.

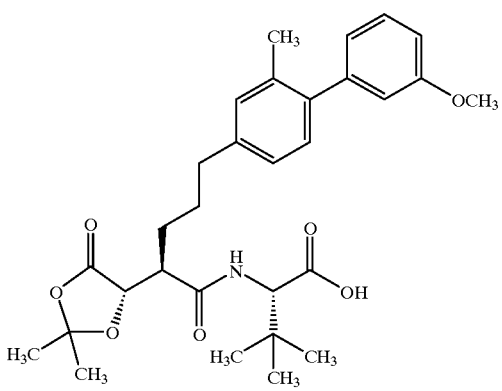

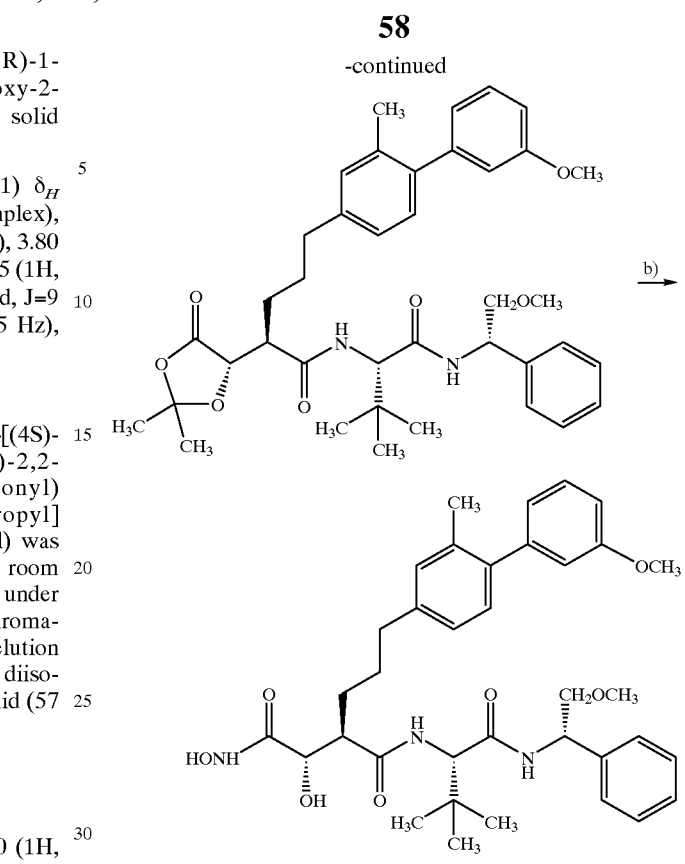

a) According to the method of Example 25(a), (2R)-N-[(1S)1-(carboxy)-2,2-dimethylpropyl]-2-[(4S)-2,2-dimethyl-5-oxo-1,3-dioxolan-4-yl]-5-[(3'-methoxy-2-methylbiphen-4-yl)propyl]pentanamide (Preparation 34) (220 mg, 0.42 mmol) was reacted with (1S)-2-methoxy-1-phenylethylamine (63 mg, 0.42 mmol) at room temperature for 2.5 h. The mixture was poured into ethyl acetate (75 mL) and washed with 0.5M aqueous sodium dihydrogenphosphate (2×50 mL) and 5% aqueous sodium bicarbonate (50 mL)(solid sodium chloride was added to give phase separation). The organic solution was dried (Na$_2$SO$_4$) and concentrated under reduced pressure. The residue was purified by flash chromatography (gradient elution with hexane:ethyl acetate=30:70 to 60:40) to give a white solid which was purified again by flash chromatography (sorbsil C$_{60}$, (20–40$\mu$) silica gel, eluting with hexane:ethyl acetate 35:65) to give (2R)-2-[(4S)-2,2-dimethyl-5-oxo-1,3-dioxolan-4-yl]-N-[(1S)-2,2-dimethyl-1-({[(1S)-2-methoxy-1-phenylethyl]amino}carbonyl)propyl]-5-[(3'-methoxy-2-methylbiphen-4-yl)propyl]pentanamide as a white solid (191 mg, 69%).

$R_f$ 0.37 (hexane:ethyl acetate=1:1)

$\delta_H$ (400 MHz, CDCl$_3$) 1.00 (9H, s), 1.50 (3H, s), 1.55 (3H, s), 1.65 (2H, m), 1.86 (2H, m), 2.20 (3H, s), 2.60 (3H, m), 3.35 (3H, s), 3.60 (2H, d, J=5 Hz), 3.80 (3H, s), 4.25 (1H, d, J=9 Hz), 4.45 (1H, d, J=6 Hz), 5.10 (1H, dt, J=5 and 7.5 Hz), 6.35 (1H, d, J=7.5 Hz), 6.50 (1H, d, J=9 Hz), 6.80–6.92 (3H, m), 6.96–7.04 (2H, m), 7.10 (1H, d, J=8 Hz), 7.15–7.35 (6H, complex).

LRMS (thermospray) m/z=659 (MH$^+$).

b) According to the method of Example 19, (2R)-2-[(4S)-2,2-dimethyl-5-oxo-1,3-dioxolan-4-yl]-N-[(1S)-2,2-dimethyl-1-({[(1S)-2-methoxy-1-phenylethyl]amino}carbonyl)propyl]-5-[(3'-methoxy-2-methylbiphen-4- yl)propyl]pentanamide (from a), above) (191 mg, 0.29 mmol) was reacted with hydroxylamine at room temperature for 17 h. The solution was concentrated under reduced pressure, the residue purified by column chromatography ($C_{18}$ silanised silica gel (40–63$\mu$) gradient elution with methanol:water=60:40 to 70:30) and then triturated with diisopropyl ether to give the title compound as a white solid (81 mg, 44%).

m.p. 82–89° C.

$R_f$ 0.40 (dichloromethane:methanol=90:10)

$\delta_H$ (400 MHz, DMSO-$d_6$) 0.90 (9H, s), 1.20 (1H, m), 1.40 (3H, m), 2.15 (3H, s), 2.38 (1H, m), 2.45 (1H, m), 2.70 (1H, m), 3.20 (3H, s), 3.44 (2H, d, J=7 Hz), 3.76 (4H, m), 4.38 (1H, d, J=9.5 Hz), 5.00 (1H, q, J=7 Hz), 5.21 (1H, d, J=7.5 Hz), 6.78 (1H, s), 6.80 (1H, d, J=8 Hz), 6.88 (2H, m), 7.00 (2H, m), 7.14 (3H, m), 7.24 (2H, m), 7.32 (1H, t), 7.58 (1H, d, J=9.5 Hz), 8.32 (1H, d, J=7 Hz), 8.80 (1H, br s), 10.58 (1H, br s).

LRMS (thermospray) m/z=634 (MH$^+$)

| Found: | C, 67.47; | H, 7.52; | N, 6.55; |
|---|---|---|---|
| $C_{36}H_{47}N_3O_7$·0.4H$_2$O requires | C, 67.46; | H, 7.52; | N, 6.56% |

Example 32

(2R)-N1-[(1S)-2,2-Dimethyl-1-({[(1S)-2methoxy-1-phenylethyl]amino}carbonyl)propyl]-(N4-hydroxy)-2{3-[3'-methoxy-2methylbiphen-4-yl]propyl}butanediamide

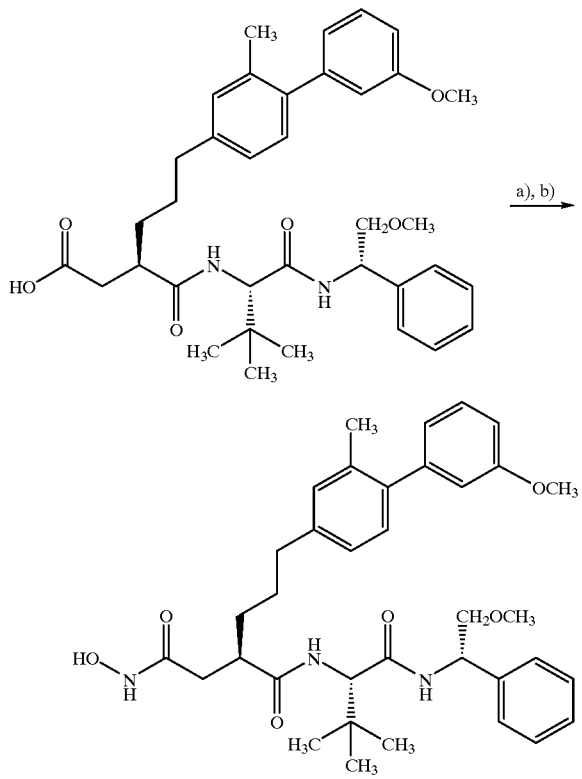

a) According to the method of Example 2, (3R)-3-({[(1S)-2,2-dimethyl-1-({[(1S)-2-methoxy-phenylethyl] amino}carbonyl)propyl]amino}carbonyl)-6-[3'-methoxy-2-methylbiphen-4-yl]hexanoic acid (Example 15) (603 mg, 1.0 mmol) was reacted with O-allylhydroxylamine hydrochloride (134 mg, 1.2 mmol). Purification of the crude product by flash chromatography (gradient elution with hexane:ethyl acetate=1:1 to 1:2) followed by repeated by flash chromatography (elution with dichloromethane:methanol:conc. aq. ammonia 95:5:0.5) gave (2R)-N1-[(1S)-2,2-dimethyl-1-({[(1S)-2-methoxy-1-phenylethyl]amino}carbonyl)propyl]-2-{3-[3'-methoxy-2-methylbiphen-4-yl]propyl}-(N4-3-propenyloxy)butanediamide (397 mg, 60%) as a colourless foam. M.p. 76–79° C.

$R_f$ 0.35 (hexane:ethyl acetate=1:2).

$\delta_H$ (300 MHz, DMSO-$d_6$) 0.92 (9H, s), 1.42 (4H, m), 2.01 (1H, dd, J=7 and 15 Hz), 2.15 (3H, s and 1H, m, overlapping), 2.44 (1H, m), 2.55 (1H, m), 2.84 (1H, m), 3.20 (3H, s), 3.47 (2H, d, J=8 Hz), 3.77 (3H, s), 4.20 (2H, m), 4.35 (1H, d, J=10 Hz), 5.02 (1H, q, J=7 Hz), 5.19 (1H, d, J=10 Hz), 5.40 (1H, d, J=17 Hz), 5.87 (1H, m), 6.78 (1H, s), 6.84(1H, d, J=8 Hz), 6.90 (2H, m), 7.00 (2H, m), 7.23 (6H, m), 7.70 (1H, br d, J=10), 8.32 (1H, br d, J=7 Hz), 10.85 (1H, br s).

LRMS (thermospray) m/z=658 (base peak, MH$^+$), 680 (MNa$^+$).

$\nu_{max.}$ (KBr disc) 3310, 2970, 2930, 1640, 1537, 1481, 700 cm$^{-1}$.

| Found: | C, 70.89; | H, 7.85; | N, 6.27; |
|---|---|---|---|
| $C_{39}H_{51}N_3O_6$ requires | C, 71.21; | H, 7.81; | N, 6.39% | b) According to the method of Example 2, (2R)-N1-[(1S)-2,2-dimethyl-1-({[(1S)-2-methoxy-1-phenylethyl]amino}carbonyl)propyl]-2-{3-[3'-methoxy-2-methylbiphen- 4-yl]propyl}-(N4-3-propenyloxy)butanediamide (380 mg, 0.58 mmol) was reacted with ammonium formate (366 mg, 5.80 mmol) in ethanol/water (4:1, 10 mL) under palladium catalysis at reflux for 1 h. After work-up, the residue was purified by reverse-phase flash chromatography ($C_{18}$ silanised silica gel 40–63$\mu$, elution with methanol:water=4:1) to give (2R)-N1-[(1S)-2,2-dimethyl-1-({[(1S)-2-methoxy-1-phenylethyl]amino}carbonyl)propyl]-(N4-hydroxy)-2-{3-[3'-methoxy-2-methylbiphen-4-yl]propyl}butanediamide (260 mg, 73% as a colourless solid.

m.p. 166–168° C.

$R_f$ 0.29 (reverse-phase tlc, methanol:water=4:1)

$\delta_H$ (300 MHz, methanol-$d_4$) 1.03 (9H, s), 1.51 (4H, m), 2.16 (3H, s, and 1H, m, overlapping), 2.35 (1H, dd, J=8 and 13 Hz), 2.48 (2H, m), 2.87 (1H, m), 3.33 (3H, s), 3.58 (2H, d, J=7 Hz), 4.40 (1H, s,), 5.10 (1H, t, J=7 Hz), 6.92 (1H, s), 6.80 (1H, d, J=8 Hz), 6.89 (2H, br d, J=8 Hz), 6.97 (1H, s), 6.98 (1H, d, J=8 Hz), 7.15 (3H, m), 7.27 (3H, m).

LRMS (thermospray) m/z=618 (MH$^+$)

$\nu_{max.}$ (KBr disc) 3290, 3240, 2960, 2930, 1644, 1531, 1481, 1226, 703 cm$^{-1}$.

| Found: | C, 69.06; | H, 7.80; | N, 6.65; |
|---|---|---|---|
| $C_{36}H_{47}N_3O_6$·0.5H$_2$O requires | C, 68.99; | H, 7.72; | N, 6.70% |

Preparation 1

(2S)-Amino-3,3-dimethyl-N-[(1R)-1-phenylethyl]butanamide,hydrochloride.

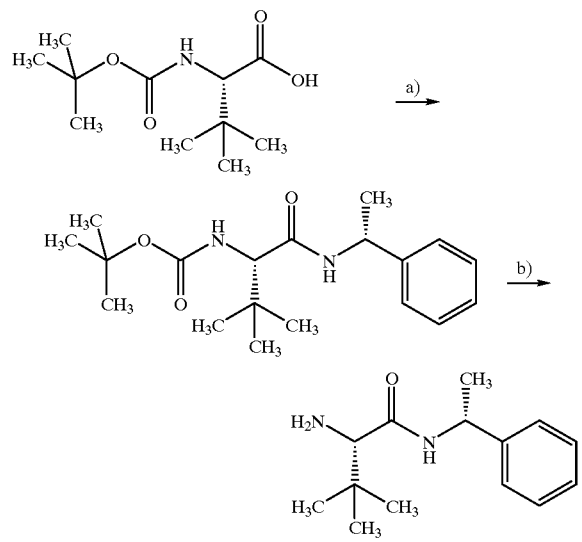

a) N-(Dimethylaminopropyl)-N'-ethylcarbodiimide hydrochloride (35.47 g, 185 mmol) was added to a stirred mixture of tert-butyl N-[(1S)-2,2-dimethyl-1-carboxy) propyl]carbamate (34.7 g, 150 mmol)(Fluka Chemicals; J. Pospisek, K. Blaha, Coll. Czech. Chem. Commun., 1977, 42, 1069–76) and 1-hydroxy-1,2,3-benzotriazole hydrate (22.3 g, 165 mmol) in anhydrous dichloromethane (350 mL) under nitrogen at 4° C. After 1 h, (R)-(1-phenyl)ethylamine (19.14 g, 158 mmol) was added, followed by N-methylmorpholine (16.7g, 165 mmol). After another 30 min, the mixture was allowed to warm to room temperature. After 17 h at room temperature, the mixture was concentrated under reduced pressure, and partitioned between ethyl acetate (400 mL) and water (400 mL). The organic layer was washed sequentially with 5% aqueous citric acid (2×400 mL) and saturated aqueous sodium bicarbonate (500 mL), dried (MgSO$_4$), and concentrated under reduced pressure. The residue was triturated with diisopropyl ether, filtered and dried to give (2S)-tert-(butoxycarbonyl)amino-3,3-dimethyl-N-[(1R)-1-phenylethyl]butanamide (47.5 g, 94%), as a colourless solid.

m.p. 166–169° C.

R$_f$ 0.7 (hexane:ether:acetic acid=30:70:1)

δ$_H$ (400 MHz, CDCl$_3$) 0.97 (9H, s), 1.39 (9H, s), 1.45 (3H, d, J=7 Hz), 3.73 (1H, br d), 5.04 (1H, pentet, J=7 Hz), 5.15 (1H, br s), 5.84 (1H, br d), 7.26 (5H, complex).

LRMS (thermospray) m/z=335 (MH$^+$)

FTIR ν$_{max.}$ (KBr disc) 3340, 3280, 2980, 1713, 1696, 1642, 1179, 700 cm$^{-1}$

| Found: | C, 68.30; | H, 9.08; | N, 8.39; |
|---|---|---|---|
| C$_{19}$H$_{30}$N$_2$O$_3$ requires | C, 68.23; | H, 9.04; | N, 8.38% | b) (2S)-tert-(Butoxycarbonyl)amino-3,3-dimethyl-N-[(1R)-1-phenylethyl]butanamide (46.4 g, 139 mmol) was dissolved in a mixture of anhydrous dichloromethane (600 mL) and dioxane (150 mL) and cooled to 4° C. Hydrogen chloride was bubbled through the solution with stirring until a saturated solution was formed. After being stirred for 4 h at 4° C., the solution was concentrated under reduced pressure. The residue was triturated with ether and filtered to give the title compound (38.0 g, 100%).

R$_f$ 0.46 (hexane/isopropanol/conc. aq. ammonia=80:20:1)

δ$_H$ (400 MHz, d$_6$-DMSO) 1.03 (9H, s), 1.37 (3H, d, J=7 Hz), 3.50 (1H, d, J=8 Hz), 4.94 (1H, pentet, J=7 Hz), 7.24 (1H, t, J=8 Hz), 7.33 (2H, t, J=8 Hz), 7.39 (2H, d, J=8 Hz), 8.10 (3H, br s), 8.88 (1H, br d).

LRMS (thermospray) m/z=235 (MH$^+$)

FTIR ν$_{max.}$ (KBr disc) 2960, 1674, 1557, 1505, 700 cm$^{-1}$

| Found: | C, 61.98; | H, 8.71; | N, 10.09; |
|---|---|---|---|
| C$_{14}$H$_{22}$N$_2$O.HCl.H$_2$O requires | C, 62.09; | H, 8.56; | N, 10.34% |

Preparation 1a (2S)-Amino-3,3-dimethyl-N-[(1S)-2methoxy-1-phenylethyl]butanamide,hydrochloride.

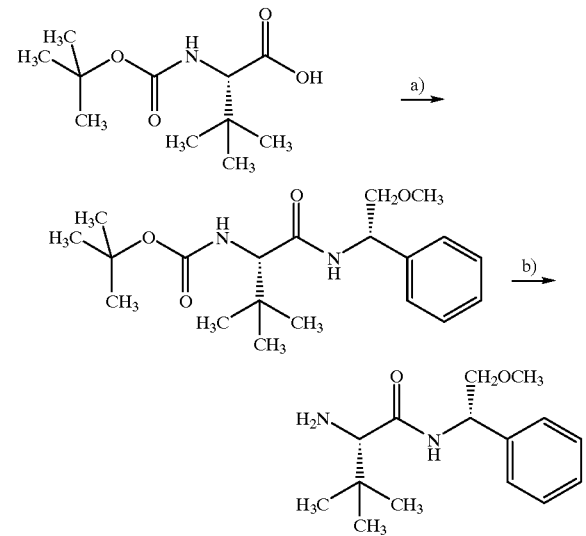

a) By the method of Preparation 1, tert-butyl N-[(1S)-2,2-dimethyl-1-(carboxy)propyl]carbamate (27.79 g, 120 mmol) was reacted with (S)-(2-methoxy-1-phenyl) ethylamine (19.12 g, 126.6 mmol). The crude product was recrystallised from hot ethyl acetate/hexane to give (2S)-tert-(butoxycarbonyl)amino-3,3-dimethyl-N-[(1S)-2-methoxy-1-phenylethyl]butanamide (20.02 g, 46%), as a colourless solid. The mother liquors were concentrated under reduced pressure and the residue triturated with ether, filtered and dried to afford an additional 15.44 g (35%) of product.

m.p. 135–137° C.

R$_f$ 0.64 (hexane:ethyl acetate=2:1)

δ$_H$ (300 MHz, CDCl$_3$) 1.02 (9H, s), 1.42 (9H, s), 3.34 (3H, s), 3.63 (2H, d, J=7 Hz), 3.86 (1H, br d, J=12 Hz), 5.14 (1H, dt, J=7 and 10 Hz), 5.21 (1H, br d, J=12 Hz), 6.34 (1H, br d, J=10 Hz), 7.30 (5H, complex).

LRMS (thermospray) m/z=365 (MH$^+$)

FTIR ν$_{max.}$ (KBr disc) 3290, 2970, 1713, 1694, 1643, 1364, 1173, 700 cm$^{-1}$

| Found: | C, 65.84; | H, 8.81; | N, 7.64; |
| --- | --- | --- | --- |
| $C_{20}H_{32}N_2O_4$ requires | C, 65.91; | H, 8.85; | N, 7.69% | b) By the method of Preparation 1, (2S)-tert-(butoxycarbonyl)amino-3,3-dimethyl-N-[(1S)-2-methoxy-1-phenylethyl]butanamide (35.0 g, 96 mmol) was treated with hydrogen chloride in a mixture of dichloromethane and dioxane (100 min at 4° C., 40 min at 20° C.). The solution was concentrated under reduced pressure. The residue was treated with ether and the solvent evaporated several times to give the title compound (36.27 g, 97%), as a slightly hygroscopic colourless solid, m.p. 197–199° C.

$R_f$ 0.45 (hexane/isopropanol/conc. aq. ammonia=80:20:1)

$\delta_H$ (300 MHz, $d_6$-DMSO) 1.03 (9H, s), 3.24 (3H, s), 3.52 (2H, m), 3.61 (1H, d, J=9 Hz), 5.12 (1H, m), 7.28 (1H, d, J=7 Hz), 7.33 (2H, t, J=7 Hz), 7.41 (2H, d, J=7 Hz), 8.06 (3H, br s), 8.87 (1H, br d, J=9 Hz).

LRMS (thermospray) m/z=265 ($MH^+$)

FTIR $\nu_{max}$ (KBr disc) 3250, 3060, 2960, 1683, 1559, 1504, 1121, 1086, 871, 700 $cm^{-1}$

| Found: | C, 58.11; | H, 8.57; | N, 7.38; |
| --- | --- | --- | --- |
| $C_{15}H_{24}N_2O_2 \cdot HCl \cdot 6/7 dioxane \cdot \frac{1}{4}H_2O$ requires | C, 62.09; | H, 8.56; | N, 10.34% |

Preparation 2 tert-Butyl(3R)-3-({[(1S)-2,2-dimethyl-1-({[(1R)-1-phenylethyl]amino}carbonyl)propyl]amino}carbonyl)hex-5-enoate

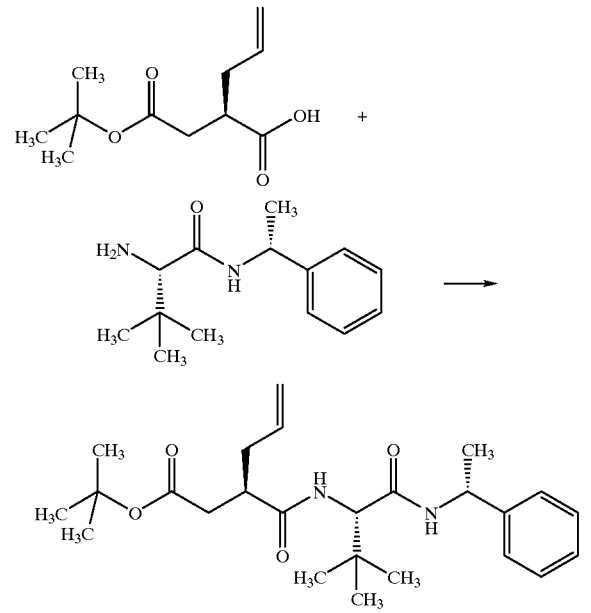

N-(Dimethylaminopropyl)-N'-ethylcarbodiimide (4.21 g, 22.0 mmol) was added to a stirred mixture of (2R)-2-[2-(tert-butoxy)-2-oxoethyl]pent-4-enoic acid (A. L. Castelhano, S. L. Bender, J. G. Deal, S. Homer, T. J. Liak, Z. Yuan, World Patent WO96/16027 (1996)) (3.80 g, 17.8 mmol) and 1-hydroxy-7-azabenzotriazole (2.49 g, 18.3 mmol) in anhydrous dimethylformamide (60 mL) under nitrogen at 4° C. After 1 h, (2S)-amino-3,3-dimethyl-N-[(1R)-1-phenylethyl]butanamide hydrochloride (Preparation 1)(5.10 g, 18.8 mmol) was added, followed by diisopropylethylamine (2.42 g, 19.2 mmol). After another 30 min, the mixture was allowed to warm to room temperature. After 17 h at room temperature, the mixture was concentrated under reduced pressure, and partitioned between ethyl acetate (400 mL) and water (400 mL). The aqueous layer was saturated with sodium bicarbonate and extracted with ethyl acetate (2×100 mL). The combined organic solutions were concentrated under reduced pressure, the residue was dissolved in ether (500 mL) and washed with water (3×200 mL), dried ($MgSO_4$), and concentrated under reduced pressure. The residue was triturated with pentane, filtered and dried to give tert-butyl (3R)-3-({[(1S)-2,2-dimethyl-1-({[(1R)-1-phenylethyl]amino}carbonyl)propyl]amino}carbonyl)hex-5-enoate (6.70 g, 88%), as a colourless solid.

m.p. 123–126° C.

$R_f$ 0.16 (hexane:isopropanol=98:2)

$\delta_H$ (400 MHz, $CDCl_3$) 0.97 (9H, s), 1.39 (9H, s), 1.46 (3H, d, J=7 Hz), 2.06 (1H, dt, 13 and 6.5 Hz), 2.09 (1H, m), 2.31 (1H, dd, J=15 and 3 Hz), 2.71 (1H, m), 2.77 (1H, m), 4.14 (1H, d, J=10 Hz), 4.90 (1H, d, J=10Hz), 4.94 (1H, d, J=15 Hz), 5.05 (1H, pentet, J=7 Hz), 5.42 (1H, m), 5.95 (1H, br d), 6.36 (1H, br d), 7.26 (5H, complex).

LRMS (thermospray) m/z=431 ($MH^+$)

FTIR $\nu_{max}$ (KBr disc) 2635, 2098, 1733, 1640, 1540, 1363, 1153, 696 $cm^{-1}$

| Found: | C, 69.30; | H, 8.96; | N, 6.54; |
| --- | --- | --- | --- |
| $C_{25}H_{38}N_2O_4$ requires | C, 69.74; | H, 8.90; | N, 6.51% |

Preparation 3 tert-Butyl(3R)-3-({[(1S)-2,2-dimethyl-1-({[(1R)-1-phenylethyl]amino}carbonyl)propyl]amino}carbonyl)-6-[3-methyl-(4-phenyl) phenyl]-hexanoate

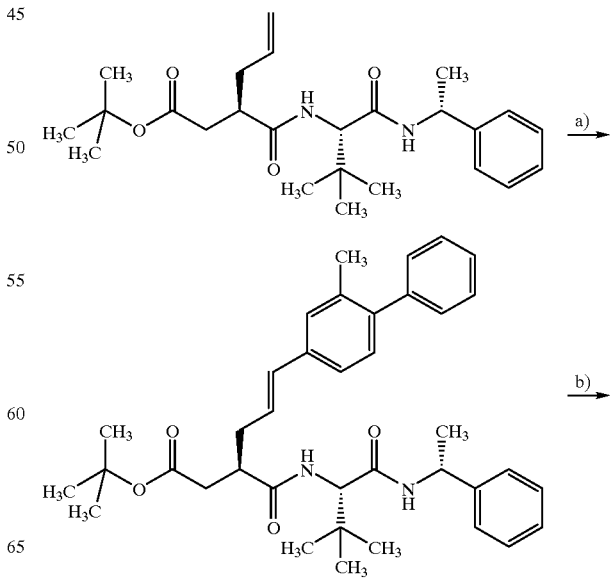

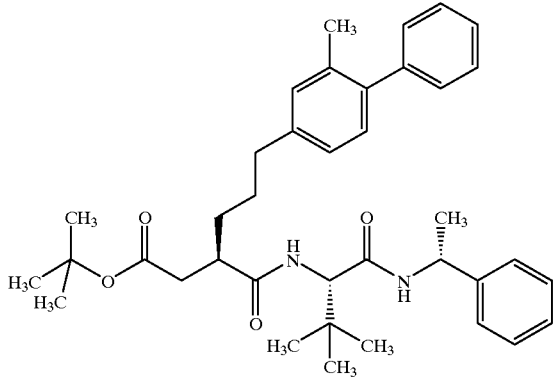

a) A mixture of palladium acetate (52 mg, 0.23 mmol) and tri-(2-methylphenyl)phosphine (141 mg, 0.46 mmol) in anhydrous acetonitrile (10 mL) was sonicated at room temperature for 1 min until a creamy-coloured suspension formed. This suspension was added via Pasteur pipette to a stirred solution of tert-butyl (3R)-3-({[(1S)-2,2-dimethyl-1-({[(1R)-1-phenylethyl]amino}carbonyl)propyl]amino}carbonyl)hex-5-enoate (Preparation 2)(861 mg, 2.0 mmol), 3-methyl-4-phenylbromobenzene (M. Gomberg, J. C. Pernert, J. Amer. Chem. Soc., 1926, 48, 1372–84, and see also Preparation 19B)(1.32 gm, 5.34 mmol), and triethylamine (1.28 mL, 9.29 mmol) in anhydrous acetonitrile (15 mL) under nitrogen. The mixture was purged with nitrogen, then heated at reflux for 24 h. The mixture was poured into ethyl acetate (200 mL) and washed with saturated aqueous sodium chloride (2×100 mL), dried (Na$_2$SO$_4$), and concentrated under reduced pressure. The residue was purified by flash chromatography (gradient elution with dichloromethane:ethyl acetate) to give mainly tert-butyl (3R,5E)-3-({[(1S)-2,2-dimethyl-1-({[(1R)-1-phenylethyl]amino}carbonyl)propyl]amino}carbonyl)-6-[3-methyl-(4-phenyl)phenyl]hex-5-enoate as a colourless foam (1.91 gm, 69%). $^1$H NMR suggests that two alkene isomers, the (5Z) and (4E) were also present. The mixture of alkenes was taken onto the next step (see b, below).

R$_f$ 0.52 (dichloromethane:ethyl acetate=9:1)

δ$_H$ (400 MHz, CDCl$_3$)(for the (5E) isomer). 1.00 (9H, s), 1.39 (9H, s), 1.47 (3H, d, J=7 Hz), 2.26 (1H, m), 2.40 (2H, m), 2.60 (1H, dd, J=9 and 15 Hz), 2.71 (1H, m), 4.20 (1H, d, J=9 Hz), 5.02 (1H, pentet, J=7 Hz), 6.04 (2H, m), 6.35 (1H, d, J=14 Hz), 6.51 (1H, br d), 7.19 (11H, complex), 7.36 (2H, t, J=8 Hz).

b) A solution of tert-butyl (3R,5E)-3-({[(1S)-2,2-dimethyl-1-({[(1R)-1-phenylethyl]amino}carbonyl)propyl]amino}carbonyl)-6-[3-methyl-(4-phenyl)phenyl]hex-5-enoate (1.91 gm, 3.2 mmol) in ethanol (80 mL) was hydrogenated over 10% palladium on charcoal (120 mg) at 3 bar and 20° C. for 16 h. The mixture was filtered through Arbocel filter aid and concentrated under reduced pressure to give tert-butyl (3R)-3-({[(1S)-2,2-dimethyl-1-({[(1R)-1-phenylethyl]amino}carbonyl)propyl]amino}carbonyl)-6-[3-methyl-(4-phenyl)phenyl]hexanoate (2.07 gm, 108%), as a colourless foam, which was taken onto the next step without purification (see Example 1).

R$_f$ 0.52 (dichloromethane:ethyl acetate=9:1)

δ$_H$ (400 MHz, CDCl$_3$) 0.99 (9H, s), 1.38 (9H, s), 1.47 (3H, d, J=7 Hz), 1.52 (4H, complex), 2.20 (3H, s), 2.29 (1H, m), 2.53 (4H, m), 4.16 (1H, d, J=9 Hz), 5.05 (1H, pentet, J=7 Hz), 5.97 (1H, br d), 6.42 (1H, br d), 6.93 (1H, d, J=8 Hz), 6.98 (1H, s), 7.07 (1H, d, J=8 Hz), 7.23 (8H, complex), 7.36 (2H, t, J=7 Hz).

LRMS (thermospray) m/z=599 (MH$^+$)

| Found: | C, 75.86; | H, 8.44; | N, 4.60; |
| C$_{38}$H$_{50}$N$_2$O$_4$ requires | C, 76.22; | H, 8.42; | N, 4.68% |

Example 33

Preparation 4

(3R)-6-[(3-Chloro-4-phenyl)phenyl]-3-({[(1S)-2,2-dimethyl-1-({[(1R)-1-phenylethyl]amino}carbonyl)propyl]amino}carbonyl)hexanoic acid

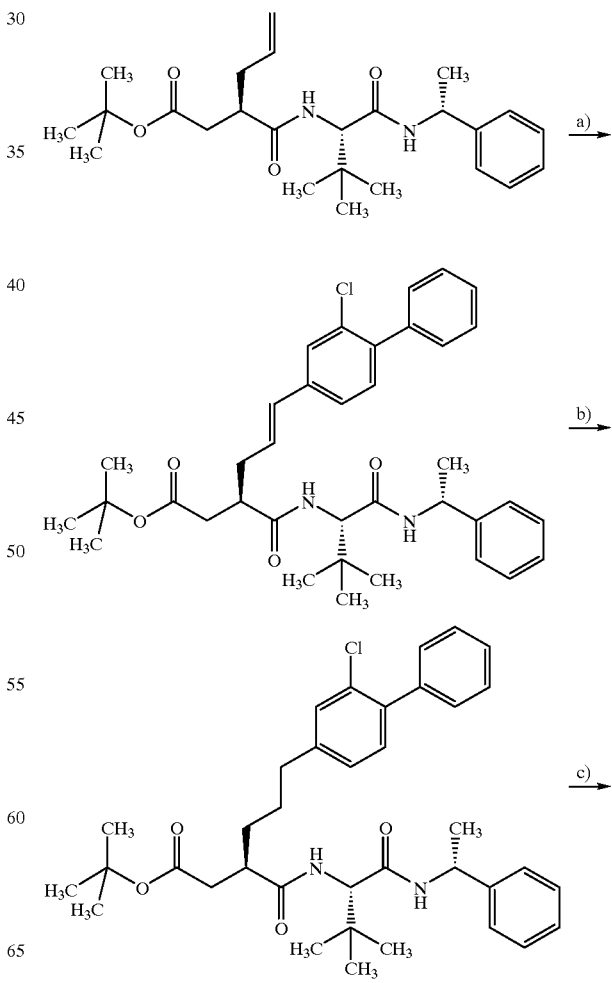

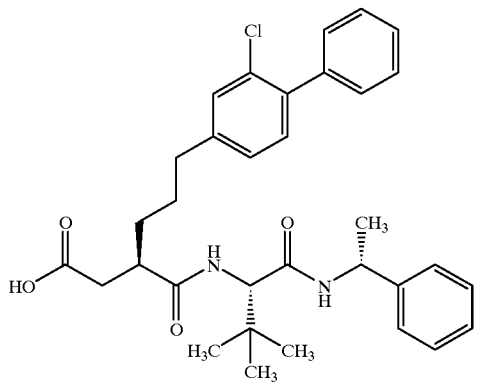

a) A mixture of palladium acetate (24 mg, 0.1 mmol) and tri-(2-methylphenyl)phosphine (61 mg, 0.2 mmol) in anhydrous acetonitrile (1 mL) was sonicated at room temperature for 1 min until a creamy-coloured suspension formed. This suspension was added via Pasteur pipette to a stirred solution of tert-butyl (3R)-3-({[(1S)-2,2-dimethyl-1-({[(1R)-1-phenylethyl]amino}carbonyl)propyl]amino}carbonyl)hex-5-enoate (Preparation 2)(861 mg, 2.0 mmol), (3-chloro-4-phenyl)phenyl trifluoromethanesulphonate (Preparation 9)(740 mg, 2.2 mmol), and triethylamine (420 μL, 3.0 mmol) in anhydrous acetonitrile (3 mL) under nitrogen. The mixture was purged with nitrogen, then heated at reflux for 22 h. Further quantities of reagents and catalyst were then added as follows: (3-chloro-4-phenyl)phenyl trifluoromethanesulphonate (200 mg, 0.59 mmol), triethylamnine (420 μL, 3.0 mmol), palladium acetate (35 mg, 0.145 mmol) and tri-(2-methylphenyl)phosphine (89 mg, 0.29 mmol), and heating was continued for a further 8 h. The mixture was poured into ethyl acetate (100 mL) and washed with saturated aqueous sodium chloride (2×50 mL), dried (MgSO$_4$), and concentrated under reduced pressure. The residue was purified by flash chromatography (eluting with toluene:ethyl acetate=9:1) to give mainly tert-butyl (3R,5E)-6-[3-chloro-(4-phenyl)phenyl]-3-({[(1S)-2,2-dimethyl-1-({[(1R)-1-phenylethyl]amino}carbonyl)propyl]amino}carbonyl)hex-5-enoate as a colourless foam (936 mg, 76%). $^1$H nmr suggested that two alkene isomers, the (5Z) and (4E) were also present. The mixture of alkenes was taken onto the next step (see b, below).

R$_f$ 0.14 (toluene:ethyl acetate=10:1)

δ$_H$ (400 MHz, CDCl$_3$)(for the (5E) isomer). 0.96 (9H, s), 1.37 (9H, s), 1.45 (3H, d, J=6.5 Hz), 2.29 (1H, m), 2.36 (1H, dd, J=3 and 15 Hz), 2.45 (1H, m), 2.61 (1H, dd, J=9 and 15 Hz), 2.73 (1H, m), 4.16 (1H, d, J=9.5 Hz), 5.02 (1H, pentet, J=6.5 Hz), 5.85 (1H, br d), 6.09 (1H, dt, J=6.5 and 15 Hz), 6.32 (1H, d, J=15 Hz), 6.49 (1H, br d), 7.18 (8H, complex), 7.37 (SH, complex).

LRMS (thermospray) m/z=617 (MH$^+$)

b) A mixture of tert-butyl (3R,5E)-6-[3-chloro-(4-phenyl)phenyl]-3-({[(1S)-2,2-dimethyl-1-({[(1R)-1-phenylethyl]amino}carbonyl)propyl]amino}carbonyl)hex-5-enoate (936 mg, 1.52 mmol) and p-toluenesulphonyl hydrazide (1.41 gm, 7.60 mmol) in toluene (15 mL) was stirred under nitrogen at reflux for 4 h. After being cooled, the mixture was diluted with ether (150 mL), and washed with water (50 mL), 0.5M hydrochloric acid (50 mL) and saturated aqueous sodium chloride (50 mL), dried (MgSO$_4$), and concentrated under reduced pressure. The residue was purified by flash chromatography (gradient elution with hexane/ethyl acetate) to give tert-butyl (3R)-6-[3-chloro-(4-phenyl)phenyl]-3-({[(1S)-2,2-dimethyl-1-({[(1R)-1-phenylethyl]amino}carbonyl)propyl]amino}carbonyl)hexanoate (701 mg, 74%), as a colourless foam.

R$_f$ 0.36 (hexane:ethyl acetate=5:1)

δ$_H$ (400 MHz, CDCl$_3$) 1.03 (9H, s), 1.43 (9H, s), 1.52 (3H, d, J=7 Hz), 1.43–1.70 (4H, complex), 2.32 (1H, m), 2.60 (4H, m), 4.18 (1H, d, J=9 Hz), 5.09 (1H, pentet, J=7 Hz), 5.95 (1H, br d), 6.47 (1H, br d), 7.03 (1H, d, J=8 Hz), 7.23 (7H, complex), 7.42 (5H, complex).

LRMS (thermospray) m/z=620 (MH$^+$)

c) tert-Butyl (3R)-6-[3-chloro-(4-phenyl)phenyl]-3-({[(1S)-2,2-dimethyl-1-({[(1R)-1-phenylethyl]amino}carbonyl)propyl]amino}carbonyl)hexanoate (665 mg, 1.07 mmol) was dissolved in anhydrous dioxane (30 mL) and cooled in an ice-water bath under nitrogen. Hydrogen chloride gas was bubbled through the stirred solution for 15 min until the solution was saturated. The solution wa stirred for 3 h, and then concentrated under reduced pressure. The residue was dissolved in toluene and concentrated under reduced pressure three times to give a colourless gum which crystallised upon addition of hexane and ethyl acetate. The white solid was recrystallised from ethyl acetate/diisopropyl ether to give the title compound (325 mg, 54%).

m.p. 154–155.5° C. (from ethyl acetate/diisopropyl ether).

R$_f$ 0.38 (ether:hexane:acetic acid=70:30:1)

δ$_H$ (400 MHz, CD$_3$OD) (only partial exchange of amide NH signals was evident) 1.03 (9H, s), 1.43 (3H, d, J=6.5 Hz), 1.48 (2H, m,), 1.52 (2H, m), 2.39 (1H, dd, J=3 and 14 Hz), 2.53 (2H, m), 2.61 (1H, dd, J=9 and 14 Hz), 2.86 (1H, m), 4.36 (1H, s), 5.00 (1H, pentet, J=6.5 Hz), 7.03 (1H, d, J=9 Hz), 7.17 (7H, complex), 7.36 (5H, complex), 7.76 (0.5H, br d) 8.47 (0.8H, br d).

LRMS (thermospray) m/z=562 (MH$^+$)

| Found: | C, 70.29; | H, 6.98; | N, 4.91; |
|---|---|---|---|
| C$_{33}$H$_{39}$ClN$_2$O$_4$ requires | C, 70.38; | H, 6.98; | N, 4.97% |

Example 34

(3R)-3-({[(1S)-2,2-Dimethyl-1-({[(1R)-1-phenylethyl]amino}carbonyl)propyl]amino}carbonyl)-6-(3-fluoro-4-phenoxyphenyl)hexanoic acid.

Preparation 5

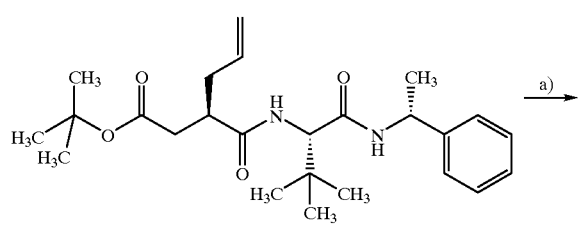

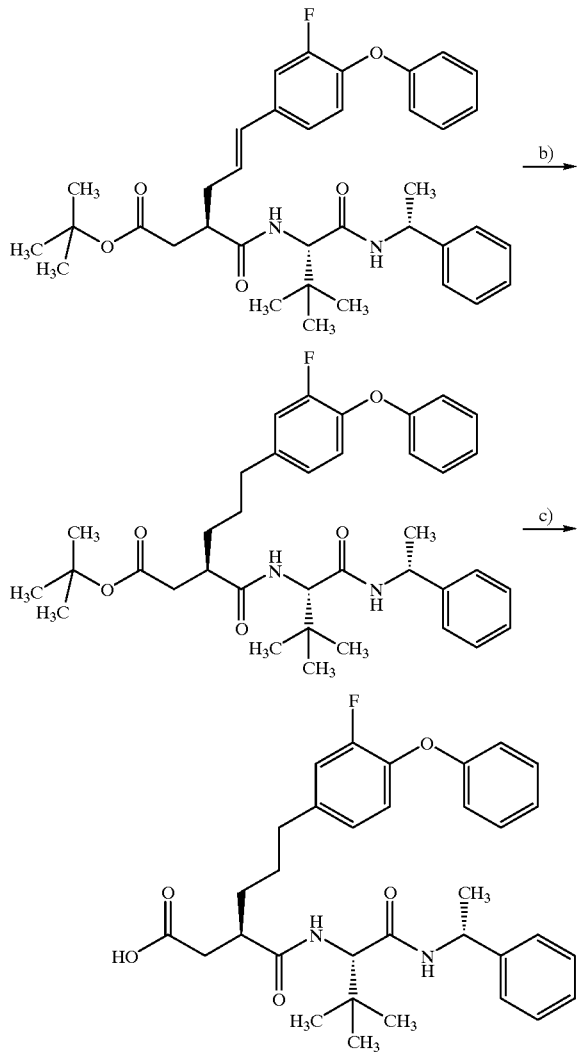

R$_f$ 0.24 (hexane:ethyl acetate=3:1)

δ$_H$ (300 MHz, CDCl$_3$)(for the (5E) isomer) 1.02 (9H, s), 1.40 (9H, s), 1.50 (3H, d, J=6 Hz), 2.26 (1H, m), 2.40 (2H, m), 2.64 (1H, dd, J=9 and 17 Hz), 2.74 (1H, m), 4.23 (1H, d, J=10 Hz), 5.06 (1H, pentet, J=6 Hz), 5.98 (1H, m), 6.02 (1H, br d), 6.30 (1H, d, J=15 Hz), 6.50 (1H, br d), 6.94 (3H, m), 7.07 (2H, complex), 7.27 (8H, complex).

LRMS (thermospray) m/z=617 (MH$^+$)

b) A solution of tert-butyl (3R)-3-({[(1S)-2,2-dimethyl-1-({[(1R)-1-phenylethyl]amino}carbonyl)propyl]amino}carbonyl)-6-(3-fluoro-4-phenoxyphenyl)hexanoate (949 mg, 1.53 mmol), ammonium formate (474 mg, 7.51 mmol) and 10% palladium on charcoal (100 mg) in methanol (10 mL) was stirred at 20° C. for 16 h. The mixture was filtered through Arbocel filter aid and concentrated under reduced pressure. The residue was dissolved in ethyl acetate and washed with saturated aqueous sodium chloride, dried (MgSO$_4$) and concentrated under reduced pressure to give tert-butyl (3R)-3-({[(1S)-2,2-dimethyl-1-({[(1R)-1-phenylethyl]amino}carbonyl)propyl]amino}carbonyl)-6-(3-fluoro-4-phenoxyphenyl)hexanoate (876 mg, 92%), as a colourless foam, which was taken onto the next step without purification.

R$_f$ 0.29 (hexane:ethyl acetate=3:1)

δ$_H$ (400 MHz, CDCl$_3$) 0.98 (9H, s), 1.26 (1H, m), 1.37 (9H, s), 1.44 (3H, m), 1.46 (3H, d, J=6.5 Hz), 2.23 (1H, m), 2.40 (2H, m), 2.52 (2H, m), 4.32 (1H, d, J=10 Hz), 5.08 (1H, pentet, J=6.5 Hz), 6.48 (1H, br d), 6.58 (1H, br d), 6.74 (1H, d, J=8 Hz), 6.87 (3H, m), 7.01 (1H, t, J=7 Hz), 7.19 (8H, complex).

LRMS (thermospray) m/z=619 (MH$^+$)

c) Trifluoroacetic acid (2 mL) was added dropwise over 5 min to a stirred solution of tert-butyl (3R)-3-({[(1S)-2,2-dimethyl-1-({[(1R)-1-phenylethyl]amino}carbonyl)propyl]amino}carbonyl)-6-(3-fluoro-4-phenoxyphenyl)hexanoate (876 mg, 1.41 mmol) in anhydrous dichloromethane (6 mL) under nitrogen at 20° C. The solution was stirred for 16 h and concentrated under reduced pressure. The residue was dissolved in toluene and concentrated under reduced pressure (twice). Purification by flash chromatography (eluting with hexane:ethyl acetate:acetic acid=75:25:1) gave the title compound as a yellow gum (784 mg, 98%).

R$_f$ 0.21 (hexane:ethyl acetate:acetic acid=75:25:1)

δ$_H$ (400 MHz, CDCl$_3$) 0.96 (9H, s), 1.40 (3H, m), 1.47 (3H, d, J=7 Hz), 1.58 (1H, m,), 2.42 (3H, m), 2.68 (2H, m), 4.32 (1H, d, J=10), 5.04 (1H, pentet, J=7 Hz), 6.35 (1H, br, d), 6.73 (1H, d, J=6 Hz), 6.82 (2H, m), 6.89 (2H, d, J=8 Hz), 7.01 (1H, t, J=6 Hz), 7.11 (1H, d, J=8 Hz), 7.20 (7H, complex).

a) A mixture of palladium acetate (20 mg, 0.08 mmol) and tri-(2-methylphenyl)phosphine (50 mg, 016 mmol) was added to a stirred solution of tert-butyl (3R)-3-({[(1S)-2,2-dimethyl-1-({[(1R)-1-phenylethyl]amino}carbonyl)propyl]amino}carbonyl)hex-5-enoate (Preparation 2)(700 mg, 1.63 mmol), 3-fluoro-4-phenoxy-bromobenzene (Preparation 10) (479 mg, 1.79 mmol), and triethylamine (340 μL, 2.43 mmol) in anhydrous acetonitrile (3 mL) under nitrogen. The mixture was purged with nitrogen, then heated at reflux for 14 h. Additional palladium acetate (20 mg, 0.08 mmol) and tri-(2-methylphenyl)phosphine (50 mg, 016 mmol) was added and the mixture was heated for a further 9 h. After being cooled, the mixture was poured into ethyl acetate (100 mL) and washed with saturated aqueous sodium chloride (2×50 mL), dried (MgSO$_4$), and concentrated under reduced pressure. The residue was purified by flash chromatography (eluting with hexane:ethyl acetate=9:1) to give mainly tert-butyl (3R,5E)-3-({[(1s)-2,2-dimethyl-1-({[(1R)-1-phenylethyl]amino}carbonyl)propyl]amino }carbonyl)-6-(3-fluoro-4-phenoxyphenyl)hex-5-enoate as a colourless oil (949 mg). $^1$H nmr suggested that two alkene isomers, the (5Z) and (4E), together with the alkene starting material (10%) were also present. The mixture of alkenes was taken onto the next step (see b, below).

LRMS (APCI) m/z=563 (MW⁺)

Example 35
Preparation 6

(3R)-3-({[(1S)-2,2-Dimethyl-1-({[(1R)-1-phenylethyl]amino}carbonyl)propyl]amino}carbonyl)-6-(3-methyl-4-phenoxyphenyl)hexanoic acid.

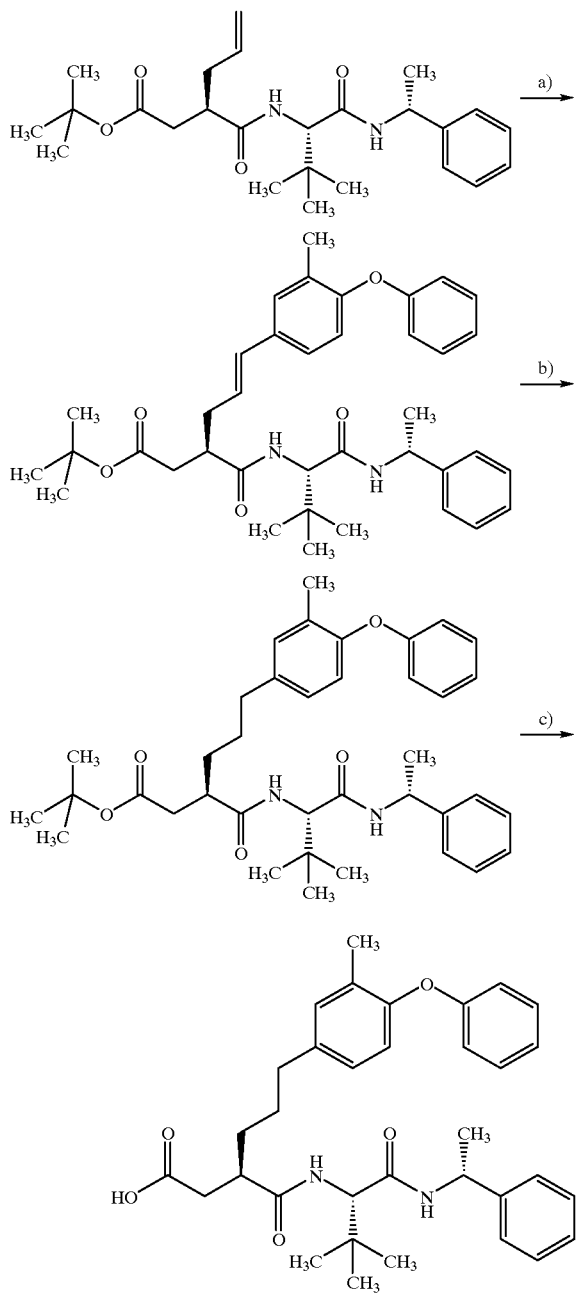

a) A mixture of palladium acetate (20 mg, 0.08 mmol) and tri-(2-methylphenyl)phosphine (50 mg, 0.16 mmol) was added to a stirred solution of tert-butyl (3R)-3-({[(1S)-2,2-dimethyl-1-({[(1R)-1-phenylethyl]amino}carbonyl)propyl]amino}carbonyl)hex-5-enoate (Preparation 2)(578 mg, 1.23 mmol), 1-iodo-3-methyl-4-phenoxybenzene (Preparation 11)(384 mg, 1.35 mmol), and triethylamine (300 µL, 2.14 mmol) in anhydrous acetonitrile (3 mL) under nitrogen. The mixture was purged with nitrogen, then heated at reflux for 24 h. After being cooled, the mixture was poured into ethyl acetate (100 mL) and washed with saturated aqueous sodium chloride (2×50 mL), dried (MgSO₄), and concentrated under reduced pressure. The residue was purified by flash chromatography (eluting with hexane:ethyl acetate=9:1 and then 4:1) to give mainly tert-butyl (3R,5E)-3-({[(1S)-2,2-dimethyl-1-({ [(1R)-1-phenylethyl]amino}carbonyl)propyl]amino}carbonyl)-6-(3-methyl-4-phenoxyphenyl)hex-5-enoate as an orange foam (615 mg). ¹H nmr suggested that two alkene isomers, the (5Z) and (4E), together with the alkene starting material (10%) were also present. The mixture of alkenes was taken onto the next step (see b, below).

R$_f$ 0.5 (hexane:ethyl acetate=3:1)

δ$_H$ (300 MHz, CDCl₃)(for the (5E) isomer) 1.02 (9H, s), 1.26 (9H, s), 1.50 (3H, d, J=7 Hz), 2.19 (3H, s), 2.29 (1H, m), 2.44 (2H, m), 2.63 (1H, m), 2.74 (1H, m), 4.19 (1H, d, J=10 Hz), 5.04 (1H, pentet, J=7 Hz), 5.91 (1H, br d), 6.00 (1H, dt, J=16 and 8 Hz), 6.35 (1H, d, J=16 Hz), 6.51 (1H, br d), 6.80 (1H, d, J=9 Hz), 6.87 (2H, d J=9 Hz), 7.06 (2H, m), 7.26 (8H, complex).

LRMS (thermospray) m/z=613 (MH⁺)

b) A solution of tert-butyl (3R,5E)-3-({[(1s)-2,2-dimethyl-1-({[(1R)-1-phenylethyl]amino}carbonyl)propyl]amino}carbonyl)-6-(3-methyl-4-phenoxyphenyl)hex-5-enoate (615 mg, 1.00 mmol), ammonium formate (310 mg, 4.9 mmol) and 10% palladium on charcoal (65 mg) in methanol (8 mL) was stirred at 20° C. for 16 h. The mixture was filtered through Arbocel filter aid and concentrated under reduced pressure. The residue was dissolved in ethyl acetate and washed with saturated aqueous sodium chloride, dried (MgSO₄) and concentrated under reduced pressure to give tert-butyl (3R)-3-({[(1S)-2,2-dimethyl-1-({[(1R)-1-phenylethyl]amino}carbonyl)propyl]amino}carbonyl)-6-(3-methyl-4 -phenoxyphenyl)hexanoate (550 mg, 90%), as a foam, which was taken onto the next step without purification.

R$_f$ 0.5 (hexane:ethyl acetate=3:1)

δ$_H$ (300 MHz, CDCl₃) 1.03 (9H, s), 1.41 (9H, s), 1.33–1.60 (4H, m, obscured by other peaks), 1.50 (3H, d, J=7 Hz), 2.16 (3H, s), 2.30 (1H, m), 2.48 (2H, m), 2.57 (2H, m), 4.26 (1H, d, J=9 Hz), 5.10 (1H, pentet, J=7 Hz), 6.22 (1H, br d), 6.44 (1H, br d), 6.77 (1H, d, J=9 Hz), 6.86 (3H, m), 6.99 (2H, m), 7.26 (7H, complex).

LRMS (thermospray) m/z=615 (M⁺)

c) Trifluoroacetic acid (2.5 mL) was added dropwise over 5 min to a stirred solution of tert-butyl (3R)-3-({[(1S)-2,2-dimethyl-1-({[(1R)-1-phenylethyl]amino}carbonyl)propyl]amino}carbonyl)-6-(3-methyl-4-phenoxyphenyl)hexanoate (550 mg, 0.9 mmol) in anhydrous dichloromethane (5 mL) under nitrogen at 20° C. The solution was stirred for 1 h and concentrated under reduced pressure. The residue was diluted with hydrochloric acid (2M) and extracted with three portions of ethyl acetate. The combined organic solutions were washed with saturated aqueous sodium chloride, dried (MgSO₄) and concentrated under reduced pressure. Two portions of toluene were added and evaporated to give the title compound as a yellow gum (640 mg), contaminated with toluene and trifluoroacetic acid.

R$_f$ 0.18 (dichloromethane:methanol=99: 1)

δ$_H$ (300 MHz, CDCl₃) 0.99 (9H, s), 1.44 (3H, m), 1.50 (3H, d, J=7 Hz), 1.57 (1H, m,), 2.15 (3H, s), 2.43 (3H, m), 2.71 (2H, m), 4.43 (1H, d, J=10 Hz), 5.06 (1H, pentet, J=7 Hz), 6.77 (2H, m), 6.84 (2H, d, J=8 Hz), 6.93 (1H, s), 7.00

(1H, t, J=8 Hz), 7.10 (8H, complex), 7.46 (1H, d, J=10 Hz), 7.74 (2H, br s).

LRMS (thermospray) m/z=558 (M⁺)

Preparation 7

Methyl(2S,3R)-3-Carboxy-2ethoxy-hex-4-enoate

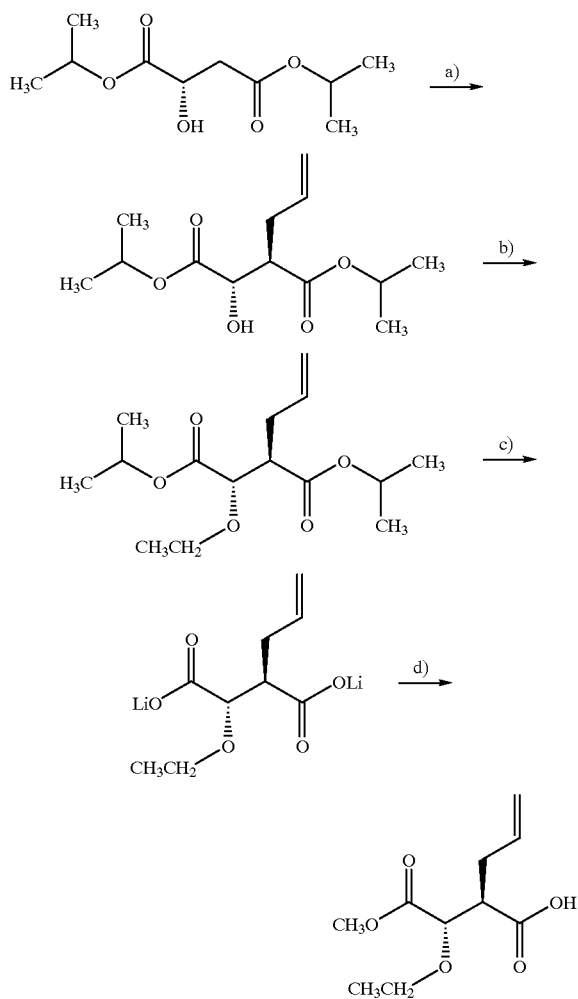

a) n-Butyllithium (23.0 mL, 2.5M in hexanes, 57.5 mmol) was added dropwise to a stirred solution of diisopropylamine (9.63 mL, 69.0 mmol) in anhydrous tetrahydrofuran (10 mL) under nitrogen at −78° C. The reaction flask was placed in an ice-water bath for 10 min, then re-cooled to −78° C. Anhydrous tetrahydrofuran (10 mL) was added, followed by dropwise addition of a solution of (S)-diisopropyl malate (6.0 gm, 27.0 mmol) in anhydrous tetrahydrofuran (20 mL). The mixture was allowed to warm to −20° C. and stirred for 8 h. The mixture was then re-cooled to −78° C. and freshly distilled allyl iodide (2.75 mL, 30 mmol) was added dropwise. The mixture was allowed to warm to −40° C. and stirred for 36 h. The mixture was poured into ice-cold 5% aqueous citric acid (150 mL), and extracted with ethyl acetate (3×150 mL). The combined organic solutions were washed with saturated aqueous sodium chloride, dried (MgSO₄), and concentrated under reduced pressure. The residue was purified by flash chromatography (eluting with hexane:ethyl acetate=80:20) to give a mixture of (2S, 3R)- and (2S, 3S)-isopropyl 2-hydroxy-3-(2-propyloxycarbonyl)-5-hexenoate (5.42 gm, 76%)(14:1), as a pale yellow oil.

$R_f$ 0.63 (hexane:ethyl acetate=1:1)

$\delta_H$ (400 MHz, CDCl₃) (major isomer) 1.19 (6H, m), 1.26 (6H, m), 2.39 (1H, m), 2.58 (1H, m), 2.87 (1H, m), 3.14 (1H, d, J=6.5 Hz, OH), 4.19 (1H, m), 4.98 (1H, m), 5.07 (2H, m), 5.13 (1H, d, J=15 Hz), 5.79 (1H, m); (peaks attributable to the minor isomer) 2.29 (1H, m), 2.50 (1H, m), 2.78 (1H, m), 3.06 (1H, d), 4.40 (1H, m).

LRMS (thermospray) m/z=276 (MNH₄⁺), 259 (MH⁺).

b) Ethyl trifluoromethanesulphonate (1.45 mL, 11.2 mmol) was added to a mixture of (2S, 3R)- and (2S, 3S)-isopropyl 2-hydroxy-3-(2-propyloxycarbonyl)-5-hexenoate (14:1)(1.45 gm, 5.6 mmol) and 2,6-di-tert-butyl-4-methylpyridine (2.88 g, 14.0 mmol) and the mixture was stirred under nitrogen at 45° C. for 5.5 h, 20° C for 18 h, and 45° C. for 24. The cooled mixture was applied to the top of a short column of silica gel and eluted with ethyl acetate. The filtrate was concentrated under reduced pressure and further purified by flash chromatography (hexane:ethyl acetate=85:15) to give (2S, 3R)-isopropyl 2-ethoxy-3-(2-propyloxycarbonyl)-5-hexenoate (627 mg, 39%).

$R_f$ 0.62 (hexane:ethyl acetate=70:30)

$\delta_H$ (400 MHz, CDCl₃) 1.13 (3H, t, J=7.5 Hz), 1.17 (6H, m), 1.24 (6H, m), 2.24 (1H, dt, J=13 and 6.5 Hz), 2.36 (1H, dt, J=13 and 6.5 Hz), 2.83 (1H, m), 3.38 (1H, dq, J=9.5 and 7.5 Hz), 3.62 (1H, J=9.5 and 7.5 Hz), 3.92 (1H, d, J=8 Hz), 5.02 (4H, m), 5.70 (1H, m).

LRMS (thermospray) m/z=304 (MNH₄⁺), 287 (MH⁺).

c) A mixture of (2S, 3R)-isopropyl 2-ethoxy-3-(2-propyloxycarbonyl)-5-hexenoate (500 mg, 1.75 mmol) and lithium hydroxide hydrate (154 mg, 3.67 mmol) in methanol:water=1:1 (6 mL) was stirred under nitrogen at room temperature for 22 h, then concentrated under reduced pressure. NMR showed incomplete reaction, so more lithium hydroxide hydrate (154 mg, 3.67 mmol) and methanol:water=1:1 (6 mL) were added, and the mixture was heated to 50° C. for 20 h. The mixture was cooled, concentrated under reduced pressure, and toluene was added and evaporated several times. The residue was dried over sodium hydroxide pellets in vacuo, and then used in the next step without purification.

$\delta_H$ (400 MHz, CD₃OD) 1.15 (3H, t, J=7.5 Hz), 2.26 (1H, m), 2.40 (1H, m), 2.46 (1H,m), 3.35 (1H, dq, J=9.5 and 7.5 Hz), 3.45 (1H, dq, J=9.5 and 7.5 Hz), 3.72 (1H, d, J=7 Hz), 4.94 (2H, partially obscured by HOD peak), 5.84 (1H, m).

d) To a stirred suspension of dilithium (2S,3R)-2-ethoxy-3-(prop-3-enyl)butanedioate (393 mg from c, above) in anhydrous tetrahydrofuran (2.6 mL) under nitrogen at 0° C. was added trifluoroacetic anhydride (2.62 mL) dropwise. The mixture was stirred for 4 h, and concentrated under reduced pressure. Toluene was added and evaporated several times. The resulting gum was dissolved in anhydrous methanol (2 mL) at 0° C. and allowed to warm to room temperature overnight. The solution was concentrated under reduced pressure, and the residue was partitioned between saturated aqueous sodium dihydrogen citrate and ethyl acetate. The aqueous layer was extracted with two portions of ethyl acetate. The combined organic solutions were washed with saturated aqueous sodium chloride, dried (NaSO₄), and concentrated under reduced pressure to give the title compound (220 mg), as a pale yellow oil. A major impurity was evident by ¹H NMR, which could be the (2S,3S) isomer.

$R_f$ 0.3 (dichloromethane:methanol:acetic acid=95:5:1)

$\delta_H$ (400 MHz, CD₃OD) 1.16 (3H, t, J=7.5 Hz), 2.32 (1H, m), 2.44 (1H, m), 2.95 (1H, m), 3.42 (1H, dq, J=9.5 and 7.5 Hz), 3.68 (m), 3.74 (3H, s), 4.01 (1H, d, J=6 Hz), 4.94 (2H, m), 5.74 (1H, m).

Example 36

Preparation 8

(2S,3R)-3-([[(1S)-2,2-Dimethyl-1-([[(1R)-1-phenylethyl]aminocarbonyl)propyl]aminocarbonyl)-2ethoxy-6-(3-fluoro-4-phenoxyphenyl)hexanoic acid.

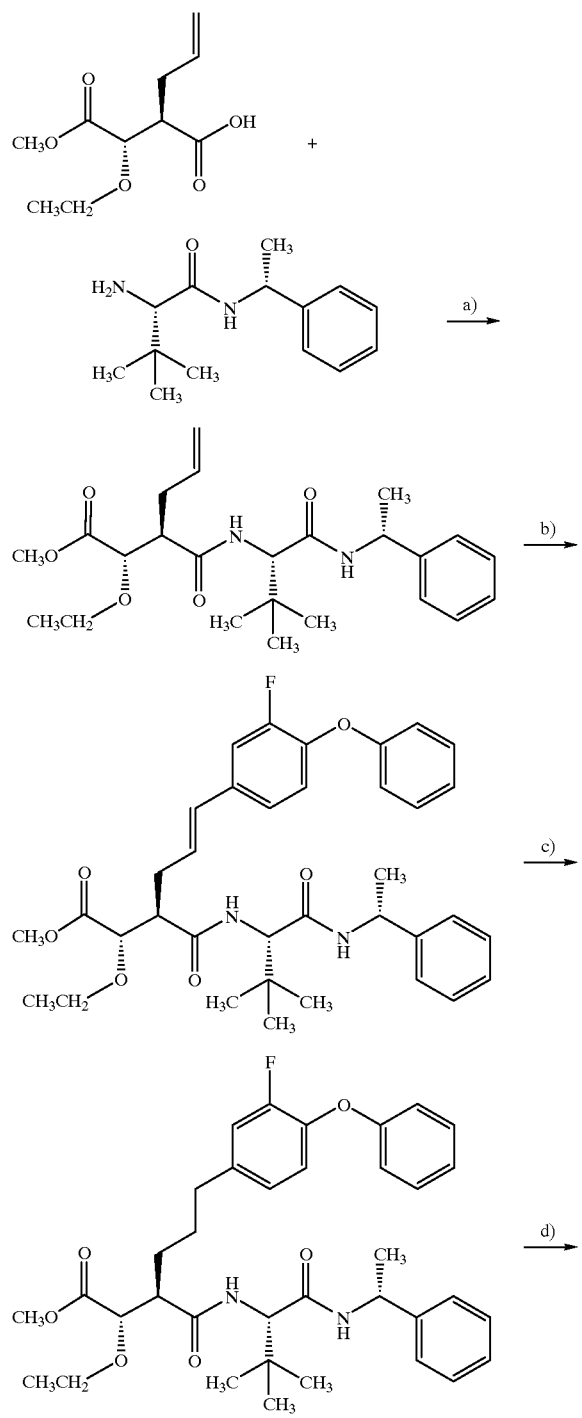

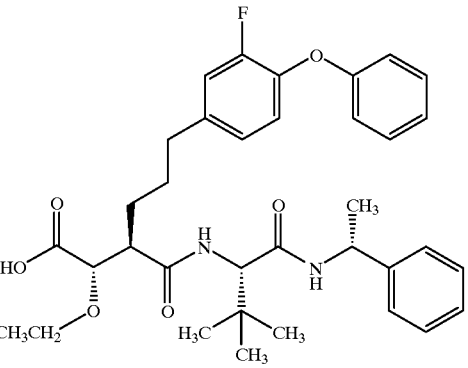

a) N-(Dimethylaminopropyl)-N'-ethylcarbodiimide hydrochloride (214 mg, 1.12 mmol) was added to a stirred mixture of methyl (2S, 3R)-3-carboxy-2-ethoxy-hex-4-enoate (Preparation 7) (210 mg, 0.97 mmol) and 1-hydroxy-7-azabenzotriazole (139 mg, 1.02 mmol) in anhydrous dimethylformamide (4 mL) under nitrogen at 0° C. After 1 h, (2S)-amino-3,3-dimethyl-N-[(1R)-1-phenylethyl] butanamide hydrochloride (Preparation 1)(276 mg, 1.02 mmol) was added, followed by diisopropylethylamine (0.18 μL, 1.02 mmol). After another 30 min, the mixture was allowed to warm to room temperature. After 17 h at room temperature, the mixture was concentrated under reduced pressure, and partitioned between ethyl acetate (50 mL) and water (50 mL). The aqueous layer was saturated with sodium bicarbonate and extracted with ethyl acetate (2×20 mL). The combined organic solutions were concentrated under reduced pressure, dissolved in ether (50 mL), washed with water (3×20 mL), dried ($Na_2SO_4$), and concentrated under reduced pressure. The residue was purified by flash chromatography (eluting with hexane:ethyl acetate=60:40) to give methyl (2S,3R)-3-({[(1S)-2,2-dimethyl-1-({[(1R)-1-phenylethyl]amino}carbonyl)propyl]amino}carbonyl)-2-ethoxy-hex-5-enoate (181 mg, 43%), as a colourless solid (single diastereomer by $^1$H NMR).

m.p. 131–134° C.

$R_f$ 0.4 (hexane:ethyl acetate=1:1)

$δ_H$ (300 MHz, $CDCl_3$) 1.00 (9H, s), 1.22 (3H, t, J=7 Hz), 1.49 (3H, d, J=6.5 Hz), 2.31 (1H, dt, 14 and 8 Hz), 2.51 (1H, dt, 14 and 6.5 Hz), 2.68 (1H, m), 3.42 (1H, dq, J=16 and 7 Hz), 3.66 (1H, dq, J=16 and 7 Hz), 3.69 (3H, s), 4.05 (1H, d, J=5 Hz), 4.13 (1H, d, J=9 Hz), 5.04 (1H, d, J=10 Hz), 5.07 (1H, d, J=18 Hz), 5.14 (1H, pentet, J=7 Hz), 5.70 (1H, dddd, J=6, 7, 10 and 18 Hz), 6.42 (1H, br d), 7.06 (1H, br d), 7.29 (5H, complex).

LRMS (thermospray) m/z=433 ($MH^+$)

b) A mixture of palladium acetate (12 mg, 0.05 mmol) and tri-(2-methylphenyl)phosphine (30 mg, 0.10 mmol) in anhydrous acetonitrile (1 mL) was sonicated at room temperature for 1 min until a creamy-coloured suspension formed. This suspension was added via Pasteur pipette to a stirred solution of methyl (2S,3R)-3-({[(1S)-2,2-dimethyl-1-({[(1R)-1-phenylethyl]amino}carbonyl)propyl]amino}carbonyl)-2-ethoxy-hex-5-enoate (415 mg, 0.96 mmol), 3-fluoro-4-phenoxy-bromobenzene (Preparation 10)(400 mg, 1.50 mmol), and triethylamine (280 μL, 2.0 mmol) in anhydrous acetonitrile (1 mL) under nitrogen. The mixture was purged with nitrogen, then heated at reflux for 16 h. After being cooled, the mixture was poured into ethyl acetate (70 mL) and washed with 5% aqueous citric acid (20 mL), saturated aqueous sodium chloride (50 mL), dried (MgSO$_4$), and concentrated under reduced pressure. The residue was purified by flash chromatography (gradient elution with dichloromethane:ethyl acetate) to give mainly methyl (2S,3R,5E)-3-({[(1S)-2,2-dimethyl-1-({[(1R)-1-phenylethyl]amino}carbonyl)propyl]amino}carbonyl)-2-ethoxy-6-(3-fluoro-4-phenoxyphenyl)hex-5-enoate as a pale yellow foam (359 mg, 69%). $^1$H nmr suggested that two alkene isomers, the (5Z) and (4E) were also present. The mixture of alkenes was taken onto the next step (see c, below).

R$_f$ 0.36 (dichloromethane:ethyl acetate=10:1)

δ$_H$ (400 MHz, CDCl$_3$)(for the (5E) isomer). 1.01 (9H, s), 1.16 (3H, t, J=7 Hz), 1.49 (3H, d, J=6.5 Hz), 2.48 (1H, m), 2.68 (1H, m), 2.80 (1H, m), 3.26 (1H, m), 3.69 (1H, m and 3H, s, overlapping), 4.06 (1H, d, J=4 Hz), 4.15 (1H, d, J=9.5 Hz), 5.10 (1H, pentet, J=6.5 Hz), 6.03 (1H, dt, 16 and 8 Hz), 6.36 (1H, d, J=16 Hz), 6.42 (1H, br d), 6.95 (3H, m), 7.01 (1H, d, J=8 Hz), 7.09 (3H, m), 7.22 (1H, m), 7.28 (6H, complex).

LRMS (thermospray) m/z=636 (MNH$_4^+$)

c) A solution of methyl (2S,3R,5E)-3-({[(1S)-2,2-dimethyl-1-({[(1R)-1-phenylethyl]amino}carbonyl)propyl]amino}carbonyl)-2-ethoxy-6-(3-fluoro-4-phenoxyphenyl)hex-5-enoate (350 mg, 0.566 mmol) in ethanol (15 mL) was hydrogenated over 10% palladium on charcoal (60 mg) at 3 bar and 20° C. for 16 h. The mixture was filtered through Arbocel filter aid and concentrated under reduced pressure. The residue was dissolved in cyclohexane and evaporated (twice) to give methyl (2S,3R)-3-({[(1S)-2,2-dimethyl-1-({[(1R)-1-phenylethyl]amino}carbonyl)propyl]amino}carbonyl)-2-ethoxy-6-(3-fluoro-4-phenoxyphenyl)hexanoate (368 gm, 105%), as a colourless foam, which was taken onto the next step without purification.

R$_f$ 0.29 (hexane:ethyl acetate=2:1)

δ$_H$ (400 MHz, CDCl$_3$) 1.01 (9H, s), 1.19 (3H, t, J=7 Hz), 1.49 (3H, d, J=6.5 Hz), 1.61 (3H, m), 1.75 (1H, m), 2.58 (3H, m), 3.41 (1H, dq, J=10 and 7 Hz), 3.61 (1H, dq, J=10 and 7 Hz), 3.70 (3H, s), 3.99 (1H, d, J=5 Hz), 4.15 (1H, d, J=9 Hz), 5.12 (1H, pentet, J=6.5 Hz), 6.38 (1H, br d), 6.83 (1H, d, J=10 Hz), 6.87 (1H, d, J=12 Hz), 6.93 (4H, m), 7.03 (1H, t, J=9.5 Hz), 7.20 (1H, m), 7.29 (6H, complex).

LRMS (thermospray) m/z=638 (MNH$_4^+$)

d) Lithium hydroxide hydrate (116 mg, 2.83 mmol) was added to a solution of methyl (2S,3R)-3-({[(1S)-2,2-dimethyl-1-({[(1R)-1-phenylethyl]amino}carbonyl)propyl]amino}carbonyl)-2-ethoxy-6-(3-fluoro-4-phenoxyphenyl)hexanoate (368 mg, 0.566 mmol) in methanol:water=10:1 (5 mL) and the mixture was stirred at room temperature for 2 h. The solution was neutralised with 5% aqueous citric acid and concentrated under reduced pressure. The residue was partitioned between ethyl acetate (100 mL) and 5% aqueous citric acid (20 mL), washed with saturated aqueous sodium chloride (20 mL), dried MgSO$_4$), and concentrated under reduced pressure. Purification by flash chromatography (eluting with dichloromethane:methanol=20:1 to 10:1) gave the title compound (62 mg, 18%) as a colourless glass, and some mixed fractions. These were combined and repurified by flash chromatography (eluting with ethyl acetate:hexane:acetic acid=33:66:1 to 50:50:1) to give the title compound (37 mg, 11%), as a white solid.

m.p. 185–187° C.

R$_f$ 0.23 (ether:hexane:acetic acid=70:30: 1)

δ$_H$ (400 MHz, CD$_3$OD) (NB some of the shifts are concentration dependant) 1.02 (9H, s), 1.15 (3H, t, J=7 Hz), 1.44 (3H, d, J=7 Hz), 1.56 (3H, m), 1.69 (1H, m), 2.54 (2H, m), 2.68 (1H, m), 3.35 (1H, dq, J=10 and 7 Hz), 3.66 (1H, dq, J=10 and 7 Hz), 4.31 (1H, s), 5.02 (1H, q, J=7 Hz), 6.87 (4H, m), 6.96 (1H, d, J=12 Hz), 7.02 (1H, t, J=7 Hz), 7.13 (1H, m), 7.19 (2H, t, J=7 Hz), 7.28 (4H, m).

LRMS (thermospray) m/z=607 (MH$^+$)

FTIR ν$_{max.}$ (KBr disc) 3330,2980, 1643,1593, 1508, 1493, 1217,700 cm$^{-1}$

Preparation 9

(3-Chloro-4-phenyl)phenyl trifluoromethanesulphonate.

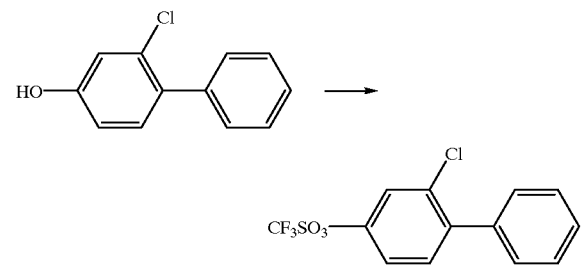

Trifluoromethanesulphonic anhydride (755 μL, 4.45 mmol) was added dropwise over 2 min to a stirred solution of (3-chloro-4-phenyl)phenol (759 mg, 3.71 mmol)(World Patent 97/20815) and anhydrous pyridine (785 μL, 9.65 mmol) in anhydrous dichloromethane under nitrogen at 0° C. The mixture was stirred for 1.5 h at 0° C. and then for 2.5 h at 20° C. The mixture was poured into a mixture of ether/hexane (200 mL, 50:50) and filtered. The filtrate was concentrated under reduced pressure, and the residue purified by flash chromatography (eluting with hexane:ether=20:1) to give the title compound as a colourless oil (1062 mg, 85%), which crystallised on standing at room temperature for several days.

m.p. 43–44° C.

R$_f$ 0.27 (hexane)

δ$_H$ (300 MHz, CDCl$_3$) 7.27 (1H, dd, J=8 and 2 Hz), 7.29 (7H, br s).

LRMS (EI) m/z=336 (M$^+$)

Preparation 10

3-Fluoro-4-phenoxy-bromobenzene

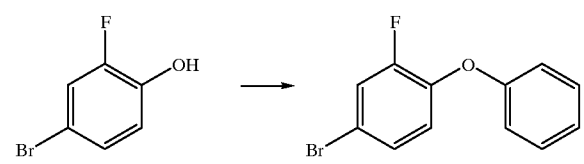

Aqueous sodium hydroxide (5.5 mL, 1M, 5.5 mmol) was added to a mixture of 4-bromo-2-fluorophenol (0.96 gm, 5.0 mmol) and diphenyliodonium bromide (1.99 gm, 5.5 mmol) in water (20 mL), and the mixture was heated under reflux for 4 h. After being cooled, the reaction mixture was diluted with ether, and filtered. The organic phase was washed with saturated aqueous sodium chloride, dried (MgSO$_4$), and concentrated under reduced pressure. The residual dark orange oil was purified by flash chromatography (eluting with hexane) to give the title compound as an orange oil (1.2 gm, 90%).

$R_f$ 0.36 (hexane)

$\delta_H$ (400 MHz, CDCl$_3$) 6.90 (3H, m), 7.06 (1H, m), 7.20 (1H, m), 7.30 (3H, m).

Preparation 11

1-Iodo-3-methyl-4-phenoxybenzene.

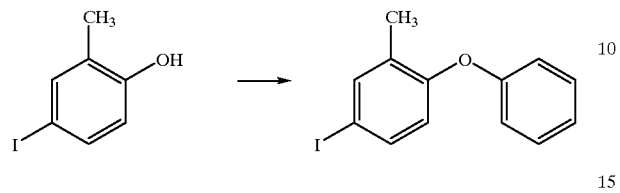

Aqueous sodium hydroxide (33 mL, 1M, 33 mmol) was added to a mixture of 4-iodo-2-methylphenol (7.0 gm, 29.9 mmol) and diphenyliodonium bromide (11.89 gm, 32.9 mmol) in water (120 mL), and the mixture was heated under reflux for 4 h. After being cooled, the reaction mixture was extracted with ethyl acetate (4×100 mL), combined extracts were washed with saturated aqueous sodium chloride, dried (MgSO$_4$), and concentrated under reduced pressure. The residual dark orange oil was purified by repeated flash chromatography (eluting with hexane for the first column, then pentane for the second) to give the title compound as an orange oil (7.84 gm, 84%).

$R_f$ 0.78 (hexane)

$\delta_H$ (400 MHz, CDCl$_3$) 2.23 (3H, s), 6.65 (1H, d, J=9 Hz), 6.94 (2H, m), 7.10 (1H, m), 7.32 (2H, m), 7.47 (1H, d, J=9 Hz), 7.59 (1H, s).

LRMS (thermospray) m/z=310 (MH$^+$)

Preparation 12 tert-Butyl(2S,3R)-3-Carboxy-2propyl-hex-5-enoate

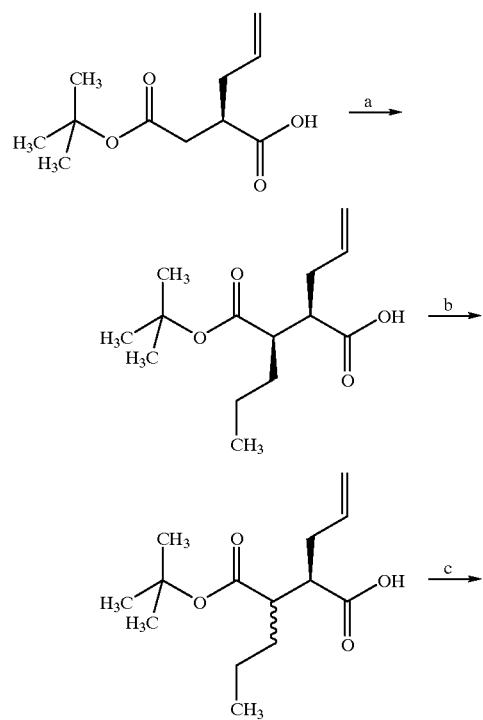

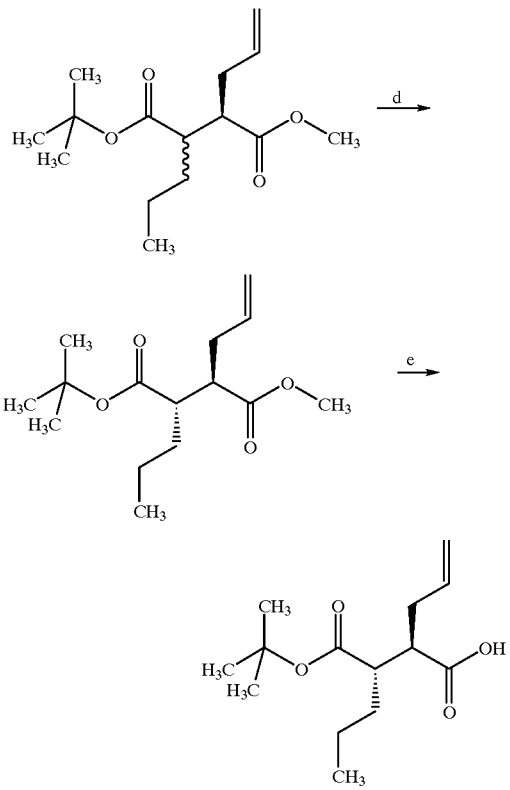

a) n-Butyllithium (2.2 mL, 2.5M in hexanes, 5.6 mmol) was added dropwise to a stirred solution of diisopropylamine (0.73 mL, 5.6 mmol) in anhydrous tetrahydrofuran (3 mL) under nitrogen at −5° C. After 1 h the solution was cooled to −70° C. and N,N'-dimethylpropyleneurea (DMPU)(3 mL) was added. Then a solution of (2R)-2-[2-(tert-butoxy)-2-oxoethyl]pent-4-enoic acid (535 mg, 2.5 mmol) in anhydrous tetrahydrofuran (6 mL) was added dropwise over 15 min keeping the reaction temperature at −70° C. After being stirred for 1 h, 1-iodopropane (680 mg, 4.0 mmol) was added dropwise and the mixture was stirred at −70° C. for 1 h, then −40° C. for 2 h and finally allowed to warm to 0° C. Methanol (1 mL) was added, and the mixture was partitioned between 5% aqueous citric acid (150 mL) and ether (200 mL). The organic layer was washed with 5% aqueous citric acid (75 mL), water (3×200 mL), dried (MgSO$_4$) and concentrated under reduced pressure to give a pale yellow oil. Purification by flash chromatography (eluting with hexane:ethyl acetate:acetic acid=80:20:2) gave (2R, 3R)- and (2R, 3S)-3-[(2-methylprop-2-yl)oxycarbonyl]-2(3-propen-1-yl)hexanoic acid (472 mg, 74%), as a colourless oil with diastereomeric ratio 97:3.

$R_f$ 0.31 (hexane:ethyl acetate:acetic acid=80:20:2)

$\delta_H$ (400 MHz, CDCl$_3$)(for 2R, 3R isomer) 0.92 (3H, t, J=7.5 Hz), 1.34 (2H, m), 1.45 (9H, s), 1.58 (2H, m), 2.39 (2H, t, J=7 Hz), 2.60 (1H, dt, J=6 and 8 Hz), 2.74 (1H, dt, 6 and 7.5 Hz), 5.06 (1H, d, J=10 Hz), 5.10 (1H, d, J=17 Hz), 5.74 (1H, ddt, J=17, 10 and 7.5 Hz).

LRMS (thermospray) m/z=256 (weak, M$^+$), 200 (base peak, MH$^+$−t-Bu)

FTIR $v_{max}$ (film) 2970, 1730, 1370, 1250, 1160 cm$^{-1}$ b) The mixture of (2R, 3R)- and (2R, 3S)-3-[(2-methylprop-2-yl)oxycarbonyl]-2-(3-propen-1-yl)hexanoic acids (97:3 from a, above) (3.05 g, 11.9 mmol) was dissolved in anhydrous tetrahydrofuran (35 mL) and added dropwise over 30 min to a stirred solution of lithium diisopropylamide (from n-butyllithium (19.2 mL, 2.5M in hexanes, 48 mmol) and diisopropylamine (7.0 mL, 50 mmol)) in anhydrous tetrahydrofuran (25 mL) at −70° C. The mixture was allowed to warm to −10° C., stirred for 30 min then allowed to warm to 0° C. for 2 h. The solution was then cooled to −70° C. and methanol (15 mL) was added rapidly via syringe. The mixture was allowed to warm to room temperature and partitioned between 5% aqueous citric acid (150 mL) and ether (200 mL). The organic layer was washed with 5% aqueous citric acid (50 mL), water (3×200 mL), dried ($MgSO_4$) and concentrated under reduced pressure to give a pale yellow oil. Purification by flash chromatography (gradient elution with hexane:ethyl acetate:acetic acid) gave (2R, 3S)- and (2R, 3R)-3-[(2-methylprop-2-yl)oxycarbonyl]-2-(3-propen-1-yl)hexanoic acid (3.05 g, 100%), as a colourless oil with diastereomeric ratio 58:42.

$R_f$ 0.31 (hexane:ethyl acetate:acetic acid=80:20:2)

The assignment of stereochemistry for the two isomers was made as follows. A mixture of (2R, 3S)- and (2R, 3R)-3-[(2-methylprop-2-yl)oxycarbonyl]-2-(3-propen-1-yl) hexanoic acids (ratio 1:3) in ethanol was hydrogenated over 10% palladium on charcoal (3 bar) and then treated with hydrogen chloride in dry dichloromethane/dioxan (4° C., 4 h) to give a mixture of (2R, 3S)- and (2R, 3R)-2,3-diprop-1-ylbutanedioic acids (ratio 1:3), which are known in the literature (Bull. Chem. Soc. (France) 1975, 2189). Examination of the proton NMR spectrum (acetone-$d_6$) showed $\delta_H$ 2.70 (2H, m, $CHCO_2H$, major isomer) and $\delta_H$ 2.55 (2H, m, $CHCO_2H$, minor isomer).

c) A solution of (2R, 3S)- and (2R, 3R)-3-[(2-methylprop-2-yl)oxycarbonyl]-2-(3-propen-1-yl)hexanoic acid (3.04 g, 11.9 mmol)(diastereomeric ratio 58:42) and caesium bicarbonate (2.30 g, 11.9 mmol) in water (35 mL) and acetonitrile (90 mL) was stirred at 20° C. for 5 min. The solution was evaporated under reduced pressure and the residue dissolved and evaporated from toluene four times. The resulting gum was dried under high vacuum for 30 min, then dissolved in anhydrous N,N-dimethylacetamide (50 mL). Iodomethane (3.41 g, 24 mmol) was added and the solution was stirred at 20° C. for 17 h. The solution was concentrated under reduced pressure and partitioned between ether (250 mL) and water (250 mL). The organic layer was washed with water (3×200 mL), dried $MgSO_4$, and concentrated under reduced pressure to give a mixture of methyl (2R, 3S)- and (2R, 3R)-3-[(2-methylprop-2-yl)oxycarbonyl]-2-(3-propen-1-yl)hexanoates as a yellow oil (3.0 g, 94%). TLC (pentane:ether=10:1) showed two product spots with $R_f$ 0.41 and 0.30.

d) The mixture of methyl (2R, 3S)- and (2R, 3R)-3-[(2-methylprop-2-yl)oxycarbonyl]-2-(3-propen-1-yl)hexanoates from c) above was separated by flash chromatography (pentane:ether=20:1 then 10:1) to give two fractions. The first eluted product was identified as methyl (2R, 3S)-3-[(2-methylprop-2-yl)oxycarbonyl]-2-(3-propen-1-yl)hexanoate (1.78 g, 56%, $R_f$ 0.41 (pentane:ether=10:1) as a colourless oil.

$\delta_H$ (400 MHz, $CDCl_3$) 0.87 (3H, t, J=7 Hz), 1.30 (3H, m), 1.46 (9H, s), 1.56 (1H, m), 2.23 (1H, m), 2.34 (1H, m), 2.54 (1H, dt, 3 and 10 Hz), 2.69 (1H, 4.5 and 10 Hz), 3.66 (3H, s), 5.00 (1H, d, J=10 Hz), 5.04 (1H, d, J=17 Hz), 5.72 (1H, ddt, J=17, 10 and 7 Hz).

| | | |
|---|---|---|
| $C_{15}H_{26}O_4$ requires | C, 66.61; | H, 9.77; |
| Found: | C, 66.64; | H, 9.69% |

FTIR $v_{max.}$ (KBr disc) 2970, 1730, 1370, 1150 $cm^{-1}$

The second eluted product was identified as methyl (2R, 3R)-3-[(2-methylprop-2-yl)oxycarbonyl]-2-(3-propen-1-yl) hexanoate (760 mg, 24%, $R_f$ 0.30 (pentane:ether=10:1) as a colourless oil.

$\delta_H$ (400 MHz, $CDCl_3$) 0.90 (3H, t, J=7 Hz), 1.27 (1H, m), 1.35 (1H, m), 1.45 (9H, s), 1.55 (2H, m), 2.36 (2H, m), 2.58 (1H, dt, J=5 and 9 Hz), 2.71 (1H, dt, 5 and 9 Hz), 3.66 (3H, s), 5.02 (1H, d, J=10 Hz), 5.08 (1H, d, J=16 Hz), 5.76 (1H, m).

| | | |
|---|---|---|
| $C_{15}H_{26}O_4$ requires | C, 66.70 | H, 9.81; |
| Found: | C, 66.64; | H, 9.69% |

FTIR $v_{max.}$ (KBr disc) 2970, 1730, 1370, 1160 $cm^{-1}$ e) A mixture of methyl (2R, 3S)-3-[(2-methylprop-2-yl)oxycarbonyl]-2-(3-propen-1-yl)hexanoate (1.49 g, 5.51 mmol) and anhydrous lithium iodide (11 g, 82 mmol) in anhydrous pyridine (50 mL) was heated at reflux under nitrogen for 17 h. After being cooled the mixture was poured into 20% aqueous citric acid (500 mL) and extracted with ethyl acetate (250 mL). The organic layer was washed with 5% aqueous citric acid (2×150 mL), water (3×250 mL), dried $MgSO_4$, and concentrated under reduced pressure. The residue was triturated with hexane, filtered and the filtrate concentrated under reduced pressure. The crude product was purified by repeated flash chromatography (first column eluted with dichloromethane:methanol:acetic acid=80:20:2, second column eluted with a hexane:ethyl acetate:acetic acid gradient) to give (2R, 3S)-3-[(2-methylprop-2-yl) oxycarbonyl]-2-(3-propen-1-yl)hexanoic acid (788 mg, 56%) as a colourless oil.

$R_f$ 0.3 (hexane:ethyl acetate:acetic acid=80:20:2)

$\delta_H$ (400 MHz, $CDCl_3$) 0.91 (3H, t, J=7 Hz), 1.35 (3H, m), 1.47 (9H, s), 1.62 (1H, m), 2.26 (1H, dt, J=10 and 7.5 Hz), 2.38 (1H, dt, J=7.5 and 10 Hz), 2.58 (1H, dt, J=3 and 10 Hz), 2.70 (1H, dt, 5 and 9 Hz), 5.04 (1H, d, J=10 Hz), 5.08 (1H, d, J=18 Hz), 5.76 (1H, ddt, J=18, 10 and 7.5 Hz).

LRMS (thermospray) m/z=257 (weak, $MH^+$)

| | | |
|---|---|---|
| Found: | C, 65.30; | H, 9.44; |
| $C_{14}H_{24}O_4$ requires | C, 65.60; | H, 9.44% |

Preparation 13 tert-Butyl(3R)-3-({[(1S)-2,2-Dimethyl-1-({[(1R)-1-phenylethyl]amino}carbonyl)propyl]amino}carbonyl)-6-(3-methyl-(4-phenyl) phenyl]-(2S)-propylhexanoate

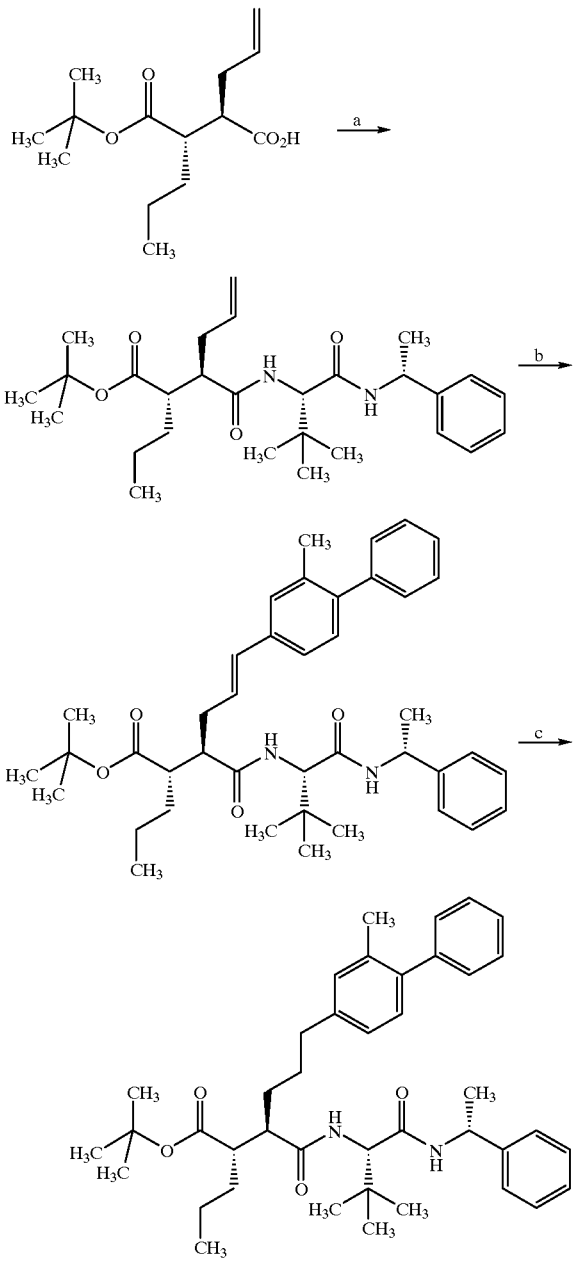

a) According to the method of Preparation 2, (2R, 3S)-3-[(2-methylprop-2-yl)oxycarbonyl]-2-(3-propen-1-yl) hexanoic acid (380 mg, 1.48 mmol) was reacted with (2S)-amino-3,3-dimethyl-N-[(1R)-1-phenylethyl] butanamide hydrochloride (P)reparation 1)(441 mg, 1.62 mmol) for 1 h at 4° C. and then 72 h at 20° C. The mixture was concentrated under reduced pressure, and partitioned between ethyl acetate (100 mL) and water (100 mL). The aqueous layer was saturated with sodium bicarbonate and extracted with ethyl acetate (2×100 mL). The combined organic solutions were concentrated under reduced pressure, the residue was dissolved in ether (500 mL) and washed with water (3×200 mL), dried (MgSO$_4$), and concentrated under reduced pressure. The residue was triturated with pentane, filtered and dried to give tert-butyl (2S, 3R)-3-({[(1S)-2,2-dimethyl-1-({[(1R)-1-phenylethyl]amino}carbonyl)propyl]amino}carbonyl)-2-(1-propyl)hex-5-enoate (579 mg, 80%), as a colourless solid.

m.p. 180–183° C.

$R_f$ 0.51 (hexane:isopropanol=90:10)

$\delta_H$ (400 MHz, CDCl$_3$) 0.84 (3H, t, J=7.5 Hz), 1.02 (9H, s), 1.22–1.50 (4H, m), 1.45 (9H, s), 1.50 (3H, d, J=7 Hz), 2.08 (1H, m), 2.22 (1H, m), 2.34 (1H, dt, J=4 and 10 Hz), 2.52 (1H, dt, J=3 and 10 Hz), 4.18 (1H, d, J=9 Hz), 4.72 (1H, d, J=9.5 Hz), 4.85 (1H, d, J=16.5 Hz), 5.09 (1H, pentet, J=7 Hz), 5.53 (1H, ddt, J=9.5, 16.5 and 7 Hz), 6.03 (1H, br, d), 6.24 (1H, br d), 7.26 (5H, complex).

LRMS (thermospray) m/z=473 (MH$^+$)

FTIR $\nu_{max.}$ (KBr disc) 3320, 2970, 2930, 1725, 1640, 1540, 1370, 1150, 700 cm$^{-1}$

| Found: | C, 71.09; | H, 9.46; | N, 6.10; |
| C$_{28}$H$_{44}$N$_2$O$_4$ requires | C, 71.15; | H, 9.38; | N, 5.93% | b) According to the method of Preparation 3, tert-butyl (2S, 3R)-3-({[(1S)-2,2-dimethyl-1-({[(1R)-1-phenylethyl]amino}carbonyl)propyl]amino}carbonyl)-2-(1-propyl)hex-5-enoate (543 mg, 1.15 mmol) was reacted with 3-methyl-4-phenylbromobenzene (356 mg, 1.44 mmol) under palladium catalysis in a mixture of anhydrous acetonitrile and dimethylformamide (2:5, 7 mL) at 90° C. for 17 h. The mixture was concentrated under reduced pressure, poured into ethyl acetate (100 mL) and washed with water (2×100 mL), dried (MgSO$_4$), and concentrated under reduced pressure. The residue was purified by flash chromatography (gradient elution with hexane:ethyl acetate) to give mainly tert-butyl (2S,3R,5E)-3-({[(1S)-2,2-dimethyl-1-({[(1R)-1-phenylethyl]amino}carbonyl)propyl]amino}carbonyl)-6-[3-methyl-(4-phenyl)phenyl]-2-(1-propyl)hex-5-enoate as a colourless gum (460 mg, 63%). $^1$H nmr suggested that two alkene isomers, the (5Z) and (4E) were also present. The mixture of alkenes was taken onto the next step (see c, below).

$R_f$ 0.46 (hexane:ethyl acetate=3:1)

$\delta_H$ (400 MHz, CDCl$_3$)(for the (5E) isomer). 0.87 (3H, t, J=7 Hz), 1.03 (9H, s), 1.32 (2H, m), 1.46 (9H, s, 3H, d, J=7 Hz, and 2H, m, overlapping), 2.22 (3H, s), 2.34 (1H, m), 2.48 (2H, m), 2.60 (1H, m), 4.19 (1H, d, J=9 Hz), 4.93 (1H, pentet, J=7 Hz), 5.85 (1H, br, d), 6.05 (1H, dt, J=14 and 7 Hz), 6.35 (1H, d, J=14 Hz), 6.27 (1H, br d), 7.20 (11H, complex), 7.37 (2H, m).

LRMS (thermospray) m/z=639 (MH$^+$)

c) tert-Butyl (2S,3R,5E)-3-({[[(1s)-2,2-dimethyl-1-({[(1R)-1-phenylethyl]amino}carbonyl)propyl]amino}carbonyl)-6-[3-methyl-(4-phenyl)phenyl]-2-(1-propyl)hex-5-enoate (437 gm, 0.68 mmol) in ethanol (50 mL) was hydrogenated over 10% palladium on charcoal (50 mg) at 3 bar and 20° C. for 17 h. The mixture was filtered through Arbocel filter aid and concentrated under reduced pressure. Flash chromatography (gradient elution with hexane:ethyl acetate) gave tert-butyl (2S,3R)-3-({[(1S)-2,2-dimethyl-1-({[(1R)-1-phenylethyl]amino}carbonyl)propyl]amino}carbonyl)-6-[3-methyl-(4-phenyl)phenyl]-2-(1-propyl)hexanoate (395 gm, 62%), as a colourless foam.

$R_f$ 0.38 (hexane:ethyl acetate=3:1)

$\delta_H$ (400 MHz, CDCl$_3$) 0.85 (3H, t, J=7 Hz), 1.03 (9H, s), 1.26 (4H, m), 1.37 (9H, s), 1.48 (4H, m, and 3H, d, J=7 Hz, overlapping), 2.20 (3H, s), 2.29 (1H, m), 2.48 (4H, m), 2.48 (4H, m), 4.24 (1H, d, J=9 Hz), 5.10 (1H, pentet, J=7 Hz), 6.02 (1H, br d), 6.29 (1H, br d), 6.94 (1H, d, J=8 Hz), 6.98 (1H, s), 7.09 (1H, d, J=8 Hz), 7.24 (7H, complex), 7.32 (1H, d, J=7 Hz), 7.39 (2H, t, J=7Hz).

LRMS (thermospray) m/z=641 (MH$^+$)

| Found: | C, 76.71; | H, 8.97; | N, 4.35; |
|---|---|---|---|
| C$_{41}$H$_{56}$N$_2$O$_4$ requires | C, 76.84; | H, 8.81; | N, 4.37% |

Preparation 14

(2R)-2[(4S)-2,2-Dimethyl-5-oxo-1,3-dioxolan-4-yl]-N-[(1S)-2,2-dimethyl-1-phenylethyl] amino}carbonyl)propyl]pent-4-enamide.

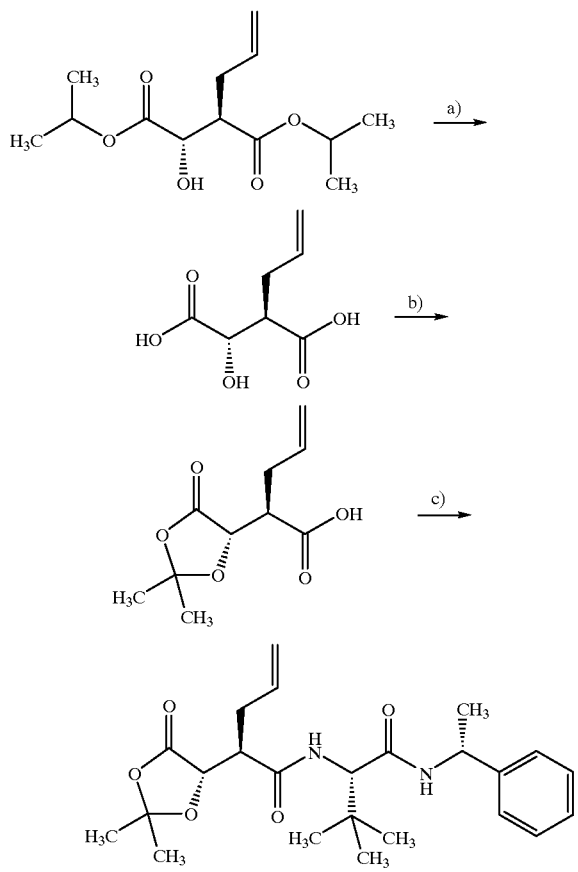

a) A mixture of isopropyl (2S, 3R)- and (2S, 3S)-2-hydroxy-3-(2-propyloxycarbonyl)-5-hexenoate (6.28 gm, 24.3 mmol)(isomeric ratio=14:1)(Preparation 7, step a) and potassium hydroxide (4.09 g, 72.9 mmol) in dioxane:water (50 mL, 5:2) was heated under nitrogen at 90° C. for 18 h. The mixture was cooled, diluted with water (200 mL) and passed down an ion-exchange column (Dowex 50X8, 300 g), eluting with water until no further diacid eluted. The eluant was concentrated under reduced pressure, dissolved and evaporated from ethanol twice, then ether (twice) and dried under vacuum to give (2S, 3R)-2-hydroxy-3-(prop-3-en-1-yl)butanedioic acid (waxy yellow solid, 4.85 g>100%, contained ethanol and ether), as the major component of an 8:1 mixture of isomers, which was used directly for the next step without further purification.

$\delta_H$ (300 MHz, CDCl$_3$) 2.47 (1H, dt, J=7.5 and 15.5 Hz), 2.60 (1H, m), 3.00 (1H, dt, J=4 and 6 Hz), 4.26 (1H, d, J=4 Hz), 5.09 (1H, d, J=10 Hz), 5.15 (1H, d, J=18 Hz), 5.83 (1H, m).

b) The crude diacid from a) above was dissolved in a mixture of dimethylformamide (36 mL) and 2,2-dimethoxypropane (133 mL) at room temperature and p-toluenesulphonic acid hydrate (231 mg) was added. The mixture was heated at 30° C. for 2.5 days. The solvents were removed under reduced pressure to give 7.5 g of an oil, which contained (4S)-4-[(1R)-1-carboxy-but-3-enyl]-2,2-dimethyl-1,3-dioxolan-5-one as the major component, together with dimethylformamide and p-toluenesulphonic acid.

$\delta_H$ (400 MHz, CDCl$_3$) 1.53 (3H, s), 1.60 (3H, s), 2.47 (1H, dt, J=7.5 and 15.5 Hz), 2.71 (1H, dt, J=7.5 and 15.5 Hz), 3.00 (1H, m), 4.30 (1H, d, J=4 Hz), 5.12 (1H, d, J=10 Hz), 5.16 (1H, d, J=16 Hz), 5.80 (1H, m).

c) A portion of the crude (4S)-4-[(1R)-1-carboxy-but-3-enyl]-2,2-dimethyl-1,3-dioxolan-5-one from b) above (calculated from the NMR to contain 1.54 g, 7.19 mmol) and 1-hydroxy-7-aza-1H-1,2,3-benzotriazole (1.09 g, 7.55 mmol) in anhydrous dichloromethane (30 mL) were mixed and cooled to 0° C. under nitrogen. N-(Dimethylaminopropyl)-N'-ethylcarbodiimide hydrochloride (1.60 g, 8.27 mmol) was added, and the mixture was stirred for 1.5 h at 0° C. (2S)-Amino-3,3-dimethyl-N-[(1R)-1-phenylethyl]butanamide hydrochloride (Preparation 1)(2.15 g, 7.55 mmol) was added, followed by diisopropylethylamine (1.37 mL, 7.55 mmol). After another 45 min, the mixture was allowed to warm to room temperature. After 3 h at room temperature, the mixture was partitioned between ethyl acetate (200 mL) and pH 7 aqueous phosphate buffer (100 mL). The organic layer was washed with sodium bicarbonate, brine, dried (Na$_2$SO$_4$), and concentrated under reduced pressure. The resulting foam crystallised upon addition of ether, and the white solid (1.89 g) was filtered off. Recrystallisation from ethyl acetate/hexane gave (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide as a white solid (1.30 g, 42%, as a single diastereomer).

m.p. 178–180° C.

$R_f$ 0.25 (dichloromethane:ether=90:10)

$\delta_H$ (300 MHz, CDCl$_3$) 1.02 (9H, s), 1.48 (3H, d, J=7 Hz), 1.51 (3H, s), 1.56 (3H, s), 2.47 (1H, dt, 15 and 7.5 Hz), 2.58 (1H, dt, 15 and 7.5 Hz), 2.70 (1H, dt, J=11 and 5 Hz), 4.15 (1H, d, J=9 Hz), 4.50 (1H, d, J=5 Hz), 4.99 (1H, d, J=10 Hz), 5.08 (2H, m), 5.67 (1H, m), 5.67 (1H, br d), 6.45 (1H, br d), 7.27 (5H, complex).

LRMS (thermospray) m/z=431 (MH⁺)

Preparation 15

(2R)-2[(4S)2,2-Dimethyl-5-oxo-1,3-dioxolan-4-yl]-
N-[(1S)-2,2-dimethyl-1-({[(1R)-1-phenylethyl]
amino}carbonyl)propyl]-5-[(3-fluoro-4-phenoxy)
phenyl]pentanamide

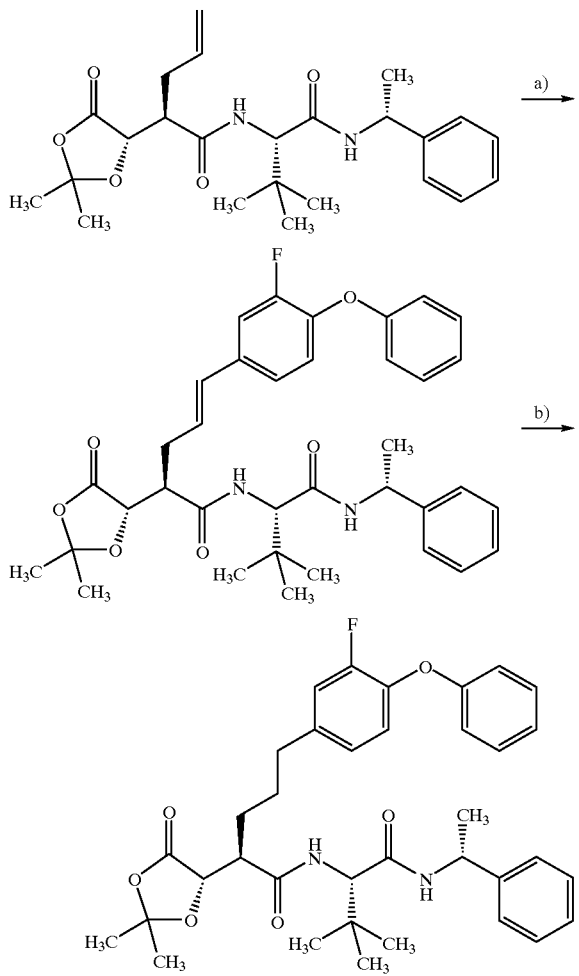

a) A mixture of palladium acetate (17 mg, 0.075 mmol) and tri-(2-methylphenyl)phosphine (46 mg, 0.15 mmol) in anhydrous acetonitrile (2 mL) was sonicated at room temperature for 1 min until a creamy-coloured suspension formed. This suspension was added via Pasteur pipette to a stirred solution of (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (650 mg, 1.5 mmol), 1-bromo-3-fluoro-4-phenoxybenzene (Preparation 10)(587 mg, 2.26 mmol), and N-ethylmorpholine (348 μL, 3.0 mmol) in anhydrous acetonitrile (2.5 mL) under nitrogen. The mixture was purged with nitrogen, then heated at reflux for 16 h. After being cooled, the mixture was poured into ethyl acetate (100 mL) and washed with 5% aqueous citric acid (30 mL), saturated aqueous sodium chloride (50 mL), dried (NaSO₄), and concentrated under reduced pressure. The residue was purified by flash chromatography (gradient elution with dichloromethane:ether) to give mainly (2R, 5E)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]-5-(3-fluoro-4-phenoxyphenyl)pent-4-enamide as a pale yellow foam (210 mg, 22%). ¹H nmr suggested that alkene isomers were also present. The mixture of alkenes was taken onto the next step (see b, below).

$R_f$ 0.36 (dichloromethane:ether=10:1)

$\delta_H$ (400 MHz, CDCl₃)(for the (5E) isomer). 1.00 (9H, s), 1.50 (3H, d, J=7 Hz), 1.53 (3H, s), 1.53 (3H, s), 1.58 (3H, s), 2.65 (1H, m), 2.77 (2H, m), 4.18 (1H, d, J=9 Hz), 4.56 (1H, d, J=5 Hz), 5.03 (1H, pentet, J=7 Hz), 5.88 (1H, br d), 6.01 (1H, dt, 16 and 7 Hz), 6.43 (1H, d, J=16 Hz), 6.58 (1H, br d), 6.94 (4H, m), 7.08 (2H, m), 7.20 (2H, m), 7.24 (5H, complex).

LRMS (thermospray) m/z=618 (MH⁺), 542 (M⁺–(CH₃)₂CO₂).

b) A solution of (2R, 5E)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]-5-(3-fluoro-4-phenoxyphenyl)pent-4-enamide (210 mg, 0.34 mmol) in ethanol:ethyl acetate=5:1 (10 mL) was hydrogenated over 10% palladium on charcoal (20 mg) at 3 bar and 20° C. for 3 h. The mixture was filtered through Arbocel filter aid and concentrated under reduced pressure to give (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]-5-(3-fluoro-4-phenoxyphenyl)pentanamide (103 mg, 49%), as a colourless solid, which was used for Example 9 without purification.

$R_f$ 0.71 (dichloromethane:methanol=90:10)

$\delta_H$ (400 MHz, CDCl₃) 1.03 (9H, s), 1.50 (3H, d, J=7 Hz), 1.52 (3H, s), 1.57 (3s, and 2H m, overlapping), 1.85 (2H, m), 2.58 (3H, m), 4.16 (1H, d, J=10 Hz), 4.45 (1H, d, J=8 Hz), 5.06 (1H, pentet, J=7 Hz), 5.92 (1H, br d), 6.55 (1H, br d,), 6.84 (1H, d, J=8 Hz), 6.94 (3H, m), 7.06 (1H, t, J=7 Hz), 7.26 (8H, complex).

LRMS (thermospray) m/z=619 (MH⁺)

Preparation 16

(2R)-2[(4S)-2,2-Dimethyl-5-oxo-1,3-dioxolan-4-yl]-
N-[(1S)-2,2-dimethyl-1-({[(1R)-1-phenylethyl]
amino}carbonyl)-5-[(3-methyl-4-phenyl)phenyl]
pentanamide

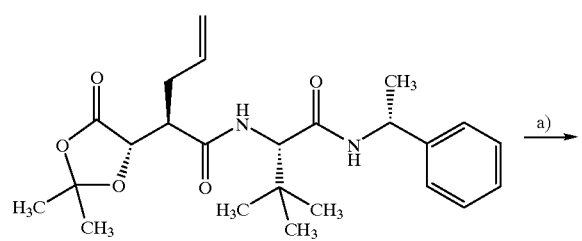

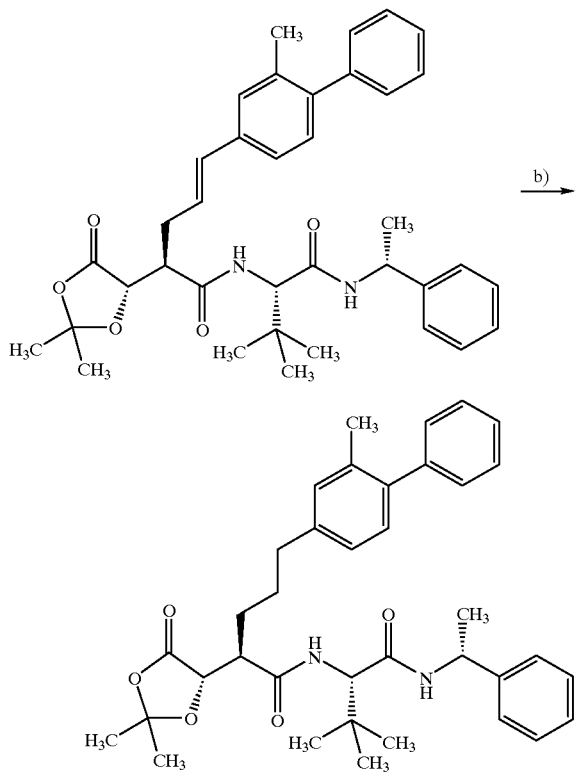

filtered through Arbocel filter aid and concentrated under reduced pressure to give (2R)-2-[(4'S)-2,2-dimethyl-5-oxo-1,3-dioxolan-4-yl]-N-[(1S)-2,2-dimethyl-1-({[(1R)-1-phenylethyl]amino}carbonyl)propyl]-5-[(3-methyl-4-phenyl)phenyl]pentanamide (440 mg, 92%), as a creamy coloured solid, which was used for Example 10 without purification.

$R_f$ 0.53 (dichloromethane:methanol=95:5)

$\delta_H$ (400 MHz, CDCl$_3$) 1.03 (9H, s), 1.50 (3H, d, J=7 Hz), 1.53 (3H, s), 1.58 (3H, s), 1.64 (2H m), 1.87 (2H, m), 2.46 (3H, m), 4.20 (1H, d, J=10Hz), 4.47 (1H, d, J=5 Hz), 5.07 (1H, pentet, J=7 Hz), 5.99 (1H, br d), 6.55 (1H, br d,), 7.00 (1H, d, J=8 Hz), 7.04 (b1H, s), 7.13 (1H, d, J=8 Hz), 7.29 (5H, complex), 7.40 (2H, m).

LRMS (thermospray) m/z=600 (MH$^+$), 523 (base peak, M$^+$–(CH$_3$)$_2$CO$_2$).

Example 37

Preparation 17

(3R)-3-({[(1S)-2,2-Dimethyl-1-({[(1R)-1-phenylethyl]amino}carbonyl)propyl]amino}carbonyl)-6-[(3-fluoro-4-phenyl)phenyl]hexanoic acid

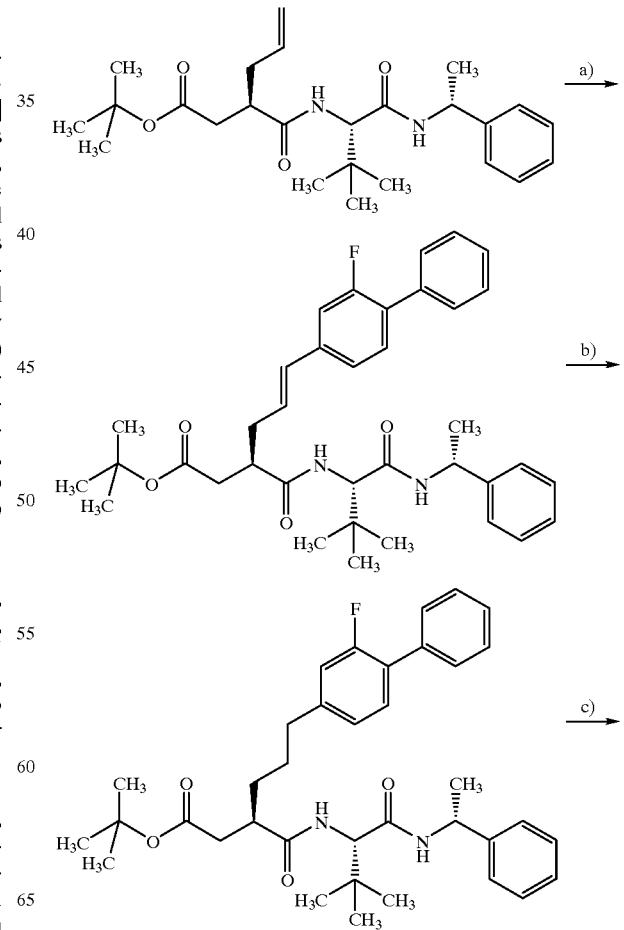

a) According to the method of Preparation 15 a), (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (Preparation 14) (860 mg, 2.0 mmol) was reacted with 1-bromo-3-methyl-4-phenylbenzene (740 mg, 3.0 mmol) under palladium catalysis at reflux in acetonitrile for 16 h. After being cooled, the mixture was partitioned between ethyl acetate (3×50 mL) and saturated aqueous sodium bicarbonate (50 mL). The combined organic solutions were dried (Na$_2$SO$_4$) and concentrated under reduced pressure. The residue was purified by flash chromatography (gradient elution with dichloromethane:methanol=97.5:2.5) to give mainly (2R, 5E)-2-[(4S)-2,2-dimethyl-5-oxo-1,3-dioxolan-4-yl]-N-[(1S)-2,2-dimethyl-1-1-({[(1R)-1-phenylethyl]amino}carbonyl)propyl]-5-[(3-methyl-4-phenyl)phenyl]pent-4-enamide as a buff foam (480 mg, 40%). $^1$H nmr suggested that alkene isomers were also present. The mixture of alkenes was taken onto the next step (see b, below).

$R_f$ 0.59 (dichloromethane:methanol=95:5)

$\delta_H$ (400 MHz, CDCl$_3$)(for the (5E) isomer). 1.03 (9H, s), 1.48 (3H, d, J=7 Hz), 1.54 (3H, s), 1.59 (3H, s), 2.25 (3H, s), 2.71 (1H, dt, J=15 and 7.5 Hz), 2.77 (1H, q, J=6 Hz), 2.85 (1H, dt, J=15 and 7.5 Hz), 4.18 (1H, d, J=9Hz), 4.58 (1H, d, J=5 Hz), 5.03 (1H, pentet, J=7 Hz), 5.87 (1H, br d), 6.13 (1H, dt, 16 and 7 Hz), 6.52 (1H, d, J=16 Hz), 6.58 (1H, br d), 7.23 (10H, complex), 7.38 (3H, m).

LRMS (thermospray) m/z=521 (M$^+$–(CH$_3$)$_2$CO$_2$).

b) A solution of (2R, 5E)-2-[(4S)-2,2-dimethyl-5-oxo-1, 3-dioxolan-4-yl]-N-[(1S)-2,2-dimethyl-1-({[(1R)-1-phenylethyl]amino}carbonyl)propyl]-5-[(3-methyl-4-phenyl)phenyl]pent-4-enamide (480 mg, 0.80 mmol) in ethanol (20 mL) was hydrogenated over 10% palladium on charcoal (48 mg) at 3 bar and 20° C. for 4 h. The mixture was

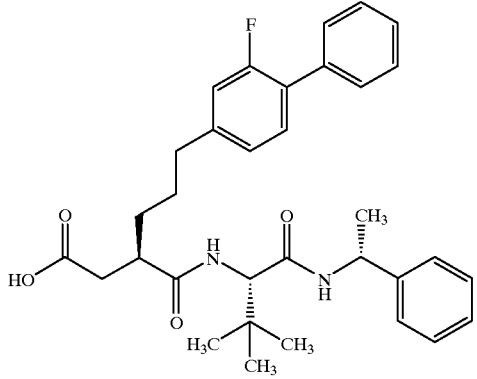

The procedures of Preparation 3 were followed for steps a) (using 1-bromo-3-fluoro-4-phenylbenzene instead of 1-bromo-3-methyl-4-phenylbenzene) and b) to give:

tert-butyl (3R,5E)-3-({[(1S)-2,2-dimethyl-1-({[(1R)-1-phenylethyl]amino}carbonyl)propyl]amino}carbonyl)-6-[3-fluoro-(4-phenyl)phenyl]hex-5-enoate as a colourless gum (997 mg, 83%). $^1$H mnr suggested that two alkene isomers, the (5Z) and (4E) were also present. The mixture of alkenes was taken onto the next step.

$R_f$ 0.23 (hexane:ethyl acetate=3:1)

$\delta_H$ (400 MHz, CDCl$_3$)(for the (5E) isomer). 0.96 (9H, s), 1.39 (9H, s), 1.47 (3H, d, J=6.5 Hz), 2.28 (1H, dt, J=14 and 7 Hz), 2.37 (1H, dd, J=4 and 15 Hz), 2.44 (1H, m), 2.62 (1H, dd, J=8 and 15 Hz), 2.73 (1H, m), 4.16 (1H, d, J=9 Hz), 5.03 (1H, pentet, J=6.5 Hz), 5.88 (1H, br d), 6.06 (1H, dt, J=7.5 and 15 Hz), 6.33 (1H, d, J=15 Hz), 6.48 (1H, br d), 7.06 (2H, m), 7.19 (5H, m), 7.30 (2H, m), 7.39 (2H, t, J=8 Hz), 7.48 (2H, d, J=8 Hz).

LRMS (thermospray) m/z=602 (MH$^+$)

and tert-butyl (3R)-3-({[(1S )-2,2-dimethyl-1-({[(1R)-1-phenylethyl]amino}carbonyl)propyl]amino}carbonyl)-6-[3-fluoro-(4-phenyl)phenyl]hexanoate (702 mg, 72%), as a colourless foam.

$R_f$ 0.28 (hexane:ethyl acetate=3:1)

$\delta_H$ (400 MHz, CDCl$_3$) 1.00 (9H, s), 1.37 (9H, s), 1.46 (3H, d, J=7 Hz), 1.50 (3H, m), 1.61 (1H, m), 2.28 (1H, m), 2.55 (4H, m), 4.16 (1H, d, J=9 Hz), 5.06 (1H, pentet, J=7 Hz), 5.90 (1H, br d), 6.42 (1H, br d), 6.89 (2H, m), 7.22 (7H, complex), 7.40 (2H, t, J=7 Hz), 7.48 (2H, d, J=7 Hz).

LRMS (thermospray) m/z 603 (MH$^+$)

| $C_{37}H_{47}FN_2O_4$ requires | C, 73.66; | H, 7.88; | N, 4.64; |
|---|---|---|---|
| Found: | C, 73.73; | H, 7.86; | N, 4.65% | c) According to the method of Preparation 1, tert-butyl (3R)-3-({[(1S)-2,2-dimethyl-1-({[(1R)-1-phenylethyl]amino}carbonyl)propyl]amino}carbonyl)-6-[3-fluoro-(4-phenyl)phenyl]hexanoate (650 mg, 1.08 mmol) was treated with trifluoroacetic acid at 20° C. for 4 h to give the title compound (470 mg, 80%).

m.p. 165–168° C. (after trituration with diisopropyl ether).

$R_f$ 0.38 (ether:hexane:acetic acid=70:30: 1)

$\delta_H$ (400 MHz, DMSO-d$_6$) 0.87 (9H, s), 1.43 (3H, d, J=7 Hz), 1.42 (4H, m), 2.20 (1H, dd, J=3 and 15 Hz), 2.44 (3H, m), 2.79 (1H, m), 4.27 (1H, d, J=10 Hz), 4.89 (1H, pentet, J=7 Hz), 6.97 (2H, m), 7.16 (5H, complex), 7.32 (2H, m), 7.45 (4H, m), 7.65 (1H, br d), 8.27 (1H, br d), 11.97 (1H, br s).

| $C_{33}H_{39}FN_2O_4$ requires | C, 72.52; | H, 7.24; | N, 5.09; |
|---|---|---|---|
| Found: | C, 72.50; | H, 7.19; | N, 5.12% |

FTIR $v_{max.}$ (KBr disc) 3300, 3070, 3030, 2965, 1710, 1633, 1543, 764, 700 cm$^{-1}$ Preparation 18

Methyl (3R)-3-({[(1S)-2,2-Dimethyl-1-({[(1R)-1-phenylethyl]amino}carbonyl)propyl] amino}carbonyl)-(2,S)-ethoxy-6-[(3-methyl-4-phenyl)phenyl]hexanoate

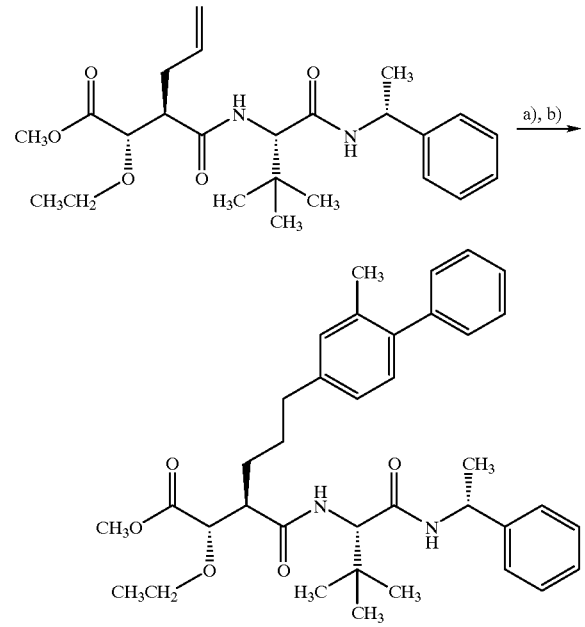

a) According to the method of Preparation 15 a), methyl (2S,3R)-3-({[(1S)-2,2-dimethyl-1-({[(1R)-1-phenylethyl] amino}carbonyl)propyl]amino}carbonyl)-2-ethoxy-hex-5-enoate (Preparation 8a) (396 mg, 0.92 mmol) was reacted with 1-bromo-3-methyl-4-phenylbenzene (340 mg, 1.37 mmol) under palladium catalysis at reflux in acetonitrile for 16 h. After being cooled, the mixture was poured into ethyl acetate (70 mL) and washed with 5% aqueous citric acid (20 mL), saturated aqueous sodium chloride (50 mL), dried (MgSO$_4$), and concentrated under reduced pressure. The residue was purified by flash chromatography (gradient elution with hexane:ethyl acetate) to give mainly methyl (2S,3R,5E)-3-({[(1S)-2,2-dimethyl-1-({[(1R)-1-phenylethyl]amino}carbonyl)propyl]amino}carbonyl)-2-ethoxy-6-[(3-methyl-4-phenyl)phenyl]hex-5-enoate as a pale yellow foam (415 mg, 75%). $^1$H nmr suggested that two alkene isomers, the (5Z) and (4E) were also present. The mixture of alkenes was taken onto the next step (see b, below).

$R_f$ 0.51 (hexane:ethyl acetate=1:1)

$\delta_H$ (400 MHz, CDCl$_3$)(for the (5E) isomer). 1.02 (9H, s), 1.26 (3H, t, J=7 Hz), 1.50 (3H, d, J=7 Hz), 2.24 (3H, s), 2.55 (1H, m), 2.73 (1H, m), 2.82 (1H, m), 3.45 (1H, pentet, J=7

Hz), 3.69 (1H, m and 3H, s, overlapping), 4.11 (1H, d, J=4 Hz), 4.14 (1H, d, J=10 Hz), 5.12 (1H, pentet, J=7 Hz), 6.14 (1H, dt, 16 and 8 Hz), 6.46 (1H, d, J=16 Hz), 6.50 (1H, br, d), 7.24 (11H, complex), 7.40 (3H, m).

b) A solution of methyl (2S,3R,5E)-3-({[(1S)-2,2-dimethyl-1-({[(1R)-1-phenylethyl]amino}carbonyl)propyl]amino}carbonyl)-2-ethoxy-6-[(3-methyl-4-phenyl)phenyl]hex-5-enoate (415 mg, 0.70 mmol) in ethanol (20 mL) was hydrogenated over 10% palladium on charcoal (40 mg) at 3 bar and 20° C. for 2 h. The mixture was filtered through Arbocel filter aid and concentrated under reduced pressure. The residue was dissolved in cyclohexane and evaporated (twice) to give methyl (2S,3R)-3-({[(1S)-2,2-dimethyl-1-({[(1R)-1-phenylethyl]amino}carbonyl)propyl]amino}carbonyl)-2-ethoxy-6-(3-fluoro-4-phenoxyphenyl)hexanoate (384 gm, 91%), as a colourless foam, which was used for Example 12 without purification.

$R_f$ 0.48 (hexane:ethyl acetate=1:1)

$\delta_H$ (400 MHz, CDCl$_3$) 1.01 (9H, s), 1.14 (3H, t, J=7 Hz), 1.49 (3H, d, J=7 Hz), 1.65 (3H, m), 1.80 (1H, m), 2.24 (3H, s), 2.60 (3H, m), 3.40 (1H, dt, J=16 and 8 Hz), 3.62 (1H, m), 3.70 (3H, s), 4.01 (1H, d, J=5 Hz), 4.15 (1H, d, J=9 Hz), 5.13 (1H, pentet, J=7 Hz), 6.41 (1H, br d), 6.92 (1H, d, J 9Hz), 7.00 (1H, d, J=7Hz), 7.03 (1H, s), 7.11 (1H, d, J=7 Hz), 7.29 (7H, complex), 7.40 (3H, m).

LRMS (thermospray) m/z 602 (MH$^+$).

Preparation 19A tert-Butyl(3R)-3-({[(1S)-2,2-dimethyl-1-({[(1S)-2methoxy-1-phenylethyl]amino}carbonyl)propyl]amino}carbonyl)-6-[3-methyl-(4-phenyl)phenyl]-hexanoate

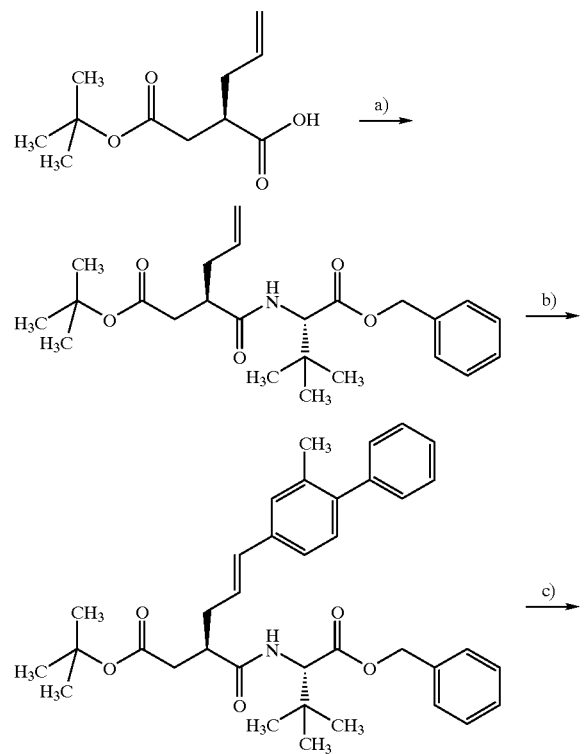

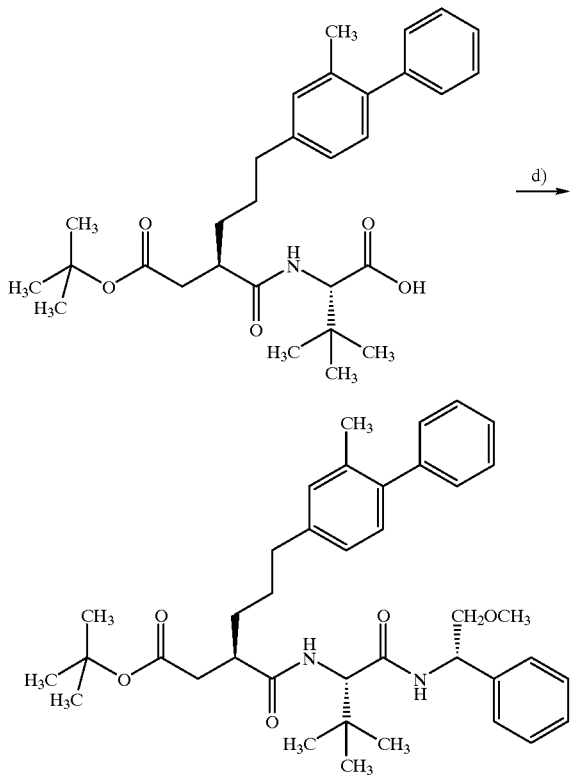

a) N-(Dimethylaminopropyl)-N'-ethylcarbodiimide (2.298 g, 12 mmol) was added to a stirred mixture of (2R)-2-[2-(tert-butoxy)-2-oxoethyl]pent-4-enoic acid (2.13 g, 10 mmol tert-leucine benzyl ester (2.834 g, 11 mmol)(N. Moss et al., J. Med. Chem., 1996, 39, 2178), N-methylmorpholine (2.40 mL, 22 mmol) and 1-hydroxybenzotriazole hydrate (1.836 g, 12 mmol) in anhydrous dichloromethane (50 mL) under nitrogen at 0° C. The mixture was allowed to warm slowly to room temperature with the cooling bath in place. After 20 h, the mixture poured into ethyl acetate (250 mL) and washed with 5% aqueous citric acid (2×100 mL), saturated aqueous sodium bicarbonate (2×70 mL), brine (70 mL), dried (MgSO$_4$), and concentrated under reduced pressure. The residual oil crystallised upon addition of pentane. The solid was filtered and dried to give tert-butyl (3R)-3-({[(1S)-2,2-dimethyl-1-(benzyloxycarbonyl)propyl]amino}carbonyl)hex-5-enoate (4.068 g, 97%), as a colourless solid.

m.p. 55–57° C.

$R_f$ 0.37 (hexane:ethyl acetate=10:1)

$\delta_H$ (300 MHz, CDCl$_3$) 0.95 (9H, s), 1.42 (9H, s), 2.15 (1H, dt, 16 and 6.5 Hz), 2.39 (2H, m), 2.59 (1H, d, J=10 Hz), 2.68 (2H, m), 4.50 (1H, d, J=10 Hz), 5.00 (1H, d, J=10 Hz), 5.04 (1H, d, J=17 Hz), 5.13 (1H, d, J=12 Hz), 5.19 (1H, d, J=12 Hz), 5.71 (1H, m), 6.35 (1H, br d), 7.34 (5H, complex).

LRMS (thermospray) m/z=418 (MH$^+$)

b) By the method of Preparation 3 a), tert-butyl (3R)-3-({[(1S)-2,2-dimethyl-1-(benzyloxycarbonyl)propyl]amino}carbonyl)hex-5-enoate (2.085 g, 5.0 mmol) was reacted with 3-methyl-4-phenylbromobenzene (1.855 g, 7.5 mmol) under palladium catalysis, using N-ethylmorpholine as base at reflux in acetonitrile for 16.5 h. Work-up as before followed by purification by repeated flash chromatography (first column hexane:ether=4:1; second column toluene:ether=20:1) gave mainly tert-butyl (3R,5E)-3-({[(1S)-2,2-dimethyl-1-(benzyloxycarbonyl)propyl]amino}carbonyl)-6-[3-methyl-(4-phenyl)phenyl]hex-5-enoate as a pale yellow gum (2.205 gm, 75%). $^1$H nmr suggested that two alkene isomers, the (5Z) and (4E) were also present. The mixture of alkenes was taken onto the next step (see c, below). $\delta_H$ (400 MHz, CDCl$_3$) 0.95 (9H, s), 1.42 (9H, s), 2.26 (3H, s), 2.35 (1H, m), 2.45 (1H, dd, 3 and 17 Hz), 2.54 (1H, dt, J=15 and 6.5),2.69 (1H, dd, J=9 and 17 Hz), 2.77 (1H, m), 4.52 (1H, d, J=10 Hz), 4.97 (1H, d, J=12 Hz), 5.06 (1H, d, J=12 Hz), 6.16 (1H, dt, J=18 and 7 Hz), 6.42 (2H, m), 7.29 (13H, complex).

c) A solution of tert-butyl (3R,5E)-3-({[(1S)-2,2-dimethyl-1-(benzyloxycarbonyl)propyl]amino}carbonyl)-6-[3-methyl-(4-phenyl)phenyl]hex-5-enoate (2.205 g, 3.78 mmol) in ethanol/water=10:1 (44 mL) was hydrogenated over 10% palladium on charcoal at 3 bar and room temperature for 6 h. The mixture was filtered through Arbocel filter aid, washing well with ethanol. The filtrate was concentrated under reduced pressure. The residue was dissolved in toluene and evaporated (three times), dissolved in ether and evaporated (twice), and finally dissolved in ether and precipitated as an oil by the addition of hexane. Removal of the solvent under reduced pressure gave tert-butyl (3R)-3-({[(1S)-2,2-dimethyl-1-(carboxy)propyl]amino}carbonyl)-6-[3-methyl-(4-phenyl)phenyl]hexanoate (1.817 g, 97%) as a colourless foam, m.p. 51–56° C.

R$_f$ 0.38 (hexane:ether:acetic acid=50:50:1)

$\delta_H$ (400 MHz, DMSO-d$_6$) 0.94 (9H, s), 1.37 (9H, s and 1H, m, overlapping), 1.50 (3H, m), 2.17 (3H, s), 2.23 (1H, m,), 2.39 (1H, dd, J=10 and 15 Hz), 2.53 (2H, m), 2.86 (1H, m), 4.10 (1H, d, J=10 Hz), 7.05 (3H, m), 7.29 (3H, m), 7.40 (2H, t, J=8 Hz), 7.90 (1H, br, d).

LRMS (thermospray) m/z=513 (MNH$_4^+$).

d) 7-Azabenzotriazol-1-yloxytris(pyrrolidino) phosphonium hexafluorophosphate (522 mg, 1.0 mmol) was added to a stirred solution of tert-butyl (3R)-3-({[(1S)-2,2-dimethyl-1-(carboxy)propyl]amino}carbonyl)-6-[3-methyl-(4-phenyl)phenyl]hexoate (496 mg, 1.0 mmol), (1S)-2-methoxy-1-phenylethylamine (151 mg, 1.0 mmol)(J. Amer. Chem. Soc., 1995, 117, 10885) and collidine (267 µL, 2.0 mmol) in anhydrous dichloromethane (5 mL) under nitrogen at 0° C. After 1 h, the solution was stirred at 20° C. for 2.75 h. The mixture was poured into ethyl acetate (70 mL) and washed sequentially with 5% aqueous citric acid (2×50 mL), saturated aqueous sodium bicarbonate (2×50 mL), and brine (50 mL). The organic solution was dried (MgSO$_4$) and concentrated under reduced pressure. The residue was purified by flash chromatography (eluting with hexane:ethyl acetate=3:1) to give tert-butyl (3R)-3-({[(1S)-2,2-dimethyl-1-({[(1s)-2-methoxy-1-phenylethyl]amino}carbonyl)propyl]amino}carbonyl)-6-[3-methyl-(4-phenyl)phenyl]-hexanoate (537 mg, 85%) as a colourless foam.

R$_f$ 0.16 (hexane:ethyl acetate=4:1)

$\delta_H$ (400 MHz, CDCl$_3$) 1.02 (9H, s), 1.40 (9H, s and 1H, m, overlapping), 1.55 (2H, m), 1.68 (1H, m), 2.23 (3H, s), 2.32 (1H, m), 2.55 (4H, m), 3.33 (3H, s), 3.62 (2H, d, J=5 Hz), 4.28 (1H, d, J=9 Hz), 5.12 (1H, dt, J=8 and 5 Hz), 6.35 (1H, br d), 6.44 (1H, br d), 6.96 (1H, d, J=8 Hz), 7.00 (1H, s), 7.10 (1H, d, J=8 Hz), 7.26 (8H, complex), 7.39 (2H, m).

LRMS (thermospray) m/z=630 (MH$^+$)

FTIR $\nu_{max.}$ (KBr disc) 3320, 2930, 1729, 1643, 1543, 1370, 1157 and 700cm$^{-1}$ Preparation 19B tert-Butyl(3R)-3-({[(1S)-2,2-Dimethyl-1-({[(1S)-2methoxy-1-phenylethyl]amino}carbonyl)propyl]amino}carbonyl)-6-(3-methyl-(4-phenyl) phenyl] hexanoate

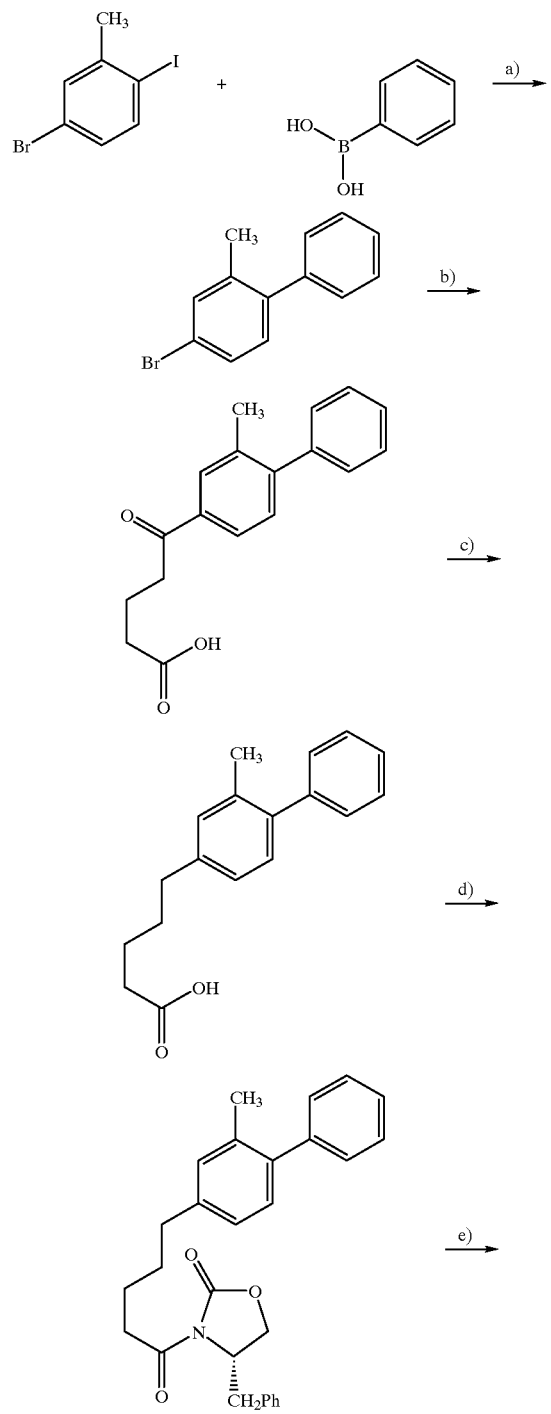

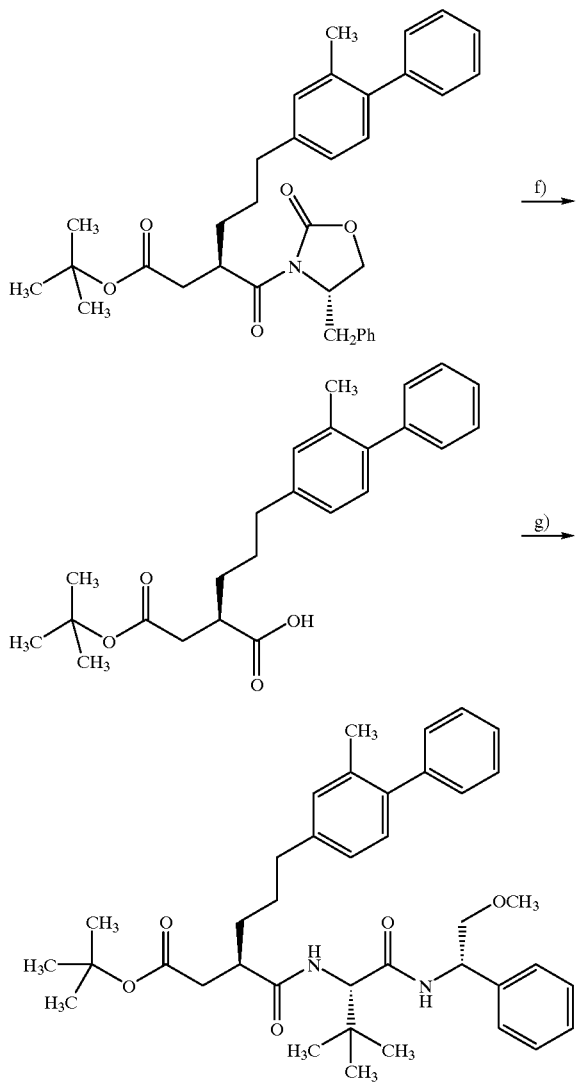

a) An alternative synthesis of 3-methyl-4-phenylbromobenzene is as follows: A mixture of 5-bromo-2-iodo-toluene (5.01 g, 16.9 mmol), phenylboronic acid (2.26 g, 18.5 mmol), palladium acetate (190 mg, 0.85 mmol), triphenylphosphine (440 mg, 1.68 mmol) and 2M aqueous sodium carbonate (25 mL) in acetone (60 mL) was degassed and heated at reflux under nitrogen for 18 h. The mixture was cooled and partitioned between ether (200 mL) and water (100 mL). The organic layer was washed with brine (100 mL), dried (MgSO₄) and concentrated under reduced pressure to give a yellow oil. Purification by flash chromatography (eluting with hexane) gave 3-methyl4-phenylbromobenzene (3.298 g, 79%).

b) A solution of 3-methyl-4-phenylbromobenzene (12.36 g, 50.0 mmol) in anhydrous tetrahydrofuran (30 mL) was added dropwise at reflux to a suspension of magnesium turnings (1.33 g, 50 mmol) in anhydrous tetrahydrofuran (23 mL) containing a crystal of iodine under nitrogen with mechanical stirring. After the addition was complete the mixture was diluted with anhydrous tetrahydroflran (55 mL) and heating continued for 1 h. The arylmagnesium bromide solution was allowed to cool to room temperature, and then added dropwise via syringe to a solution of glutaric anhydride (6.27 g, 55 mmol) in anhydrous tetrahydrofuran (125 mL) under nitrogen at −40° C. After 90 min at −40° C., the mixture was allowed to warm to 0° C., and hydrochloric acid (1M, 250 mL) was added. The mixture was extracted with ether (500 mL), washed with brine (200 mL), dried (MgSO₄) and concentrated under reduced pressure. The residue was purified by flash chromatography (eluting with dichoromethane:methanol=95:5) to give 5-(3-methyl-4-phenyl)phenyl-5-oxopentanoic acid as a pale brown oil, (8.6 g, 60%) which subsequently crystallised. m.p. 91–94° C.

R$_f$ 0.26 (dichoromethane:methanol=95:5)

δ$_H$ (400 MHz, CDCl₃) 2.11 (2H, pentet, J=7 Hz), 2.33 (3H, s), 2.50 (2H, t, J=7 Hz), 3.11 (2H, t, J=7 Hz), 7.31 (3H, m), 7.42 (3H, m), 7.84 (1H, d, J=8 Hz), 7.90 (1H, s).

LRMS (thermospray) m/z=283 (MH⁺).

| Found: | C, 76.49; | H, 6.48; |
|---|---|---|
| C₁₈H₁₈O₃ requires | C, 76.57; | H, 6.43% | c) Triethylsilane (1.4 mL, 8.75 mmol) was added dropwise over 2 min to a stirred solution of 5-(3-methyl-4-phenyl)phenyl-5-oxopentanoic acid (1.0 g, 3.5 mmol) in trifluoroacetic acid (5 mL) under nitrogen at 0° C. The mixture was then allowed to warm to room temperature and stirred for 2 h. The mixture was poured into water (20 mL) and extracted with dichloromethane (3×15 mL). The combined organic solutions were washed with brine, dried (MgSO₄) and concentrated under reduced pressure. The mixture was purified by flash chromatography (eluting with dichloromethane:methanol=95:5) to give a 3:1 mixture of [5-(3-methyl-4-phenyl)phenyl]pentanoic acid and triethylsilanol (1.1 g). This material was dissolved in hexane (5 mL) and sodium hydrogen carbonate (290 mg, 3.5 mmol) was added. The mixture was stirred overnight at room temperature, and then concentrated under reduced pressure. The solid residue was triturated with ethyl acetate and filtered to give sodium [5-(3-methyl-4-phenyl)phenyl] pentanoate (820 mg, 80%). Treatment of this material with hydrochloric acid and solvent extraction gave the free acid as a viscous, colourless gum.

δ$_H$ (400 MHz, CDCl₃) 1.74 (4H, m), 2.27 (3H, s), 2.43 (2H, m), 2.65 (2H, m), 7.06 (1H, d, J=8 Hz), 7.11 (1H, s), 7.16 (1H, d, J=8 Hz), 7.33 (3H, m), 7.42 (2H, m).

LRMS (thermospray) m/z=286 (MNH₄⁺).

| Found: | C, 80.40; | H, 7.59; |
|---|---|---|
| C₁₈H₂₀O₂ requires | C, 80.56; | H, 7.51% | d) Oxalyl chloride (3.1 mL, 35.5 mmol) was added dropwise to a stirred solution of [5-(3-methyl-4-phenyl)phenyl]pentanoic acid (6.80 g, 25.3 mmol) in anhydrous dichloromethane (60 mL) under nitrogen at −10° C. Dimethylformamide (2 drops) was added, and after 10 min the mixture was allowed to warm to room temperature. After 5 h, the solution was concentrated under reduced pressure, and the residue dissolved in anhydrous toluene and concentrated under reduced pressure (twice). The residue was dissolved in hexane (150 mL), allowed to stand for 17 h, then filtered through Arbocel filter aid, washing the filter cake with more hexane. The filtrate was concentrated under reduced pressure to give 5-[(3-methyl-4-phenyl)phenyl]pentanoyl chloride (7.1 g, 97%).

δ$_H$ (400 MHz, CDCl$_3$) 1.77 (4H, m), 2.26 (3H, s), 2.63 (2H, t, J=6.5 Hz), 2.95 (2H, t, J=6.5 Hz), 7.06 (1H, d, J=8 Hz), 7.10 (1H, s), 7.36 (5H, m).

A solution of n-butyllithium (9.92 mL, 2.5M in hexanes, 24.8 mmol) was added dropwise over 15 min to a solution of 4-(S)-benzyloxazolidin-2-one (4.39 g, 24.8 mmol) in anhydrous tetrahydrofuran (70 mL) under nitrogen at −70° C. The mixture was allowed to warm to −50° C. for 30 min, then re-cooled to −70° C. A solution of [5-(3-methyl-4-phenyl)phenyl]pentanoyl chloride (7.1 g, 24.8 mmol) in anhydrous tetrahydrofuran (10 mL) was added dropwise over 15 min. After 1 h, the mixture was allowed to warm to 0° C. whereupon 20% aqueous ammonium chloride (75 mL) was added rapidly. After being stirred for 15 min, the mixture was extracted with ethyl acetate (250 mL), and the organic phase washed with water (3×250 mL), dried (MgSO$_4$), and concentrated under reduced pressure. The residue was purified by flash chromatography (gradient elution with pentane:ethyl acetate=20:1 to 2:1) to give 4-(S)-benzyl-3-{[5-(3-methyl-4-phenyl)phenyl]pentanoyl}oxazolidin-2-one (9.66 g, 91%) as a colourless oil.

R$_f$ 0.4 (pentane:ethyl acetate=3:1)

δ$_H$ (300 MHz, CDCl$_3$) 1.79 (4H, m), 2.28 (3H, s), 2.70 (2H, m), 2.79 (1H, dd, J=10 and 13 Hz), 3.01 (2H, m), 3.32 (1H, dd, J=3 and 13 Hz), 4.19 (2H, m), 4.70 (1H, m), 7.06–7.43 (13H, complex).

LRMS (thermospray) m/z=445 (MNH$_4^+$).

FTIR (KBr disc) 2930, 1784, 1700, 1387, 1350, 1211, 702 cm$^{-1}$.

| Found: | C, 75.43; | H, 6.65; | N, 3.08 |
|---|---|---|---|
| C$_{28}$H$_{29}$NO$_3$.0.3CH$_2$Cl$_2$ requires | C, 75.03; | H, 6.59; | N, 3.09% | e) A solution of sodium hexamethyldisilazide (31.3 mL, 1M in tetrahydrofuran, 31.3 mmol) was added dropwise over 30 min to a stirred solution of 4-(S)-benzyl-3-{[5-(3-methyl-4-phenyl)phenyl]pentanoyl}oxazolidin-2-one (13.39 g, 31.3 mmol) in anhydrous tetrahydrofuran (100 mL) at −75° C. After 1 h, a solution of tert-butyl bromoacetate (4.95 mL, 33.5 mmol) in anhydrous tetrahydrofuran (10 mL) was added dropwise over 20 min, keeping the temperature below −70° C. The mixture was stirred at this temperature for 2 h, then allowed to warm to −50° C. at which point 20% aqueous ammonium chloride (150 mL) was added with rapid stirring. The mixture was allowed to warm to 10° C., and then poured into a mixture of ethyl acetate (400 mL) and water (200 mL). The organic phase was separated, washed with water (3×250 mL), dried (MgSO$_4$) and concentrated under reduced pressure. The residue was purified by flash chromatography (gradient elution with pentane:ether=20:1 to 1:1) to give tert-butyl (3R)-3-[(4-(S)-4-benzyl-2-oxo-1,3-oxazolidin-3-yl)carbonyl]-6-(3-methyl-4-phenyl)phenyl)hexanoate as a colourless oil (10.4 g, 61%).

R$_f$ 0.6 (pentane:ether=1:1)

δ$_H$ (300 MHz, CDCl$_3$) 1.45 (9H, s), 1.58 (1H, m), 1.74 (3H, m), 2.27 (3H, s), 2.51 (1H, dd, J=5 and 18 Hz), 2.65 (2H, m), 2.80 (2H, m), 3.38 (1H, dd, J=3 and 15 Hz), 4.16 (2H, d, J=5 Hz), 4.25 (1H, m), 4.68 (1H, m), 7.04 (1H, d, J=8 Hz), 7.08 (1H, s), 7.14 (1H, d, J=8 Hz), 7.35 (10H, complex).

LRMS (thermospray) m/z=542 (MH$^+$), 560 (MNH$_4^+$).

| Found: | C, 74.55; | H, 7.40; | N, 2.44 |
|---|---|---|---|
| C$_{34}$H$_{39}$NO$_5$.0.1ether.0.2EtOAc requires | C, 74.60; | H, 7.40; | N, 2.47% |

FTIR ν$_{max.}$ (KBr disc) 2980, 2930, 1780, 1725, 1700, 1388, 1350, 1157, 768, 702 cm$^{-1}$.

f) 30% Aqueous hydrogen peroxide (12.75 ml, 114 mmol) was added dropwise to a solution of tert-butyl (3R)-3-[(4-benzyl-2oxo-1,3-oxazolidin-3-yl)carbonyl]-6-(3-methyl-4-phenyl)phenyl)hexanoate (10.3 g, 19.0 mmol) in tetrahydrofuran:water (3:1, 400 mL) at 0° C. Then lithium hydroxide monohydrate (1.595 g, 38.0 mmol) was added in one portion. The mixture was stirred for 2 h at 0° C. and 1 h at 20° C. the reaction mixture was re-cooled to 0° C. and a solution of sodium sulphite (15.56 g, 123.5 mmol) in water (80 mL) was added dropwise over 15 min. The mixture was stirred rapidly at 0° C. for 2.5 h, then 2M hydrochloric acid (ca. 8 mL) was added to adjust the pH to 6. The mixture was concentrated under reduced pressure to half volume, acidified to pH 2 by the addition of 2M hydrochloric acid, and extracted with dichloromethane (400 mL and 2×200 mL). The combined extracts were dried (MgSO$_4$), concentrated under reduced pressure and the residue purified by flash chromatography (gradient elution with pentane:ether=15:1 to 1:4) to give tert-butyl (3R)-3-(carboxy)-6-(3-methyl-4-phenyl)phenyl)hexanoate (7.05 g, 97%) as a colourless oil.

Rf 0.5 (pentane:ether:acetic acid=30:70:1)

δ$_H$ (300 MHz, CDCl$_3$) 1.45 (9H, s), 1.63 (1H, m), 1.77 (4H, m), 2.26 (3H, m), 2.42 (dd, J=5 and 17 Hz), 2.65 (3H, m), 2.87 (1H, m), 7.06 (2H, m), 7.15 (1H, d, J=8 Hz), 7.34 (5H, m).

LRMS (thermospray) m/z=400 (MNH$_4^+$).

[α]$_D$=+12.9° C.(c=0.716, methanol, 25° C.)

FTIR ν$_{max.}$ (film) 2980, 2930, 1730, 1705, 1485, 1368, 1157, 764, 702 cm$^{-1}$.

| Found: | C, 74.96; | H, 8.06; |
|---|---|---|
| C$_{24}$H$_{30}$O$_4$.0.1H$_2$O requires | C, 75.01; | H, 7.92% | g) N-(Dimethylaminopropyl)-N'-ethylcarbodiimide hydrochloride (3.50 g, 1826 mmol) was added to a stirred mixture of (2S)-amino-3,3-dimethyl-N-[(1S)-2-methoxy-1-phenylethyl]butanamide hydrochloride (Preparation 1a) (6.78 g, 17.43 mmol—contains 1 mol. equiv. dioxane), tert-butyl (3R)-3-(carboxy)-6-(3-methyl-4-phenyl)phenyl) hexanoate (6.35 g, 16.6 mmol), 1-hydroxy-1,2,3-benzotriazole hydrate (2.80 g, 20.75 mmol) and diisopropylethylamine (5.9 mL, 34.03 mmol) in anhydrous dichloromethane (82 mL) under nitrogen at 4° C. After 2 h, the mixture was allowed to warm to room temperature. After 17 h at room temperature, the mixture was poured into ethyl acetate (600 mL) and washed sequentially with 5% aqueous citric acid (2×250 mL), saturated aqueous sodium bicarbonate (2×250 mL), brine (200 mL), dried (MgSO$_4$), and concentrated under reduced pressure. The residue was redissolved in ether and evaporated to give tert-butyl (3R)-3-({[(1S)-2,2-dimethyl-1-({[(1S)-2-methoxy-1-phenylethyl]amino}carbonyl)propyl]amino}carbonyl)-6-[3-methyl-(4-phenyl)phenyl]-hexanoate (10.35 g, 99%), as a colourless foam.

| | | | |
|---|---|---|---|
| Found: | C, 73.99; | H, 8.31; | N, 4.51 |
| $C_{39}H_{52}N_2O_5 \cdot 0.04$EtOAc requires | C, 74.38; | H, 8.34; | N, 4.43% |

Preparation 20

4-Iodo-1-(3-methoxyphenyl)-2methylbenzene

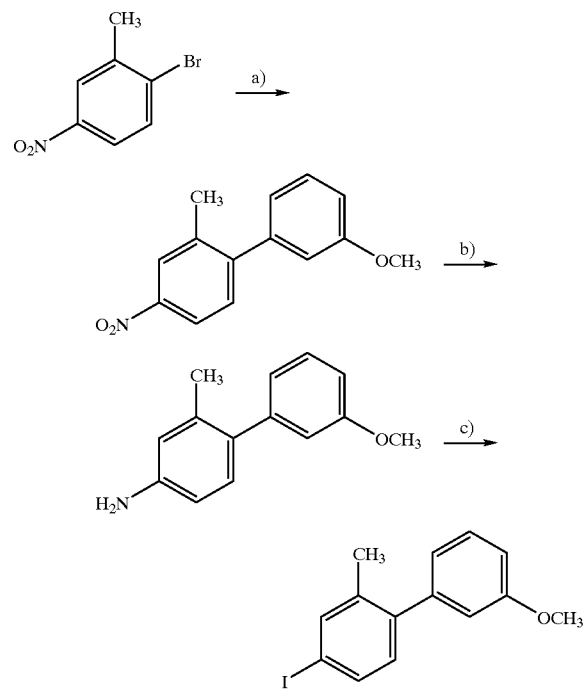

a) A solution of 2-bromo-5-nitrotoluene (40.0 gm, 185 mmol) in 1,2-dimethoxyethane (600 mL) was added to tetrakis(triphenylphosphine)palladium(0) (9.77 gm, 9.25 mmol) under nitrogen at room temperature. A solution of 3-methoxyphenylboronic acid (31.5 gm, 207 mmol) in ethanol (150 mL) was added. Finally, 2M aqueous sodium carbonate (800 mL) was added and the mixture was heated under reflux with rapid mechanical stirring for 18 h. After being cooled, the mixture was partitioned between ethyl acetate and water and the organic phase was dried ($Na_2SO_4$) and concentrated under reduced pressure. Purification by column chromatography on silica gel eluting with hexane:ethyl acetate=98:2 then 95:5 gave 1-(3-methoxyphenyl)-2-methyl-4-nitrobenzene (40.55 gm, 90%).

$R_f$ 0.22 (hexane:ethyl acetate=95:5)

$\delta_H$ (400 MHz, $CDCl_3$) 2.38 (3H, s), 3.85 (3H, s), 6.83 (1H, s), 6.88 (1H, d, J=8 Hz), 6.96 (1H, d, J=8 Hz), 7.38 (2H, m), 8.02 (1H, d, J=8 Hz), 8.14 (1H, s).

LRMS (thermospray) m/z=261 ($MNH_4^+$)

b) 1-(3-Methoxyphenyl)-2-methyl-4-nitrobenzene(23.4 gm, 96 mmol) was dissolved in a mixture of ethanol and ethyl acetate (3:1, 470 mL) and hydrogenated over 10% palladium on charcoal (2.3 gm) at 3 bar and 20° C. for 2 h. The mixture was filtered through Arbocel filter aid, washing with ethyl acetate. The filtrate was concentrated under reduced pressure to give 4-amino-1-(3-methoxyphenyl)-2-methylbenzene (20.8 gm, 100%) as a pinkish-brown oil.

$R_f$ 0.06 (hexane:ethyl acetate=90:10) $\delta_H$ (400 MHz, $CDCl_3$) 2.22 (3H, s), 3.65 (2H, br s), 3.84 (3H, s), 6.59 (2H, m), 6.87 (3H, m), 7.04 (1H, d, J=8 Hz), 7.28 (1H, m).

c) A stirred solution of 4-amino-1-(3-methoxyphenyl)-2-methylbenzene (5.0 gm 23.4 mmol) and iodine (2.97 gm, 25.8 mmol) in toluene (120 mL) was heated to 50° C. and a solution of iso-amyl nitrite (3.46 mL, 25.8 mmol) in toluene (50 mL) was added. The mixture was heated at 90° C. for 2 h and cooled. The toluene was removed under reduced pressure and the residue was dissolved in dichloromethane and washed with excess 5% aqueous sodium metabisulphite to remove iodine. The organic solution was dried ($Na_2SO_4$) and concentrated under reduced pressure. The residue was purified by repeated flash chromatography (first column gradient elution with hexane:ethyl acetate starting with neat hexane; second column eluted with hexane) to give 4-iodo-1-(3-methoxyphenyl)-2-methylbenzene as a pale orange oil (5.63 gm, 74%).

$R_f$ 0.49 (hexane:ethyl acetate=90:10)

$\delta_H$ (400 MHz, $CDCl_3$) 2.23 (3H, s), 3.84 (3H, s), 6.81 (1H, s), 6.86 (1H, d, J=8 Hz), 6.90 (1H, d, J=8 Hz), 6.95 (1H, d, J=8 Hz), 7.32 (1H, t, J=8 Hz), 7.55 (1H, d, J=8 Hz), 7.47 (1H, s).

Preparation 21 tert-Butyl(3R)-3-({[(1S)-2,2-Dimethyl-1-({[(1S)-2methoxy-1-phenylethyl]amino}carbonyl)propyl]amino}carbonyl)-6-(3'-methoxy-2methylbiphen-4-yl)hexanoate

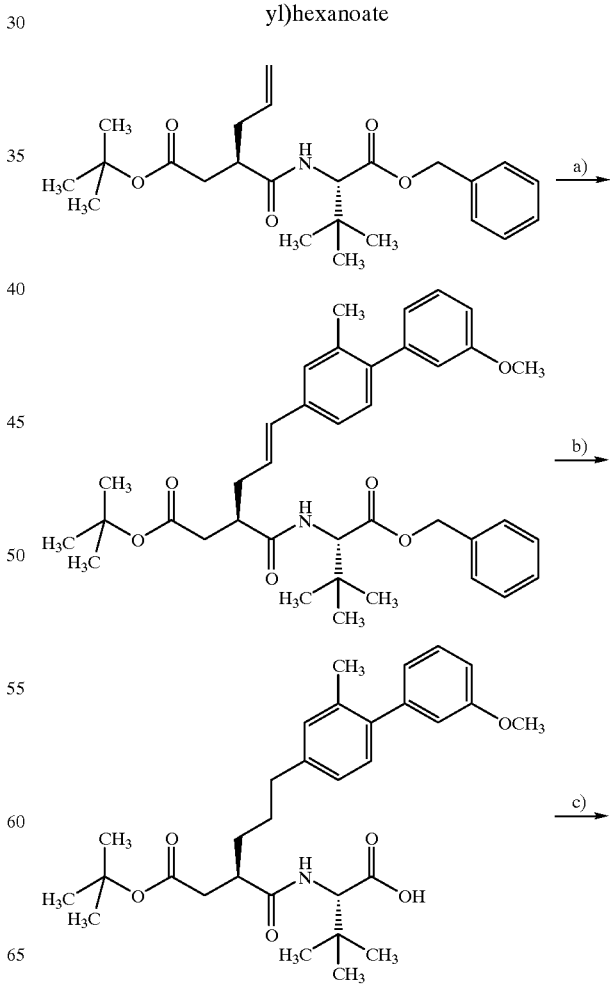

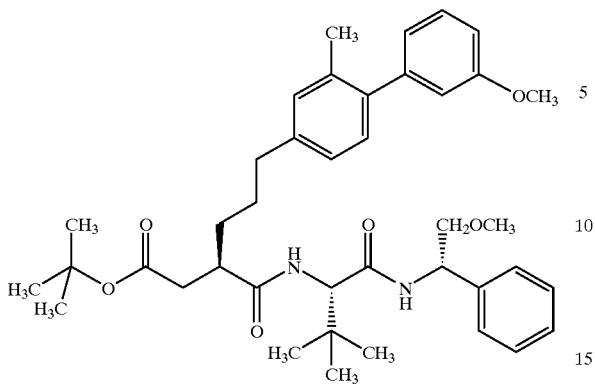

a) By the method of Preparation 3 a), tert-butyl (3R)-3-({[(1S)-2,2-dimethyl-1-(benzyloxycarbonyl)propyl]amino}carbonyl)hex-5-enoate (2.085 g, 5.0 mmol) was reacted with 4-iodo-1-(3-methoxyphenyl)-2-methylbenzene (Preparation 20) (889 mg, 2.13 mmol) under palladium catalysis, using N-ethylmorpholine as base at reflux in acetonitrile for 14.5 h. Work-up as before followed by purification by flash chromatography (hexane:ethyl acetate= 10:1) gave mainly tert-butyl (3R,5E)-3-({[(1S)-2,2-dimethyl-1-(benzyloxycarbonyl)propyl]amino}carbonyl)-6-(3'-methoxy-2-methylbiphen-4-yl)hex-5-enoate as a pale yellow gum (1.043 gm, 80%). $^1$H nmr suggested that two alkene isomers, the (5Z) and (4E) were also present. The mixture of alkenes was taken onto the next step (see b, below).

$\delta_H$ (400 MHz, CDCl$_3$) 0.95 (9H, s), 1.43 (9H, s), 2.26 (3H, s), 2.36 (1H, m), 2.45 (1H, dd, 3 and 17 Hz), 2.55 (1H, dt, J=14 and 7), 2.68 (1H, dd, J=9 and 17 Hz), 2.77 (1H, m), 3.80 (3H, s), 4.50 (1H, d, J=10 Hz), 4.97 (1H, d, J=12 Hz), 5.07 (1H, d, J=12 Hz), 6.16 (1H, dt, J=18 and 7 Hz), 6.40 (2H, m), 6.85 (3H, m), 7.30 (9H, complex).

LRMS (thermospray) m/z=614 (MH$^+$)

b) According to the method of Preparation 19 c), tert-butyl (3R,5E)-3-({[(1S)-2,2-dimethyl-1-(benzyloxycarbonyl)propyl]amino}carbonyl)-6-(3'-methoxy-2-methylbiphen-4-yl]hex-5-enoate (1.040 g, 1.69 mmol) was hydrogenated over 10% palladium on charcoal to give tert-butyl (3R)-3-({[(1S)-2,2-dimethyl-1-(carboxy)propyl]amino}carbonyl)-6-(3'-methoxy-2-methylbiphen-4-yl)hexanoate (664 g, 75%) as a colourless foam.

R$_f$ 0.33 (hexane:ether:acetic acid=50:50:1)

$\delta_H$ (400 MHz, CDCl$_3$) 1.02 (9H, s), 1.42 (9H, s), 1.47 (1H, m), 1.66 (2H, m), 1.77 (1H, m), 2.25 (3H, s), 2.37 (1H, m,), 2.63 (3H, m), 3.83 (3H, s), 4.48 (1H, d, J=10 Hz), 6.43 (1H, br d), 6.87 (3H, m), 7.03 (2H, m), 7.13 (1H, d, J=8 Hz), 7.28 (1H,m).

LRMS (thermospray) m/z=526 (MH$^+$)

c) According to the procedure of Preparation 19 d), tert-butyl (3R)-3-({[(1S)-2,2-dimethyl-1-(carboxy)propyl]amino}carbonyl)-6-(3'-methoxy-2-methylbiphen-4-yl)hexanoate (660 mg, 1.26 mmol) was reacted with (1S)-2-methoxy-1-phenylethylamine (190 mg, 1.260 mmol). Work-up as above, followed by flash chromatography (eluting with hexane:ethyl acetate=3:1) to give tert-butyl (3R)-3-({[(1S)-2,2-dimethyl-1-({[(1s)-2-methoxy-1-phenylethyl]amino}carbonyl)propyl]amino}carbonyl)-6-(3'-methoxy-2-methylbiphen-4-yl)hexanoate (672 mg, 81%) as a colourless foam.

R$_f$ 0.16 (hexane:ethyl acetate=4:1)

$\delta_H$ (400 MHz, CDCl$_3$) 1.02 (9H, s), 1.40 (9H, s and 1H, m, overlapping), 1.55 (2H, m), 1.68 (1H, m), 2.23 (3H, s), 2.33 (1H, m), 2.56 (4H, m), 3.33 (3H, s), 3.63 (2H, m), 3.82 (3H, s), 4.29 (1H, d, J=9 Hz), 5.13 (1H, dt, J=8 and 5 Hz), 6.35 (1H, br d), 6.45 (1H, br d), 6.86 (3H, m), 6.96 (1H, d, J=8 Hz), 7.00 (1H, s), 7.10 (1H, d, J=8 Hz), 7.26 (6H, complex).

LRMS (thermospray) m/z=659 (MH$^+$)

| Found: | C, 72.15; | H, 8.21; | N, 4.17; |
| C$_{40}$H$_{54}$N$_2$O$_6$.½H$_2$O requires | C, 71.93; | H, 8.30; | N, 4.19% |

Preparation 22

(2R)-5-{[4-(4-Cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide.

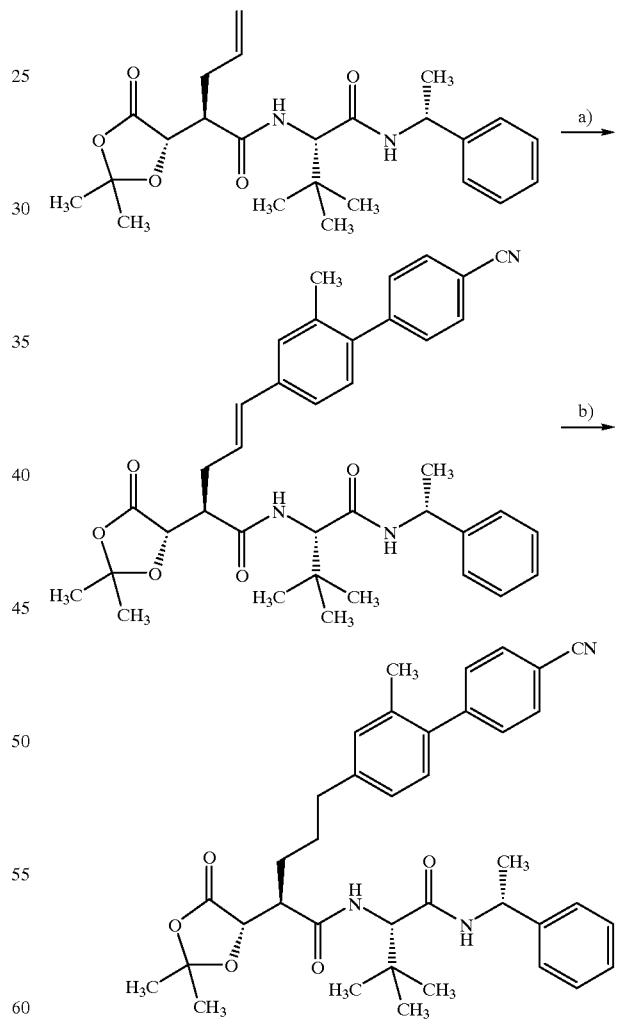

a) According to the method of Preparation 15 a), (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (Preparation 14) (430 mg, 1.0 mmol) was reacted with 1-(4-cyanophenyl)-4-iodo-2-methylbenzene

105

(Preparation 23)(479 mg, 1.5 mmol) under palladium catalysis at reflux in acetonitrile for 16 h. After being cooled, the mixture was partitioned between ethyl acetate (3×30 mL) and saturated aqueous sodium bicarbonate (30 mL). The combined organic solutions were dried (Na$_2$SO$_4$) and concentrated under reduced pressure. The residue was purified by flash chromatography (eluting with dichloromethane:methanol=97.5:2.5) to give mainly (2R, 4E)-5-{[4-(4-cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide as a buff foam (403 mg, 65%). $^1$H nmr suggested that alkene isomers were also present. The mixture of alkenes was taken onto the next step (see b, below).

R$_f$ 0.41 (dichloromethane:methanol=95:5)

$\delta_H$ (400 MHz, CDCl$_3$)(for the (4E) isomer). 1.00 (9H, s), 1.46 (3H, d, J=7.5 Hz), 1.54 (3H, s), 1.59 (3H, s), 2.20 (3H, s), 2.70 (1H, m), 2.81 (2H, m), 4.20 (1H, d, J=9 Hz), 4.60 (1H, d, J=4.5 Hz), 5.04 (1H, pentet, J=7.5 Hz), 5.82 (1H, d, J=7.5 Hz), 6.62 (1H, dt, 16 and 7 Hz), 6.50 (1H, d, J=16 Hz), 6.58 (1H, d, J=9 Hz), 7.10 (1H, d, J=8 Hz), 7.15–7.30 (7H, m), 7.38 (2H, d, J=8 Hz), 7.70 (2H, d, J=8 Hz).

LRMS (thermospray) m/z=564 (MH$^+$–acetone), 547.

b) A solution of (2R, 4E)-5-{[4-(4-cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (403 mg, 0.65 mmol) in ethanol (70 mL) was hydrogenated over 10% palladium on charcoal (40 mg) at 3 bar and 20° C. for 5.5 h. The mixture was filtered through Arbocel filter aid and concentrated under reduced pressure to give (2R)-5-{[4-(4-cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide (384 mg, 61%), as a colourless solid, which was used for Example 17 without purification.

$\delta_H$ (400 MHz, CDCl$_3$) 1.00 (9H, s), 1.48 (3H, d, J=7 Hz), 1.50 (3H, s), 1.55 (3H, s), 1.62 (2H, m), 1.68 (2H, m), 2.20 (3H, s), 2.60 (3H, m), 4.18 (1H, d, J=9.5 Hz), 4.45 (1H, d, J=6 Hz), 5.08 (1H, pentet, J=7 Hz), 5.86 (1H, d, J=7 Hz), 6.50 (1H, d, J=9.5 Hz), 7.00–7.10 (3H, m), 7.15–7.30 (5H, m), 7.40 (2H, d, J=7.5 Hz), 7.70 (2H, d, J=7.5 Hz).

LRMS (thermospray) m/z=624 (MH$^+$), 641 (MNH$_4^+$).

Preparation 23

1-(4-Cyanophenyl)-4-iodo-2methylbenzene.

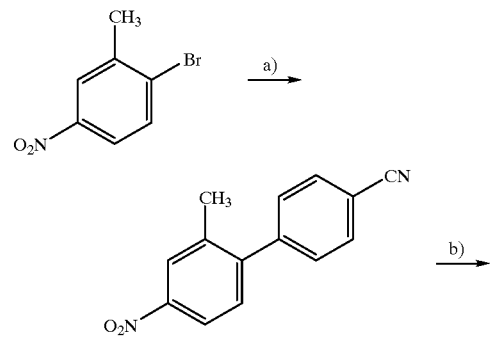

106

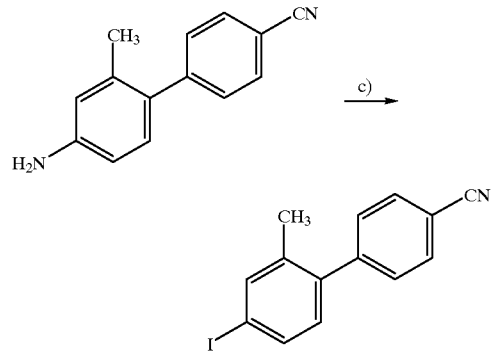

a) A mixture of 2-bromo-5-nitrotoluene (7.05 gm, 32.67 mmol), 4-cyanophenylboronic acid (Tet. Lett., 1993, 34, 8237)(6.0 gm, 40.83 mmol), caesium fluoride (11.02 gm, 72.53 mmol) and tri-(2-methylphenyl)phosphine (1.0 gm, 3.27 mmol) in 1,2-dimethoxyethane (240 mL) were stirred under an atmosphere of nitrogen at room temperature for 40 mins. Tris(dibenzylideneacetone)dipalladiumn (1.50 gm, 1.63 mmol) was added and stirred for 10 mins at room temperature, then heated at 80° C. for 4 h. After being cooled, the mixture was partitioned between ethyl acetate and saturated aqueous sodium bicarbonate. The organic phase was separated, washed with water, then dried (Na$_2$SO$_4$) and concentrated under reduced pressure to give crude 1-(4-cyanophenyl)-2-methyl-4-nitrobenzene (9.78 gm) which was used without further purification.

R$_f$ 0.89 (dichloromethane)

$\delta$H(300 MHz, CDCl$_3$) 2.35 (3H, s), 7.35 (1H, d, J=8 Hz), 7.45 (2H, d, J=8 Hz), 7.68 (2H, d, J=8 Hz), 8.10 (1H, d, J=8 Hz), 8.18 (1H, s).

b) 1-(4-Cyanophenyl)-2-methyl-4-nitrobenzene (9.7 gm, 40.76 mmol) was dissolved in a mixture of methanol and dichloromethane (1:1, 400 mL) and hydrogenated over 10% palladium on charcoal (970 mg) at 3 bar and 20° C. for 18 h. The mixture was filtered through Arbocel filter aid and concentrated under reduced pressure. The residue was purified by flash chromatography (gradient elution with hexane-:ethyl acetate 20:1 to 1:1) to give 4-amino-1-(4-cyanophenyl)-2-methylbenzene (2.5 gm, 30%) as a brown oil.

R$_f$ 0.20 (hexane:ethyl acetate=3:1)

$\delta_H$ (400 MHz, CDCl$_3$) 2.20 (3H, s), 3.75 (2H, br s), 6.60 (2H, m), 7.00 (1H, d, J=8 Hz), 7.40 (2H, d, J=8 Hz), 7.66 (2H, d, J=8 Hz).

LRMS (thermospray) m/z=226 (MNH$_4^+$).

c) A suspension of 4-amino-1-(4-cyanophenyl)-2-methylbenzene (250 mg 1.2 mmol) in conc. hydrochloric acid (1.3 mL) and water (1.6 mL) at 0° C., was treated with a solution of sodium nitrite (183 mg, 2.65 mmol) in water (1 mL) over 10 mins. The mixture was stirred for 20 mins and then a solution of potassium iodide (840 mg, 5.06 mmol) in water (2 mL) was added, over 10 mins. The resultant mixture was heated at 90° C. for 2 h, then cooled. The residue was extracted with dichloromethane (3×30 mL) and the combined organic extracts were washed with 5% aqueous sodium metabisulphite (4×30 mL), to remove iodine. The organic solution was dried (Na$_2$SO$_4$) and concentrated under reduced pressure. The residue was purified by flash chromatography (gradient elution with hexane:ethyl acetate 20:1 to 10:1) to give 1-(4-cyanophenyl)-4-iodo-2-methylbenzene as a white solid (263 mg, 69%).

$R_f$ 0.62 (hexane:ethyl acetate=4:1)

$\delta_H$ (300 MHz, CDCl$_3$) 2.20 (3H, s), 6.92 (1H, d, J=8 Hz), 7.40 (2H, d, J=8 Hz), 7.60 (1H, d, J=8 Hz), 7.68 (1H, s), 7.74 (2H, d, J=8 Hz).

LRMS (thermospray) m/z=319 (MH$^+$).

Preparation 24

(2R)-5-{[4-(3-Cyanophenyl)-3-methyl]phenyl}-2 [(4S)-2,2-dimethyl-5-oxo-1,3-dioxolan-4-yl]-N-[(1S)-2,2-dimethyl-1-({[(1R)-1-phenylethyl] amino}carbonyl)propyl]pentanamide.

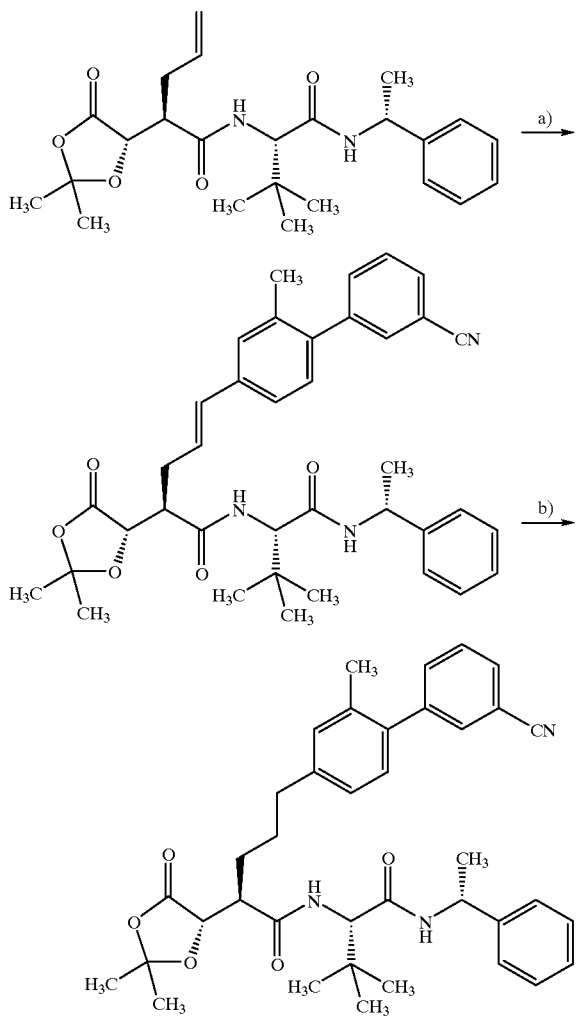

a) Palladium acetate (12.2 mg, 0.050 mmol) was added to a stirred solution of (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (Preparation 14)(430 mg, 1.0 mmol), 1-(3-cyanophenyl)-4-iodo-2-methylbenzene (Preparation 25)(457 mg, 1.50 mmol), tri-(2-methylphenyl)phosphine (30 mg, 0.10 mmol), and N-ethylmorpholine (190 μL, 1.5 mmol) in anhydrous acetonitrile (3 mL), under nitrogen. The mixture was purged with nitrogen, then heated at reflux for 14 h. After being cooled, the mixture was dissolved in ethyl acetate (100 mL), washed with water (100 mL), 0.5M aqueous sodium dihydrogenphosphate (50 mL) and saturated aqueous sodium bicarbonate (50 mL). The organic solution was dried (Na$_2$SO$_4$) and concentrated under reduced pressure. The residue was purified by flash chromatography (gradient elution with hexane:ethyl acetate=3:1 to 1:1) to give mainly (2R, 4E)-5-{[4-(3-cyanophenyl)-3-methyl]phenyl}-2-[(4S)-2,2-dimethyl-5-oxo-1,3-dioxolan-4-yl]-N-[(1S), -2,2-dimethyl-1-({[(1R)-1-phenylethyl]amino}carbonyl)propyl] pent-4-enamide as a buff foam (385 mg, 62%). $^1$H nmr suggested that alkene isomers were also present. The mixture of alkenes were taken onto the next step (see b, below).

$R_f$ 0.27 (dichloromethane:ethyl acetate=10:1)

$\delta_H$ (400 MHz, CDCl$_3$)(for the (4E) isomer). 1.01 (9H, s), 1.50 (3H, d, J=7 Hz), 1.55 (3H, s), 1.60 (3H, s), 2.20 (3H, s), 2.70 (1H, m), 2.82 (2H, m), 4.18 (1H, d, J=8.5 Hz), 4.58 (1H, d, J=5 Hz), 5.04 (1H, pentet, J=7 Hz), 5.84 (1H, d, J=7 Hz), 6.16 (1H, dt, 16 and 7 Hz), 6.50 (1H, d, J=16 Hz), 6.58 (1H, d, J=8.5 Hz), 7.05 (1H, d, J=8 Hz), 7.10–7.40 (8H, complex), 7.54 (2H, m), 7.62 (1H, m).

LRMS (thermospray) m/z=639 (MNH$_4^+$).

| Found: | C, 72.88; | H, 7.05; | N, 6.63; |
|---|---|---|---|
| C$_{38}$H$_{43}$N$_3$O$_5$.0.25H$_2$O requires | C, 72.88; | H, 7.00; | N, 6.71% | b) A solution of (2R, 4E)-5-{[4-(3-cyanophenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl] amino}carbonyl)propyl]pent-4-enamide (359 mg, 0.58 mmol) in ethanol (35 mL) was hydrogenated over 10% palladium on charcoal (35 mg) at 3 bar and 20° C. for 6 h. The mixture was filtered through Arbocel filter aid, concentrated under reduced pressure and azeotroped with ethyl acetate, then diethyl ether. The residual oil was purified by flash chromatography (gradient elution with hexane:ethyl acetate 5:1 to 1:1), then triturated with pentane and crystallised to give (2R)-5-{[4-(3-cyanophenyl)-3-methyl] phenyl}]-2-[(4S)-2,2-dimethyl-5-oxo-1,3-dioxolan-4-yl]-N-[(1S)-2,2-dimethyl-1-({[(1R)-1-phenylethyl] amino}carbonyl)propyl]pentanamide (139 mg, 38%), as a white solid, which was used for Example 19.

$R_f$ 0.40 (hexane:ethyl acetate=1:1)

δH(400 MHz, CDCl$_3$) 1.02 (9H, s), 1.52 (3H, d, J=7 Hz), 1.55 (3H, s), 1.58 (3H, s), 1.64 (2H, m), 1.90 (2H, m), 2.20 (3H, s), 2.60 (3H, m), 4.20 (1H, d, J=9.5 Hz), 4.46 (1H, d, J=7.5 Hz), 5.08 (1H, pentet, J=7 Hz), 5.86 (1H, d, J=7 Hz), 6.50 (1 H, d, J9.5 Hz), 6.98–7.08 (3H, m), 7.20 (5H, m), 7.50 (2H, m), 7.55 (1H, s), 7.60 (1H, m).

LRMS (thermospray) m/z=641 (MNH4+).

| Found: | C, 72.99; | H, 7.36; | N, 6.75; |
|---|---|---|---|
| C$_{38}$H$_{45}$N$_3$O$_5$ requires | C, 73.17; | H, 7.27; | N, 6.74% |

Preparation 25

1-(3-Cyanophenyl)-4-iodo-2methylbenzene.

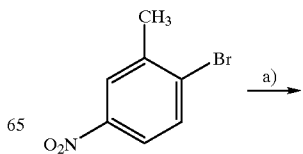

109

-continued

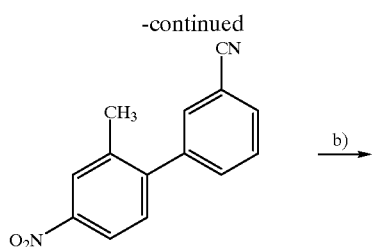

b)

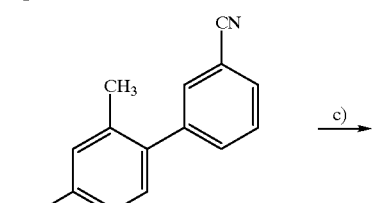

c)

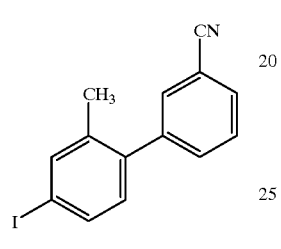

a) A solution of 2-bromo-5-nitrotoluene (8.82 gm, 40.83 mmol) in 1,2-dimethoxyethane (150 mL) was added to a solution of tetrakis(triphenylphosphine)palladium(0) (2.35 gm, 2.04 mmol) in 1,2-dimethoxyethane (100 mL) under nitrogen at room temperature. A solution of 3-cyanophenylboronic acid (J. Med.Chem., 1997, 40, 4208) (9.0 gm, 61.25 mmol) in ethanol (45 mL) was added and stirred for 10 mins. Finally, 2M aqueous sodium carbonate (234 mL) was added and the mixture was heated under reflux for 18 h. After being cooled, the mixture was partitioned between ethyl acetate and saturated aqueous sodium bicarbonate. The organic phase was washed with water, dried (Na$_2$SO$_4$), concentrated under reduced pressure and triturated with diethyl ether to give 1-(3-cyanophenyl)-2-methyl-4-nitrobenzene (8.48 gm, 87%) as a brown solid.

R$_f$ 0.74 (hexane:ethyl acetate 1:1)

$\delta_H$ (300 MHz, CDCl$_3$) 2.35 (3H, s), 7.38 (1H, d, J=8 Hz), 7.52–7.68 (3H, m), 7.75 (1H, d, J=8 Hz), 8.15 (1H, d, J=8 Hz), 8.20 (1H, s).

LRMS (thermospray) m/z=239 (M$^+$).

b) 1-(3-Cyanophenyl)-2-methyl-4-nitrobenzene (3.0 gm, 12.61 mmol) and tin(II) chloride dihydrate were suspended in ethanol (30 mL) and heated to 70° C. for 30 mins. After being cooled, the mixture was poured onto ice, and neutralised by the addition of sodium bicarbonate. The mixture was then extracted with dichloromethane (3×50 mL). The combined organic layers were dried (Na$_2$SO$_4$) and concentrated under reduced pressure to give 4-amino-1-(3-cyanophenyl)-2-methylbenzene (1.8 gm, 69%) as a yellow oil.

R$_f$ 0.36 (hexane:ethyl acetate=2:1)

$\delta_H$ (300 MHz, CDCl$_3$) 2.20 (3H, s), 3.75 (2H, br s), 6.60 (2H, m), 7.00 (1H, d, J=8 Hz), 7.42–7.60 (4H, m).

c) A suspension of 4-amino-1-(3-cyanophenyl)-2-methylbenzene (2.5 gm, 12.0 mmol) in conc. hydrochloric acid (13 mL) and water (16 mL) at 0° C., was treated with a solution of sodium nitrite (1.83 gm, 26.5 mmol) in water (10 mL) over 10 mins. The mixture was stirred for 20 mins and then a solution of potassium iodide (8.40 gm, 50.6 mmol) in water (20 mL) was added over 10 mins. The resultant mixture was heated at 80° C. for 2 h then cooled. The residue was extracted with dichloromethane and the combined organic extracts were washed with excess 5% aqueous sodium metabisulphite, to remove iodine. The organic solution was dried (Na2SO$_4$) and concentrated under reduced pressure. The residue was purified by flash chromatography (gradient elution with hexane:ethyl acetate 20:1 to 10:1) to give 1-(3-cyanophenyl)-4-iodo-2-methylbenzene as a white solid (1.105 gm, 29%).

R$_f$ 0.67 (hexane:ethyl acetate=4:1)

$\delta_H$ (300 MHz, CDCl$_3$) 2.20 (3H, s), 6.90 (1H, d, J=8 Hz), 7.45–7.75 (6H, complex).

LRMS (APCI) m/z=319 (MH$^+$).

Preparation 26

(2R)-5-{[4-(3-Carbamoylphenyl)-3-methyl]phenyl}-2[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide.

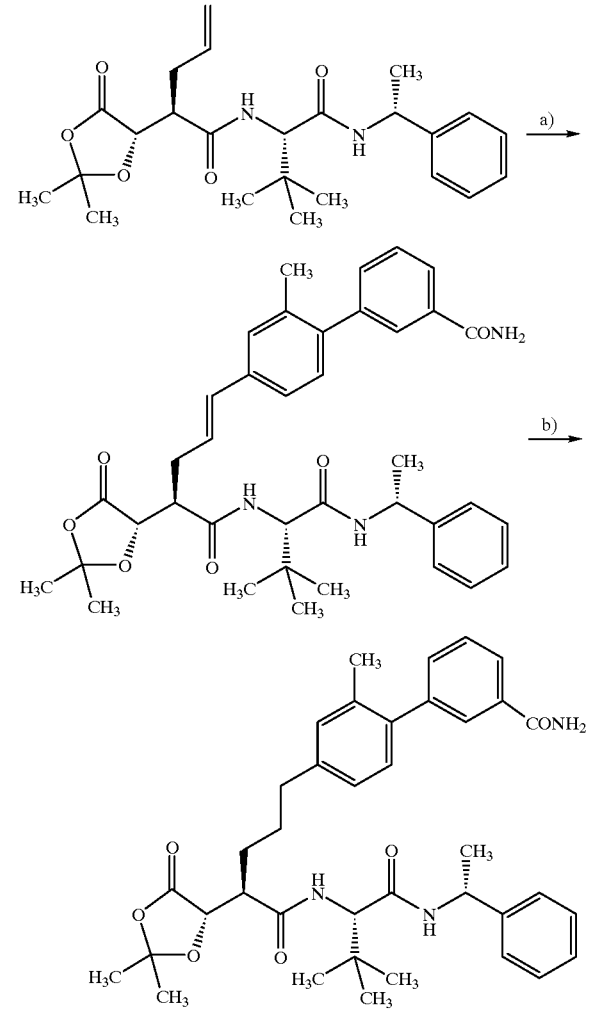

a) Palladium acetate (10.4 mg, 0.042 mmol) was added to a stirred solution of (2R)-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (Preparation 14)(366 mg, 0.85 mmol), 1-(3- carbamoylphenyl)-4-iodo-2-methylbenzene (Preparation 27)(300 mg, 0.89 mmol), tri-(2-methylphenyl)phosphine (27 mg, 0.09 mmol), and N-ethylmorpholine (115 µL, 0.89 mmol) in anhydrous acetonitrile (3 mL), under nitrogen. The mixture was purged with nitrogen, then heated at reflux for 3 h. Palladium acetate (10.4 mg, 0.042 mmol) was added and refluxed for 60 mins. Further portions of palladium acetate (10.4 mg, 0.042 mmol) were added at 60 mins intervals, followed by refluxing until reaction had been refluxed for 8 hr. The reaction was cooled, diluted with acetonitrile (10 mL) and filtered through Arbocel filter aid, washing with ethyl acetate (100 mL). The filtrate was washed with 5% aqueous sodium bicarbonate (50 mL), dried ($Na_2SO_4$) and concentrated under reduced pressure. The residue was purified by flash chromatography (gradient elution with dichloromethane:ethyl acetate=10:1 to 1:1) to give (2R, 4E)-5-{[4-(3-carbamoylphenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide as a yellow foam (175 mg, 32%).

$R_f$ 0.20 (dichloromethane:ethyl acetate=1:1)

$\delta_H$ (400 MHz, $CDCl_3$) 1.02 (9H, s), 1.50 (3H, d, J=7 Hz), 1.54 (3H, s), 1.60 (3H, s), 2.20 (3H, s), 2.70 (1H, m), 2.78 (1H, m), 2.88 (1H, m), 4.22 (1H, d, J=8.5 Hz), 4.60 (1H, d, J=5.5 Hz), 5.04 (1H, pentet, J=7 Hz), 5.94 (2H, br s), 6.00 (1H, d, J=7 Hz), 6.12 (1H, dt, J=16 and 7 Hz), 6.48 (1H, d, J=16 Hz), 6.82 (1H, d, J=8.5 Hz), 7.08 (1H, d, J=7.5 Hz), 7.14 (1H, m), 7.18–7.36 (5H, complex), 7.40–7.52 (3H, m), 7.60 (1H, s), 7.80 (1H, d,J=7.5 Hz).

LRMS (thermospray) m/z=657 ($MNH_4^+$).

| Found: | C, 70.59; | H, 7.16; | N, 6.42; |
| $C_{38}H_{45}N_3O_6$.0.2EtOAc requires | C, 70.89; | H, 7.14; | N, 6.39% | b) A solution of (2R, 4E)-5-{[4-(3-carbamoylphenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pent-4-enamide (160 mg, 0.25 mmol) in ethanol (50 mL) was hydrogenated over 10% palladium on charcoal (25 mg) at 3 bar and 20° C. for 8 h. The mixture was filtered through Arbocel filter aid, concentrated under reduced pressure and azeotroped with ethyl acetate, then diethyl ether. The residue was purified by flash chromatography (gradient elution with hexane:ethyl acetate 5:1 to 1:3), then azeotroped with diethyl ether to give (2R)-5-{[4-(3-carbamoylphenyl)-3-methyl]phenyl}-2-[(4S)-2,2-dimethyl-5-oxo-1,3-dioxolan-4-yl]-N-[(1S)-2,2-dimethyl-1-({[(1R)-1-phenylethyl]amino}carbonyl)propyl]pentanamide (82 mg, 51%), as a white solid, which was used for Example 20.

$R_f$ 0.17 (hexane:ethyl acetate=1:3)

$\delta_H$ (400 MHz, DMSO) 0.92 (9H, s), 1.30 (3H, d, J=7 Hz), 1.40–1.60 (9H, complex), 1.78 (1H, m), 2.15 (3H, s), 2.40–2.60 (2H, m), 2.98 (1H, m), 4.38 (1H, d, J=9 Hz), 4.46 (1H, d, J=9 Hz), 4.92 (1H, pentet, J=7 Hz), 6.98 (1H, d, J=7.5 Hz), 7.02 (2H, m), 7.12 (3H, m), 7.20 (2H, m), 7.30 (1H, br s), 7.40 (1H, d, J=7.5 Hz), 7.50 (1H, t, J=7.5 Hz), 7.80 (3H, m), 8.00 (1H, br s), 8.40 (1H, d, J=7 Hz).

LRMS (thermospray) m/z=664 ($MNa^+$).

| Found: | C, 70.26; | H, 7.59; | N, 6.36; |
| $C_{38}H_{47}N_3O_6$.0.25EtOAc requires | C, 70.56; | H, 7.44; | N, 6.33% |

Preparation 27

1-(3-Carbamoylphenyl)-4-iodo-2methylbenzene.

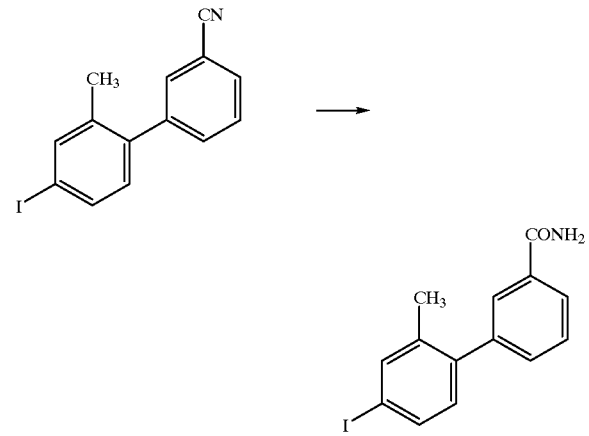

Potassium hydroxide (1.21 gm, 21.6 mmol) was added to a solution of 1-(3-cyanophenyl)-4-iodo-2-methylbenzene (1.27 gm, 4.0 mmol) in ethanol (50 mL) and heated under reflux for 16 h. After being cooled, the mixture was diluted with water (100 mL) and extracted with ethyl acetate (3×50 mL). The combined organic extracts were dried ($Na_2SO_4$) and concentrated under reduced pressure to give crude product (1.08 gm). The crude product (540 mg) was purified by flash chromatography (gradient elution with dichloromethane:sat. methanolic ammonia 100:2.5 to dichloromethane:ethyl acetate 1:1 to dichloromethane:ethyl acetate:acetic acid 100:100:4), then azeotroped with ethanol, ethyl acetate and diethyl ether to give 1-(3-carbamoylphenyl)-4-iodo-2-methylbenzene (310 mg, 46%) as a buff solid.

m.p. 138–141° C.

$R_f$ 0.40 (dichloromethane:ethyl acetate:acetic acid= 50:50:2.5)

$\delta_H$ (400 MHz, DMSO) 2.18 (3H, s), 7.00 (1H, d, J=8 Hz), 7.38 (1H, br s), 7.48 (2H, m), 7.62 (1H, d, J=8 Hz), 7.72 (1H, s), 7.80 (1H, s), 7.86 (1H, d, J=8 Hz), 8.00 (1H. br s).

LRMS (thermospray) m/z=355 ($MNH_4^+$).

Preparation 28 tert-Butyl(3R)-3-[({({[(1S)-2methoxy-1-phenylethyl]amino}carbonyl)-[(1S)-2methyl]-1-propyl}amino)carbonyl]-6-[3-methyl-(4-phenyl)phenyl]hexanoate.

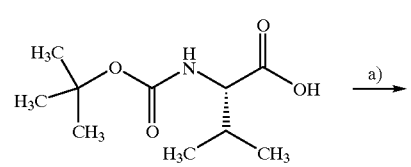

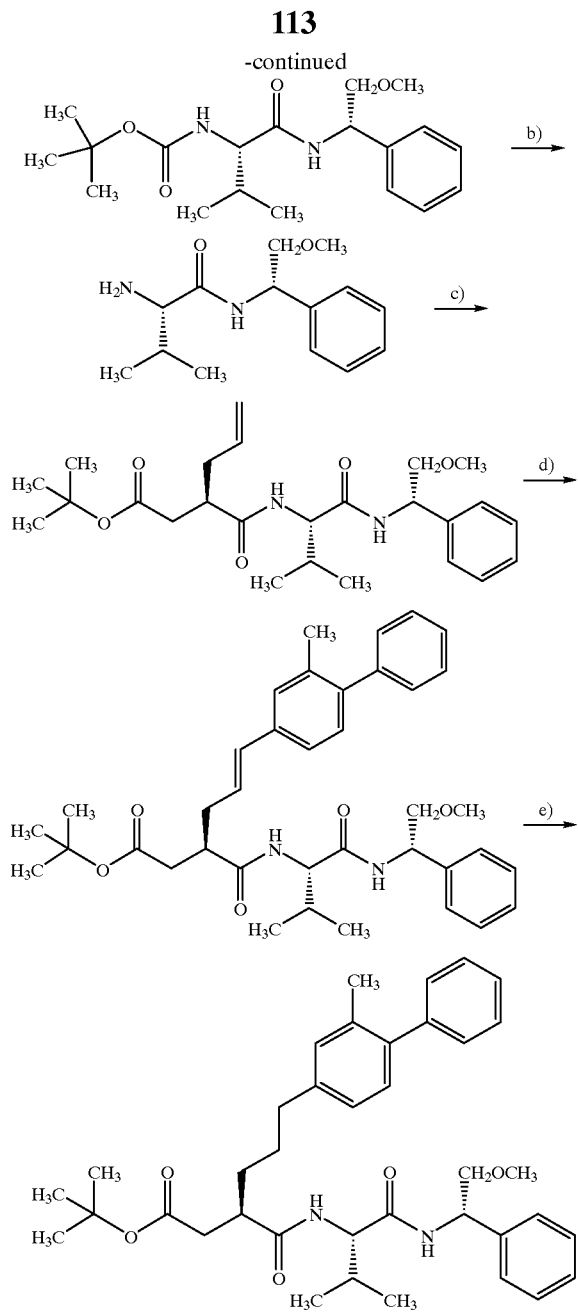

a) According to the procedure of Preparation 19 a), N-tert-butoxycarbonyl-L-valine (868 mg, 4.0 mmol) was reacted with (1S)-2-methoxy-1-phenylethylamine (604 mg, 4.0 mmol) for 72 h. The mixture was concentrated under reduced pressure and partitioned between ethyl acetate (200 mL) and water (200 mL). The organic layer was washed with 5% aqueous citric acid (100 mL), saturated aqueous sodium bicarbonate (100 mL), dried (MgSO$_4$), and concentrated under reduced pressure. The product was triturated with diisopropyl ether, filtered and dried to give (2S)-tert-(butoxycarbonyl)amino-N-[(1S)-2-methoxy-1-phenylethyl]-3-methylbutanamide (1.11 g, 79%) as a colourless solid.

m.p. 112–113° C.

R$_f$ 0.71 (dichloromethane:methanol:conc. aq. ammonia=90:10:1)

δ$_H$ (400 MHz, CDCl$_3$) 0.96 (6H, d, J=7 Hz), 1.45 (9H, s), 2.18 (1H, m), 3.35 (3H, s), 3.64 (2H, m), 3.92 (1H, m), 5.00 (1H, br s), 5.18 (1H, m), 6.60 (1H, m), 7.32 (5H, m).

LRMS (thermospray) m/z=351 (MH$^+$).

b) (2S)-tert-(Butoxycarbonyl)amino-N-[(1S)-2-methoxy-1-phenylethyl]-3-methylbutanamide (1.11 g, 3.17 mmol) was dissolved in a mixture of anhydrous dichloromethane (15 mL) and dioxane (15 mL) and cooled to 4° C. Hydrogen chloride was bubbled through the solution, with stirring, until a saturated solution was formed. After being stirred for 4 h at 4° C., the solution was concentrated under reduced pressure. The residue was azeotroped with dichloromethane to give (2S)-amino-N-[(1S)-2-methoxy-1-phenylethyl]-3-methylbutanamide hydrochloride (948 mg, 104%), as a pale yellow foam.

δ$_H$ (400 MHz, CDCl$_3$) 0.95 (3H, d, J=7.5 Hz), 1.00 (3H, d, J=7.5 Hz), 2.20 (1H, m), 3.15 (3H, s), 3.56 (1H, m), 3.66 (1H, m), 4.02 (1H, m), 5.10 (1H, m), 7.20–7.35 (3H, m), 7.40 (2H, d, J=8 Hz), 7.90 (3H, brs), 8.18 (1H, d, J=7.5 Hz).

LRMS (thermospray) m/z=251 (MH$^+$).

c) According to the method of Preparation 2, (2R)-2-[2-(tert-butoxy)-2-oxoethyl]pent-4-enoic acid (646 mg, 3.02 mmol) was reacted with (2S)-amino-N-[(1S)-2-methoxy-1-phenylethyl]-3-methylbutanamide hydrochloride (from b) above)(908 mg, 3.17 mmol) for 1 h at 4° C. and then 18 h at 20° C. The mixture was concentrated under reduced pressure, and partitioned between ethyl acetate (100 mL) and saturated aqueous sodium bicarbonate (100 mL). The layers were separated and aqueous layer extracted again with ethyl acetate (100 mL). The combined organic layers were dried (MgSO$_4$), and concentrated under reduced pressure. The residue was purified by flash chromatography (eluting with dichloromethane:methanol 98:2) to give tert-butyl (3R)-3-({[({[(1S)-2-methoxy-1-phenylethyl]amino}carbonyl)-(1S)-2-methyl-1-propyl]amino}carbonyl)hex-5-enoate (1.08 g, 80%), as a white solid.

m.p. 155–157° C.

R$_f$ 0.36 (dichloromethane:methanol=95:5)

δ$_H$ (400 MHz, CDCl$_3$) 0.94 (3H, d, J=7 Hz), 0.97 (3H, d, J=7 Hz), 1.40 (9H, s), 2.15 (2H, m), 2.35 (2H, m), 2.65 (2H, m), 3.15 (3H, s), 3.65 (2H, d, J=5 Hz), 4.26 (1H, t, J=7.5), 4.96 (1H, d, J=9 Hz), 5.00 (1H, d, J=18 Hz), 5.15 (1H, dt, J=5 and 7 Hz), 5.66 (1H, m), 6.26 (1H, d, J=7.5 Hz), 6.55 (1H, d, J=7 Hz), 7.30 (5H, m).

LRMS (thermospray) m/z=447 (MH$^+$).

d) According to the method of Preparation 15 a), tert-butyl (3R)-3-({[({[(1S)-2-methoxy-1-phenylethyl]amino}carbonyl)-(1S)-2-methyl-1-propyl]amino}carbonyl)hex-5-enoate (from c) above) (1.08 g, 2.42 mmol) was reacted with 4-iodo-2-methyl-1-phenylbenzene (Preparation 29)(1.07 g, 3.63 mmol) under palladium catalysis at reflux in acetonitrile for 18 h. After being cooled, the mixture was diluted with ethyl acetate (200 mL) and washed sequentially with 5% aqueous citric acid (50 mL), saturated aqueous sodium bicarbonate (50 mL), saturated aqueous brine (50 mL), dried (Na$_2$SO$_4$) and concentrated under reduced pressure. The residue was purified by flash chromatography (gradient elution with dichloromethane:ethyl acetate=30:1 to 3:1) to give tert-butyl (3R, 5E)-3-({[({[(1S)-2-methoxy-1-phenylethyl]amino}carbonyl)-(1S)-2-methyl-1-propyl]amino}carbonyl)-6-[3-methyl-(4-phenyl)phenyl]hex-5-enoate as a pale brown foam (980 mg, 66%).

R$_f$ 0.35 (dichloromethane:ethyl acetate=4:1)

δ$_H$ (400 MHz, CDCl$_3$). 0.96 (3H, d, J=7 Hz), 0.98 (3H, d, J=7 Hz), 1.40 (9H, s), 2.18 (1H, m), 2.22 (3H, s), 2.36 (1H, m), 2.40–2.58 (2H, m), 2.66 (1H, m), 2.75 (1H, m), 3.35 (3H, s), 3.62 (2H, d, J=4.5 Hz), 4.30 (1H, t, J=7.5 Hz), 5.12 (1H, dt, J=4.5 and 7 Hz), 6.10 (1H, m), 6.36 (1H, d, J=7 Hz), 6.40 (1H, d, J=16 Hz), 6.55 (1H, d, J=7.5 Hz), 7.10 (2H, m), 7.20–7.38 (9H, complex), 7.40 (2H, m).

| Found:              | C, 74.43; | H, 7.85; | N, 4.57;  |
| $C_{38}H_{48}N_2O_5$ requires | C, 74.48; | H, 7.90; | N, 4.57% | e) A solution of tert-butyl (3R, 5E)-3-({[({[(1S)-2-methoxy-1-phenylethyl]amino}carbonyl)-(1S-2-methyl-1-propyl]amino}carbonyl)-6-[3-methyl-(4-phenyl)phenyl]hex-5-enoate (from d) above)(930 mg, 1.51 mmol) in ethanol (50 mL) was hydrogenated over 10% palladium on charcoal (75 mg) at 3 bar and 20° C. for 17 h. The mixture was filtered through Arbocel filter aid and concentrated under reduced pressure. The residue was purified by flash chromatography (gradient elution with pentane:ethyl acetate 10:1 to 2:1) and triturated with diethyl ether to give tert-butyl (3R)-3-({[({[(1S)-2-methoxy-1-phenylethyl]amino}carbonyl)-(1S)-2-methyl-1-propyl]amino}carbonyl)-6-[3-methyl-(4-phenyl)phenyl]hexanoate (748 mg, 81 %), as a colourless foam, which was used in Example 21.

$R_f$ 0.35 (pentane:ethyl acetate=2:1)

$\delta_H$ (400 MHz, CDCl$_3$) 0.95 (3H, d, J=7 Hz), 0.98 (3H, d, J=7 Hz), 1.40 (9H, s), 1.42 (1H, m), 1.60 (2H, m), 1.70 (1H, m), 2.18 (1H, m), 2.22 (3H, s), 2.38 (1H, m), 2.45–2.66 (4H, complex), 3.32 (3H, s), 3.60 (2H, d, J=4.5 Hz), 4.28 (1H, t, J=7.5 Hz), 5.15 (1H, dt, J=4.5 and 7 Hz), 6.30 (1H, d, J=7.5 Hz), 6.55 (1H, d, J=7 Hz), 6.98 (1H, d, J=8 Hz), 7.00 (1H, s), 7.10 (1H, d, J=8 Hz), 7.20–7.36 (8H, complex), 7.40 (2H, m).

| Found:              | C, 74.39; | H, 8.24; | N, 4.59;  |
| $C_{38}H_{50}N_2O_5$ requires | C, 74.32; | H, 8.27; | N, 4.61% |

Preparation 29

4-Iodo-2methyl-1-phenylbenzene.

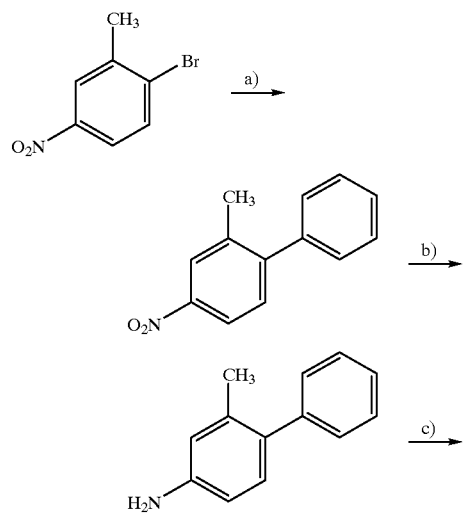

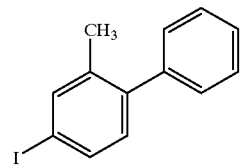

a) According to the method of Preparation 25(a), 2-bromo-5-nitrotoluene (15 gm, 69.4 mmol) was treated with phenyl boronic acid (12.7 gm, 104.1 mmol) under palladium catalysis, using 2M aqueous sodium carbonate as base at reflux in dimethoxyethane for 16 h. After being cooled, the mixture was separated the organic layer was diluted with diethyl ether and washed with water (twice). The organic layer was dried (Na$_2$SO$_4$) and concentrated under reduced pressure. The residue was purified by flash chromatography (gradient elution with hexane to hexane-:ethyl acetate 95:5) to give 2-methyl-4-nitro-1-phenylbenzene as a yellow solid (12.7gm, 86%).

$R_f$ 0.33 (hexane:ethyl acetate=95:5)

$\delta_H$ (300 MHz, CDCl$_3$) 2.40 (3H, s), 7.20–7.50 (6H, complex), 8.10 (1H, d, J=8 Hz), 8.15 (1H, s).

b) 2-Methyl-4-nitro-1-phenylbenzene (12.7 gm, 60 mmol) was dissolved in ethanol (260 mL) and hydrogenated over 10% palladium on charcoal (1.27gm) at 3 bar and 20° C. for 2 h. The mixture was filtered through Arbocel filter aid, washing with ethyl acetate. The filtrate was concentrated under reduced pressure to give 4-amino-2-methyl-1-phenylbenzene (10.49 gm, 95%) as a pinkish brown oil.

$\delta_H$ (400 MHz, CDCl$_3$) 2.20 (3H, s), 3.60 (2H, br s), 6.60 (2H, m), 7.05 (1H, d, J=8 Hz), 7.30 (3H, m), 7.40 (2H, m).

c) A stirred solution of 4-amino-2-methyl-1-phenylbenzene (10.49 gm, 57.2 mmol) in diiodomethane (100 mL) was treated with iso-amyl nitrite (27 mL, 200.2 mmol) over 5 mins. The mixture was heated to 75° C. for 45 mins, then at 65° C. for 1 h. After being cooled, the mixture was concentrated under reduced pressure (95° C./30 mmHg) and the residue was purified by flash chromatography (eluting with hexane) to give 4-iodo-2-methyl-1-phenylbenzene (11.6 gm, 66%) as an oil.

$R_f$ 0.33 (hexane)

$\delta_H$ (400 MHz, DMSO-d$_6$) 2.20 (3H, s), 6.98 (1H, d, J=8 Hz), 7.30 (2H, m), 7.35 (1H, m), 7.45 (2H, m), 7.60 (1H, d, J=8 Hz), 7.70 (1H, s).

Preparation 30 tert-Butyl(3R)-3-({[({[(1S)-2methoxy-1-phenylethyl]amino}carbonyl)-(1S)-2phenylethyl]amino}carbonyl)-6-[3-methyl-(4-phenyl)phenyl]hexanoate.

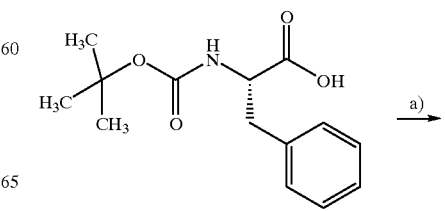

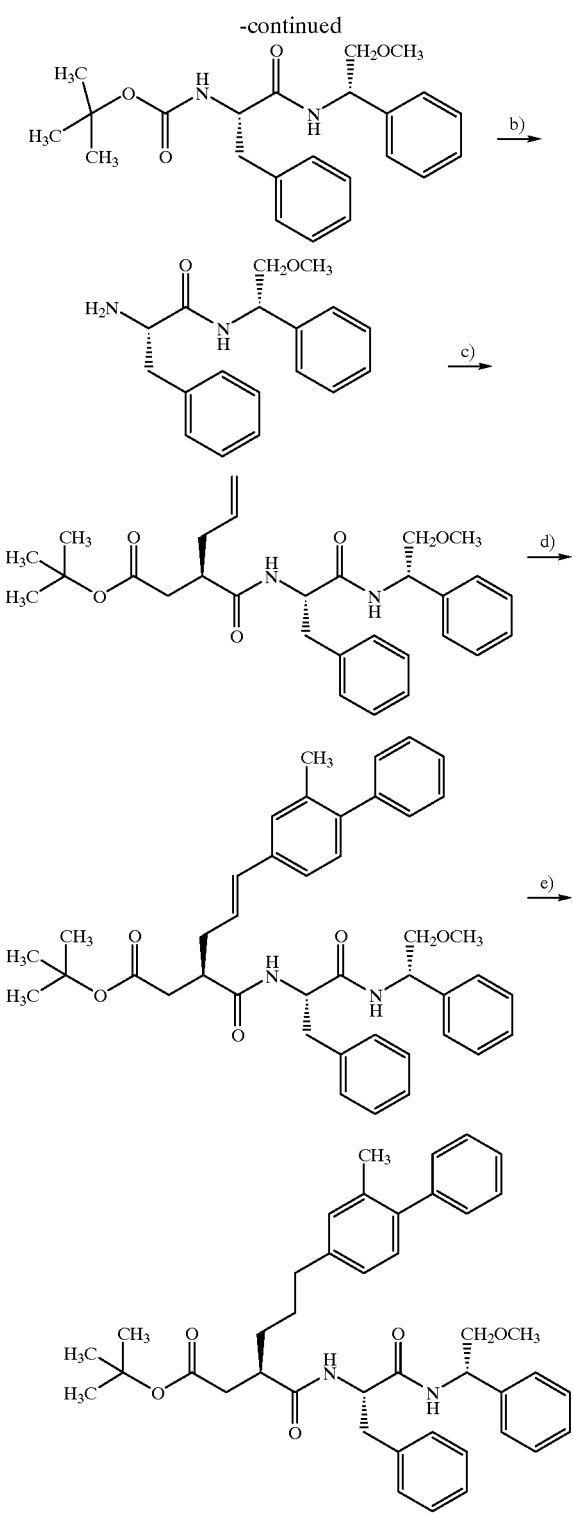

a) According to the procedure of Preparation 19 a) N-tert-butoxycarbonyl-1-phenylalanine (1.06 mg, 4.0 mmol) was reacted with (1S)-2-methoxy-1-phenylethylamine (604 mg, 4.0 mmol) for 72 h. The mixture was concentrated under reduced pressure and partitioned between ethyl acetate (200 mL) and water (200 mL). The organic layer was washed with 5% aqueous citric acid (100 mL), saturated aqueous sodium bicarbonate (100 mL), dried (MgSO$_4$), and concentrated under reduced pressure. The product was triturated with diisopropyl ether, filtered and dried to give (2S)-tert-(butoxycarbonyl)amino-N-[(1S)-2-methoxy-1-phenylethyl]-3-phenylpropionamide (1.28 g, 81%) as a white solid.

m.p. 133–134 ° C.

R$_F$ 0.76 (dichloromethane:methanol:conc. aq. ammonia= 90:10:1)

δ$_H$ (400 MHz, CDCl$_3$) 1.40 (9H, s), 3.02 (1H, dd, J=7 and 13 Hz), 3.16 (1H, dd, J=6 and 13 Hz), 3.22 (3H, s), 3.40 (1H, m), 3.56 (1H, dd, J=4.5 and 10 Hz), 4.38 (1H, m), 5.05 (2H, m), 6.45 (1H, d, J=8 Hz), 7.18–7.36 (10H, complex).

LRMS (thermospray) m/z=399 (MH$^+$).

b) (2S)-tert-(Butoxycarbonyl)amino-N-[(1S)-2-methoxy-1-phenylethyl]-3-phenylpropanamide (1.28 g, 3.2 mmol) was dissolved in a mixture of anhydrous dichloromethane (15 mL) and dioxane (15 mL) and cooled to 4° C. Hydrogen chloride was bubbled through the solution, with stirring, until a saturated solution was formed. After being stirred for 4 h at 4° C., the solution was concentrated under reduced pressure. The residue was azeotroped with dichloromethane to give (2S)-amino-N-[(1S)-2-methoxy-1-phenylethyl]-3-phenylpropanamide hydrochloride (1.11 g, 103%), as a pale yellow foam.

δ$_H$ (400 MHz, CDCl$_3$) 3.08 (1H, dd, J=13 and 10 Hz), 3.20 (3H, s), 3.32 (2H, m), 3.50 (1H, dd, J=7.5 and 6.5 Hz), 4.44 (1H, m), 5.00 (1H, m), 7.18 (1H, m), 7.20 (2H, m), 7.20 (2H, m), 7.25 (7H, complex), 7.64 (1H, d, J=8 Hz), 7.80 (3H, br s).

LRMS (thermospray) m/z=299 (MH$^+$).

c) According to the method of Preparation 2, (2R)-2-[2-(tert-butoxy)-2-oxoethyl]pent-4-enoic acid 658 mg, 3.07 mmol) was reacted with (2S)-amino-N-[(1S)-2-methoxy-1-phenylethyl]-3-phenylpropanamide hydrochloride (from b) above)(1.08 mg, 3.23 mmol) for 1 h at 4° C. and then 18 h at 20° C. The mixture was concentrated under reduced pressure, and partitioned between ethyl acetate (100 mL) and saturated aqueous sodium bicarbonate (100 mL). The layers were separated and aqueous layer extracted again with ethyl acetate (100 mL). The combined organic layers were dried (MgSO$_4$) and concentrated under reduced pressure. The residue was triturated with diisopropyl ether to give tert-butyl (3R)-3-({[({[(1S)-2-methoxy-1-phenylethyl]amino}carbonyl)-(1S)-2-phenylethyl]amino}carbonyl)hex-5-enoate (1.35 g, 85%), as a white solid.

m.p. 122–125 ° C.

R$_f$ 0.47 (dichloromethane:methanol=95:5)

δ$_H$ (400 MHz, CDCl$_3$) 1.40 (9H, s), 2.12 (1H, m), 2.26–2.40 (2H, m), 2.5014 2.60 (2H, m), 3.00 (1H, dd, 8.5 and 14 Hz), 3.19 (1H, dd, 5.5 and 14 Hz), 3.20 (3H, s), 3.36 (1H, dd, 4.5 and 9.5 Hz), 3.50 (1H, dd, 4.8 and 9.5), 4.65 (1H, q, J=7.5 Hz), 4.94–5.04 (3H, m), 5.60 (1H, m), 6.37 (2H, m), 7.18–7.35 (10H, complex).

LRMS (thermospray) m/z=495 (MH$^+$).

d) According to the method of Preparation 15 a), give tert-butyl (3R)-3-({[({[(1S)-2-methoxy-1-phenylethyl]amino}carbonyl)-(1S)-2-phenylethyl]amino}carbonyl)hex-5-enoate (from c) above) (1.35 g, 2.73 mmol) was reacted with 4-iodo-2-methyl-1-phenylbenzene (Preparation 29) (1.21 g, 4.09 mmol) under palladium catalysis at reflux in acetonitrile for 18 h. After being cooled, the mixture was diluted with ethyl acetate (200 mL) and washed with 5% aqueous citric acid (50 mL), saturated aqueous sodium bicarbonate (50 mL), saturated brine (50 mL), dried (Na$_2$SO$_4$) and concentrated under reduced pressure. The residue was purified by flash chromatography (gradient elution with dichloromethane:ethyl acetate=50:1 to 5:1) to give tert-butyl (3R, 5E)-3-({[({[(1S)-2-methoxy-1-phenylethyl]amino}carbonyl) -(1S)-2-phenylethyl]amino}carbonyl)-6-[3-methyl-(4-phenyl)phenyl]hex-5-enoate as a pale brown foam (1.1 g, 61%).

$R_f$ 0.35 (dichloromethane:ethyl acetate=5:1)

$\delta_H$ (400 MHz, CDCl$_3$) 1.40 (9H, s), 2.22 (3H, s), 2.34 (1H, m), 2.40–2.56 (2H, m), 2.56–2.75 (2H, m), 3.00 (1H, dd, J=7.5 and 14 Hz), 3.19 (1H, dd, J=6 and 14 Hz), 3.20 (3H, s), 3.35 (1H, dd, J=4.5 and 10 Hz), 3.50 (1H, dd,, J=4.5 and 10 Hz), 4.65 (1H, q, J=7.5 Hz), 5.00 (1H, dt, J=4.5 and 7.5 Hz), 6.06 (1H, dt, J=7 and 14 Hz), 6.34 (1H, d, J=7.5 Hz), 6.38 (1H, d, J=14 Hz), 6.44 (1H, d, J=7.5 Hz), 7.10–7.38 (16H, complex), 7.40 (2H, m).

| Found: | C, 76.10; | H, 7.27; | N, 4.20; |
|---|---|---|---|
| C$_{42}$H$_{48}$N$_2$O$_5$ requires | C, 76.33; | H, 7.32; | N, 4.24% | e) A solution of tert-butyl (3R, 5E)-3-({[({[(1S)-2-methoxy-1-phenylethyl]amino}carbonyl)-(1S)-2-phenylethyl]amino}carbonyl)-6-[3-methyl-(4-phenyl)phenyl]hex-5-enoate (1.03 g, 1.56 mmol) in ethanol (100 mL) was hydrogenated over 10% palladium on charcoal (125 mg) at 3 bar and 20° C. for 18 h. The mixture was filtered through Arbocel filter aid and concentrated under reduced pressure. The residue was purified by flash chromatography (gradient elution with pentane:ethyl acetate 10:1 to 2:1)and triturated with diethyl ether to give tert-butyl (3R)-3-({[({[(1S)-2-methoxy-1-phenylethyl]amino}carbonyl)-(1S)-2-phenylethyl]amino}carbonyl)-6-[3-methyl-(4-phenyl)phenyl]hexanoate (980 mg, 95%), as a colourless foam, which was used in Example 22.

$R_f$ 0.35 (pentane:ethyl acetate=2:1)

$\delta_H$ (400 MHz, CDCl$_3$) 1.40 (9H, s), 1.42 (1H, m), 1.48–1.70 (3H, m), 2.20 (3H, s), 2.38 (1H, 2.56 (4H, m), 3.00 (1H, dd, J=8 and 13 Hz), 3.20 (3H, s, and 1H, dd, J=5.5 and 13 Hz overlapping), 3.36 (1H, dd, J 5 and 9 Hz), 3.50 (1H, dd, J=5 and 9 Hz), 4.65 (1H, q, J=8 Hz), 5.00 (1H, dt, J=5 and 8 Hz), 6.38 (2H, d, J=8 Hz), 6.95 (1H, d, J=8 Hz), 7.00 (1H, s), 7.10 (1H, d, J=8 Hz), 7.14–7.35 (13H, complex), 7.40 (2H, m).

| Found: | C, 76.03; | H, 7.70; | N, 4.25; |
|---|---|---|---|
| C$_{42}$H$_{50}$N$_2$O$_5$ requires | C, 76.10; | H, 7.60; | N, 4.23% |

Preparation 31 tert-Butyl-(3R)-3-({[(1S)-2,2-dimethyl-1-}[(1R)-1-(4-pyridyl)ethylamino]carbonyl}propyl]amino}carbonyl)-6-[(3-methyl-4-phenyl)phenyl]hexanoate

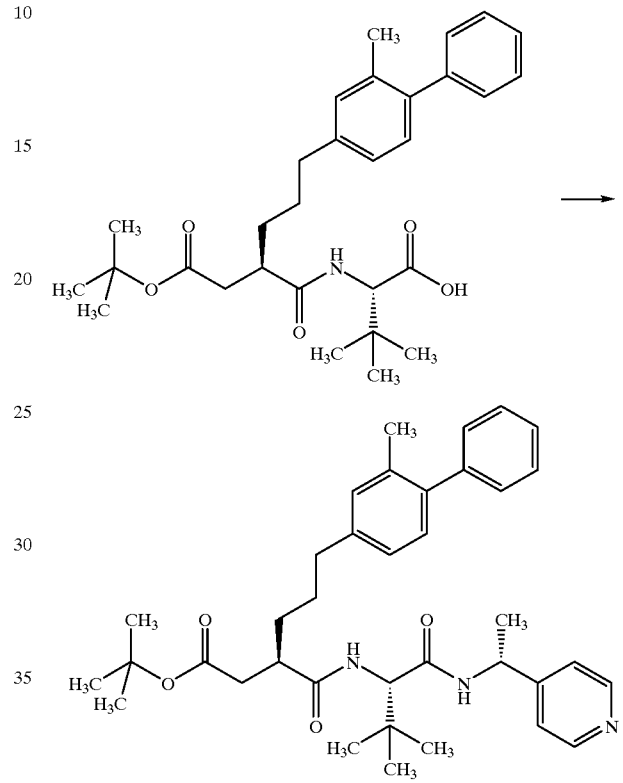

According to the method of Example 25(a), tert-butyl (3R)-3-({[(1S)-1-(carboxy)-2,2-dimethylpropyl]amino}carbonyl)-6-[(3-methyl-4-phenyl)phenyl]hexanoate (Preparation 19A, part (c))(497 mg, 1.0 mmol) was reacted with (R)-(+)-1-(4-pyridyl)ethylamine (122 mg, 1.0 mmol) at room temperature for 2.5 h, followed by the same work up, to give tert-butyl-(3R)-3-({[(1S-2,2-dimethyl-1-{[(1R)-1-(4-pyridyl)ethylamino]carbonyl}propyl]amino}carbonyl)-6-[(3-methyl-4-phenyl)phenyl]-hexanoate (460 mg, 77%) as a white solid.

$R_f$ 0.21 (hexane:ethyl acetate=1:2)

$\delta_H$ (400 MHz, CDCl$_3$) 1.01 (9H, s), 1.40 (9H, s), 1.45 (3H, d, J=7.5 Hz), 1.50–1.65 (4H, m), 2.22 (3H, s), 2.38 (1H, m), 2.50–2.65 (4H, m), 4.20 (1H, d, J=9 Hz), 5.04 (1H, pentet, J=7.5 Hz), 6.15 (1H, d, J=7.5 Hz), 6.45 (1H, d, J=9 Hz), 7.00 (2H, m), 7.14 (3H, m), 7.30 (3H, m), 7.38 (2H, m), 8.45 (2H, d, J=7.5 Hz).

121

LRMS (thermospray) m/z=600 (MH⁺)

Example 38
Preparation 32

(3R)-3-({[(1S)-2,2-Dimethyl-1-}[(1R)-1-(3-pyridyl)ethylamino]carbonyl}propyl]amino}carbonyl)-6-[(3-methyl-4-phenyl)phenyl]hexanoic acid.

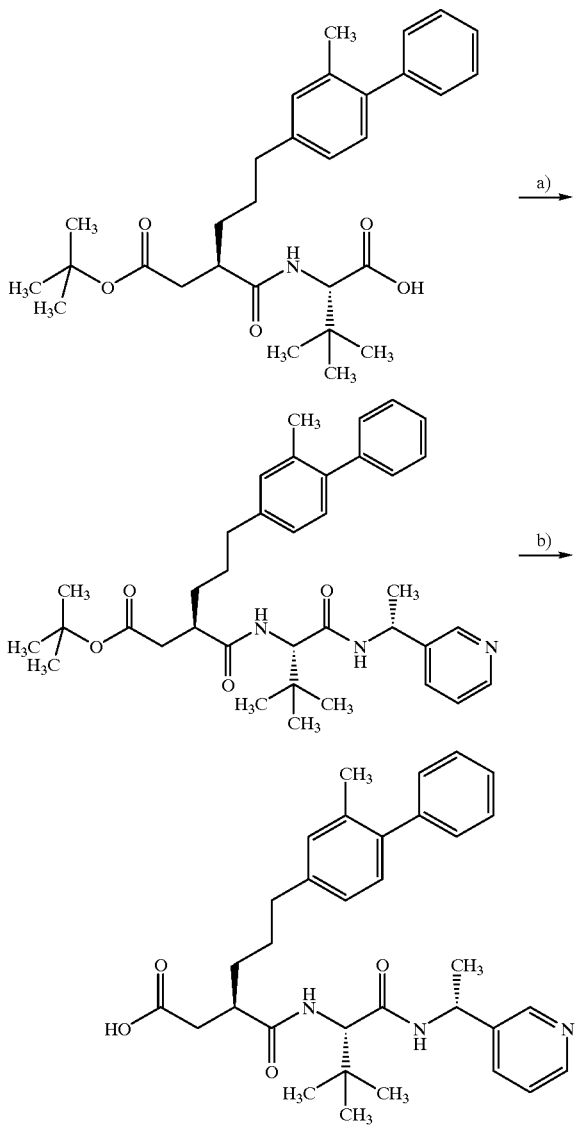

a) According to the method of Example 25(a), tert-butyl (3R)-3-({[(1S)-1-(carboxy)-2,2-dimethylpropyl]amino}carbonyl)-6-[3-methyl-(4-phenyl)phenyl]hexanoate (Preparation 19c)(497 mg, 1.0 mmol) was reacted with (R)-(+)-1-(3-pyridyl)ethylamine (122 mg, 1.0 mmol) at room temperature for 2.5 h, followed by the same work up and purification by flash chromatography (gradient elution with hexane:ethyl acetate 4:1 to 100% ethyl acetate) gave tert-butyl-(3R)-3-({[(1S)-2,2-dimethyl-1-{[(1R)-1-(3-pyridyl)ethylamino]carbonyl}propyl]amino}carbonyl)-6-[3-methyl-(4-phenyl)phenyl]-hexanoate (537 mg, 89%) as a colourless foam.

$R_f$ 0.33 (ethyl acetate)

$\delta_H$ (400 MHz, DMSO-$d_6$) 0.90 (9H, s), 1.02 (3H, d, J=7.5 Hz), 1.34 (9H, s), 1.20–1.34 (4H, m), 2.14 (3H, s), 2.20 (1H, m), 2.30–2.50 (3H, m), 2.80 (1H, m), 4.30 (1H, d, J=9.5 Hz), 4.95 (1H, pentet, J=7.5 Hz), 6.92 (1H, d, J=8 Hz), 7.00 (2H, m), 7.18 (1H, m), 7.24 (2H, m), 7.32 (1H, m), 7.40 (2H, m), 7.60 (1H, d, J=8 Hz), 7.75 (1H, d, J=9.5 Hz), 8.35 (1H, m), 8.42 (1H, d, J=7.5 Hz), 8.46 (1H, s).

LRMS (thermospray) m/z=600 (MH⁺).

b) Hydrogen chloride gas was bubbled in to a solution of tert-butyl-(3R)-3-({[(1S)-2,2-dimethyl-1-{[(1R)-1-(3-pyridyl)ethylamino]carbonyl}propyl]amino}carbonyl)-6-[(3-methyl-4-phenyl)phenyl]-hexanoate (285 mg, 0.47 mmol) in dioxane (15 mL) under nitrogen at 0° C., until saturated. The solution was stirred for 3 h at 0° C., then concentrated under reduced pressure. The residue was dissolved in methanol (3 mL), diethyl ether (3 mL) was added, the mixture was filtered and filtrate concentrated under reduced pressure. The residue was dissolved in methanol (3 mL), toluene (3 mL) was added and concentrated under reduced pressure. Finally, diethyl ether (5 mnL) was added to the residue which was sonicated to give a white solid which was filtered and dried to give the title compound as a white solid (338 mg, 65%).

$R_f$ 0.06 (ethyl acetate:hexane:acetic acid=50:50:1)

$\delta^H$ (400 MHz, CD₃OD) 1.02 (9H, s), 1.40–1.60 (4H, m), 1.54 (3H, d, J=7.5 Hz), 2.16 (3H, s), 2.30–2.58 (3H, m), 2.62 (1H, m), 2.90 (1H, m), 4.20 (1H, m), 5.15 (1H, pentet, J=7.5 Hz), 6.90 (1H, d, J=8 Hz), 6.98 (2H, m), 7.22 (2H, d, J=8 Hz), 7.32 (1H, m), 7.40 (2H, d, J=8 Hz), 7.80 (1H, m), 7.85 (1H, d, J=9.5 Hz), 8.50 (2H, m), 8.80 (2H, m).

LRMS (thermospray) m/z=544 (MH⁺)

| Found: | C, 65.78; | H, 7.26; | N, 6.72; |
|---|---|---|---|
| C₃₃H₄₁N₃O₄.HCl.1.25H₂O requires | C, 65.74; | H, 7.63; | N, 6.76% |

Preparation 33

(2R)-N-[(1S)-1-(Carboxy)-2,2-dimethylpropyl]-2[(4S)-2,2-dimethyl-5-oxo-1,3-dioxolan-4-yl]-5-[(3-methyl-4-phenyl)phenyl]pentanamide.

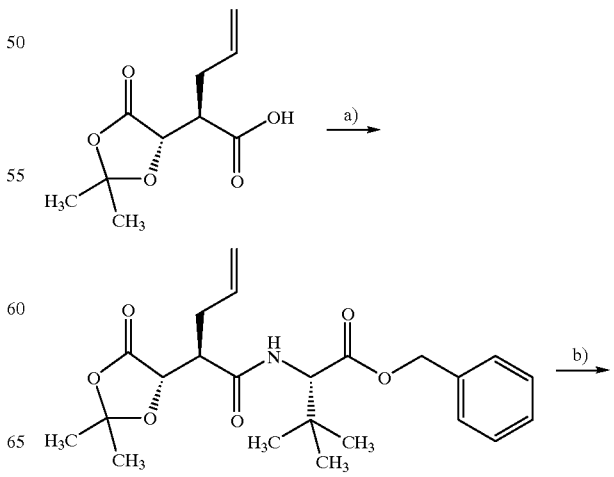

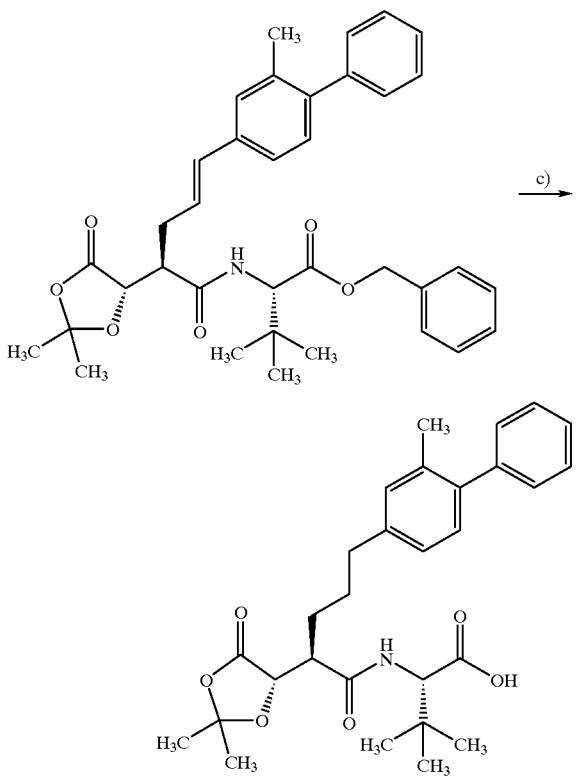

a) According to the method of Preparation 2, (4S)-4-[(1R)-1-carboxy-but-3-enyl]-2,2-dimethyl-1,3-dioxolan-5-one (Preparation 14b)(2.39 g, 11.20 mmol) was reacted with L-tert-leucine benzyl ester hydrochloride (3.03 g, 11.76 mmol) for 1 h at 4° C. and then 17 h at 20° C. The mixture was concentrated under reduced pressure, dissolved in ethyl acetate (200 mL), washed with 0.5M aqueous sodium dihydrogenphosphate (2×200 mL), 5% saturated sodium bicarbonate (200 mL), water, dried (MgSO$_4$), and concentrated under reduced pressure. The residue was purified by flash chromatography (gradient elution with hexane:ethyl acetate 10:1 to 1:1) to give (2R)-N-[(1S)-1-[(benzyloxy)carbonyl]-2,2-dimethylpropyl]-2-[(4S)-2,2-dimethyl-5-oxo-1,3-dioxolan-4-yl]pent-4-enamide (4.06 g, 87%), as a white solid.

m.p. 67–70 ° C.

R$_f$ 0.30 (hexane:diethyl ether=1:1)

δ$_H$ (400 MHz, DMSO-d$_6$) 0.95 (9H, s), 1.45 (3H, s), 1.54 (3H, s), 2.30 (1H, m), 2.45 (1H, m), 3.00 (1H, m), 4.02 (1H, d, J=8 Hz), 4.50 (1H, d, J=8 Hz), 4.85 (1H, d, J=8 Hz), 5.00 (1H, d, J=16 Hz), 5.10 (2H, s), 5.60 (1H, m), 7.34 (5H, m), 8.12 (1H, d, J=8 Hz).

LRMS (thermospray) m/z=418 (MH$^+$)

| Found: | C, 66.13; | H, 7.50; | N, 3.36; |
| C$_{23}$H$_{31}$NO$_6$ requires | C, 66.17; | H, 7.48; | N, 3.35% | b) Palladium acetate (58 mg, 0.24 mmol) was added to a stirred solution of (2R)-2-[(4S)-2,2-dimethyl-5-oxo-1,3-dioxolan-4-yl]-N-{(1S)-2,2-dimethyl-1-[(benzyloxy)carbonyl]propyl}pent-4-enamide (2.0 g, 4.8 mmol), 4-iodo-2-methyl-1-phenylbenzene (Preparation 29)(2.1 g, 7.20 mmol) and N-ethylmorpholine (920 μL, 7.20 mmol) in anhydrous acetonitrile (15 mL), under nitrogen. The mixture was purged with nitrogen, then heated under reflux. After 1 h, due to the precipitation of palladium, palladium acetate (58 mg, 0.24 mmol) was added and refluxed continued. After a further 2 h, another 58 mg of palladium acetate was added. After another 2 h, tri-(2-methylphenyl)phosphine (304 mg, 1.0 mmol) and palladium acetate (58 mg, 0.24 mmol) were added and the mixture refluxed for 2 h, after which time, again tri-(2-methylphenyl)phosphine (304 mg, 1.0 mmol) and palladium acetate (58 mg, 0.24 mmol) were added and the mixture refluxed for 8 hr. The reaction mixture was cooled, diluted with ethyl acetate (200 mL) and water (200 mL) and filtered through Arbocel filter aid to remove palladium. The layers were separated and organic layer washed with water (2×100 mL), dried (Na$_2$SO$_4$) and concentrated under reduced pressure. The crude product was purified by flash chromatography. Firstly, chromatography eluting with a gradient elution with dichloromethane:ethyl acetate=50:1 to 15:1 gave a yellow gum. Further purification by flash chromatography (gradient elution with hexane:diethyl ether 10:1 to 1:1) and trituration with pentane:diethyl ether gave (2R, 4E)-N-{(1S)-1-[(benzyloxy)carbonyl]-2,2-dimethylpropyl}-2-[(4S)-2,2-dimethyl-5-oxo-1,3-dioxolan-4-yl]-5-[(3-methyl-4-phenyl)phenyl]pent-4-enamide as a white solid (710 mg, 25%).

m.p. 115° C.–118° C.

R$_f$ 0.30 (hexane:ethyl acetate=1:1)

δ$_H$ (300 MHz, CDCl$_3$) 0.96 (9H, s), 1.54 (3H, s), 1.60 (3H, s), 2.24 (3H, s), 2.65–2.90 (3H, m), 4.50 (1H, d, J=9.5 Hz), 4.60 (1H, d, J=7.5 Hz), 5.0 (1H, d, J=9.5 Hz), 5.3 (1H, d, J=9.5 Hz), 6.20 (1H, m), 6.44 (1H, d, J=9.5 Hz), 6.52 (1H, d, J=16 Hz), 7.10–7.42 (13H, complex).

LRMS (thermospray) m/z=584 ((M$^+$).

| Found: | C, 73.96; | H, 7.02; | N, 2.41; |
| C$_{36}$H$_{41}$NO$_6$ requires | C, 74.08; | H, 7.08; | N, 2.40% | c) A solution of (2R, 4E)-N-{(1S)-1-[(benzyloxy)carbonyl]-2,2-dimethylpropyl}-2-[(4S)-2,2-dimethyl-5-oxo-1,3-dioxolan-4-yl]-5-[(3-methyl-4-phenyl)phenyl]pent-4-enamide (1.24 gm, 2.12 mmol) in ethanol (50 mL) was hydrogenated over 10% palladium on charcoal (100 mg) at 3 bar and room temperature for 6 h. The mixture was filtered through Arbocel filter aid and concentrated under reduced pressure. The residue was azeotroped with diethyl ether to give (2R)-N-[(1S)-1-(carboxy)2,2-dimethylpropyl]-2-[(4S)-2,2-dimethyl-5-oxo-1,3-dioxolan-4-yl]-5-[(3-methyl-4-phenyl)phenyl]pentanamide (1.08 gm, 103%) as a colourless foam.

R$_f$ 0.40 (hexane:ethyl acetate:acetic acid=50:50:1)

δ$_H$ (400 MHz, DMSO-d$_6$) 0.95 (9H, s), 1.46 (3H, s), 1.55 (3H, s), 1.50–1.66 (3H, m), 1.80 (1H, m,), 2.20 (3H, s), 2.50 (1H, m), 2.60 (1H, m), 3.00 (1H, m), 4.15 (1H, d, J=8 Hz), 4.50 (1H, d, J=8 Hz), 7.05 (3H, m), 7.30 (3H, m), 7.40 (2H, m), 7.95 (1H, d, J=8 Hz).

| Found: | C, 69.50; | H, 7.69; | N, 2.69; |
| C$_{29}$H$_{37}$NO$_6$·0.3H$_2$O requires | C, 69.52; | H, 7.56; | N, 2.80% |

Preparation 34

(2R)-N-[(1S)-1-(Carboxy)-2,2-dimethylpropyl]-2-[(4S)-2,2-dimethyl-5-oxo-1,3-dioxolan-4-yl]-5-[(3'-methoxy-2methylbiphen-4-yl)propyl]pentanamide.

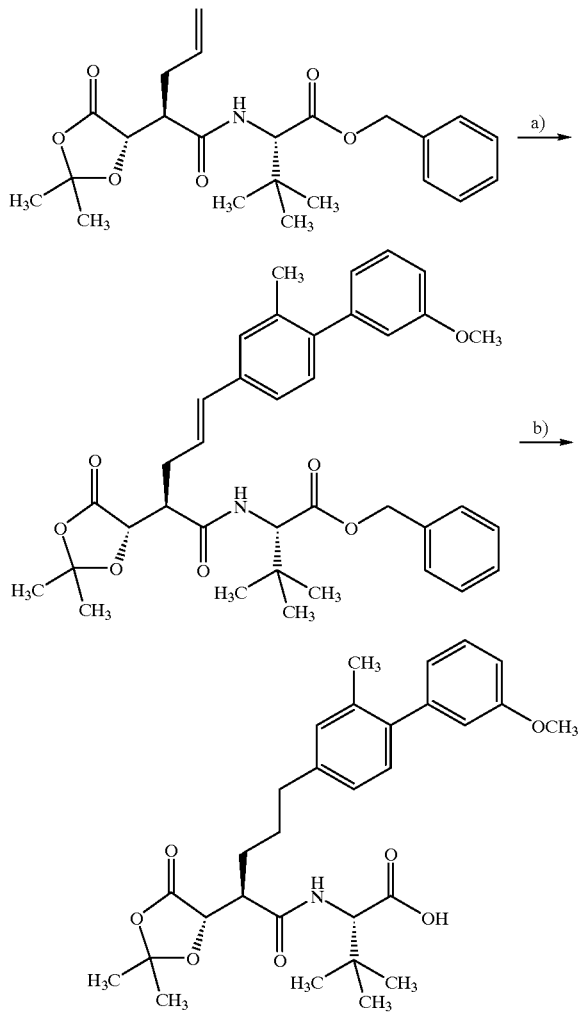

a) According to the method of Preparation 15 a), (2R)-N-[(1S)-1-[(benzyloxy)carbonyl]-2,2-dimethylpropyl]-2-[(4S)-2,2-dimethyl-5-oxo-1,3-dioxolan-4-yl]pent-4-enamide (Preparation 33a) (1.0 g, 2.4 mmol) was reacted with 4-iodo-1-(3-methoxyphenyl)-2-methylbenzene (Preparation 20)(1.16 g, 3.59 mmol) under palladium catalysis at reflux in acetonitrile for 16 h. After being cooled, the mixture was partitioned between ethyl acetate (3×75 mL) and saturated aqueous sodium bicarbonate (75 mL). The combined organic solutions were dried ($Na_2SO_4$) and concentrated under reduced pressure. The residue was purified by flash chromatography (eluting with dichloromethane:diethyl ether=97.5:2.5) to give (2R, 4E)-N-{(1S)-1-[(benzyloxy)carbonyl]-2,2-dimethylpropyl}-2-[(4S)-2,2-dimethyl-5-oxo-1,3-dioxolan-4-yl]-5-[(3'-methoxy-2-methylbiphen-4-yl)propyl]pent-4-enamide as a solid (1.08 mg, 74%). $^1$H nmr suggested that alkene isomers were also present. The mixture of alkenes was taken onto the next step (see b, below).

$R_f$ 0.44 (dichloromethane:diethyl ether=95:5)

$\delta_H$ (400 MHz, $CDCl_3$)(for the (4E) isomer). 0.95 (9H, s), 1.52 (3H, s), 1.60 (3H, s), 2.54–2.90 (3H, m), 3.80 (3H, s), 4.50 (1H, d, J=9.5 Hz), 4.60 (1H, d, J=5 Hz), 4.98 (1H, d, J=12 Hz), 5.07 (1H, d, J=12 Hz), 6.20 (1H, m), 6.45 (1H, d, J=9 Hz), 6.50 (1H, d, J=16 Hz), 6.86 (3H, m), 7.12–7.40 (9H, complex).

LRMS (thermospray) m/z=613 (MHF), 630 ($MNH_4^+$).

b) A solution of (2R, 4E)-N-{(1S)-1-[(benzyloxy)carbonyl]-2,2-dimethylpropyl}-2-[(4S)-2,2-dimethyl-5-oxo-1,3-dioxolan-4-yl]-5-[(3'-methoxy-2-methylbiphen-4-yl)propyl]pent-4-enamide (534 mg, 0.87 mmol) in ethanol (75 mL) was hydrogenated over 10% palladium on charcoal (50 mg) at 3 bar and 20° C. for 5.75 h. The mixture was filtered through Arbocel filter aid, concentrated under reduced pressure and azeotroped with ethyl acetate to give (2R)-N-[(1s)-1-(carboxy)-2,2-dimethylpropyl]-2-[(4S)-2,2-dimethyl-5-oxo-1,3-dioxolan-4-yl]-5-[(3'-methoxy-2-methylbiphen-4-yl)propyl]pentanamide (384 mg, 61%), as a white solid, which was used for Examples 30 and 31 without purification.

$\delta_H$ (400 MHz, DMSO-$d_6$) 0.96 (9H, s), 1.45 (3H, s), 1.55 (3H, s), 1.50–1.65 (3h, m), 1.80 (1H, m), 2.20 (3H, s), 2.50 (1H, m), 2.60 (1H, m), 2.96 (1H, m), 3.78 (3H, s), 4.15 (1H, d, J=9 Hz), 4.50 (1H, d, J=9 Hz), 6.85 (3H, m), 7.00 (1H, m), 7.05 (2H, m), 7.32 (1H, t, J=8 Hz), 7.96 (1H, d, J=9 Hz), 12.50 (1H, br s).

LRMS (thermospray) m/z=526 ($MH^+$).

All patents, patent applications, and publications cited above are incorporated herein by reference in their entirety.

The present invention is not to be limited in scope by the specific embodiments described, which are intended as single illustrations of individual aspects of the invention. Functionally equivalent compositions and methods are within the scope of the invention.

What is claimed is:

1. A compound of formula (I):

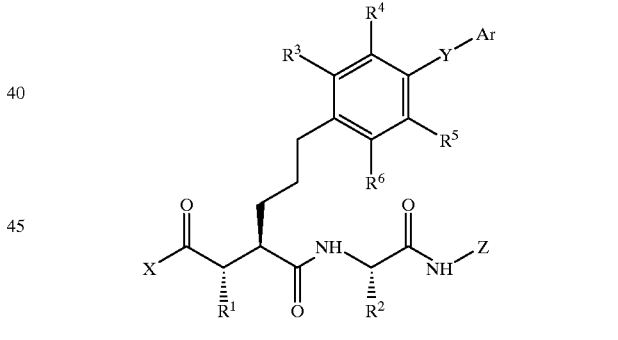

(I)

or a pharmaceutically acceptable salt thereof, or solvate of either entity, wherein $R^1$ is H, OH, $C_{1-4}$ alkyl, $C_{1-4}$ alkoxy, or $C_{2-4}$ alkenyl, $R^2$ is $C_{1-6}$ akyl optionally substituted by fluoro, indolyl, imidazolyl, $SO_2(C_{1-4}$ alkyl), $C_{5-7}$ cycloalkyl, or by an optionally protected OH, SH, $CONH_2$, $CO_2H$, $NH_2$ or NHC(=NH)$NH_2$ group, $C_{5-7}$ cycloalkyl optionally substituted by $C_{1-6}$ alkyl, or is benzyl optionally substituted by optionally protected OH, $C_{1-6}$ alkoxy, benzyloxy or benzylthio, wherein the optional protecting groups for said OH, SH, $CONH_2$, $NH_2$ and NHC(=NH)$NH_2$ groups are selected from $C_{1-6}$ alkyl, benzyl, $C_{1-6}$ alkanoyl, and where the optional protecting groups for said $CO_2H$ is selected from $C_{1-6}$ alkyl or benzyl, $R^3$, $R^5$ and $R^6$ are each independently selected from H and F, $R^4$ is $CH_3$, Cl or F,
X is HO or HONH,
Y is a direct link or O,
Z is either a group of formula (a):

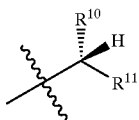

where $R^{10}$ is $C_{1-4}$ alkyl, $C_{1-4}$ alkoxymethyl, hydroxy($C_{2-4}$ alkyl), carboxy($C_{1-4}$ alkyl) or (amino or dimethylamino)$C_{2-4}$ alkyl,
and $R^{11}$ is phenyl, naphthyl or pyridyl optionally substituted by up to three substituents independently selected from halo and methyl;
or(b)

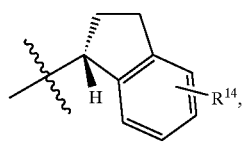

$R^{14}$ is H, OH, CH, or halo,
Ar is a group of formula (c), (d) or (e):

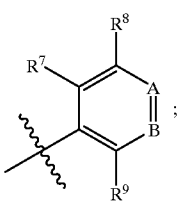

(c)

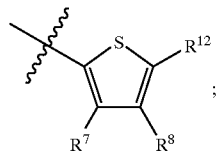

(d)

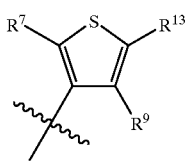

(e)

wherein
A is N or $CR^{12}$,
B is N or $CR^{13}$,
provided that A and B are not both N,
$R^7$ and $R^9$ are each independently H or F,
and $R^8$, $R^{12}$ and $R^{13}$ are H, CN, $C_{1-6}$ alkyl, hydroxy($C_{1-6}$ alkyl), hydroxy($C_{1-6}$)alkoxy, $C_{1-6}$ alkoxy($C_{1-6}$)alkoxy, (amino or dimethylamino)$C_{1-6}$ alkyl, $CONH_2$, OH, halo, $C_{1-6}$ alkoxy, ($C_{1-6}$ alkoxy)methyl, piperazinylcarbonyl, piperidinyl, $C(NH_2)=NOH$ or $C(=NH)NHOH$, with the proviso that at least two of $R^8$, $R^{12}$ and $R^{13}$ are H.

2. The compound according to claim 1 wherein $R^1$ is H, OH, $C_{1-4}$ alkyl or $C_{1-4}$ alkoxy.

3. The compound according to claim 1 wherein $R^2$ is $C_{1-6}$ alkyl optionally substituted by indolyl, $C_{1-6}$ alkylthio, $SO_2$($C_{1-4}$ alkyl), $C_{5-7}$ cycloalkyl, OH or SH, $C_{5-7}$ cycloalkyl optionally substituted by $C_{1-6}$ alkyl,
or $R^2$ is benzyl.

4. The compound according to claim 1 wherein Z is a group of formula (a):

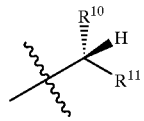

where $R^{10}$ is $C_{1-4}$ alkyl, $C_{1-4}$ alkoxymethyl or hydroxy($C_{2-4}$ alkyl)
and $R^{11}$ is phenyl or pyridyl, optionally substituted by up to three substituents independently selected from halo and methyl,
or Z is

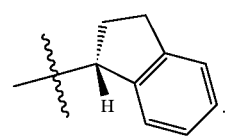

5. The compound according to claim 1 wherein $R^3$ is H.
6. The compound according to claim 1 wherein $R^4$ is F when Y is O, and $R^4$ is Cl or $CH_3$ when Y is a direct link.
7. The compound according to claim 1 wherein $R^5$ is H.
8. The compound according to claim 1 wherein $R^6$ is H.
9. The compound according to claim 1 wherein Ar is a group of formula (c),

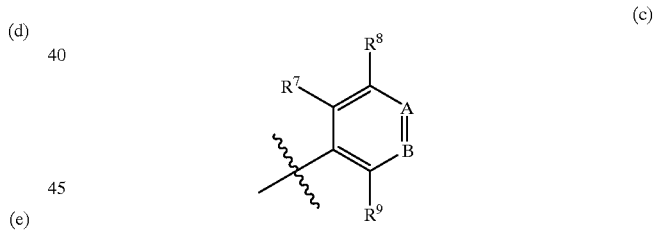

(c)

wherein
A is $CR^{12}$ and B is $CR^{13}$,
$R^7$ and $R^9$ are each independently H or F,
$R^8$ and $R^{13}$ are each independently H, F, Cl, CN, $CONH_2$, $CH_3$ or $OCH_3$, and
$R^{12}$ is H, $C_{1-6}$ alkyl, CN, hydroxy($C_{2-6}$ alkyl), (amino or dimethylamino)$C_{2-6}$ alkyl, $CONH_2$, OH, halo, $C_{1-6}$ alkoxy, ($C_{1-6}$ alkoxy)methyl, piperazinylcarbonyl, piperidinyl, $C(NH_2)NOH$ or $C(=NH)NHOH$.

10. The compound according to claim 1 wherein $R^1$ is H, OH, n-propyl or ethoxy.

11. The compound according to claim 1 wherein $R^2$ is $C_{1-6}$ alkyl optionally substituted by OH, $SO_2$($C_{1-4}$ alkyl) or $C_{5-7}$ cycloalkyl, cyclohexyl optionally substituted by $C_{1-6}$ alkyl,
or $R^2$ is benzyl.

12. The compound according to claim 1 wherein Z is a group of formula (a):

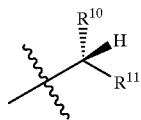

where $R^{10}$ is $C_{1-4}$ alkyl, $C_{1-4}$ alkoxymethyl or hydroxy($C_{24}$ alkyl), and $R^{11}$ is phenyl, pyridin-4-yl or pyridin-3-yl, or Z is

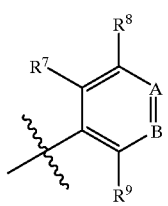

13. The compound according to claim 1 wherein Ar is a group of formula (c),

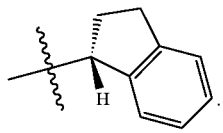 (c)

wherein

A is $CR^{12}$, B is $CR^{13}$, and $R^7$, $R^8$ and $R^9$ are H.

14. The compound according to claim 1 wherein $R^1$ is H.

15. The compound according to claim 1 wherein $R^2$ is cyclohexylmethyl, isopropyl, 1-methylcyclohexyl, t-butyl, $C(CH_3)_2SO_2CH_3$, benzyl or $C(CH_3)_2OH$.

16. The compound according to claim 1 wherein Z is a group of formula (a):

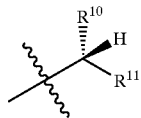

where $R^{10}$ is $CH_3$, $CH_2OCH_3$, or $CH_2OH$, and $R^{11}$ is phenyl, pyridin-4-yl or pyridin-3-yl, or Z is

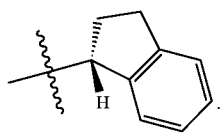

17. The compound according to claim 1 wherein Ar is a group of formula (c),

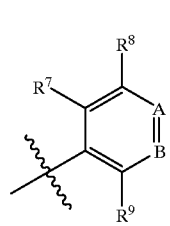 (c)

wherein

A is $CR^{12}$, B is $CR^{13}$, $R^7$, $R^8$ and $R^9$ are H, $R^{12}$ is H, $C_{1-6}$ alkyl, CN, hydroxy($C_{2-6}$ alkyl), (amino or dimethylamino)$C_{2-6}$ alkyl, $CONH_2$, OH, halo, $C_{1-6}$ alkoxy, ($C_{1-6}$ alkoxy)methyl, $C(NH_2)=NOH$ or $C(=NH)NHOH$, and $R^{13}$ is H, $OCH_3$, CN, $CONH_2$, $CH_3$ or F.

18. The compound according to claim 1 wherein $R^2$ is isopropyl, t-butyl or benzyl.

19. The compound according to claim 1 wherein Z is a group of formula

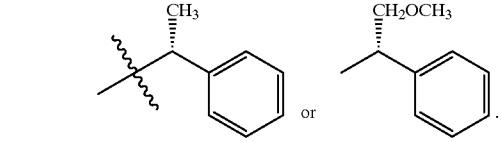

20. The compound according to claim 1 wherein Ar is phenyl, 3-methoxyphenyl, 4-cyanophenyl, 3-cyanophenyl, 3-carbamoylphenyl or 4-hydroxyamidinophenyl.

21. The compound according to claim 1 wherein $R^2$ is t-butyl.

22. The compound according to claim 1 wherein Ar is phenyl or 3-methoxyphenyl.

23. The compound according to claim 1 wherein $R^1$ is H, OH, n-propyl or ethoxy, $R^2$ is t-butyl, isopropyl or benzyl, Z is a group of formula

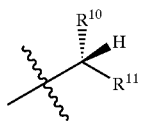

where $R^{10}$ is CH, $CH_2OCH_3$, or $CH_2OH$, and $R^{11}$ is phenyl, pyridin-4-yl or pyridin-3-yl, or Z is

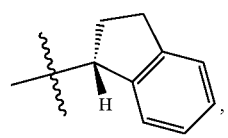

$R^3$ is H, $R^4$ is $CH_3$, Cl or F, $R^5$ is H, $R^6$ is H, and Ar is phenyl, 3-methoxyphenyl, 4-cyanophenyl, 3-cyanophenyl, 3-carbamoylphenyl or 4-hydroxyamidinophenyl.

24. A pharmaceutical composition comprising the compound according to claim 1, in admixture with a compatible adjuvant, diluent or carrier.

25. A method of treating a condition mediated by MMPs, which comprises administering to a patient in need of said treatment an effective amount of a compound according to claim 1.

26. A process for making a compound according to claim 1 where X is OH, comprising transforming a compound of formula (II)

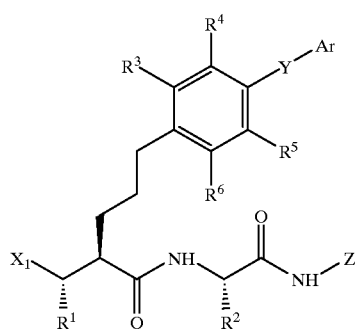

(II)

where $X_1$ is a group capable of being transformed to a carboxy, and the other substituents are as defined in claim 1.

27. A process for making a compound according to claim 1 where X is NHOH and $R^1$, $R^2$, $R^3$, $R^4$, $R^5$, $R^6$, Y, Ar and Z are as defined in claim 1, comprising reacting a compound of formula (I) according to claim 1 where X is OH with hydroxylamine or a hydroxylamine derivative.

28. A process for making a compound according to claim 1 where X is NHOH and $R^1$, $R^2$, $R^3$, $R^4$, $R^5$, $R^6$, Y, Ar and Z are as defined in claim 1, comprising reacting a compound of formula (I) where X is OH with O-allylhydroxylamine or a salt thereof, in the presence of a peptide coupling agent to give a compound of formula (III):

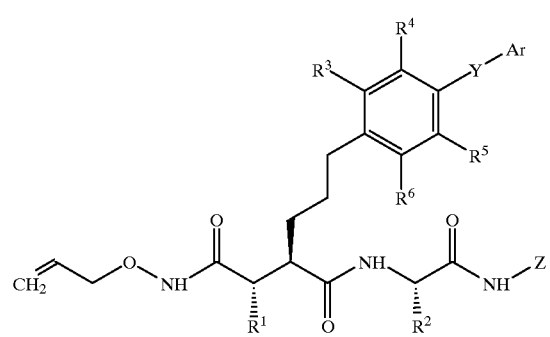

(III)

followed by treating the compound of formula (III) with ammonium formate in the presence of a suitable catalyst.

29. A process for making a compound according to claim 1 where X is NHOH, $R^1$ is OH and $R^2$, $R^3$, $R^4$, $R^5$, $R^6$, Y, Ar and Z are as defined in claim 1, comprising reacting a compound of formula (IV)

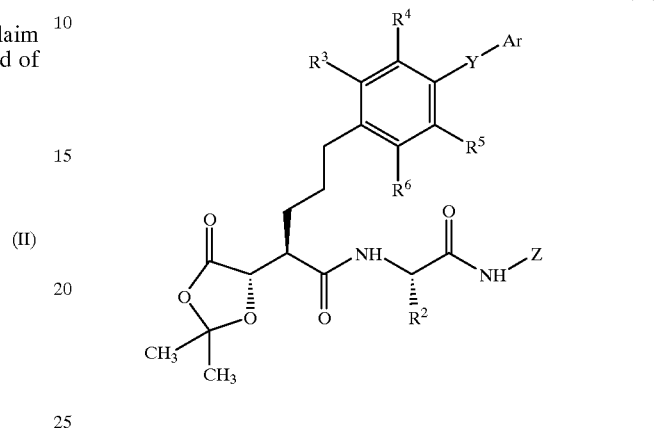

(IV)

with hydroxylamine or a salt thereof.

30. A process for making the compound according to claim 1 where X is OH and $R^1$, $R^2$, $R^3$, $R^4$, $R^5$, $R^6$, Y, Ar and Z are as defined in claim 1, which comprises cross-coupling a compound of formula (V) with a compound of formula (VI):

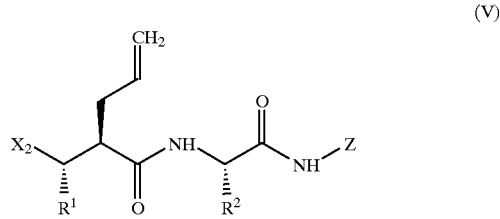

(V)

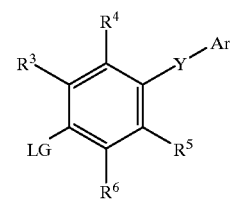

(VI)

where $X_2$ is a protected acid such as a $CO_2CH_3$ or $CO_2$(t-butyl) group and LG is a cross-coupling leaving group such as I, Br or $OSO_2CF_3$, and $R^1$, $R^2$, $R^3$, $R^4$, $R^5$, $R^6$, Y, Ar, and Z are as defined in claim 1, in the presence of a catalyst, to produce a compound or compounds of formula (VIIa) and/or (VIIb) wherein $X_2$ is defined as above for compounds of formula (V) and $R^1$, $R^2$, $R^3$, $R^4$, $R^5$, $R^6$, Y, Ar and Z are as defined in claim 1,

32. A compound of formula (I)

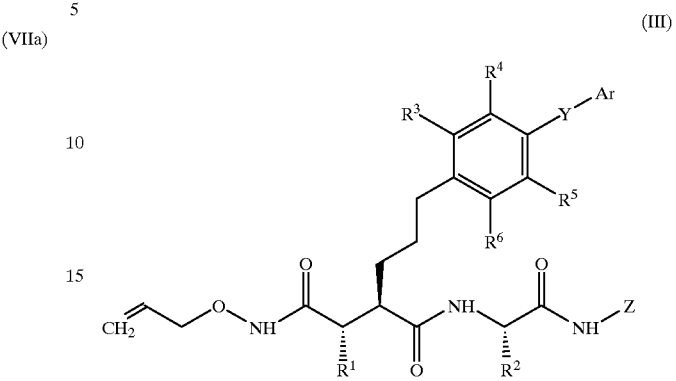

where $R^1$, $R^2$, $R^3$, $R^4$, $R^5$, $R^6$, Y, Ar and Z are as defined in claim 28, or salt thereof, or solvate of either entity.

33. A compound of formula (IV)

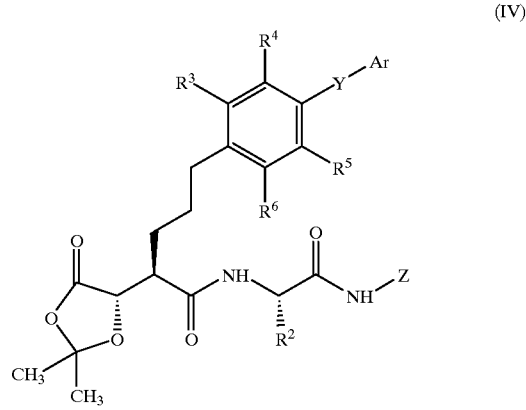

where $R^2$, $R^{3l}$, $^{R4}$, $R^5$, $R^6$, Y, Ar and Z are as defined in claim 29, or salt thereof, or solvate of either entity.

34. A compound of formula (VIIa) or (VIIb)

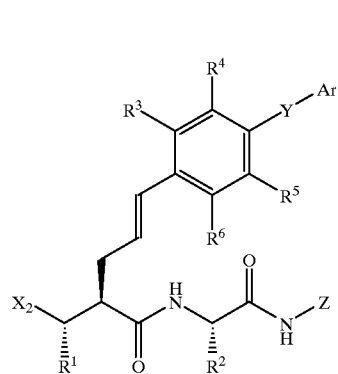

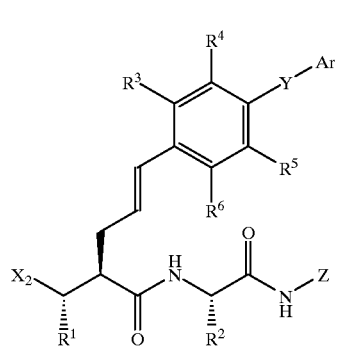

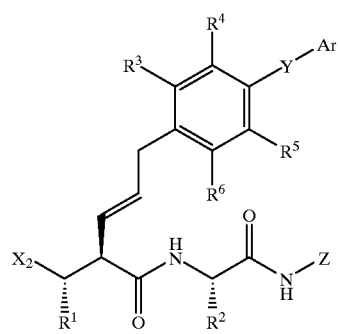

followed by reducing the olefinic moiety and deprotecting the protected acid moiety $X_2$.

31. A compound of formula (II)

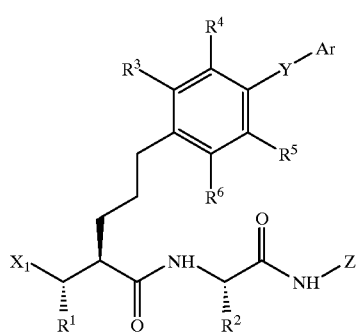

where the $X_1$, $R^1$, $R^2$, $R^3$, $R^4$, $R^5$, $R^6$, Y, Ar and Z are as defined in claim 26, or salt thereof, or solvate of either entity.

(VIIb)

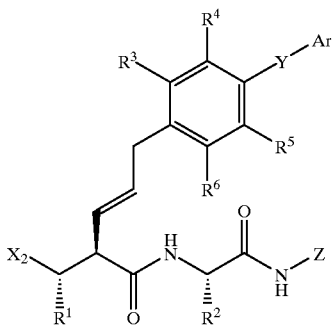

wherein $X_2$, $R^1$, $R^2$, $R^3$, $R^4$, $R^5$, $R^6$, Y, Ar and Z are as defined in claim 30, or salt thereof, or solvate of either entity.

35. The method of claim 25 wherein the condition is mediated by MMP-3, MMP-12, or MMP-13, or a combination thereof.

36. The process of claim 26 wherein $X_1$ is a $CO_2$(t-butyl or methyl) moiety, and the transformation of the compound of formula (II) takes place by hydrolysis.

37. A compound according to claim 1, selected from the group consisting of:

N1-[(1S)-2,2-dimethyl-1-({[(1R)-1-phenylethyl]amino}carbonyl)propyl]-(N4-hydroxy)-(2R)-2-{3-[3-methyl-(4-phenyl)phenyl]propyl}butanediamide;

N1-[(1S)-2,2-dimethyl-1-({[(1R)-1-phenylethyl]amino}carbonyl)propyl]-(2R)-2-[3-(3-fluoro-4-phenoxyphenyl)propyl]-(N4-hydroxy)butanediamide;

N1-[(1S)-2,2-dimethyl-1-({[(1R)-1-phenylethyl]amino}carbonyl)propyl]-(N4-hydroxy)-(2R)-2-{3-[3-methyl-(4-phenyl)phenyl]propyl}-(3S)-propylbutanediamide;

(3R)-3-({[(1S)-2,2-dimethyl-1-({[(1S)-2-methoxy-1-phenylethyl]amino}carbonyl)-propyl]amino}carbonyl)-6-[(3-methyl-4-phenyl)phenyl]hexanoic acid;

(3R)-3-({[(1S)-2,2-dimethyl-1-({[(1S)-2-methoxy-1-phenylethyl]amino}carbonyl)-propyl]amino}carbonyl)-6-[(3'-methoxy-2-methylbiphen-4-yl)hexanoic acid;

(2R)-N-1-[(1S)-2,2-dimethyl-1-({[(1S)-2-methoxy-1-phenylethyl]amino}carbonyl)propyl]-2-{3-[(3-methyl-4-phenyl)phenyl]propyl}-(N-4-hydroxy)butanediamide;

(3R)-3-({[({[(1S)-2-methoxy-1-phenylethyl]amino}carbonyl)-(1S)-2-phenylethyl]amino}carbonyl)-6-[3-methyl-(4-phenyl)phenyl]hexanoic acid;

(N4,3S)-dihydroxy-N1-[(1S)-2,2-dimethyl-1-({[(1S)-2-methoxy-1-phenylethyl]amino}carbonyl)propyl]-(2R)-2-{3-[3-methyl-(4-phenyl)phenyl]propylbutanediamide;

(N4,3S)-dihydroxy-N1-[(1S)-2,2-dimethyl-1-({[(1R)-1-phenylethyl]amino}carbonyl)propyl]-(2R)-2-{3-[3'-methoxy-2-methylbiphen-4-yl) propyl]}butanediamide;

(N4,3S)-dihydroxy-N1-[(1S)-2,2-dimethyl-1-({[(1S)-2-methoxy-1-phenylethyl]amino}carbonyl)propyl]-(2R)-2-{3-[(3'-methoxy-2-methylbiphen-4-yl)propyl]}butanediamide;

(2R)-N1-[(1S)-2,2-dimethyl-1-({[(1S)-2-methoxy-1-phenylethyl]amino}carbonyl)propyl]-(N4-hydroxy)-2-{3-[3'-methoxy-2-methylbiphen-4-yl]propyl}butanediamide;

and the salts and solvates thereof.

* * * * *